(12) United States Patent
Siu et al.

(10) Patent No.: US 8,349,865 B2
(45) Date of Patent: *Jan. 8, 2013

(54) INHIBITORS OF JANUS KINASES

(75) Inventors: Tony Siu, Brookline, MA (US); Jonathan Young, Southborough, MA (US); Michael Altman, Cambridge, MA (US); Alan Northrup, Reading, MA (US); Matthew Katcher, Brookline, MA (US); Ellalahewage Sathyajith Kumarasinghe, Franklin, MA (US); Ekaterina Kozina, Evanston, IL (US); Scott Peterson, Somerville, MA (US); Matthew Childers, Newton Highlands, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 352 days.

This patent is subject to a terminal disclaimer.

(21) Appl. No.: 12/677,375

(22) PCT Filed: Sep. 8, 2008

(86) PCT No.: PCT/US2008/010507
§ 371 (c)(1),
(2), (4) Date: Mar. 10, 2010

(87) PCT Pub. No.: WO2009/035575
PCT Pub. Date: Mar. 19, 2009

(65) Prior Publication Data
US 2010/0197634 A1 Aug. 5, 2010

Related U.S. Application Data

(60) Provisional application No. 60/993,224, filed on Sep. 11, 2007.

(51) Int. Cl.
*C07D 471/06* (2006.01)
*A61K 31/4375* (2006.01)

(52) U.S. Cl. ............ 514/292; 514/293; 546/81; 546/82
(58) Field of Classification Search ................ 546/81, 546/82; 514/292, 293
See application file for complete search history.

(56) References Cited

U.S. PATENT DOCUMENTS
2005/0153966 A1 7/2005 Gangloff et al.

FOREIGN PATENT DOCUMENTS
| WO | 03/011285 A1 | 2/2003 |
| WO | 2005/105814 A1 | 11/2005 |
| WO | 2007/008502 A2 | 1/2007 |
| WO | 2008112217 | * 9/2008 |

OTHER PUBLICATIONS

Dorwald F. A. Side Reactions in Organic Synthesis, 2005, Wiley: VCH, Weinheim p. IX of Preface.*
Matsui, T et al., Journal of Medicinal Chemistry, American Cancer Society, vol. 35, No. 18, pp. 3307-3319 (1992), "Novel 5-HT3 Antagonists. Isoquinolinones and 3-Aryl-1-pyridones".
Ried, W et al., Liebigs Annalen Der Chemie, vol. 707, pp. 242-249 (1967), "Chinoline aus Isatin und aliphatischen Iminoverbindungen".
Rajamanickam, P et al., Synthesis, vol. 5, pp. 541-543 (1985), "A convenient synthesis of benzo[c][2,6]naphthyridines".
Dhanabal, T et al., Tetrahedron, vol. 62, pp. 6258-6263 (2006), "Heteroatom directed photoannulation: synthesis of indoloquinoline alkaloids: cryptolepine, cryptotackieine, cryptosanguinolentine, and their methyl derivatives".

* cited by examiner

*Primary Examiner* — Rita Desai
(74) *Attorney, Agent, or Firm* — Laura M. Ginkel; David A. Muthard

(57) ABSTRACT

The instant invention provides for compounds that inhibit the four known mammalian JAK kinases (JAK1, JAK2, JAK3 and TYK2) and PDK1. The invention also provides for compositions comprising such inhibitory compounds and methods of inhibiting the activity of JAK1, JAK2, JAK3 TYK2 and PDK1 by administering the compound to a patient in need of treatment for myeloproliferative disorders or cancer.

7 Claims, No Drawings

INHIBITORS OF JANUS KINASES

CROSS REFERENCE TO RELATED APPLICATIONS

This application is a U.S. National Phase application under 35 U.S.C. §371 of PCT Application No. PCT/US2008/010507 filed Sep. 08, 2008, which claims priority from U.S. Provisional Application Ser. No. 60/993,224, filed Sep. 11, 2007.

REFERENCE TO SEQUENCE LISTING SUBMITTED ELECTRONICALLY

The sequence listing of the present application is being submitted electronically via EFS-Web as an ASCII formatted sequence listing with a file name "MRLONC22400USPCT-SEQTXT -10MAR2010", creation date of Feb. 25, 2010 and a size of 862 bytes. This sequence listing submitted via EFS-Web is part of the specification and is herein incorporated by reference in its entirety.

BACKGROUND OF THE INVENTION

Janus kinase (JAK) is a family of intracellular non-receptor tyrosine kinases, ranging from 120-140 kDa, that transduce cytokine-mediated signals via the JAK-STAT pathway. The JAK family plays a role in the cytokine-dependent regulation of proliferation and function of cells involved in immune response. Currently, there are four known mammalian JAK family members: JAK1, JAK2, JAK3 and TYK2.

JAK1, JAK2 and TYK2 are ubiquitously expressed whereas JAK3 is expressed in the myeloid and lymphoid lineages. The JAK family members are non-receptor tyrosine kinases that associate with many hematopoietin cytokines, receptor tyrosine kinases and GPCR's. JAK1(−/−) mice were found to be developmentally similar to the JAK1(+/+) although they weighed 40% less than the wild-type and failed to nurse at birth. These pups were not viable and died within 24 hours of birth (Meraz et al Cell, 1998, 373-383). JAK1 deficiency led to reduced number of thymocytes, pre-B cells and mature T and B lymphocytes. TYK2(−/−) mice, on the other hand, are viable, demonstrating subtle defects in their response to IFN-α/β and IL-10 and profound defects to the response of IL-12 and LPS.

The breast cancer susceptibility protein (BRCA1) acts as a tumor suppressor and contributes to cell proliferation, cycle regulation, as well as DNA damage and repair. BRCA1 (−/−) mice develop normally but die by 7.5 days post embryo suggesting a key role of BRCA1 for development. Mice in which the BRCA1 protein was over expressed led to inhibition of cell growth and sensitized cells to cytotoxic reagents. In the human prostate cancer cell line Du-145 (Gao FEBS Letters 2001, 488, 179-184), enhanced expression of BRCA1 was found to correlate with constitutive activation of STAT3 as well as activation of JAK1 and JAK2. Moreover, antisense oligonucleotides selective for STAT3 led to significant inhibition of cell proliferation and apoptosis in Du-145 cells. This data supports the potential utility of JAK1 and JAK2 inhibitors in the treatment of prostate cancer.

Campbell et al (Journal of Biological Chemistry 1997, 272, 2591-2594) has reported that STAT3 is constitutively activated in v-Src transformed cells. To test whether STAT3 activation resulted via signaling through the JAK-STAT pathway, three fibroblast cell lines (NIH3T3, Balb/c, and 3Y1) were transformed with v-Src. The level of JAK1 phosphorylation in NIH3T3 cells was markedly increased in cells over-expressed with v-Src or mutant c-Src (Y527F) compared to those in the less transforming c-Src. This result correlated with increased JAK1 enzymatic activity. Similar results were observed with JAK2 albeit to a lesser extent. These results are consistent with constitutive activation of JAK1 and possibly JAK2 which contribute to the hyperactivation of STAT3 in Src-transformed cells.

Asthma is a disease that is increasing in prevalence and results in "airway obstruction, airway hyperresponsiveness, and airway inflammation and remodeling" (Pernis The Journal of Clinical Investigation 2002, 109, 1279-1283). A common cause is the inappropriate immune responses to environmental antigens usually involving CD4+ T helper cells (TH2) which are triggered from cytokines IL-4, IL-5, IL-6, IL-10, and IL-13 which signal through JAK1/JAK3-STAT6 pathway. Th1 cells are thought to be involved with the "delayed-type hypersensitivity responses" which secrete IL-2, IFN-γ, and TNF-β and signal through the JAK2/TYK2-STAT4 pathway. STAT6 (−/−) mice were protected from AHR when challenged with environmental antigens and showed no increase in IgE levels or the quantity of mucous containing cells.

JAK2 is a cytoplasmic protein-tyrosine kinase that catalyzes the transfer of the gamma-phosphate group of adenosine triphosphate to the hydroxyl groups of specific tyrosine residues in signal transduction molecules. JAK2 mediates signaling downstream of cytokine receptors after ligand-induced autophosphorylation of both receptor and enzyme. The main downstream effectors of JAK2 are a family of transcription factors known as signal transducers and activators of transcription (STAT) proteins. Studies have disclosed an association between an activating JAK2 mutation (JAK2V617F) and myeloproliferative disorders. The myeloproliferative disorders, a subgroup of myeloid malignancies, are clonal stem cell diseases characterized by an expansion of morphologically mature granulocyte, erythroid, megakaryocyte, or monocyte lineage cells. Myeloproliferative disorders (MPD) include polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), juvenile myelomonocytic leukemia (JMML) and systemic mast cell disease (SMCD). It has been suggested that abnormalties in signal transduction mechanisms, including constitutive activation of protein tyrosine kinases, initiate MPD.

JAK3 associates with the common gamma chain of the extracellular receptors for the following interleukins: IL-2, IL-4, IL-7, IL-9 and IL-15. A JAK3 deficiency is associated with an immune compromised (SCID) phenotype in both rodents and humans. The SCID phenotype of JAK3 (−/−) mammals and the lymphoid cell specific expression of JAK3 are two favorable attributes of a target for an immune suppressant. Data suggests that inhibitors of JAK3 could impede T-cell activation and prevent rejection of grafts following transplant surgery, or to provide therapeutic benefit to patients suffering autoimmune disorders.

SUMMARY OF THE INVENTION

The instant invention provides for compounds that inhibit mammalian JAK kinases (such as JAK1, JAK2, JAK3 and TYK2). The invention also provides for compositions comprising such inhibitory compounds and methods of inhibiting the activity of JAK1, JAK2, JAK3 and TYK2 by administering the compound to a patient in need of treatment for myeloproliferative disorders or cancer. One embodiment of the invention is illustrated by a compound of the following formula, and the pharmaceutically acceptable salts and stereoisomers thereof:

DETAILED DESCRIPTION OF THE INVENTION

The instant invention provides for compounds that inhibit the four known mammalian JAK kinases (JAK1, JAK2, JAK3 and TYK2). The invention also provides for compositions comprising such inhibitory compounds and methods of inhibiting the activity of JAK1, JAK2, JAK3 and TYK2 by administering the compound to a patient in need of treatment for myeloproliferative disorders or cancer. One embodiment of the invention is illustrated by a compound of formula I:

I wherein D is N, NO or $CR^3$;
E is N, NO or $CR^3$;
G is N, NO or $CR^3$;
J is N, NO or $CR^3$;
L is a single bond, —NH—, —O—, —C(O)— or —SO$_m$—;
M is
(a) hydrogen,
(b) halo,
(c) hydroxyl,
(d) $C_{1-6}$ alkyl, optionally substituted with one to four substituents independently selected from the group consisting of halo, hydroxyl, $SO_2NR^4R^5$, $Si(CH_3)_3$ and $Si(CH_3)_3O(C_{1-6}$ haloalkyl),
(e) $C_{2-6}$ alkenyl,
(f) $C_{1-6}$ haloalkyl, which is optionally substituted with $C_{3-8}$ cycloalkyl,
(g) $C_{3-8}$ cycloalkyl,
(h) $(C_{1-6}$ alkyl)$C_{3-8}$ cycloalkyl,
(i) aryl, which is optionally substituted with one to four substituents independently selected from the group consisting of halo, hydroxyl, cyano, $C_{1-6}$ alkyl (which is optionally substituted with one to three substituents independently selected from the group consisting of cyano, halo, hydroxyl and $NR^4R^5$), $C_{2-6}$ alkenyl (which is optionally substituted with hydroxyl), $C_{2-6}$ alkynyl (which is optionally substituted with hydroxyl or $Si(CH_3)_3$), $O(C_{1-6}$ haloalkyl), $C_{3-8}$ cycloalkyl (which is optionally substituted with hydroxyl), heteroaryl (which is optionally substituted on either the carbon or heteroatom with $R^8$), $SO_mNHR^7$, $SO_mR^7$, $(C_{1-6}$ alkyl)$NHSO_mR^7$, (C=O)$R^8$, (C=O)$OR^8$, (C=O)$NHR^8$, (C=O)NH—$C_{1-3}$ alkyl-heterocyclyl, (C=NH)$NHR^8$, (C=NOR$^8$)$C_{1-3}$ alkyl, (C=NO—$C_{1-3}$ alkyl-(C=O)heterocyclyl)$C_{1-3}$ alkyl, and (C=NO—$C_{2-6}$ alkenyl)$C_{1-3}$ alkyl,
(j) heteroaryl, which optionally substituted on either the carbon or heteroatom with one to three substituents independently selected from the group consisting of halo, oxo, aryl and $R^8$;
(k) heterocyclyl,
(l) $(C_{1-6}$ alkyl)aryl, which is optionally substituted on either the alkyl or aryl group with a substituent selected from the group consisting of one to two halo and $SO_mNHR^7$,
(m) C(O)$R^8$, or
(n) $NR^4R^5$;
$R^1$ is hydrogen, halo, $C_{1-6}$ alkyl, $C_{1-6}$ haloalkyl, O($C_{1-6}$ alkyl), O($C_{1-6}$ haloalkyl), aryl, heteroaryl, heterocyclyl, or $NR^4R^5$;
$R^2$ is hydrogen, halo, $C_{1-6}$ alkyl, $C_{1-6}$ haloalkyl, O($C_{1-6}$ alkyl), O($C_{1-6}$ haloalkyl), aryl, heteroaryl, heterocyclyl, or $NR^4R^5$;
$R^3$ is
(a) hydrogen,
(b) halo,
(c) hydroxyl,
(d) $C_{1-6}$ alkyl,
(e) $C_{2-6}$ alkenyl, optionally substituted with one to three hydroxyl,
(f) $C_{2-6}$ alkynyl, optionally substituted with one to two substituents independently selected from the group consisting of hydroxyl, heteroaryl and $NR^4R^5$,
(g) $C_{1-6}$ haloalkyl,
(h) O($C_{1-6}$ alkyl),
(i) O($C_{1-6}$ haloalkyl),
(j) aryl,
(k) heteroaryl, optionally substituted on either the carbon or heteroatom with one to three substituents independently selected from the group consisting of hydroxyl, $R^8$, $C_{1-6}$ alkyl(heterocyclyl), $CH_2$(C=O)$OR^8$ and $NR^4R^5$,
(l) heterocyclyl,
(m) B(OH)$_2$,
(n) $NR^4R^5$,
(o) $NHR^6$ or
(p) NH(C=O)$R^6$;
$R^4$ is hydrogen or $C_{1-6}$ alkyl;
$R^5$ is hydrogen or $C_{1-6}$ alkyl;
$R^6$ is hydrogen, $C_{1-6}$ alkyl, $NR^4R^5$, —NH($C_{1-6}$ alkyl)$OR^8$, aryl, heteroaryl or heterocyclyl (which is optionally substituted on either the carbon or heteroatom with $R^8$), wherein said alkyl groups are optionally substituted with one to four substituents selected from hydroxy, halo, $OR^8$, $NR^8SO_2NR^4R^5$, heteroaryl or heterocyclyl;
m is an integer from zero to two;
or a pharmaceutically acceptable salt or stereoisomer thereof.
$R^7$ is hydrogen, $C_{1-6}$ alkyl, ($C_{3-6}$ cycloalkyl), heterocyclyl, ($C_{1-6}$ alkyl)heterocyclyl or ($C_{1-6}$ alkyl)heteroaryl, wherein said alkyl group is optionally substituted with one to four substituents selected from the group consisting of halo and hydroxy, and said heteroaryl group is optionally substituted with $C_{1-6}$ alkyl;

R⁸ is hydrogen or $C_{1-6}$ alkyl, wherein said alkyl is optionally substituted with one to two hydroxyl;

m is an integer from zero to two;

or a pharmaceutically acceptable salt or stereoisomer thereof.

In an embodiment of the invention, $R^1$ is hydrogen.

In an embodiment of the invention, $R^2$ is hydrogen.

In an embodiment of the invention, $R^3$ is hydrogen, halo, $C_{2-6}$ alkenyl (optionally substituted with one to three hydroxyl), $C_{2-6}$ alkynyl (optionally substituted with one to two substituents independently selected from the group consisting of hydroxyl, heteroaryl and $NR^4R^5$), heteroaryl (optionally substituted on either the carbon or heteroatom with one to three substituents independently selected from the group consisting of hydroxyl, $R^8$, $C_{1-6}$ alkyl(heterocyclyl), $CH_2(C=O)OR^8$ and $NR^4R^5$) or $B(OH)_2$.

In an embodiment of the invention, L is —NH—.

In an embodiment of the invention, D is $CR^3$.

In an embodiment of the invention, E is $CR^3$. In another embodiment of the invention, E is N.

In an embodiment of the invention, G is $CR^3$.

In an embodiment of the invention, J is $CR^3$.

In an embodiment of the invention, M is $C_{1-6}$ alkyl, optionally substituted with one to four substituents independently selected from the group consisting of halo, hydroxyl and $SO_2NR^4R^5$; aryl, which is optionally substituted with one to four substituents independently selected from the group consisting of halo, hydroxyl, cyano, $C_{1-6}$ alkyl (which is optionally substituted with one to three substituents independently selected from the group consisting of halo and hydroxyl), $O(C_{1-6}$ haloalkyl), $C_{3-8}$ cycloalkyl (which is optionally substituted with hydroxyl), heteroaryl (which is optionally substituted on either the carbon or heteroatom with $R^8$) and $SO_mNHR^7$; or heteroaryl, which is optionally substituted with halo. In a class of the embodiment, M is aryl, which is optionally substituted with one to four substituents independently selected from the group consisting of halo, hydroxyl, cyano, $C_{1-6}$ alkyl (which is optionally substituted with one to three substituents independently selected from the group consisting of halo and hydroxyl), $O(C_{1-6}$ haloalkyl), $C_{3-8}$ cycloalkyl (which is optionally substituted with hydroxyl), heteroaryl and $SO_mNHR^7$. In a subclass of the embodiment, M is aryl, which is optionally substituted with one to four substituents independently selected from the group consisting of halo, $C_{1-6}$ alkyl (which is optionally substituted with one to three substituents independently selected from the group consisting of halo and hydroxyl), heteroaryl and $SO_mNHR^7$.

In an embodiment of the invention, m is two.

Reference to the preferred embodiments set forth above is meant to include all combinations of particular and preferred groups unless stated otherwise.

Specific embodiments of the present invention include, but are not limited to:

5-(Cyclopropylamino)-9-fluorobenzo[c]-2,6-naphthyridin-1(2H)-one;

9-Fluoro-5-{[(1S)-2-methyl-1-(trifluoromethyl)propyl]amino}benzo[c]-2,6-naphthyridin-1(2H)-one;

9-Bromo-5-[(2,4,6-trifluorophenyl)amino]benzo[c]-2,6-naphthyridin-1(2H)-one;

5-[(5-tert-Butyl-2-methylphenyl)amino]-9-fluorobenzo[c]-2,6-naphthyridin-1(2H)-one;

9-Fluoro-5-[(1,2,2-trimethylpropyl)amino]benzo[c]-2,6-naphthyridin-1(2H)-one;

5-[(2,2-Dimethylpropyl)amino]-9-fluorobenzo[c]-2,6-naphthyridin-1(2H)-one;

5-[(2,6-Dichlorobenzyl)amino]-9-fluorobenzo[c]-2,6-naphthyridin-1(2H)-one;

9-Fluoro-5-{[(1R)-2-methyl-1-(trifluoromethyl)propyl]amino}benzo[c]-2,6-naphthyridin-1(2H)-one;

5-[(2-Chloro-3,6-difluorophenyl)amino]-9-fluorobenzo[c]-2,6-naphthyridin-1(2H)-one;

9-Fluoro-5-{[(1S)-1-(trifluoromethyl)propyl]amino}benzo[c]-2,6-naphthyridin-1(2H)-one;

9-Fluoro-5-{[(1R)-1-(trifluoromethyl)propyl]amino}benzo[c]-2,6-naphthyridin-1(2H)-one;

9-Fluoro-5-{[(trimethylsilyl)methyl]amino}benzo[c]-2,6-naphthyridin-1(2H)-one;

9-Fluoro-5-[(1-methylprop-2-en-1-yl)amino]benzo[c]-2,6-naphthyridin-1(2H)-one;

9-Fluoro-5-[(3,3,3-trifluoro-2-hydroxypropyl)amino]benzo[c]-2,6-naphthyridin-1(2H)-one;

5-[(2-Chloro-4,6-difluorophenyl)amino]-9-fluorobenzo[c]-2,6-naphthyridin-1(2H)-one;

9-Bromo-5-{[(1S)-1-cyclopropyl-2,2,2-trifluoroethyl]amino}benzo[c]-2,6-naphthyridin-1(2H)-one;

9-Bromo-5-{[(1R)-1-cyclopropyl-2,2,2-trifluoroethyl]amino}benzo[c]-2,6-naphthyridin-1(2H)-one;

9-Fluoro-5-[(1,3,5-trimethyl-1H-pyrazol-4-yl)amino]benzo[c]-2,6-naphthyridin-1(2H)-one;

5-[(1-Ethyl-3,5-dimethyl-1H-pyrazol-4-yl)amino]-9-fluorobenzo[c]-2,6-naphthyridin-1(2H)-one;

5-[(5-Tert-butylisoxazol-4-yl)amino]-9-fluorobenzo[c]-2,6-naphthyridin-1(2H)-one;

5-[(2,6-Difluorophenyl)amino]-9-fluorobenzo[c]-2,6-naphthyridin-1(2H)-one;

9-Bromo-5-{[(1S)-1-(trifluoromethyl)propyl]amino}benzo[c]-2,6-naphthyridin-1(2H)-one;

9-Fluoro-5-(methylamino)benzo[c]-2,6-naphthyridin-1(2H)-one;

5-{[2-(2,3-Difluorophenyl)ethyl]amino}-9-fluorobenzo[c]-2,6-naphthyridin-1(2H)-one;

5-{[2-(2,5-Difluorophenyl)ethyl]amino}-9-fluorobenzo[c]-2,6-naphthyridin-1(2H)-one;

5-{[2-(3,4-Difluorophenyl)ethyl]amino}-9-fluorobenzo[c]-2,6-naphthyridin-1(2H)-one;

9-Fluoro-5-{[2-(3,4,5-trifluorophenyl)ethyl]amino}benzo[c]-2,6-naphthyridin-1(2H)-one;

5-{[2-(3-Chloro-2-fluorophenyl)ethyl]amino}-9-fluorobenzo[c]-2,6-naphthyridin-1(2H)-one;

5-{[(1S)-1-(2,6-Dichlorophenyl)ethyl]amino}-9-fluorobenzo[c]-2,6-naphthyridin-1(2H)-one;

5-{[(1R)-1-(2,6-Dichlorophenyl)ethyl]amino}-9-fluorobenzo[c]-2,6-naphthyridin-1(2H)-one;

9-Bromo-5-{[(1R)-1-(2,6-dichlorophenyl)ethyl]amino}benzo[c]-2,6-naphthyridin-1(2H)-one;

9-Bromo-5-{[(1S)-1-(2,6-dichlorophenyl)ethyl]amino}benzo[c]-2,6-naphthyridin-1(2H)-one;

4-{[(9-Bromo-1-oxo-1,2-dihydrobenzo[c]-2,6-naphthyridin-5-yl)amino]methyl}benzenesulfonamide;

3,5-Dichloro-4-[(9-fluoro-1-oxo-1,2-dihydrobenzo[c]-2,6-naphthyridin-5-yl)amino]benzenesulfonamide;

5-{[2,6-Dichloro-4-(ethylthio)phenyl]amino}-9-fluorobenzo[c]-2,6-naphthyridin-1(2H)-one;

4-[(9-Bromo-1-oxo-1,2-dihydrobenzo[c]-2,6-naphthyridin-5-yl)amino]-3,5-dichlorobenzenesulfonamide;

9-Bromo-5-[(2-methyl-1-naphthyl)amino]benzo[c]-2,6-naphthyridin-1(2H)-one;

9-Bromo-5-[(2,6-dichlorophenyl)amino]benzo[c]-2,6-naphthyridin-1(2H)-one;

9-Fluoro-5-[(4-fluoro-2,6-dimethylphenyl)amino]benzo[c]-2,6-naphthyridin-1(2H)-one;

5-[(2-Chloro-6-methylphenyl)amino]-9-fluorobenzo[c]-2,6-naphthyridin-1(2H)-one;

9-Fluoro-5-[(2-methyl-1-naphthyl)amino]benzo[c]-2,6-naphthyridin-1(2H)-one;
5-[(2,6-Dichlorophenyl)amino]-9-fluorobenzo[c]-2,6-naphthyridin-1(2H)-one;
5-[(2-tert-Butylpyridin-4-yl)amino]-9-fluorobenzo[c]-2,6-naphthyridin-1(2H)-one;
3-[(9-Bromo-1-oxo-1,2-dihydrobenzo[c]-2,6-naphthyridin-5-yl)amino]-4-methylbenzonitrile;
9-Bromo-5-[(2,5-dimethylphenyl)amino]benzo[c]-2,6-naphthyridin-1(2H)-one;
3-[(9-Bromo-1-oxo-1,2-dihydrobenzo[c]-2,6-naphthyridin-5-yl)amino]-4-chlorobenzonitrile;
5-[(3-tert-Butyl-1-methyl-1H-pyrazol-5-yl)amino]-9-fluorobenzo[c]-2,6-naphthyridin-1(2H)-one;
9-Fluoro-5-[(2-phenylpyridin-4-yl)amino]benzo[c]-2,6-naphthyridin-1(2H)-one;
9-Bromo-5-[(2-chloro-5-methylphenyl)amino]benzo[c]-2,6-naphthyridin-1(2H)-one;
5-[(4-Bromo-5-tert-butyl-2-methylphenyl)amino]-9-fluorobenzo[c]-2,6-naphthyridin-1(2H)-one;
9-Fluoro-5-[(5-isopropyl-2-methylphenyl)amino]benzo[c]-2,6-naphthyridin-1(2H)-one;
2-{3-[(9-Bromo-1-oxo-1,2-dihydrobenzo[c]-2,6-naphthyridin-5-yl)amino]-4-chlorophenyl}-2-methylpropanenitrile;
9-Bromo-5-[(5-tert-butyl-2-methylphenyl)amino]benzo[c]-2,6-naphthyridin-1(2H)-one;
5-Anilino-9-fluorobenzo[c]-2,6-naphthyridin-1(2H)-one;
9-Fluoro-5-[(5-methyl-1,1-dioxido-2,3-dihydro-1-benzothien-6-yl)amino]benzo[c]-2,6-naphthyridin-1(2H)-one;
5-{[2,4-Dimethyl-5-(methylsulfonyl)phenyl]amino}-9-fluorobenzo[c]-2,6-naphthyridin-1(2H)-one;
5-[(Cyclohexylmethyl)amino]-9-fluorobenzo[c]-2,6-naphthyridin-1(2H)-one;
9-Fluoro-5-{[(1R)-1-phenylethyl]amino}benzo[c]-2,6-naphthyridin-1(2H)-one;
5-{[1-(2,6-Dichlorophenyl)ethyl]amino}-9-fluorobenzo[c]-2,6-naphthyridin-1(2H)-one;
5-(Benzylamino)-9-bromobenzo[c]-2,6-naphthyridin-1(2H)-one;
9-Bromo-5-{[(1R)-1-phenylethyl]amino}benzo[c]-2,6-naphthyridin-1(2H)-one;
9-Bromo-5-{[(1S)-1-phenylethyl]amino}benzo[c]-2,6-naphthyridin-1(2H)-one;
9-Bromo-5-{[1-(2,6-dichlorophenyl)ethyl]amino}benzo[c]-2,6-naphthyridin-1(2H)-one;
9-Bromo-5-[(2-phenylethyl)amino]benzo[c]-2,6-naphthyridin-1(2H)-one;
5-{[2-Chloro-5-(methylsulfonyl)phenyl]amino}-9-fluorobenzo[c]-2,6-naphthyridin-1(2H)-one;
9-Fluoro-5-{[2-fluoro-4-methyl-5-(methylsulfonyl)phenyl]amino}benzo[c]-2,6-napthyridin-1(2H)-one;
9-Fluoro-5-{[2-fluoro-5-(methylsulfonyl)phenyl]amino}benzo[c]-2,6-naphthyridin-1(2H)-one;
5-[(5-Acetyl-2-methylphenyl)amino]-9-fluorobenzo[c]-2,6-naphthyridin-1(2H)-one;
5-[(5-Acetyl-2-chlorophenyl)amino]-9-fluorobenzo[c]-2,6-naphthyridin-1(2H)-one;
9-Fluoro-5-{[5-(1-hydroxyethyl)-2-methylphenyl]amino}benzo[c]-2,6-naphthyridin-1(2H)-one;
5-{[2-Chloro-5-(1-hydroxyethyl)phenyl]amino}-9-fluorobenzo[c]-2,6-naphthyridin-1(2H)-one;
5-{[2-Chloro-4-fluoro-5-(1-hydroxyethyl)phenyl]amino}-9-fluorobenzo[c]-2,6-naphthyridin-1(2H)-one;
5-[(9-Fluoro-1-oxo-1,2-dihydrobenzo[c]-2,6-naphthyridin-5-yl)amino]-2,4-dimethyl-N-(pyridin-3-ylmethyl)benzenesulfonamide;
4-[(9-Bromo-1-oxo-1,2-dihydrobenzo[c]-2,6-naphthyridin-5-yl)amino]-3,5-dichloro-N-[(1H-methyl-1H-imidazol-2-yl)methyl]benzenesulfonamide;
3,5-Dichloro-4-[(9-fluoro-1-oxo-1,2-dihydrobenzo[c]-2,6-naphthyridin-5-yl)amino]-N-isobutylbenzenesulfonamide;
3,5-Dichloro-4-[(9-fluoro-1-oxo-1,2-dihydrobenzo[c]-2,6-naphthyridin-5-yl)amino]-N-(2-pyrrolidin-1-ylethyl)benzenesulfonamide;
3,5-Dichloro-4-[(9-fluoro-1-oxo-1,2-dihydrobenzo[c]-2,6-naphthyridin-5-yl)amino]-N-[(1-methyl-1H-imidazol-2-yl)methyl]benzenesulfonamide;
3,5-Dichloro-4-[(9-fluoro-1-oxo-1,2-dihydrobenzo[c]-2,6-naphthyridin-5-yl)amino]-N-[(2R)-2-hydroxypropyl]benzenesulfonamide;
5-[(9-Fluoro-1-oxo-1,2-dihydrobenzo[c]-2,6-naphthyridin-5-yl)amino]-2,4-dimethyl-N-(pyridin-3-ylmethyl)benzenesulfonamide;
5-{[2,4-Dimethyl-5-(morpholin-4-ylsulfonyl)phenyl]amino}-9-fluorobenzo[c]-2,6-naphthyridin-1(2H)-one;
5-{[2,4-Dimethyl-5-(piperidin-1-ylsulfonyl)phenyl]amino}-9-fluorobenzo[c]-2,6-naphthyridin-1(2H)-one;
N-Cyclopropyl-5-[(9-fluoro-1-oxo-1,2-dihydrobenzo[c]-2,6-naphthyridin-5-yl)amino]-2,4-dimethylbenzenesulfonamide;
5-[(9-Fluoro-1-oxo-1,2-dihydrobenzo[c]-2,6-naphthyridin-5-yl)amino]-2,4-dimethyl-N-[(1-methyl-1H-imidazol-2-yl)methyl]benzenesulfonamide;
3-[(9-Fluoro-1-oxo-1,2-dihydrobenzo[c]-2,6-naphthyridin-5-yl)amino]-4-methylbenzoic acid;
Methyl 3-[(9-fluoro-1-oxo-1,2-dihydrobenzo[c]-2,6-naphthyridin-5-yl)amino]-4-methylbenzoate;
3-[(9-Fluoro-1-oxo-1,2-dihydrobenzo[c]-2,6-naphthyridin-5-yl)amino]-N-[(2R)-2-hydroxypropyl]-4-methylbenzamide;
3-[(9-Fluoro-1-oxo-1,2-dihydrobenzo[c]-2,6-naphthyridin-5-yl)amino]-4-methyl-N-(morpholin-2-ylmethyl)benzamide;
9-Fluoro-5-{[5-(hydroxymethyl)-2-methylphenyl]amino}benzo[c]-2,6-naphthyridin-1(2H)-one;
9-Bromo-5-{[5-(hydroxymethyl)-2-methylphenyl]amino}benzo[c]-2,6-naphthyridin-1(2H)-one;
5-{[2-Chloro-4-fluoro-5-(hydroxymethyl)phenyl]amino}-9-fluorobenzo[c]-2,6-naphthyridin-1(2H)-one;
5-({2-Chloro-5-[5-(hydroxymethyl)-2-furyl]phenyl}amino)-9-fluorobenzo[c]-2,6-naphthyridin-1(2H)-one;
1,1,1-Trifluoro-N-{3-[(9-fluoro-1-oxo-1,2-dihydrobenzo[c]-2,6-naphthyridin-5-yl)amino]-4-methylbenzyl}methanesulfonamide;
9-(1-Methyl-1H-pyrazol-4-yl)-5-{[(1S)-1-(trifluoromethyl)propyl]amino}benzo[c]-2,6-naphthyridin-1(2H)-one;
5-({2,6-Dichloro-4-[(1R)-1-hydroxyethyl]phenyl}amino)-9-(3-hydroxy-3-methylbut-1-yn-1-yl)benzo[c]-2,6-naphthyridin-1(2H)-one;
5-({2,6-Dichloro-4-[(1S)-1-hydroxyethyl]phenyl}amino)-9-(3-hydroxy-3-methylbut-1-yn-1-yl)benzo[c]-2,6-naphthyridin-1(2H)-one;
5-({2,6-Dichloro-4-[(1R)-1-hydroxyethyl]phenyl}amino)-9-[(3R)-3-hydroxybut-1-yn-1-yl]benzo[c]-2,6-naphthyridin-1(2H)-one;
5-({2,6-Dichloro-4-[(1S)-1-hydroxyethyl]phenyl}amino)-9-[(3R)-3-hydroxybut-1-yn-1-yl]benzo[c]-2,6-naphthyridin-1(2H)-one;

5-({2,6-Dichloro-4-[(1R)-1-hydroxyethyl]phenyl}amino)-9-(1-methyl-1H-pyrazol-4-yl)benzo[c]-2,6-naphthyridin-1(2H)-one;

5-({2,6-Dichloro-4-[(1S)-1-hydroxyethyl]phenyl}amino)-9-(1-methyl-1H-pyrazol-4-yl)benzo[c]-2,6-naphthyridin-1(2H)-one;

5-{[2,6-Dichloro-4-(1H-pyrazol-5-yl)phenyl]amino}-9-(3-hydroxy-3-methylbut-1-yn-1-yl)benzo[c]-2,6-naphthyridin-1(2H)-one;

5-{[2,6-Dichloro-4-(1H-pyrazol-5-yl)phenyl]amino}-9-[(1E)-3-hydroxy-3-methylbut-1-en-1-yl]benzo[c]-2,6-naphthyridin-1(2H)-one;

(5-{[2,6-Dichloro-4-(1H-pyrazol-5-yl)phenyl]amino}-1-oxo-1,2-dihydrobenzo[c]-2,6-naphthyridin-9-yl)boronic acid;

9-Bromo-5-{[2,6-dichloro-4-(1-hydroxy-1-methylethyl)phenyl]amino}benzo[c]-2,6-naphthyridin-1(2H)-one;

5-{[2,6-Dichloro-4-(1-hydroxy-1-methylethyl)phenyl]amino}-9-hydroxybenzo[c]-2,6-naphthyridin-1(2H)-one;

5-{[2,6-Dichloro-4-(1-hydroxy-1-methylethyl)phenyl]amino}-9-[2-(1-hydroxy-1-methylethyl)-1,3-thiazol-4-yl]benzo[c]-2,6-naphthyridin-1(2H)-one;

5-[(2-Chloro-4,6-difluorophenyl)amino]-9-(1H-pyrazol-5-yl)benzo[c]-2,6-naphthyridin-1(2H)-one;

9-(1-Methyl-1H-pyrazol-4-yl)-5-[(2,4,6-trifluorophenyl)amino]benzo[c]-2,6-naphthyridin-1(2H)-one;

9-(2-Aminopyrimidin-5-yl)-5-[(2,4,6-trifluorophenyl)amino]benzo[c]-2,6-naphthyridin-1(2H)-one;

9-[6-(Hydroxymethyl)pyridin-3-yl]-5-[(2,4,6-trifluorophenyl)amino]benzo[c]-2,6-naphthyridin-1(2H)-one;

9-(1-Methyl-1H-pyrazol-4-yl)-5-{[(1S)-2-methyl-1-(trifluoromethyl)propyl]amino}benzo[c]-2,6-naphthyridin-1(2H)-one;

9-(1H-Pyrazol-5-yl)-5-[(2,4,6-trifluorophenyl)amino]benzo[c]-2,6-naphthyridin-1(2H)-one;

5-{[2,6-Dichloro-4-(1-hydroxy-1-methylethyl)phenyl]amino}-9-[(3R)-3-hydroxybut-1-yn-1-yl]benzo[c]-2,6-naphthyridin-1(2H)-one;

5-{[2,6-Dichloro-4-(1-hydroxy-1-methylethyl)phenyl]amino}-9-[(3S)-3-hydroxybut-1-yn-1-yl]benzo[c]-2,6-naphthyridin-1(2H)-one;

9-Bromo-5-{[2,6-dichloro-4-(1-hydroxy-1-methylethyl)phenyl](methyl)amino}benzo[c]-2,6-naphthyridin-1(2H)-one;

5-{[2,6-Dichloro-4-(1H-pyrazol-5-yl)phenyl]amino}-9-(3-hydroxy-3-methylbut-1-yn-1-yl)benzo[c]-2,6-naphthyridin-1(2H)-one;

5-{[2,6-Dichloro-4-(1H-pyrazol-5-yl)phenyl]amino}-9-[(1E)-3-hydroxy-3-methylbut-1-en-1-yl]benzo[c]-2,6-naphthyridin-1(2H)-one;

5-{[2,6-Dichloro-4-(1H-pyrazol-5-yl)phenyl]amino}-9-[(3R)-3-hydroxybut-1-yn-1-yl]benzo[c]-2,6-naphthyridin-1(2H)-one;

5-{[2,6-Dichloro-4-(1-hydroxy-1-methylethyl)phenyl]amino}-9-(1H-pyrazol-5-yl)benzo[c]-2,6-naphthyridin-1(2H)-one;

5-{[2,6-Dichloro-4-(1-hydroxy-1-methylethyl)phenyl]amino}-9-(1-methyl-1H-pyrazol-4-yl)benzo[c]-2,6-naphthyridin-1(2H)-one;

5-{[2,6-Dichloro-4-(1-hydroxy-1-methylethyl)phenyl]amino}-9-(1,3-thiazol-2-yl)benzo[c]-2,6-naphthyridin-1(2H)-one;

5-{[2,6-Dichloro-4-(1-hydroxy-1-methylethyl)phenyl]amino}-9-(3-hydroxy-3-methylbut-1-yn-1-yl)benzo[c]-2,6-naphthyridin-1(2H)-one;

5-{[2,6-Dichloro-4-(1-hydroxy-1-methylethyl)phenyl]amino}-9-[(1E)-3-hydroxy-3-methylbut-1-en-1-yl]benzo[c]-2,6-naphthyridin-1(2H)-one;

9-(2-Aminopyrimidin-5-yl)-5-{[2,6-dichloro-4-(1-hydroxy-1-methylethyl)phenyl]amino}benzo[c]-2,6-naphthyridin-1(2H)-one;

5-{[2,6-Dichloro-4-(1-hydroxy-1-methylethyl)phenyl]amino}-9-(pyridin-2-ylethynyl)benzo[c]-2,6-naphthyridin-1(2H)-one;

9-(3-Amino-3-methylbut-1-yn-1-yl)-5-{[2,6-dichloro-4-(1-hydroxy-1-methylethyl)phenyl]amino}benzo[c]-2,6-naphthyridin-1(2H)-one;

5-{[2,6-Dichloro-4-(1-hydroxy-1-methylethyl)phenyl]amino}-9-[1-(1,3-dioxolan-2-ylmethyl)-1H-pyrazol-4-yl]benzo[c]-2,6-naphthyridin-1(2H)-one;

5-{[2,6-Dichloro-4-(1-hydroxy-1-methylethyl)phenyl]amino}-9-(1-isobutyl-1H-pyrazol-4-yl)benzo[c]-2,6-naphthyridin-1(2H)-one;

Ethyl [4-(5-{[2,6-dichloro-4-(1-hydroxy-1-methylethyl)phenyl]amino}-1-oxo-1,2-dihydrobenzo[c]-2,6-naphthyridin-9-yl)-1H-pyrazol-1-yl]acetate;

5-{[2,6-Dichloro-4-(1-hydroxy-1-methylethyl)phenyl]amino}-9-[1-(2-morpholin-4-ylethyl)-1H-pyrazol-4-yl]benzo[c]-2,6-naphthyridin-1(2H)-one;

3,5-Dichloro-4-[{9-(3-hydroxy-3-methylbut-1-yn-1-yl)-1-oxo-1,2-dihydrobenzo[c]-2,6-naphthyridin-5-yl]amino}benzenesulfonamide;

3,5-Dichloro-4-[[1,2-dihydro-9-(1-methyl-1H-pyrazol-4-yl)-1-oxobenzo[c][2,6]napthyridin-5-yl]amino]-benzenesulfonamide;

5-{[2,6-Dichloro-4-(1-hydroxy-1-methylethyl)phenyl]amino}-9-[6-(1-hydroxy-1-methylethyl)pyridin-2-yl]benzo[c]-2,6-naphthyridin-1(2H)-one;

6-[(2-Chloro-4,6-difluorophenyl)amino]pyrido[4,3-c]-1,6-naphthyridin-10(9H)-one;

6-[(2,6-Dichloro-4-fluorophenyl)amino]pyrido[4,3-c]-1,6-naphthyridin-10(9H)-one;

6-[(2,4,6-Trifluorophenyl)amino]pyrido[4,3-c]-1,6-naphthyridin-10(9H)-one;

6-{[2-Fluoro-6-(Trifluoromethyl)phenyl]amino}pyrido[4,3-c]-1,6-naphthyridin-10(9H)-one;

6-{[2,6-Dichloro-4-(trifluoromethyl)phenyl]amino}pyrido[4,3-c]-1,6-naphthyridin-10(9H)-one;

6-{[2,6-Dichloro-4-(trifluoromethoxy)phenyl]amino}pyrido[4,3-c]-1,6-naphthyridin-10(9H)-one;

3,5-Dichloro-4-[(10-oxo-9,10-dihydropyrido[4,3-c]-1,6-naphthyridin-6-yl)amino]benzenesulfonamide;

6-{[(1S)-1-(Trifluoromethyl)propyl]amino}pyrido[4,3-c]-1,6-naphthyridin-10(9H)-one;

6-{[(1S)-2,2,2-Trifluoro-1-methylethyl]amino}pyrido[4,3-c]-1,6-naphthyridin-10(9H)-one;

6-[(3,5-Dichloropyridin-4-yl)amino]pyrido[4,3-c]-1,6-naphthyridin10(9H)-one;

4-Methyl-3-[(10-oxo-9,10-dihydropyrido[4,3-c]-1,6-naphthyridin-6-yl)amino]benzonitrile;

6-({2,6-Dichloro-4-[(1R)-1-hydroxyethyl]phenyl}amino)pyrido[4,3-c]-1,6-naphthyridin-10(9H)-one;

6-({2,6-Dichloro-4-[(1S)-1-hydroxyethyl]phenyl}amino)pyrido[4,3-c]-1,6-naphthyridin-10(9H)-one;

6-{[2,6-Dichloro-4-(1-hydroxy-1-methylethyl)phenyl]amino}pyrido[4,3-c]-1,6-naphthyridin-10(9H)-one;

5-{[2-Chloro-5-(1-hydroxy-1-methylethyl)phenyl]amino}-9-fluorobenzo[c]-2,6-naphthyridin-1(2H)-one;

5-{[2-Chloro-4-fluoro-5-(1-hydroxy-1-methylethyl)phenyl]amino}-9-fluorobenzo[c]-2,6-naphthyridin-1(2H)-one;

9-Fluoro-5-{[5-(1-hydroxy-1-methylethyl)-2-methylphenyl]amino}benzo[c]-2,6-naphthyridin-1(2H)-one;

6-{[2,6-Dichloro-4-(1-hydroxy-1-methylethyl)phenyl]
  amino}pyrido[4,3-c]-1,6-naphthyridin-10(9H)-one 2-oxide;
7-Bromo-6-{[2,6-dichloro-4-(1-hydroxy-1-methylethyl)
  phenyl]amino}pyrido[4,3-c]-1,6-naphthyridin-10(9H)-
  one;
6-{[2,6-Dichloro-4-(1H-pyrazol-5-yl)phenyl]amino}pyrido
  [4,3-c]-1,6-naphthyridin-10(9H)-one;
6-{[2-Chloro-6-fluoro-4-(1H-pyrazol-5-yl)phenyl]
  amino}pyrido[4,3-c]-1,6-naphthyridin-10(9H)-one;
6-{[2,6-Dichloro-4-(1-hydroxycyclopropyl)phenyl]
  amino}pyrido[4,3-c]-1,6-naphthyridin-10(9H)-one;
{3,5-Dichloro-4-[(10-oxo-9,10-dihydropyrido[4,3-c]-1,6-
  naphthyridin-6-yl)amino]phenyl}(trifluoromethyl)sulfoniumolate;
6-{[2,6-Dichloro-4-(3-hydroxy-3-methylbut-1-yn-1-yl)phenyl]amino}pyrido[4,3-c]-1,6-naphthyridin-10(9H)-one;
6-({2,6-Dichloro-4-[(1E)-3-hydroxy-3-methylbut-1-en-1-
  yl]phenyl}amino)pyrido[4,3-c]-1,6-naphthyridin-10(9H)-
  one;
6-({2,6-Dichloro-4-[(1S)-2,2-difluoro-1-hydroxyethyl]
  phenyl}amino)pyrido[4,3-c]-1,6-naphthyridin-10(9H)-
  one;
6-({2,6-Dichloro-4-[(1R)-2,2-difluoro-1-hydroxyethyl]
  phenyl}amino)pyrido[4,3-c]-1,6-naphthyridin-10(9H)-
  one;
3,5-Dichloro-4-[(10-oxo-9,10-dihydropyrido[4,3-c]-1,6-
  naphthyridin-6-yl)amino]benzonitrile;
6-{[4-(1-Amino-1-methylethyl)-2,6-dichlorophenyl]
  amino}pyrido[4,3-c]-1,6-naphthyridin-10(9H)-one;
5-{[5-(1-Amino-1-methylethyl)-2-methylphenyl]amino}-9-
  bromobenzo[c]-2,6-naphthyridin-1(2H)-one;
6-({2,6-Dichloro-4-[5-(1-hydroxy-1-methylethyl)-1,2,4-
  oxadiazol-3-yl]phenyl}amino)pyrido[4,3-c]-1,6-naphthyridin-10(9H)-one;
6-{[2,6-Dichloro-4-(1H-1,2,3-triazol-4-yl)phenyl]
  amino}pyrido[4,3-c]-1,6-naphthyridin-10(9H)-one;
6-{[2-Chloro-6-fluoro-4-(1H-1,2,3-triazol-4-yl)phenyl]
  amino}pyrido[4,3-c]-1,6-naphthyridin-10(9H)-one;
3,5-Dichloro-4-[(10-oxo-9,10-dihydropyrido[4,3-c]-1,6-
  naphthyridin-6-yl)amino]benzenecarboximidamide;
6-({2,6-Dichloro-4-[N-ethoxyethanimidoyl]phenyl}amino)
  pyrido[4,3-c]-1,6-naphthyridin-10(9H)-one;
6-({2,6-Dichloro-4-[(N-(2-morpholin-4-yl-2-oxoethoxy)
  ethanimidoyl]phenyl}amino)pyrido[4,3-c]-1,6-naphthyridin-10(9H)-one;
6-({2,6-Dichloro-4-[(N-(2-hydroxy-2-methylpropoxy)ethanimidoyl]phenyl}amino)pyrido[4,3-c]-1,6-naphthyridin-10(9H)-one;
6-({4-[N-(tert-Butoxy)ethanimidoyl]-2,6-
  dichlorophenyl}amino)pyrido[4,3-c]-1,6-naphthyridin-10
  (9H)-one;
6-({4-[N-(Allyloxy)ethanimidoyl]-2,6-
  dichlorophenyl}amino)pyrido[4,3-c]-1,6-naphthyridin-10
  (9H)-one;
5-[(2,6-Dichloro-4-fluorophenyl)amino]-9-morpholin-4-yl-
  benzo[c]-2,6-naphthyridin-1(2H)-one;
4-(2-Hydroxyethyl)-N-{1-oxo-5-[(2,4,6-trifluorophenyl)
  amino]-1,2-dihydrobenzo[c]-2,6-naphthyridin-9-
  yl}piperazine-1-carboxamide;
N3-[(Dimethylamino)sulfonyl]-N3-methyl-N-{1-oxo-5-[(2,
  4,6-trifluorophenyl)amino]-1,2-dihydrobenzo[c]-2,6-
  naphthyridin-9-yl}-b-alaninamide;
3-Hydroxy-N-{1-oxo-5-[(2,4,6-trifluorophenyl)amino]-1,2-
  dihydrobenzo[c]-2,6-naphthyridin-9-yl}propanamide;
N-{5-[(2,6-Dichloro-4-fluorophenyl)amino]-1-oxo-1,2-dihydrobenzo[c]-2,6-naphthyridin-9-yl}-2-morpholin-4-ylacetamide;
N-{5-[(2,6-Dichloro-4-fluorophenyl)amino]-1-oxo-1,2-dihydrobenzo[c]-2,6-naphthyridin-9-yl}pyrazine-2-carboxamide;
N-{5-[(2,6-Dichloro-4-fluorophenyl)amino]-1-oxo-1,2-dihydrobenzo[c]-2,6-naphthyridin-9-yl}-N'-(2-methoxyethyl)urea;
N'-{5-[(2,6-Dichloro-4-fluorophenyl)amino]-1-oxo-1,2-dihydrobenzo[c]-2,6-naphthyridin-9-yl}-N,N-dimethylurea;
N-{5-[(2,6-Dichloro-4-fluorophenyl)amino]-1-oxo-1,2-dihydrobenzo[c]-2,6-naphthyridin-9-yl}-2-methyl-2-morpholin-4-ylpropanamide;
5-[(2,6-Dichloro-4-fluorophenyl)amino]-9-[(2-hydroxy-2-pyrazin-2-ylethyl)amino]benzo[c]-2,6-naphthyridin-1
  (2H)-one;
5-[(2,6-Dichloro-4-fluorophenyl)amino]-9-[(2-morpholin-4-ylethyl)amino]benzo[c]-2,6-naphthyridin-1(2H)-one;
5-[(2,6-Dichloro-4-fluorophenyl)amino]-9-[(3,3,3-trifluoro-2-hydroxypropyl)amino]benzo[c]-2,6-naphthyridin-1
  (2H)-one;
5-[(2,6-Dichloro-4-fluorophenyl)amino]-9-[(2,3-dihydroxypropyl)amino]benzo[c]-2,6-naphthyridin-1(2H)-one;
5-[(2,6-Dichloro-4-fluorophenyl)amino]-9-[(2-hydroxy-3-methoxypropyl)amino]benzo[c]-2,6-naphthyridin-1(2H)-
  one;
5-[(2,6-Dichloro-4-fluorophenyl)amino]-9-{[2-hydroxy-2-
  (tetrahydro-2H-pyran-4-yl)ethyl]amino}benzo[c]-2,6-
  naphthyridin-1(2H)-one;
5-[(2,6-Dichloro-4-fluorophenyl)amino]-9-[(2-hydroxy-2-
  pyrazin-2-ylethyl)amino]benzo[c]-2,6-naphthyridin-1
  (2H)-one;
5-[(2,6-Dichloro-4-fluorophenyl)amino]-9-({[3-(hydroxymethyl)oxetan-3-yl]methyl}amino)benzo[c]-2,6-
  naphthyridin-1(2H)-one;
5-[(2,6-Dichloro-4-fluorophenyl)amino]-9-[(2-methyl-2-
  morpholin-4-ylpropyl)amino]benzo[c]-2,6-naphthyridin-
  1(2H)-one;
or a pharmaceutically acceptable salt or stereoisomer thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, single enantiomers, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted. For example the following is within the scope of the instant invention:

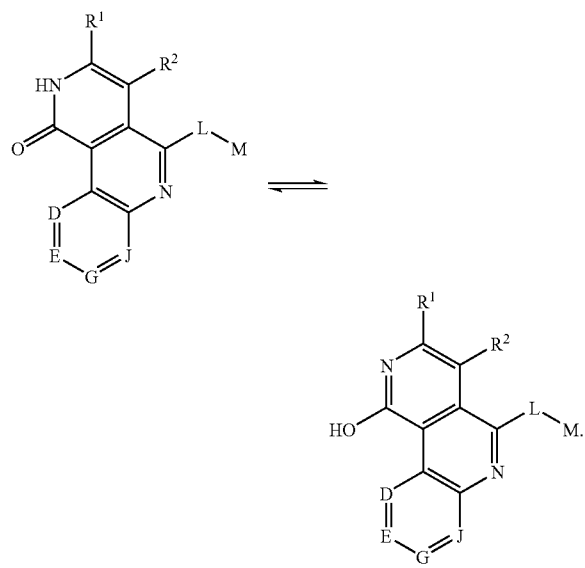

When any variable (e.g. R³, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to four substituents, and the more preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "($C_1$-$C_{10}$)alkyl" is defined to include groups having 1, 2, 3, 4, 5, 6, 7, 8, 9 or 10 carbons in a linear or branched arrange-ment. For example, "($C_1$-$C_{10}$)alkyl" specifically includes methyl, ethyl, n-propyl, i-propyl, n-butyl, t-butyl, i-butyl, pentyl, hexyl, heptyl, octyl, nonyl, decyl, and so on.

The term "haloalkyl" means an alkyl radical as defined above, unless otherwise specified, that is substituted with one to five, preferably one to three halogen. Representative examples include, but are not limited to trifluoromethyl, dichloroethyl, and the like.

As used herein, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

As used herein, the term "alkynyl" refers to a non-aromatic hydrocarbon radical, straight or branched, containing from 2 to 10 carbon atoms and at least 1 carbon to carbon triple bond. Preferably 1 carbon to carbon triple bond is present, and up to 4 non-aromatic carbon-carbon triple bonds may be present. Thus, "$C_2$-$C_6$ alkynyl" means an alkynyl radical having from 2 to 6 carbon atoms. Alkynyl groups include ethynyl, propynyl, butynyl and the like. As described above with respect to alkyl, the straight, branched or cyclic portion of the alkynyl group may contain triple bonds and may be substituted if a substituted alkynyl group is indicated.

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

"Alkoxy" represents either a cyclic or non-cyclic alkyl group of indicated number of carbon atoms attached through an oxygen bridge. "Alkoxy" therefore encompasses the definitions of alkyl and cycloalkyl above.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively. Such heteroaryl moieties for substituent Q include but are not limited to: 2-benzimidazolyl, 2-quinolinyl, 3-quinolinyl, 4-quinolinyl, 1-isoquinolinyl, 3-isoquinolinyl and 4-isoquinolinyl.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro (Cl), fluoro (F), bromo (Br) and iodo (I).

Whenever the term "alkyl" or "aryl" or either of their prefix roots appear in a name of a substituent (e.g., ($C_{1-6}$ alkyl) aryl) it shall be interpreted as including those limitations given above for "alkyl" and "aryl." Designated numbers of carbon atoms (e.g., $C_{1-6}$) shall refer independently to the number of carbon atoms in an alkyl or cyclic alkyl moiety or to the alkyl portion of a larger substituent in which alkyl appears as its prefix root.

Included in the instant invention is the free form of compounds of the instant invention, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of the instant invention. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Utility

The compounds of the present invention are inhibitors of JAK 1, JAK2, JAK 3 and TYK2, and are therefore useful to treat or prevent myeloproliferative disorders or cancer in mammals, preferably humans.

An embodiment of the invention provides a method for inhibiting JAK1 tyrosine kinase, comprising administering to the mammal a therapeutically effective amount of any of the compounds or any of the pharmaceutical compositions described above.

An embodiment of the invention provides a method for inhibiting JAK2 tyrosine kinase, comprising administering to the mammal a therapeutically effective amount of any of the compounds or any of the pharmaceutical compositions described above.

An embodiment of the invention provides a method for inhibiting wild type or mutant JAK2 tyrosine kinase, comprising administering to the mammal a therapeutically effective amount of any of the compounds or any of the pharmaceutical compositions described above.

An embodiment of the invention provides a method for inhibiting JAK2V617F tyrosine kinase, comprising administering to the mammal a therapeutically effective amount of any of the compounds or any of the pharmaceutical compositions described above.

The compounds, compositions and methods provided herein are particularly deemed useful for the treatment of myeloproliferative disorder(s). Myeloproliferative disorders that may be treated include polycythemia vera (PV), essential thrombocythemia (ET), myeloid metaplasia with myelofibrosis (MMM), chronic myelogenous leukemia (CML), myelomonocytic leukemia (CMML), hypereosinophilic syndrome (HES), juvenile myelomonocytic leukemia (JMML), and systemic mast cell disease (SMCD).

It is known in the literature that inhibitors of JAK2 are useful in the treatment and/or prevention of myeloproliferative disorders. See, e.g., Tefferi, A. and Gilliland, D. G. *Mayo Clin. Proc.* 80(7): 947-958 (2005); Fernandez-Luna, J. L. et al. *Haematologica* 83(2): 97-98 (1998); Harrison, C. N. *Br. J. Haematol.* 130(2): 153-165 (2005); *Leukemia (*2005) 19, 1843-1844; and Tefferi, A. and Barbui, T. *Mayo Clin. Proc.* 80(9): 1220-1232 (2005).

The compounds, compositions and methods provided herein are also deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma; and Adrenal glands: neuroblastoma. Thus, the term "cancerous cell" as provided herein, includes a cell afflicted by any one of the above-identified conditions.

The compounds, compositions and methods of the invention may also be useful in treating the following disease states: keloids and psoriasis.

Cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

Cancers that may be treated by the compounds, compositions and methods of the invention include: breast, prostate, colon, ovarian, colorectal and lung (non-small cell lung).

Cancers that may be treated by the compounds, compositions and methods of the invention include: breast, colon, colorectal and lung.

Cancers that may be treated by the compounds, compositions and methods of the invention include: lymphoma and leukemia.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge et al., *Expert Opin. Biol. Ther.* (2002) 2(8):953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

Further included within the scope of the invention is a method of treating hyperproliferative disorders such as restenosis, inflammation, autoimmune diseases and allergy/asthma.

Further included within the scope of the instant invention is the use of the instant compounds to coat stents and therefore the use of the instant compounds on coated stents for the treatment and/or prevention of restenosis (WO03/032809).

Further included within the scope of the instant invention is the use of the instant compounds for the treatment and/or prevention of osteoarthritis (WO03/035048).

Further included within the scope of the invention is a method of treating hypoinsulinism.

An embodiment of the invention provides a method for inhibiting JAK3 tyrosine kinase, comprising administering to the mammal a therapeutically effective amount of any of the compounds or any of the pharmaceutical compositions described above.

An embodiment of the invention provides a method for inhibiting TYK2 tyrosine kinase, comprising administering to the mammal a therapeutically effective amount of any of the compounds or any of the pharmaceutical compositions described above.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compounds of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

When a composition according to this invention is administered into a human subject, the daily dosage will normally be determined by the prescribing physician with the dosage generally varying according to the age, weight, and response of the individual patient, as well as the severity of the patient's symptoms.

In an embodiment, a suitable amount of an inhibitor of JAK2 is administered to a mammal undergoing treatment for cancer. Administration occurs in an amount of inhibitor of between about 0.1 mg/kg of body weight to about 60 mg/kg of body weight per day, or between 0.5 mg/kg of body weight to about 40 mg/kg of body weight per day. Another therapeutic dosage that comprises the instant composition includes from about 0.01 mg to about 1000 mg of inhibitor of JAK2. In another embodiment, the dosage comprises from about 1 mg to about 5000 mg of inhibitor of JAK2.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans,trans,trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxy-carminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydrO0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J.Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in U.S. Ser. No. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signaling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134, 142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with y-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with inhibitors of Akt. Such inhibitors include compounds described in, but not limited to, the following publications: WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469.

A compound of the instant invention may also be useful for treating or preventing cancer in combination with PARP inhibitors.

A compound of the instant invention may also be useful for treating cancer in combination with the following therapeutic agents: abarelix (Plenaxis depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®);

carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tosittunomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); and zoledronate (Zometa®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

All patents, publications and pending patent applications identified are hereby incorporated by reference.

The abbreviations used herein have the following tabulated meanings. Abbreviations not tabulated below have their meanings as commonly used unless specifically stated otherwise.

| | |
|---|---|
| Ac = | Acetyl |
| Bn = | Benzyl |
| CAMP | cyclic adenosine-3',5'-monophosphate |
| DBU = | 1,8-diazabicyclo[5.4.0]undec-7-ene |
| DIBAL = | diisobutylaluminum hydride |
| DMAP = | 4-(dimethylamino)pyridine |
| DMF = | N,N-dimethylformamide |
| $Et_3N$ = | Triethylamine |
| GST | glutathione transferase |
| HMDS | Hexamethyldisilazide |
| LDA = | lithium diisopropylamide |
| m-CPBA = | metachloroperbenzoic acid |
| MMPP = | monoperoxyphthalic acid |
| MPPM = | monoperoxyphthalic acid, magnesium salt $6H_2O$ |
| Ms = | methanesulfonyl = mesyl = $SO_2Me$ |
| MsO = | methanesulfonate = mesylate |
| NSAID = | non-steroidal anti-inflammatory drug |
| o-Tol = | ortho-tolyl |
| OXONE ® = | $2KHSO_5 \cdot KHSO_4 \cdot K_2SO_4$ |
| PCC = | pyridinium chlorochromate |
| PDC = | pyridinium dichromate |
| PDE | Phosphodiesterase |
| Ph = | Phenyl |
| Phe = | Benzenediyl |
| PMB = | para-methoxybenzyl |
| Pye = | Pyridinediyl |
| r.t. = | room temperature |
| Rac. = | Racemic |
| SAM = | aminosulfonyl or sulfonamide or $SO_2NH_2$ |
| SEM = | 2-(trimethylsilyl)ethoxymethoxy |
| SPA = | scintillation proximity assay |
| TBAF = | tetra-n-butylammonium fluoride |
| TEA = | triethylamine |
| Th = | 2- or 3-thienyl |
| TFA = | trifluoroacetic acid |
| TFAA = | trifluoroacetic acid anhydride |
| THF = | Tetrahydrofuran |
| Thi = | Thiophenediyl |
| TLC = | thin layer chromatography |
| TMS-CN = | trimethylsilyl cyanide |
| TMSI | trimethylsilyl iodide |
| Tz = | 1H (or 2H)-tetrazol-5-yl |
| CAN | ceric ammonium nitrate |
| $C_3H_5$ = | Allyl |

Alkyl Group Abbreviations

| | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | Cyclobutyl |
| c-Pen = | cyclopentyl |
| c-Hex = | cyclohexyl |

The compounds of the present invention may be conveniently prepared as described below.

METHODS OF SYNTHESIS

Method 1

Scheme 1 details the synthesis of the core 1-9. 2-ethyoxy nicotinic acid 1-1 was chlorinated with oxalyl chloride followed by the addition of diisopropyl amine to afford amide 1-2. Directed ortho lithiation with sec-BuLi followed by trapping with trimethylborate furnished boronic acid 1-3. With boronic acid 1-3 in hand, Suzuki coupling with commercially available anilines 1-4 and with tetrakis palladium (0) triphenylphosphine provided the coupled biaryl product 1-5. Base induced ring closure with NaHMDS gave the tricyclic core 1-6. Heating tricyclic 1-6 in $POCl_3$ resulted in the double chlorination intermediate and sometimes monochlorination 1-7. A variety of amines were added into the core either via thermally at high temperature in a microwave reactor or base assisted addition using lithium bis(trimethylsilylamide) or sodium tert-butoxide at elevated temperature to provide 1-8. Acid hydrolysis or boron tribromide dealkylation of 1-8 afforded pyridone 1-9.

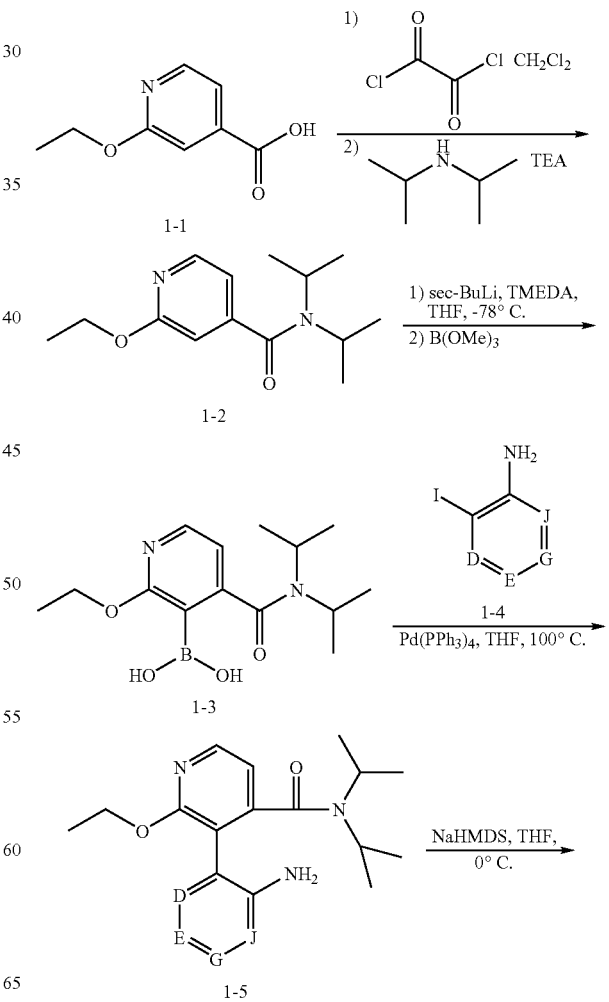

SCHEME 1

-continued

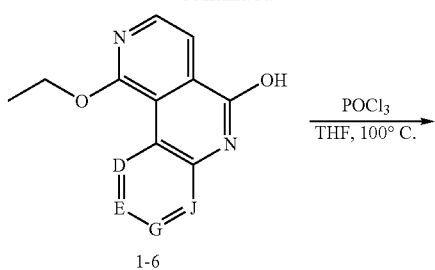
1-6

POCl₃
THF, 100° C.

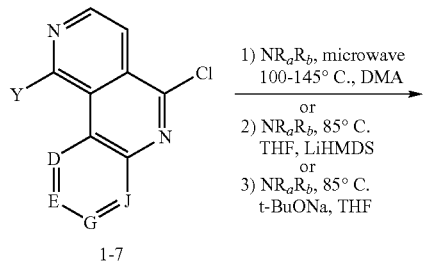
1-7

1) NR_aR_b, microwave
100-145° C., DMA
or
2) NR_aR_b, 85° C.
THF, LiHMDS
or
3) NR_aR_b, 85° C.
t-BuONa, THF

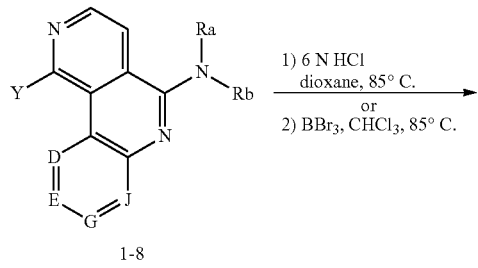
1-8

1) 6 N HCl
dioxane, 85° C.
or
2) BBr₃, CHCl₃, 85° C.

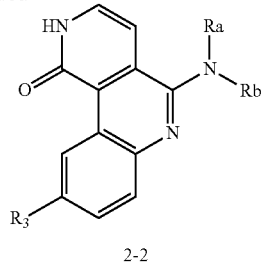
1-9

D, E, G, J = C—F, C—Br, N
Y = EtO or Cl

Method 2

Scheme 2 details a general method for substitution on the phenyl ring of intermediate 2-1. Suzuki reactions with a variety of boronic acids and boronate esters provide intermediate 2-2.

SCHEME 2

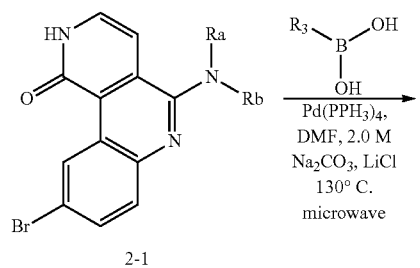
2-1

R₃—B(OH)₂
———————→
Pd(PPh₃)₄,
DMF, 2.0 M
Na₂CO₃, LiCl
130° C.
microwave

-continued

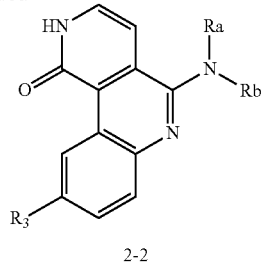
2-2

Method 3

Scheme 3 details a general method for substitution on the phenyl ring of intermediate 3-1 using palladium (Yin, J.; Buchwald, S. L.; *JACS* 2002, 124, 6043) or copper catalyzed cross coupling methods (Zhang, H.; Cai, Q.; Ma, D.; *J. Org. Chem.* 2005, 70, 5164).

SCHEME 3

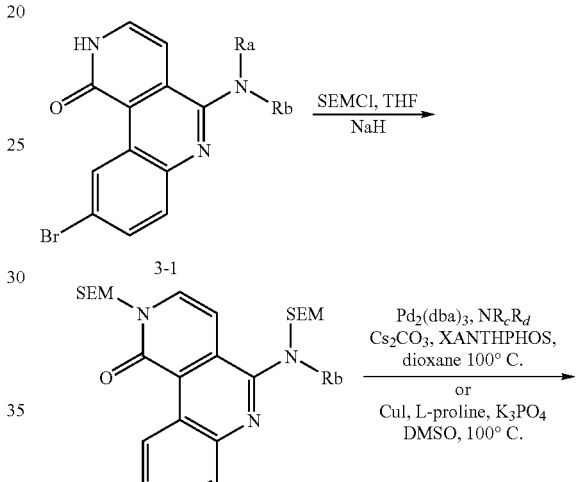
3-1

SEMCl, THF
————→
NaH 3-2

Pd₂(dba)₃, NR_cR_d
Cs₂CO₃, XANTHPHOS,
dioxane 100° C.
or
CuI, L-proline, K₃PO₄
DMSO, 100° C.

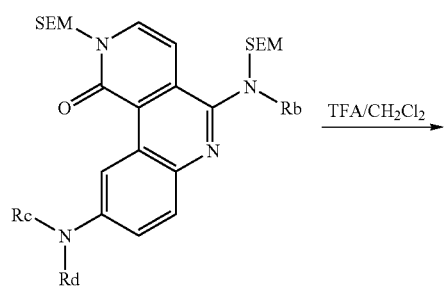
3-3

TFA/CH₂Cl₂

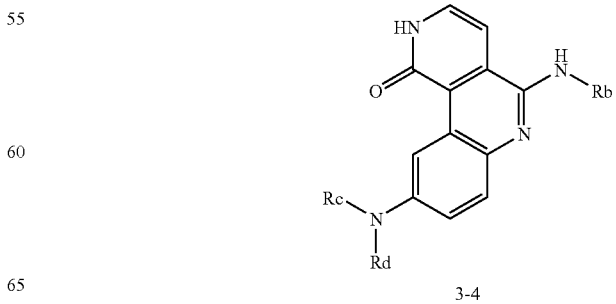
3-4

The invention will now be illustrated in the following non-limiting Examples in which, unless otherwise stated:

1. All the end products of the formula I were analyzed by NMR, TLC, HPLC and/or MS.

2. Intermediates were analyzed by NMR and/or MS and/or TLC.

3. Most compounds were purified by flash chromatography on silica gel, recrystallization and/or swish (suspension in a solvent followed by filtration of the solid).

4. The course of reactions was followed by thin layer chromatography (TLC) and reaction times are given for illustration only.

EXAMPLE 1

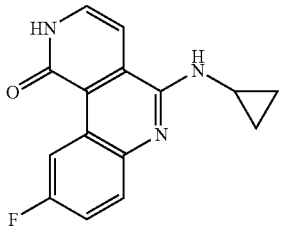 [SMILES: O=c1[nH]ccc2c(NC3CC3)nc3ccc(F)cc3c12]

5-(Cyclopropylamino)-9-fluorobenzo[c]-2,6-naphthyridin-1(2H)-one

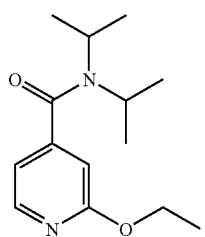 [SMILES: CCOc1cc(C(=O)N(C(C)C)C(C)C)ccn1]

Step 1: 2-Ethoxy-N,N-diisopropylisonicotinamide

To a solution of 2-ethoxyisonicotinic acid (20 g, 120 mmol) in CH$_2$Cl$_2$ (500 mL) was added oxalyl chloride (10.4 mL) followed by one drop of DMF. The solution was stirred for 2 hr then triethylamine (33.4 mL, 239 mmol) and diisopropyl amine (25 mL, 179 mmol) were added dropwise. The solution was allowed to stir for 12 hr then worked up with CH$_2$Cl$_2$ and sat. NaHCO$_3$. The crude mixture was purified by silica gel chromatography (100% hexanes to 100% EtOAc) to afford the title compound.

$^1$H NMR (600 MHz, CDCl$_3$) δ 8.14 (d, 1H); 6.74 (dd, 1H); 6.60 (d, 1H); 4.06 (q, 2H); 3.54 (br s, 1H); 3.51 (br s, 1H); 1.5 (br s, 6H); 1.45 (t, 3H), 1.10 (br s, 6H). LRMS (ESI) calculated for C$_{14}$H$_{23}$N$_2$O$_2$ [M+H]+, 251.3; found 251.2.

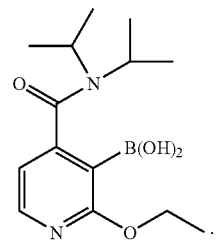 [SMILES: CCOc1nccc(C(=O)N(C(C)C)C(C)C)c1B(O)O]

Step 2: {4-[(Diisopropylamino)carbonyl]-2-ethoxypyridin-3-yl}boronic acid

To a solution of N,N,N',N'-tetramethylethylenediamine (7.46 ml, 49.4 mmol) in THF (105 ml) at −78° C., sec-butyl lithium (35.3 ml, 49.4 mmol, 1.4 M in cyclohexane) was added. 2-Ethoxy-N,N-diisopropylisonicotinamide (8.25 g, 33.0 mmol) in THF (10 mL) was added slowly over 5 min. After 15 min, trimethyl borate (11.23 ml, 101 mmol) was added and after an additional 30 min, the mixture was allowed to warm to 0° C. To this mixture, aqueous ammonium chloride (saturated, 35 mL) and hydrochloric acid (1 M, 140 mL) were added. The reaction mixture was then allowed to warm to room temperature. After 1 h, the aqueous layer was extracted with CH$_2$Cl$_2$ (140 mL). The organic extract was then washed with aqueous sodium hydroxide (1M, 2×120 mL). The combined aqueous extracts were washed with CH$_2$Cl$_2$ (100 mL), acidified with hydrochloric acid (12 M), and extracted with CH$_2$Cl$_2$ (2×120 mL). The combined organic extracts were washed with brine (100 mL), dried over sodium sulfate, and concentrated under reduced pressure to afford the title compound as a white solid.

$^1$H NMR (600 MHz, CD$_3$OD) δ 8.14 (d, 1H); 6.86 (d, 1H); 4.38 (q, 2H); 3.88 (m, 1H); 3.65 (m, 1H); 1.49 (d, 6H); 1.37 (t, 3H); 1.21 (d, 6H). LRMS (ESI) calculated for C$_{14}$H$_{23}$BN$_2$O$_4$ [M+H]$^+$, 295.2; found 295.2.

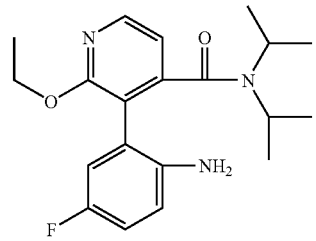 [SMILES: CCOc1nccc(C(=O)N(C(C)C)C(C)C)c1-c1cc(F)ccc1N]

Step 3: 3-(2-Amino-5-fluorophenyl)-2-ethoxy-N,N-diisopropylisonicotinamide

To a solution of {4-[(diisopropylamino)carbonyl]-2-ethoxypyridin-3-yl}boronic acid (8.19 g, 27.8 mmol) in THF (45 mL), were added 2-iodo-4-fluoro-aniline (3 g, 12.7 mmol), sodium carbonate (2.0 M, 10 mL), and tetrakis(triphenylphosphine)palladium (2.93 g, 2.53 mmol). The solution was degassed by bubbling nitrogen through the flask and subsequently heated to 100° C. for 2 hr. The solution was cooled and worked up with EtOAc and water, dried over MgSO$_4$, filtered, and concentrated. Column chromatography on silica gel (100% hexanes to 100% EtOAc) provided the title product.

LRMS (ESI) calculated for $C_{20}H_{27}FN_3O_2$ [M+H]$^+$, 360.5; found 360.2.

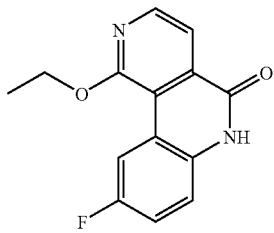 [SMILES: CCOc1nccc2c(=O)[nH]c3ccc(F)cc3c12]

Step 4: 1-Ethoxy-9-fluorobenzo[c]-2,6-naphthyridin-5(6H)-one

To a solution of 3-(2-amino-5-fluorophenyl)-2-ethoxy-N, N-diisopropylisonicotinamide (170 mg, 0.473 mmol) in THF (3153 μl), was added sodium hexamethyldisilazane (946 μl, 0.946 mmol, 1.0 M in THF). The reaction mixture was stirred at room temperature for 30 min. Methanol was added and the mixture was concentrated under reduced pressure. The residue was then triturated with diethyl ether (25 mL) and stirred for 1 h. The mixture was filtered through a frit, and the filter cake was collected and dried to afford the title compound as a beige solid.

LRMS (ESI) calculated for $C_{14}H_{11}FN_2O_2$ [M+H]+, 259.1; found 259.0.

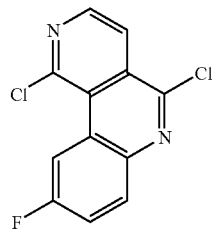 [SMILES: Fc1ccc2nc(Cl)c3ccnc(Cl)c3c2c1]

Step 5: 1,5-Dichloro-9-fluorobenzo[c]-2,6-naphthyridine

In a sealed reaction vessel 1-ethoxy-9-fluorobenzo[c]-2,6-naphthyridin-5(6H)-one (150 mg, 0.581 mmol) was dissolved in acetonitrile (10 mL) and phosphorus oxychloride (0.54 ml, 5.81 mmol) was added. The mixture was stirred at 100° C. overnight. The reaction mixture was cooled to room temperature and concentrated under reduced pressure. The residue was dissolved in acetonitrile (30 mL), and triethylamine was added until gas stopped evolving. To this mixture were added dichloromethane (100 mL) and aqueous sodium hydrogen carbonate (saturated, 100 mL). The aqueous layer was extracted with dichloromethane (2×100 mL). The combined organic extracts were washed with brine (50 mL), dried over sodium sulfate, and concentrated under reduced pressure to afford the title compound as a brown solid.

$^1$H NMR (600 MHz, CDCl$_3$) δ 9.48 (dd, 1H); 8.73 (d, 1H); 8.32 (d, 1H); 8.18 (q, 1H); 7.62 (m, 1H). LRMS (ESI) calculated for $C_{12}H_5Cl_2FN_2$ [M+H]$^+$, 267.0; found 267.0.

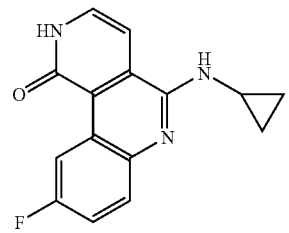 [SMILES: O=c1[nH]ccc2c(NC3CC3)nc3ccc(F)cc3c12]

Method A, Step 6: 5-(Cyclopropylamino)-9-fluorobenzo[c]-2,6-naphthyridin-1(2H)-one To a solution of 1,5-dichloro-9-fluorobenzo[c]-2,6-naphthyridine (40 mg, 0.15 mmol) in DMA (1.5 mL) was added cyclopropylamine (42.2 μl, 0.60 mmol) and the solution was heated to 100° C. for 30 min. The reaction mixture was cooled to room temperature and added to ethyl acetate (50 mL). The organic layer was washed with aqueous sodium hydrogen carbonate (saturated, 50 mL) and brine (50 mL). The combined organic extracts were dried over sodium sulfate and concentrated under reduced pressure to afford the crude mixture as a yellow oil. The oil was dissolved in THF followed by the addition of hydrochloric acid (2 mL, 12.0 mmol, 6.0 M). The mixture was then refluxed at 100° C. for 3 hr. After cooling to room temperature, the reaction mixture was added to aqueous sodium hydrogen carbonate (saturated, 50 mL). The aqueous layer was extracted with dichloromethane (2×50 mL). The combined organic extracts were washed with brine (50 mL), dried over sodium sulfate, and concentrated under reduced pressure. The residue was dissolved in water and DMSO and purified by preparative HPLC Reverse phase (C-18; eluting with acetonitrile/water+0.05% TFA), which afforded the title compound as a yellow solid.

$^1$H NMR (600 MHz, DMSO-D6) δ 12.11 (s, 1H); 9.41 (d, 1H); 7.64 (t, 1H); 7.57 (t, 1H); 7.44 (s, 1H); 7.38 (m, 1H); 6.98 (d, 1H); 2.98 (m, 1H); 0.75 (d, 2H); 0.57 (d, 2H). LRMS (ESI) calculated for $C_{15}H_{12}FN_3O$ [M+H]+, 270.1; found 270.1.

EXAMPLE 2

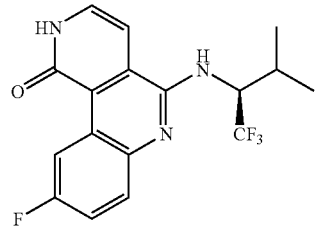 [SMILES: CC(C)[C@H](Nc1nc2ccc(F)cc2c2c(=O)[nH]ccc12)C(F)(F)F]

9-Fluoro-5-{[(1S)-2-methyl-1-(trifluoromethyl)propyl]amino}benzo[c]-2,6-naphthyridin-1(2H)-one Method B, Step 1: To a solution of 1,5-dichloro-9-fluorobenzo[c]-2,6-naphthyridine (50 mg, 0.19 mmol) (Example 1, Step 5) in THF (3 mL), were added (2S)-1,1,1-trifluoro-3-methylbutan-2-amine (26 mg, 0.19 mmol) and lithium bis(trimethylsilyl)amide (0.56 mL, 1.0 M in THF, 0.56 mmol). The solution was heated to 85° C. for 1 hr then cooled to room temperature. The reaction mixture was quenched with methanol and concentrated under reduced pressure. The crude mixture was taken up in THF (1 mL) and HCl (1 mL, 6 N) and heated to 85° C. for 1.5 hr. The solution was cooled and worked up with EtOAc and saturated NaHCO₃. The organic layers were combined, dried over MgSO₄, filtered, and concentrated to afford the title product.

LRMS (ESI) calc'd for (C$_{17}$H$_{16}$FN$_3$O) [M+H]+, 354.3; found 354.1.

EXAMPLE 3

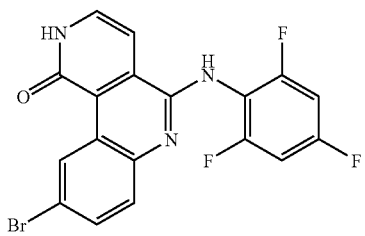 [SMILES: O=c1[nH]ccc2c(Nc3c(F)cc(F)cc3F)nc3ccc(Br)cc3c12]

9-Bromo-5-[(2,4,6-trifluorophenyl)amino]benzo[c]-2,6-naphthyridin-1(2H)-one

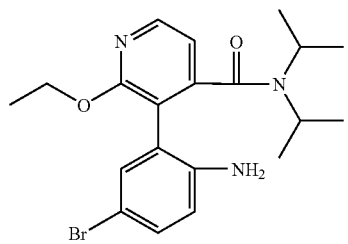 [SMILES: CCOc1nccc(C(=O)N(C(C)C)C(C)C)c1-c1cc(Br)ccc1N]

Step 1: 3-(2-Amino-5-bromophenyl)-2-ethoxy-N,N-diisopropylisonicotinamide

To a solution of 4-[(Diisopropylamino)carbonyl]-2-ethoxypyridin-3-yl}boronic acid (9.5 g, 32.2 mmol) in dioxane (95 mL) were added 2-iodo-4-bromo aniline (8.0 g, 27 mmol), potassium phosphate tribasic (15.4 g, 89 mmol), and tetrakis(triphenylphosphine)palladium (0) (3.1 g, 2.7 mmol). The solution was degassed by bubbling nitrogen gas for 5 min through the vessel which was subsequently sealed and heated to 100° C. for 2 hr. The reaction was cooled and extracted with EtOAc and water. The organic layers were dried with MgSO₄, filtered, and concentrated to afford the crude product. The oily residue was purified by silica gel chromatography (100% hexanes to 100% EtOAc, gradient elution) to afford the title compound.

LRMS (ESI) calc'd for C$_{20}$H$_{27}$BrN$_3$O$_2$ [M+H]⁺, 420.1; found 420.0.

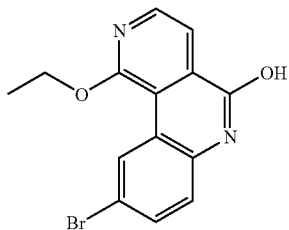 [SMILES: CCOc1nccc2c(O)nc3ccc(Br)cc3c12]

Step 2: 9-Bromo-1-ethoxybenzo[c]-2,6-naphthyridin-5-ol

To a solution of 3-(2-amino-5-bromophenyl)-2-ethoxy-N,N-diisopropylisonicotinamide (17.9 g, 43 mmol) in THF (213 mL) at 0° C. was added sodium bis(trimethylsilyl) amide (1.0 M in THF, 85 mL, 85 mmol). The solution was stirred for 2 hr and monitored by LCMS. Another 10 mL of sodium bis(trimethylsilyl) amide was added and stirred for an additional 30 min. The solution was quenched with methanol and concentrated to a slurry which was subsequently triturated with water and filtered to provide the title compound.

¹H NMR (600 MHz, CD$_6$SO) δ 9.08 (d, 1H), 8.25 (d, 1H), 7.74 (d, 1H), 7.54 (d, 1H), 7.24 (d, 1H), 4.60 (q, 2H), 1.50 (t, 3H). LRMS (ESI) calc'd for C$_{14}$H$_{12}$BrN$_2$O$_2$ [M+H]⁺, 319.0; found 319.0.

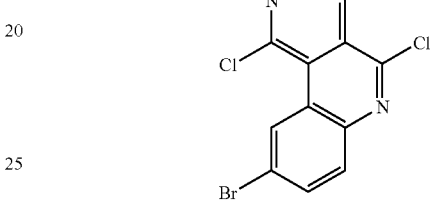

Step 3: 9-Bromo-1,5-dichlorobenzo[c]-2,6-naphthyridine

To a solution of 9-bromo-1-ethoxybenzo[c]-2,6-naphthyridin-5-ol (2.0 g, 6.3 mmol) in MeCN (50 mL) in a sealed tube was added phosphorus oxychloride (5.8 mL, 63 mmol) and heated at 100° C. overnight. The solution was carefully quenched by pouring it into an ice bath containing ammonium hydroxide. The precipitate was filtered and dried overnight on high vacuum to afford the title compound. ¹H NMR (600 MHz, CD$_6$SO) δ 9.75 (d, 1H), 8.80 (d, 1H), 8.36 (d, 1H), 8.12 (m, 1H), 8.04, (d, 1H) LRMS (ESI) calc'd for (C$_{12}$H$_6$BrCl$_2$N$_2$) [M+H]⁺, 326.9; found 326.9.

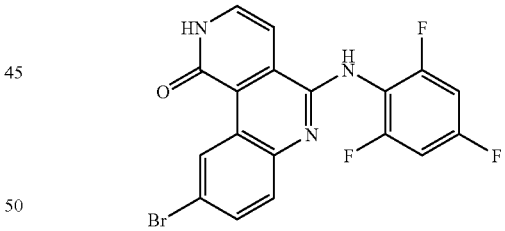

Method C, Step 4: 9-Bromo-5-[(2,4,6-trifluorophenyl)amino]benzo[c]-2,6-naphthyridin-1(2H)-one To a solution of 9-bromo-1,5-dichlorobenzo[c]-2,6-naphthyridine (800 mg, 2.4 mmol) in THF (10 mL) were added 2,4,6 trifluoroaniline (359 mg, 2.4 mmol) and sodium tert-butoxide (703 mg, 7.32 mmol) and the reaction mixture was heated to 85° C. for 45 min. The solution was cooled to room temperature, quenched with methanol and concentrated under reduced pressure. The residue was purified by silica gel chromatography (100% hexane to 100% EtOAc, gradient elution) to afford 9-bromo-1-chloro-N-(2,4,6-trifluorophenyl)benzo[c]-2,6-naphthyridin-5-amine. 9-Bromo-1-chloro-N-(2,4,6-trifluorophenyl)benzo[c]-2,6-naphthyridin-5-amine was taken up in THF (10 mL) and 6 N HCl (10 mL) and heated to 85° C. for 2 hr. The reaction was cooled to room temperature, neutralized with saturated NaHCO₃ and extracted with EtOAc. The organic layers were dried over Mg₂SO₄, filtered, and concentrated. Column chromatography on silica gel (100% hexane to 100% EtOAc) provided the title compound.

¹H NMR (600 MHz, CD₆SO) δ 12.3 (br s, 1H), 9.90 (d, 1H), 7.78 (d, 1H), 7.6 (dd, 1H), 7.35 (m, 3H), 7.20 (d, 1H). LRMS (ESI) calc'd for $C_{18}H_{10}BrF_3N_3O$ [M+H]⁺, 420.0; found 420.0.

EXAMPLE 4

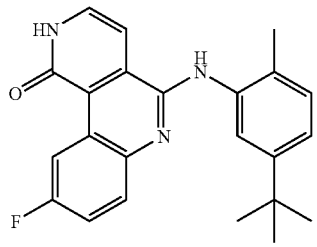 [SMILES: Cc1ccc(C(C)(C)C)cc1Nc1nc2ccc(F)cc2c2c(=O)[nH]ccc12]

5-[(5-tert-Butyl-2-methylphenyl)amino]-9-fluorobenzo[c]-2,6-naphthyridin-1(2H)-one

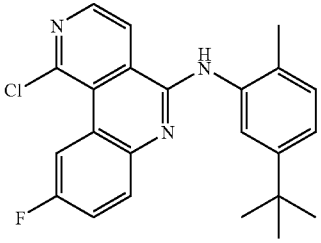 [SMILES: Cc1ccc(C(C)(C)C)cc1Nc1nc2ccc(F)cc2c2c(Cl)nccc12]

Method D, Step 1: N-(5-tert-Butyl-2-methylphenyl)-1-chloro-9-fluorobenzo[c]-2,6-naphthyridin-5-amine To a solution of 1,5-dichloro-9-fluorobenzo[c]-2,6-naphthyridin (Example 1, Step 5) (150 mg, 0.56 mmol) and 5-tert-butyl-2-methylaniline (101 mg, 0.62 mmol) in DMA (2.8 mL) was added NaHMDS (1 M in THF, 1.2 mL, 1.2 mmol) at 0° C. After stirring for 45 minutes, the reaction was quenched by the addition of sat. aq. NaHCO₃. The reaction was then extracted with EtOAc and water. The organic extracts were dried over MgSO₄ and concentrated in vacuo. Column chromatography on silica gel (100% hexane to 100% EtOAc) provided the title compound.

¹H NMR (600 MHz, CD₆SO) δ 9.26 (s, 1H), 9.12 (dd, 1H), 8.73 (d, 1H), 8.55 (d, 1H), 7.50 (m, 2H), 7.39 (d, 1H), 7.18 (m, 2H), 2.11 (s, 3H), 1.27 (s, 9H). LRMS (ESI) calc'd for $C_{23}H_{21}ClFN_3$ [M+H]⁺, 394.1; found 394.1.

Step 2: 5-[(5-tert-Butyl-2-methylphenyl)amino]-9-fluorobenzo[c]-2,6-naphthyridin-1(2H)-one N-(5-tert-butyl-2-methylphenyl)-1-chloro-9-fluorobenzo[c]-2,6-naphthridin-5-amine (110 mg, 0.28 mmol) was taken up in THF (3.5 mL) and 6 N HCl (3.5 mL) and heated to 85° C. for 2 hr. The reaction was cooled to room temperature, neutralized with saturated NaHCO₃ and extracted with EtOAc. The organic layers were dried over Mg₂SO₄, filtered, and concentrated. Column chromatography on silica gel (100% hexane to 100% EtOAc) provided the title compound.

¹H NMR (600 MHz, CD₆SO) δ 12.21 (s(br), 1H) 9.45 (dd, 1H), 8.78 (s, 1H), 7.67 (d, 1h) 7.42 (m, 1H), 7.39 (d, 1H), 7.35 (m, 1H), 7.21 (d, 1H), 7.15 (m, 2H), 2.09 (s, 3H), 1.27 (s, 9H). LRMS (ESI) calc'd for $C_{23}H_{22}FN_3O$ [M+H]⁺, 376.2; found 376.2.

Additional analogues shown below were prepared using procedures similar to those described in the above examples.

TABLE 1

| Example | Structure | Compound Name | LCMS (M + H)⁺ | Method |
|---|---|---|---|---|
| 5 | 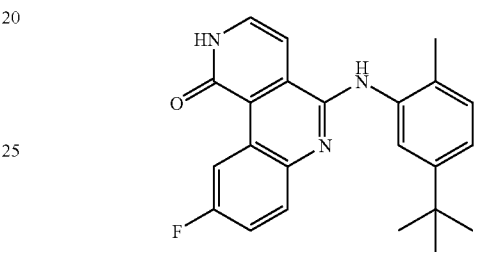 | 9-Fluoro-5-[(1,2,2-trimethylpropyl)amino]benzo[c]-2,6-naphthyridin-1(2H)-one | Calc'd: 314.2, found: 314.2 | A |

TABLE 1-continued

| Example | Structure | Compound Name | LCMS (M + H)+ | Method |
|---|---|---|---|---|
| 6 | 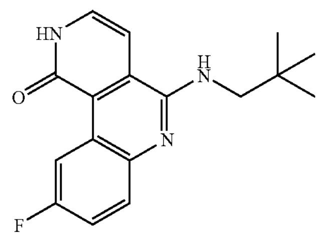 [SMILES: CC(C)(C)CNc1nc2ccc(F)cc2c2c(=O)[nH]ccc12] | 5-[(2,2-Dimethylpropyl)amino]-9-fluorobenzo[c]-2,6-naphthyridin-1(2H)-one | Calc'd: 300.2, found: 300.1 | A |
| 7 | 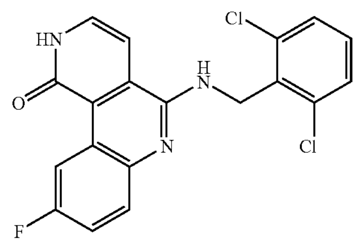 [SMILES: O=c1[nH]ccc2c(NCc3c(Cl)cccc3Cl)nc3ccc(F)cc3c12] | 5-[(2,6-Dichlorobenzyl)amino]-9-fluorobenzo[c]-2,6-naphthyridin-1(2H)-one | Calc'd: 388.0, found: 388.0 | A |
| 8 | 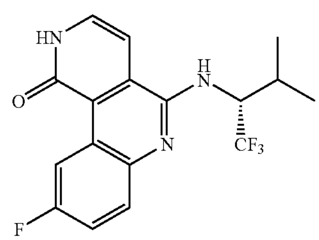 [SMILES: CC(C)[C@@H](Nc1nc2ccc(F)cc2c2c(=O)[nH]ccc12)C(F)(F)F] | 9-Fluoro-5-{[(1R)-2-methyl-1-(trifluoromethyl)propyl]amino}benzo[c]-2,6-naphthyridin-1(2H)-one | Calc'd: 354.1, found: 354.1 | B |
| 9 | 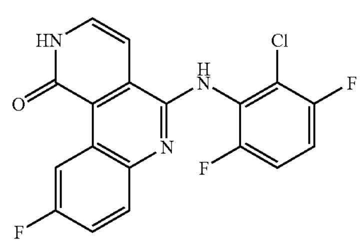 [SMILES: O=c1[nH]ccc2c(Nc3c(F)ccc(F)c3Cl)nc3ccc(F)cc3c12] | 5-[(2-Chloro-3,6-difluorophenyl)amino]-9-fluorobenzo[c]-2,6-naphthyridin-1(2H)-one | Calc'd: 376.1, found: 376.0 | C |
| 10 | 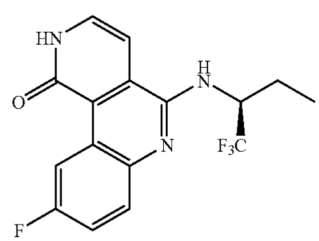 [SMILES: CC[C@H](Nc1nc2ccc(F)cc2c2c(=O)[nH]ccc12)C(F)(F)F] | 9-Fluoro-5-{[(1S)-1-(trifluoromethyl)propyl]amino}benzo[c]-2,6-naphthyridin-1(2H)-one | Calc'd: 340.1, found: 340.1 | B |
| 11 | 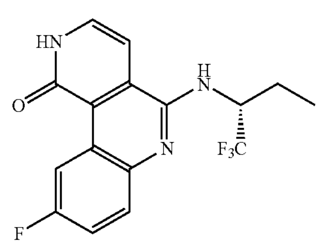 [SMILES: CC[C@@H](Nc1nc2ccc(F)cc2c2c(=O)[nH]ccc12)C(F)(F)F] | 9-Fluoro-5-{[(1R)-1-(trifluoromethyl)propyl]amino}benzo[c]-2,6-naphthyridin-1(2H)-one | Calc'd: 340.1, found: 340.1 | B |

TABLE 1-continued

| Example | Structure | Compound Name | LCMS (M + H)+ | Method |
|---|---|---|---|---|
| 12 | 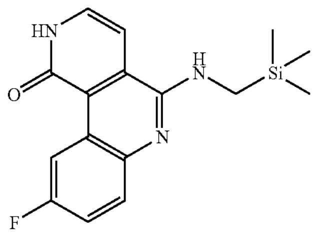 [SMILES: C[Si](C)(C)CNc1nc2ccc(F)cc2c2c(=O)[nH]ccc12] | 9-Fluoro-5-{[(trimethylsilyl)methyl]amino}benzo[c]-2,6-naphthyridin-1(2H)-one | Calc'd: 316.1, found: 316.1 | A |
| 13 | 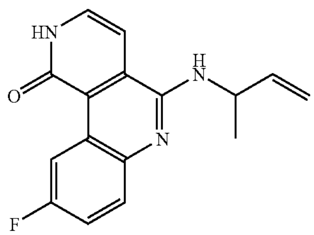 [SMILES: C=CC(C)Nc1nc2ccc(F)cc2c2c(=O)[nH]ccc12] | 9-Fluoro-5-[(1-methylprop-2-en-1-yl)amino]benzo[c]-2,6-naphthyridin-1(2H)-one | Calc'd: 284.1, found: 284.1 | A |
| 14 | 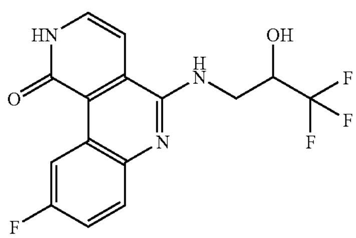 [SMILES: O=c1[nH]ccc2c(NCC(O)C(F)(F)F)nc3ccc(F)cc3c12] | 9-Fluoro-5-[(3,3,3-trifluoro-2-hydroxypropyl)amino]benzo[c]-2,6-naphthyridin-1(2H)-one | Calc'd: 342.1, found: 342.0 | A |
| 15 | 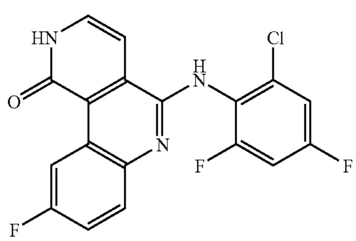 [SMILES: O=c1[nH]ccc2c(Nc3c(F)cc(F)cc3Cl)nc3ccc(F)cc3c12] | 6-[(2-Chloro-4,6-difluorophenyl)amino]-9-fluorobenzo[c]-2,6-naphthyridin-1(2H)-one | Calc'd: 376.1, found: 376.0 | C |
| 16 | 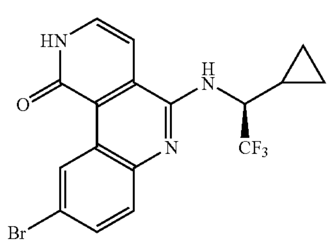 [SMILES: O=c1[nH]ccc2c(N[C@@H](C3CC3)C(F)(F)F)nc3ccc(Br)cc3c12] | 9-Bromo-5-{[(1S)-1-cyclopropyl-2,2,2-trifluoroethyl]amino}benzo[c]-2,6-naphthyridin-1(2H)-one | Calc'd: 412.3, found: 412.0 | B |
| 17 | 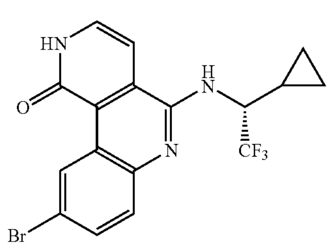 [SMILES: O=c1[nH]ccc2c(N[C@H](C3CC3)C(F)(F)F)nc3ccc(Br)cc3c12] | 9-Bromo-5-{[(1R)-1-cyclopropyl-2,2,2-trifluoroethyl]amino}benzo[c]-2,6-naphthyridin-1(2H)-one | Calc'd: 412.3, found: 412.0 | B |

TABLE 1-continued

| Example | Structure | Compound Name | LCMS (M + H)⁺ | Method |
|---|---|---|---|---|
| 18 | 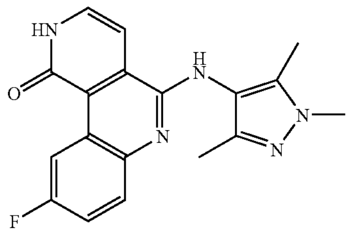 [SMILES: Cc1nn(C)c(C)c1Nc1nc2ccc(F)cc2c2c(=O)[nH]ccc12] | 9-Fluoro-5-[(1,3,5-trimethyl-1H-pyrazol-4-yl)amino]benzo[c]-2,6-naphthyridin-1(2H)-one | Calc'd: 338.4, found: 338.1 | B |
| 19 | 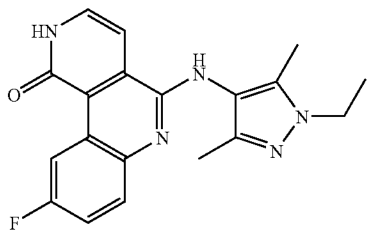 [SMILES: CCn1nc(C)c(Nc2nc3ccc(F)cc3c3c(=O)[nH]ccc23)c1C] | 5-[(1-Ethyl-3,5-dimethyl-1H-pyrazol-4-yl)amino]-9-fluorobenzo[c]-2,6-naphthyridin-1(2H)-one | Calc'd: 352.4, found: 352.1 | B |
| 20 | 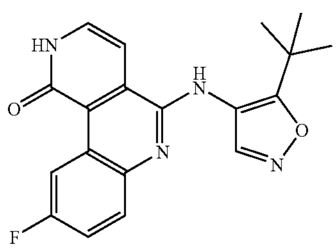 [SMILES: CC(C)(C)c1oncc1Nc1nc2ccc(F)cc2c2c(=O)[nH]ccc12] | 5-[(5-Tert-butylisoxazol-4-yl)amino]-9-fluorobenzo[c]-2,6-naphthyridin-1(2H)-one | Calc'd: 353.4, found: 353.1 | B |
| 21 | 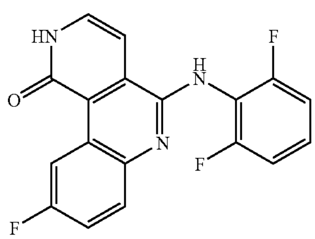 [SMILES: O=c1[nH]ccc2c(Nc3c(F)cccc3F)nc3ccc(F)cc3c12] | 5-[(2,6-Difluorophenyl)amino]-9-fluorobenzo[c]-2,6-naphthyridin-1(2H)-one | Calc'd: 342.1, found: 342.1 | C |
| 22 | 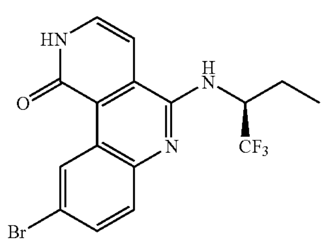 [SMILES: CC[C@H](Nc1nc2ccc(Br)cc2c2c(=O)[nH]ccc12)C(F)(F)F] | 9-Bromo-5-{[(1S)-1-(trifluoromethyl)propyl]amino}benzo[c]-2,6-naphthyridin-1(2H)-one | Calc'd: 400.3, found: 400.0 | B |
| 23 | 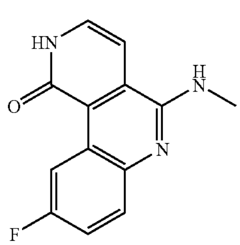 [SMILES: CNc1nc2ccc(F)cc2c2c(=O)[nH]ccc12] | 9-Fluoro-5-(methylamino)benzo[c]-2,6-naphthyridin-1(2H)-one | Calc'd: 244.1, found: 244.1 | A |

TABLE 1-continued

| Example | Structure | Compound Name | LCMS (M + H)+ | Method |
|---|---|---|---|---|
| 24 | 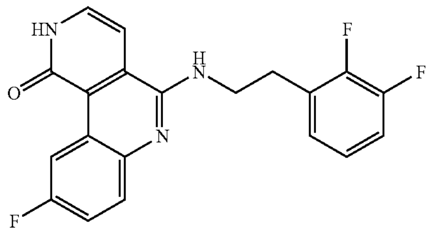 [SMILES: O=c1[nH]ccc2c(NCCc3cccc(F)c3F)nc3ccc(F)cc3c12] | 5-{[2-(2,3-difluorophenyl)ethyl]amino}-9-fluorobenzo[c]-2,6-naphthyridin-1(2H)-one | Calc'd 370.1, found 370.1 | D |
| 25 | 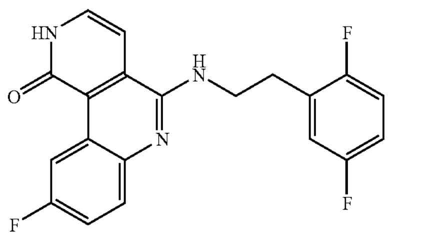 [SMILES: O=c1[nH]ccc2c(NCCc3cc(F)ccc3F)nc3ccc(F)cc3c12] | 5-{[2-(2,5-difluorophenyl)amino]amino}-9-fluorobenzo[c]-2,6-naphthyridin-1(2H)-one | Calc'd 370.1, found 370.1 | D |
| 26 | 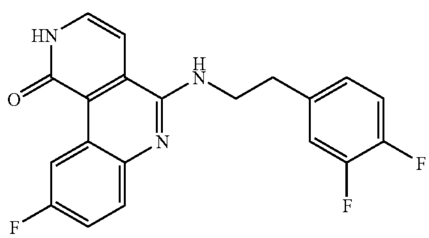 [SMILES: O=c1[nH]ccc2c(NCCc3ccc(F)c(F)c3)nc3ccc(F)cc3c12] | 5-{[2-(3,4-difluorophenyl)ethyl]amino}-9-fluorobenzo[c]-2,6-naphthyridin-1(2H)-one | Calc'd 370.1, found 370.1 | D |
| 27 | 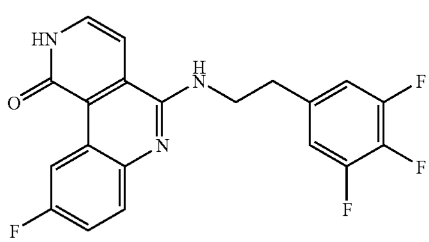 [SMILES: O=c1[nH]ccc2c(NCCc3cc(F)c(F)c(F)c3)nc3ccc(F)cc3c12] | 9-fluoro-5-{[2-(3,4,5-trifluorophenyl)amino}benzo[c]-2,6-naphthyridin-1(2H)-one | Calc'd 388.1, found 388.1 | D |
| 28 | 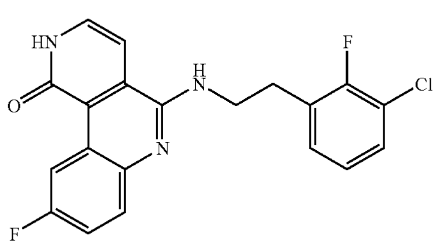 [SMILES: O=c1[nH]ccc2c(NCCc3cccc(Cl)c3F)nc3ccc(F)cc3c12] | 5-{[2-(3-chloro-2-fluorophenyl)ethyl]amino}-9-fluorobenzo[c]-2,6-naphthyridin-1(2H)-one | Calc'd 386.1, found 386.1 | D |
| 29 | 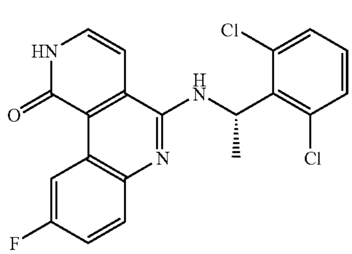 [SMILES: C[C@H](Nc1nc2ccc(F)cc2c2c(=O)[nH]ccc12)c1c(Cl)cccc1Cl] | 5-{[(1S)-1-(2,6-dichlorophenyl)ethyl]amino}-9-fluorobenzo[c]-2,6-naphthyridin-1(2H)-one | Calc'd 402.1, found 402.1 | D |

TABLE 1-continued

| Example | Structure | Compound Name | LCMS (M + H)+ | Method |
|---------|-----------|---------------|---------------|--------|
| 30 | 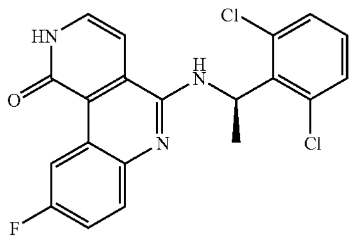 [SMILES: C[C@@H](Nc1nc2ccc(F)cc2c2c(=O)[nH]ccc12)c1c(Cl)cccc1Cl] | 5-{[(1R)-1-(2,6-dichlorophenyl)ethyl]amino}-9-fluorobenzo[c]-2,6-naphthyridin-1(2H)-one | Calc'd 402.1, found 402.1 | D |
| 31 | 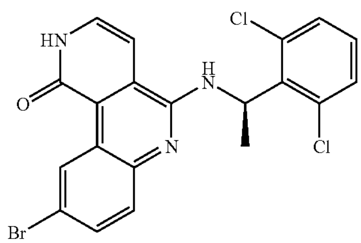 [SMILES: C[C@@H](Nc1nc2ccc(Br)cc2c2c(=O)[nH]ccc12)c1c(Cl)cccc1Cl] | 9-bromo-5-{[(1R)-1-(2,6-dichlorophenyl)ethyl]amino}benzo[c]-2,6-naphthyridin-1(2H)-one | Calc'd 462.0, found 462.0 | D |
| 32 | 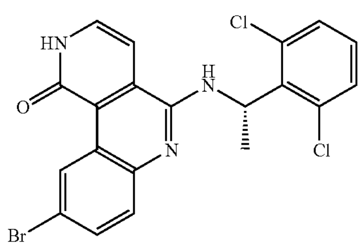 [SMILES: C[C@H](Nc1nc2ccc(Br)cc2c2c(=O)[nH]ccc12)c1c(Cl)cccc1Cl] | 9-bromo-5-{[(1S)-1-(2,6-dichlorophenyl)ethyl]amino}benzo[c]-2,6-naphthyridin-1(2H)-one | Calc'd 462.0, found 462.0 | D |
| 33 | 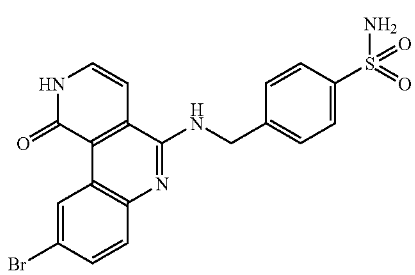 [SMILES: NS(=O)(=O)c1ccc(CNc2nc3ccc(Br)cc3c3c(=O)[nH]ccc23)cc1] | 4-{[(9-bromo-1-oxo-1,2-dihydrobenzo[c]-2,6-naphthyridin-5-yl)amino]methyl}benzenesulfonamide | Calc'd 459.0, found 459.0 | D |
| 34 | 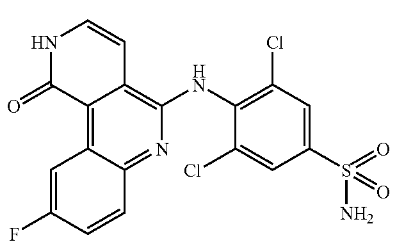 [SMILES: NS(=O)(=O)c1cc(Cl)c(Nc2nc3ccc(F)cc3c3c(=O)[nH]ccc23)c(Cl)c1] | 3,5-dichloro-4-[(9-fluoro-1-oxo-1,2-dihydrobenzo[c]-2,6-naphthyridin-5-yl)amino]benzenesulfonamide | Calc'd 453.0, found 452.9 | D |
| 35 | 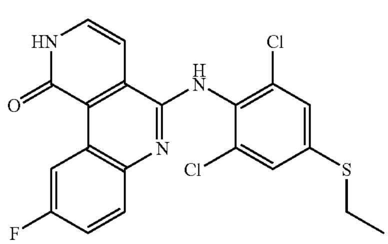 [SMILES: CCSc1cc(Cl)c(Nc2nc3ccc(F)cc3c3c(=O)[nH]ccc23)c(Cl)c1] | 5-{[2,6-dichloro-4-(ethylthio)phenyl]amino}-9-fluorobenzo[c]-2,6-naphthyridin-1(2H)-one | Calc'd 434.0, found 434.0 | D |

TABLE 1-continued

| Example | Structure | Compound Name | LCMS (M + H)+ | Method |
|---|---|---|---|---|
| 36 | 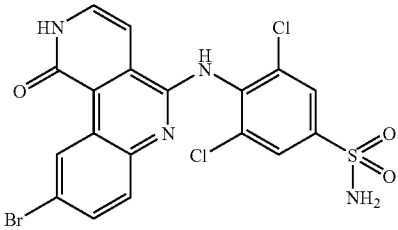 [SMILES: NS(=O)(=O)c1cc(Cl)c(Nc2nc3ccc(Br)cc3c3c(=O)[nH]ccc23)c(Cl)c1] | 4-[(9-bromo-1-oxo-1,2-dihydrobenzo[c]-2,6-naphthyridin-5-yl)amino]-3,5-dichlorobenzenesulfonamide | Calc'd 512.9, found 512.8 | D |
| 37 | 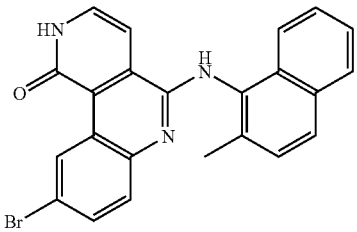 [SMILES: Cc1ccc2ccccc2c1Nc1nc2ccc(Br)cc2c2c(=O)[nH]ccc12] | 9-bromo-5-[(2-methyl-1-naphthyl)amino]benzo[c]-2,6-naphthyridin-1(2H)-one | Calc'd 430.1, found 430.0 | D |
| 38 | 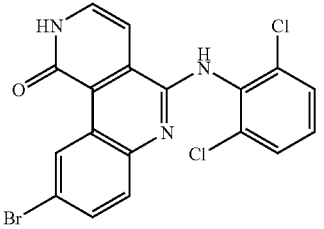 [SMILES: O=c1[nH]ccc2c(Nc3c(Cl)cccc3Cl)nc3ccc(Br)cc3c12] | 9-bromo-5-[(2,6-dichlorophenyl)amino]benzo[c]-2,6-naphthyridin-1(2H)-one | Calc'd 433.9, found 433.9 | D |
| 39 | 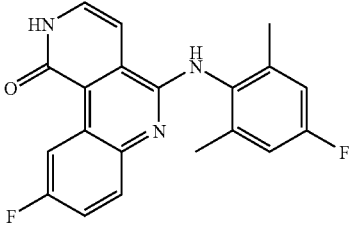 [SMILES: Cc1cc(F)cc(C)c1Nc1nc2ccc(F)cc2c2c(=O)[nH]ccc12] | 9-fluoro-5-[(4-fluoro-2,6-dimethylphenyl)amino]benzo[c]-2,6-naphthyridin-1(2H)-one | Calc'd 352.1, found 352.1 | D |
| 40 | 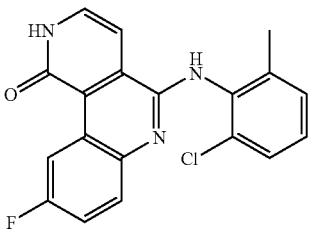 [SMILES: Cc1cccc(Cl)c1Nc1nc2ccc(F)cc2c2c(=O)[nH]ccc12] | 5-[(2-chloro-6-methylphenyl)amino]-9-fluorobenzo[c]-2,6-naphthyridin-1(2H)-one | Calc'd 354.1, found 354.1 | D |
| 41 | 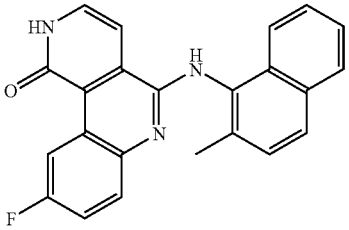 [SMILES: Cc1ccc2ccccc2c1Nc1nc2ccc(F)cc2c2c(=O)[nH]ccc12] | 9-fluoro-5-[(2-methyl-1-naphthyl)amino]benzo[c]-2,6-naphthyridin-1(2H)-one | Calc'd 370.1, found 370.1 | D |

TABLE 1-continued

| Example | Structure | Compound Name | LCMS (M + H)+ | Method |
|---|---|---|---|---|
| 42 | 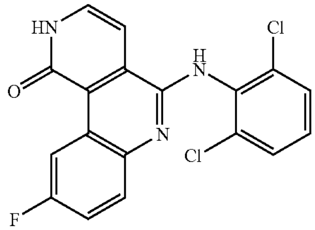 [SMILES: O=c1[nH]ccc2c(Nc3c(Cl)cccc3Cl)nc3ccc(F)cc3c12] | 5-[(2,6-dichlorophenyl)amino]-9-fluorobenzo[c]-2,6-naphthyridin-1(2H)-one | Calc'd 374.0, found 374.0 | D |
| 43 | 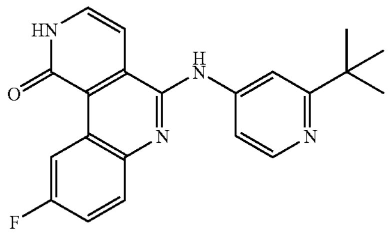 [SMILES: CC(C)(C)c1cc(Nc2nc3ccc(F)cc3c3c(=O)[nH]ccc23)ccn1] | 5-[(2-tert-butylpyridin-4-yl)amino]-9-fluorobenzo[c]-2,6-naphthyridin-1(2H)-one | Calc'd 363.2, found 363.2 | D |
| 44 | 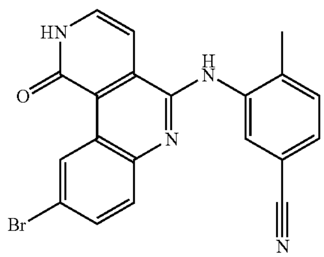 [SMILES: Cc1ccc(C#N)cc1Nc1nc2ccc(Br)cc2c2c(=O)[nH]ccc12] | 3-[(9-bromo-1-oxo-1,2-dihydrobenzo[c]-2,6-naphthyridin-5-yl)amino]-4-methylbenzonitrile | Calc'd 405.0, found 405.0 | D |
| 45 | 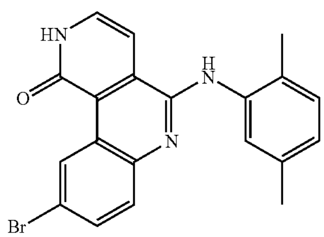 [SMILES: Cc1ccc(C)c(Nc2nc3ccc(Br)cc3c3c(=O)[nH]ccc23)c1] | 9-bromo-5-[(2,5-dimethylphenyl)amino]benzo[c]-2,6-naphthyridin-1(2H)-one | Calc'd 394.1, found 394.0 | D |
| 46 | 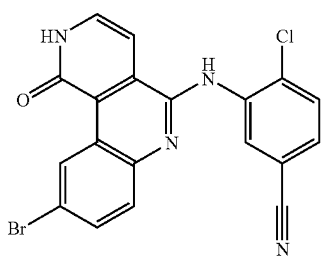 [SMILES: N#Cc1ccc(Cl)c(Nc2nc3ccc(Br)cc3c3c(=O)[nH]ccc23)c1] | 3-[(9-bromo-1-oxo-1,2-dihydrobenzo[c]-2,6-naphthyridin-5-yl)amino]-4-chlorobenzonitrile | Calc'd 425.0, found 425.0 | D |
| 47 | 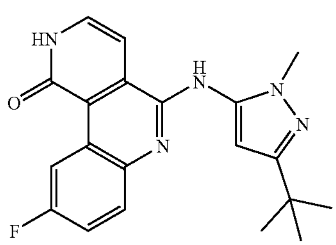 [SMILES: Cn1nc(C(C)(C)C)cc1Nc1nc2ccc(F)cc2c2c(=O)[nH]ccc12] | 5-[(3-tert-butyl-1-methyl-1H-pyrazol-5-yl)amino]-9-fluorobenzo[c]-2,6-naphthyridin-1(2H)-one | Calc'd 366.2, found 366.2 | D |

TABLE 1-continued

| Example | Structure | Compound Name | LCMS (M + H)+ | Method |
|---|---|---|---|---|
| 48 | 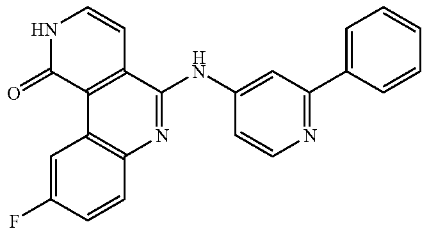 [SMILES: O=c1[nH]ccc2c(Nc3ccnc(-c4ccccc4)c3)nc3ccc(F)cc3c12] | 9-fluoro-5-[(2-phenylpyridin-4-yl)amino]benzo[c]-2,6-naphthyridin-1(2H)-one | Calc'd 383.1, found 383.1 | D |
| 49 | 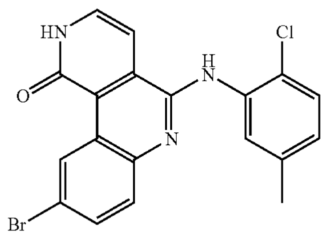 [SMILES: Cc1ccc(Cl)c(Nc2nc3ccc(Br)cc3c3c(=O)[nH]ccc23)c1] | 9-bromo-5-[(2-chloro-5-methylphenyl)amino]benzo[c]-2,6-naphthyridin-1(2H)-one | Calc'd 414.0, found 414.0 | D |
| 50 | 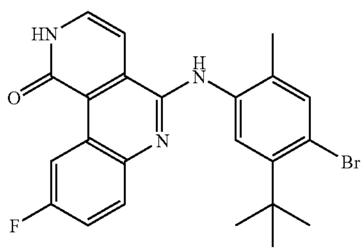 [SMILES: Cc1cc(Br)c(C(C)(C)C)cc1Nc1nc2ccc(F)cc2c2c(=O)[nH]ccc12] | 5-[(4-bromo-5-tert-butyl-2-methylphenyl)amino]-9-fluorobenzo[c]-2,6-naphthyridin-1(2H)-one | Calc'd 454.1, found 454.1 | D |
| 51 | 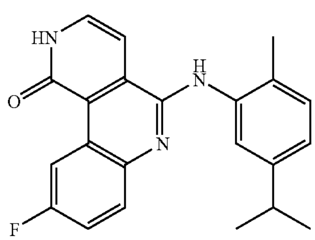 [SMILES: Cc1ccc(C(C)C)cc1Nc1nc2ccc(F)cc2c2c(=O)[nH]ccc12] | 9-fluoro-5-[(5-isopropyl-2-methylphenyl)amino]benzo[c]-2,6-naphthyridin-1(2H)-one | Calc'd 362.2, found 362.2 | D |
| 52 | 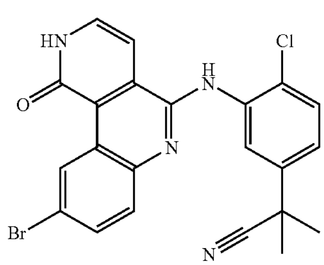 [SMILES: CC(C)(C#N)c1ccc(Cl)c(Nc2nc3ccc(Br)cc3c3c(=O)[nH]ccc23)c1] | 2-{3-[(9-bromo-1-oxo-1,2-dihydrobenzo[c]-2,6-naphthyridin-5-yl)amino]-4-chlorophenyl}-2-methylpropanitrile | Calc'd 467.0, found 467.0 | D |
| 53 | 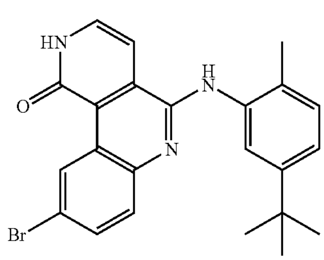 [SMILES: Cc1ccc(C(C)(C)C)cc1Nc1nc2ccc(Br)cc2c2c(=O)[nH]ccc12] | 9-bromo-5-[(5-tert-butyl-2-methylphenyl)amino]benzo[c]-2,6-naphthyridin-1(2H)-one | Calc'd 436.1, found 436.1 | D |

TABLE 1-continued

| Example | Structure | Compound Name | LCMS (M + H)+ | Method |
|---|---|---|---|---|
| 54 | 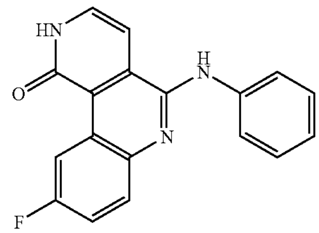 [SMILES: O=c1[nH]ccc2c(Nc3ccccc3)nc3ccc(F)cc3c12] | 5-anilino-9-fluorobenzo[c]-2,6-naphthyridin-1(2H)-one | Calc'd 306.1, found 306.1 | D |
| 55 | 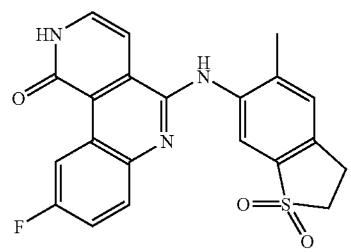 [SMILES: Cc1cc2c(cc1Nc1nc3ccc(F)cc3c3c(=O)[nH]ccc13)S(=O)(=O)CC2] | 9-fluoro-5-[(5-methyl-1,1-dioxido-2,3-dihydro-1-benzothien-6-yl)amino]benzo[c]-2,6-naphthyridin-1(2H)-one | Calc'd 410.1, found 410.0 | D |
| 56 | 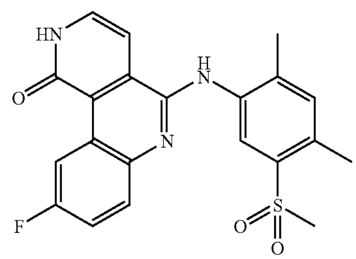 [SMILES: Cc1cc(C)c(S(C)(=O)=O)cc1Nc1nc2ccc(F)cc2c2c(=O)[nH]ccc12] | 5-{[2,4-dimethyl-5-(methylsulfonyl)phenyl]amino}-9-fluorobenzo[c]-2,6-naphthyridin-1(2H)-one | Calc'd 412.1, found 412.1 | D |
| 57 | 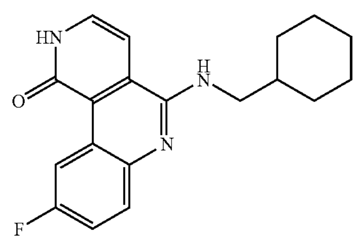 [SMILES: O=c1[nH]ccc2c(NCC3CCCCC3)nc3ccc(F)cc3c12] | 5-[(cyclohexylmethyl)amino]-9-fluorobenzo[c]-2,6-naphthyridin-1(2H)-one | Calc'd 326.2, found 326.2 | D |
| 58 | 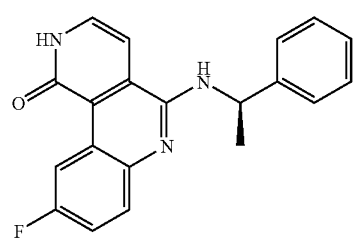 [SMILES: C[C@@H](Nc1nc2ccc(F)cc2c2c(=O)[nH]ccc12)c1ccccc1] | 9-fluoro-5-{[(1R)-1-phenylethyl]amino}benzo[c]-2,6-naphthyridin-1(2H)-one | Calc'd 334.1, found 334.1 | D |
| 59 | 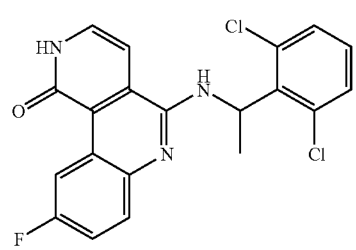 [SMILES: CC(Nc1nc2ccc(F)cc2c2c(=O)[nH]ccc12)c1c(Cl)cccc1Cl] | 5-{[1-(2,6-dichlorophenyl)ethyl]amino}-9-fluorobenzo[c]-2,6-naphthyridin-1(2H)-one | Calc'd 402.1, found 402.0 | D |

TABLE 1-continued

| Example | Structure | Compound Name | LCMS (M + H)+ | Method |
|---|---|---|---|---|
| 60 | 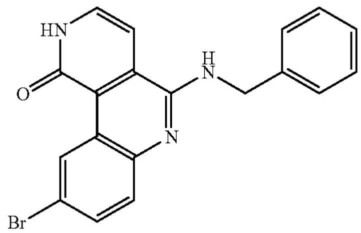 [SMILES: O=c1[nH]ccc2c(NCc3ccccc3)nc3ccc(Br)cc3c12] | 5-(benzylamino)-9-bromobenzyl[c]-2,6-naphthyridin-1(2H)-one | Calc'd 380.0, found 380.0 | D |
| 61 | 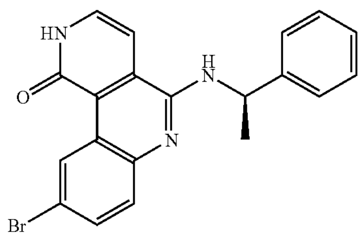 [SMILES: C[C@@H](Nc1nc2ccc(Br)cc2c2c(=O)[nH]ccc12)c1ccccc1] | 9-bromo-5-{[(1R)-1-phenylethyl]amino}benzo[c]-2,6-naphthyridin-1(2H)-one | Calc'd 394.1, found 394.0 | D |
| 62 | 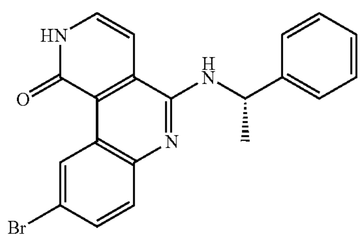 [SMILES: C[C@H](Nc1nc2ccc(Br)cc2c2c(=O)[nH]ccc12)c1ccccc1] | 9-bromo-5-{[(1S)-1-phenylethyl]amino}benzo[c]-2,6-naphthyridin-1(2H)-one | Calc'd 394.1, found 394.0 | D |
| 63 | 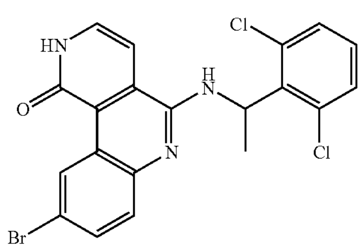 [SMILES: CC(Nc1nc2ccc(Br)cc2c2c(=O)[nH]ccc12)c1c(Cl)cccc1Cl] | 9-bromo-5-{[1-(2,6-dichlorophenyl)ethyl]amino}benzo[c]-2,6-naphthyridin-1(2H)-one | Calc'd 462.0, found 461.9 | D |
| 64 | 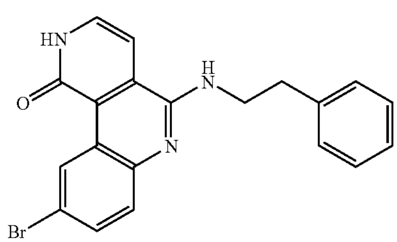 [SMILES: O=c1[nH]ccc2c(NCCc3ccccc3)nc3ccc(Br)cc3c12] | 9-bromo-5-[(2-phenylethyl)amino]benzo[c]-2,6-naphthyridin-1(2H)-one | Calc'd 394.1, found 394.0 | D |
| 65 | 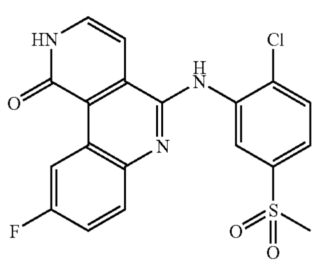 | 5-{[2-chloro-5-(methylsulfonyl)phenyl]amino}-9-fluorobenzo[c]-2,6-naphthyridin-1(2H)-one | Calc'd 418.0, found 418.0 | D |

TABLE 1-continued

| Example | Structure | Compound Name | LCMS (M + H)+ | Method |
|---|---|---|---|---|
| 66 | 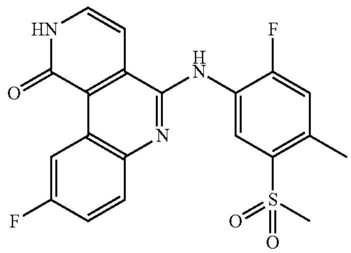 [SMILES: Cc1cc(F)c(Nc2nc3ccc(F)cc3c3c(=O)[nH]ccc23)cc1S(C)(=O)=O] | 9-fluoro-5-{[2-fluoro-4-methyl-5-(methylsulfonyl)phenyl]amino}benzo[c]-2,6-naphthyridin-1(2H)-one | Calc'd 416.1, found 416.1 | D |
| 67 | 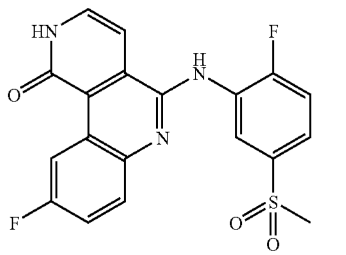 [SMILES: CS(=O)(=O)c1ccc(F)c(Nc2nc3ccc(F)cc3c3c(=O)[nH]ccc23)c1] | 9-fluoro-5-{[2-fluoro-5-(methylsulfonyl)phenyl]amino}benzo[c]-2,6-naphthyridin-1(2H)-one | Calc'd 402.1, found 402.0 | D |
| 68 | 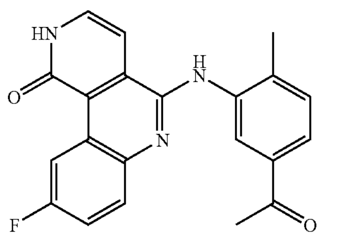 [SMILES: CC(=O)c1ccc(C)c(Nc2nc3ccc(F)cc3c3c(=O)[nH]ccc23)c1] | 5-[(5-acetyl-2-methylphenyl)amino]-9-fluorobenzo[c]-2,6-naphthyridin-1(2H)-one | Calc'd 362.1, found 362.1 | D |
| 69 | 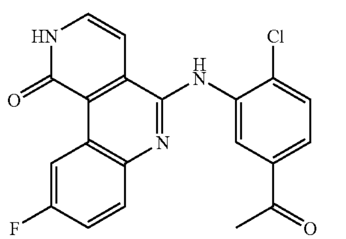 [SMILES: CC(=O)c1ccc(Cl)c(Nc2nc3ccc(F)cc3c3c(=O)[nH]ccc23)c1] | 5-[(5-acetyl-2-chlorophenyl)amino]-9-fluorobenzo[c]-2,6-naphthyridin-1(2H)-one | Calc'd 382.1, found 382.1 | D |
| 70 | 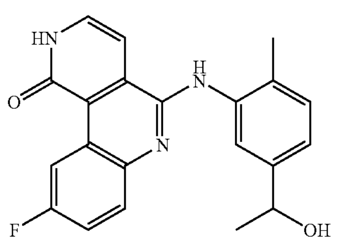 [SMILES: Cc1ccc(C(C)O)cc1Nc1nc2ccc(F)cc2c2c(=O)[nH]ccc12] | 9-fluoro-5-{[5-(1-hydroxyethyl)-2-methylphenyl]amino}benzo[c]-2,6-naphthyrin-1(2H)-one | Calc'd 364.1, found 364.1 | D |
| 71 | 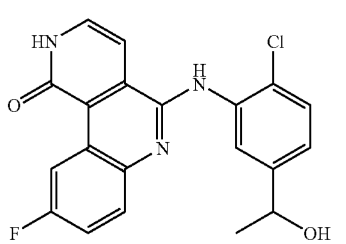 [SMILES: CC(O)c1ccc(Cl)c(Nc2nc3ccc(F)cc3c3c(=O)[nH]ccc23)c1] | 5-{[2-chloro-5-(1-hydroxyethyl)phenyl]amino}-9-fluorobenzo[c]-2,6-naphthyridin-1(2H)-one | Calc'd 384.1, found 384.0 | D |

| Example | Structure | Compound Name | LCMS (M + H)+ | Method |
|---|---|---|---|---|
| 72 | 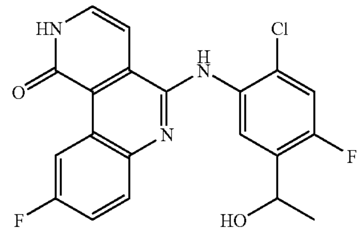 [SMILES: CC(O)c1cc(Nc2nc3ccc(F)cc3c3c(=O)[nH]ccc23)c(Cl)cc1F] | 5-{[2-chloro-4-fluoro-5-(1-hydroxyethyl)phenyl]amino}-9-fluorobenzo[c]-2,6-naphthyridin-1(2H)-one | Calc'd 402.1, found 402.1 | D |

EXAMPLE 73

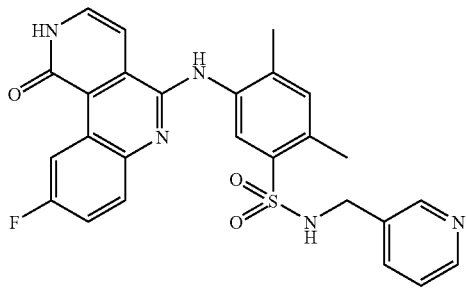 [SMILES: Cc1cc(C)c(S(=O)(=O)NCc2cccnc2)cc1Nc1nc2ccc(F)cc2c2c(=O)[nH]ccc12]

5-[(9-Fluoro-1-oxo-1,2-dihydrobenzo[c]-2,6-naphthyridin-5-yl)amino]-2,4-dimethyl-N-(pyridin-3-ylmethyl)benzenesulfonamide

Step 1: 5-{[(9H-Fluoren-9-ylmethoxy)carbonyl]amino}-2,4-dimethylbenzenesulfonic acid

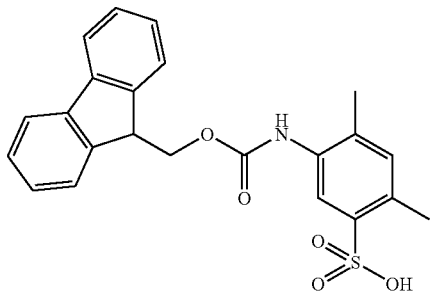 [SMILES: Cc1cc(C)c(S(=O)(=O)O)cc1NC(=O)OCC1c2ccccc2-c2ccccc21]

To a solution of 5-amino-2,4-dimethylbenzenesulfonic acid sodium salt (3.0 g, 13.4 mmol) in dioxane (37 mL) and water (37 ml) was added NaHCO₃ (2.5 g, 29.6 mmol) and 9-fluoreneylmethyl chloroformate. The mixture was then stirred at room temperature overnight and then quenched with 1N HCl and extracted with EtOAc. The organic layers were concentrated in vacuo. Purification by silica gel chromatography (0-10% MeOH/DCM) resulted in the title compound.

¹H NMR (600 MHz, CD₆SO) δ 8.92 (s(br), 1H), 7.86 (d, 1H) 7.72 (s(br), 2H), 7.56 (s, 1H) 7.38 (m, 2H), 7.31 (m, 2H) 6.92 (s, 1H) 4.34 (s (br), 1H) 4.23 (s (br), 1H) 3.12 (m, 1H), 2.41 (s, 3H), 2.08 (s, 3H).

Step 2: 9H-Fluoren-9-ylmethyl[5-(chlorosulfonyl)-2,4-dimethylphenyl]carbamate To a solution of 5-{[(9H-fluoren-9-ylmethoxy)carbonyl]amino}-2,4-dimethylbenzenesulfonic acid (5 g, 11.8 mmol) in DMF (5.9 mL) was added thionyl chloride (4.3 mL, 59.0 mmol). The reaction was stirred at room temperature for three hours and then quenched by the addition of water. The colorless precipitate was then collected by filtration and dried in vacuo to afford 9H-fluoren-9-ylmethyl[5-(chlorosulfonyl)-2,4-dimethylphenyl]carbamate as a colorless solid.

¹H NMR (600 MHz, CD₆SO) δ 8.92 (s(br), 1H), 7.86 (d, 1H) 7.72 (s(br), 2H), 7.56 (s, 1H) 7.38 (m, 2H), 7.31 (m, 2H) 6.92 (s, 1H) 4.39 (s (br), 2H), 2.41 (s, 3H), 2.08 (s, 3H).

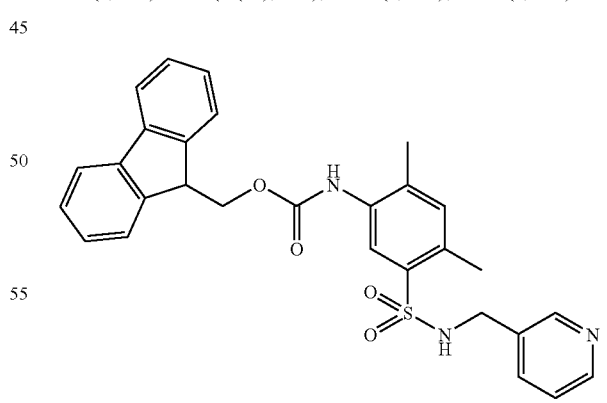

Step 3: 9H-Fluoren-9-ylmethyl(2,4-dimethyl-5-{[(pyridin-3-ylmethyl)amino]sulfonyl}phenyl)carbamate To a solution of 9H-fluoren-9-ylmethyl[5-(chlorosulfonyl)-2,4-dimethylphenyl]carbamate (1.0 g, 2.3 mmol) in CH$_2$Cl$_2$ (23 mL) was added 1-pyridin-3-ylmethanamine (0.46 mL, 4.5 mmol) and pyridine (0.55 mL, 6.8 mmol). The bright yellow solution was then stirred at room temperature overnight and then quenched by the addition of sat. aq. NaHCO$_3$ solution. The reaction was extracted with EtOAc and the organic extracted were dried over Na$_2$SO$_4$ and concentrated in vacuo. Purification by silica gel column chromatography (0-5% MeOH/DCM) afforded the title compound.

$^1$H NMR (600 MHz, CD$_6$SO) δ 9.14 (s(br), 1H), 8.53 (dd, 1H), 8.36 (dd, 1H) 8.35 (s, 1H), 8.19 (s(br), 1H), 7.84 (d, 2H), 7.13 (m, 3H), 7.54 (d, 1H), 7.39 (m, 3H), 7.21 (m, 7.14 (s, 1H), 4.41 (s (br), 1H), 4.27 (s (br), 1H), 3.95 (s, 1H), 2.42 (s, 3H), 2.17 (s, 3H). LRMS (ESI) calc'd for C$_{29}$H$_{27}$N$_3$O$_4$S [M+H]$^+$, 514.2; found 514.1.

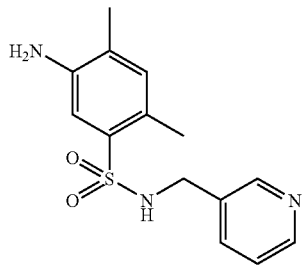 [SMILES: Cc1cc(C)c(S(=O)(=O)NCc2cccnc2)cc1N]

Step 4: 5-Amino-2,4-dimethyl-N-(pyridin-3-ylmethyl)benzenesulfonamide

To a solution of 9H-fluoren-9-ylmethyl(2,4-dimethyl-5-{[(pyridin-3-ylmethyl)amino]sulfonyl}phenyl)carbamate (1.2 g, 2.3 mmol) in DMA (4.5 mL) was added piperidine (0.8 mL, 7.9 mmol). The reaction stirred at room temperature for one hour and was then poured into a separatory funnel containing water and EtOAc. The reaction was extracted with EtOAc and the organic extracts were dried over Na$_2$SO$_4$ and concentrated in vacuo.

Purification by silica gel column chromatography (0-5% MeOH/DCM) afforded the title compound as a colorless solid.

$^1$H NMR (600 MHz, CD$_6$SO) δ 8.38 (dd, 1H), 8.36 (d, 1H), 7.93 (s, 1H) 7.56 (d, 1H) 7.26 (m, 1H), 7.13 (s, 1H), 6.85 (s, 1H) 5.03 (s, 2H), 3.93 (s, 2H), 2.30 (s, 3H), 2.02 (s, 2H). LRMS (ESI) calc'd for C$_{14}$H$_{17}$N$_3$O$_2$S [M+H]$^+$, 292.1; found 292.1.

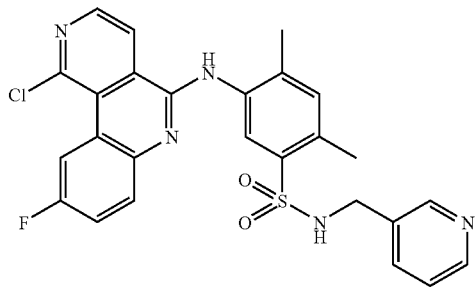 [SMILES: Cc1cc(C)c(S(=O)(=O)NCc2cccnc2)cc1Nc1nc2ccc(F)cc2c2c(Cl)nccc12]

Step 5: 5-[(1-Chloro-9-fluorobenzo[h]isoquinolin-5-yl)amino]-2,4-dimethyl-N-(pyridin-3-ylmethyl)benzenesulfonamide To a solution of 5-amino-2,4-dimethyl-N-(pyridin-3-ylmethyl)benzenesulfonamide (300 mg, 1.0 mmol) and 1,5-dichloro-9-fluorobenzo[c]-2,6-naphthyridine (Example 1, Step 5) (250 mg, 0.94 mmol) in THF (4.7 mL) at 0° C. was added NaHMDS (2.8 mL, 1 M in THF, 2.8 mmol). The deep red solution was stirred at 0° C. for ten minutes and then quenched by the addition of sat. aq. NaHCO$_3$ solution. The reaction was extracted with EtOAc and the organic extracts were dried over Na$_2$SO$_4$ and concentrated in vacuo. Purification by silica gel column chromatography (0-5% MeOH/DCM) afforded the title compound.

$^1$H NMR (600 MHz, CD$_6$SO) δ 9.39 (s, 1H), 9.13 (dd, 1H), 8.76 (d, 1H), 8.54 (d, 1H), 8.37 (m, 2H), 8.24 (s, 1H), 7.91 (s, 1H), 7.47-7.59 (m, 3H), 7.27 (s, 1H), 7.24 (m, 1H), 4.05 (s, 2H), 2.49 (s, 3H), 2.19 (s, 3H). LRMS (ESI) calc'd for C$_{26}$H$_{21}$ClFN$_5$O$_2$S [M+H]$^+$, 522.1; found 522.1.

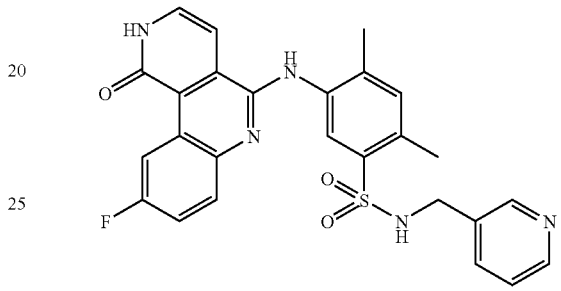

Step 6: 5-[(9-Fluoro-1-oxo-1,2-dihydrobenzo[c]-2,6-naphthyridin-5-yl)amino]-2,4-dimethyl-N-(pyridin-3-ylmethyl)benzenesulfonamide A solution of 5-[(1-chloro-9-fluorobenzo[h]isoquinolin-5-yl)amino]-2,4-dimethyl-N-(pyridin-3-ylmethyl)benzenesulfonamide (240 mg, 0.46 mmol) in THF (2.5 mL) and 6N HCl (2.5 mL) was heated to 50° C. for 12 hours. The reaction was then cooled to RT and quenched with sat. aq. NaHCO$_3$ solution. The mixture was extracted with 3:1 CHCl$_3$:iPrOH and the organic extracts were washed with brine, dried over Na$_2$SO$_4$ and concentrated in vacuo. Purification of the residue with silica gel column chromatography (0 to 10% iPrOH/CHCl$_3$) afforded the title compound as a colorless solid. $^1$H NMR (600 MHz, CD$_6$SO) δ 9.46 (dd, 1H), 8.93 (s, 1H), 8.38 (d, 1H), 8.22 (s(br), 1H), 7.90 (s, 1H), 7.70 (d, 1H), 7.58 (d, 1H), 7.45 (m, 1H), 7.33 (m, 1H), 7.21-7.25 (m, 3H), 4.05 (s, 2H), 2.48 (s, 3H), 2.18 (s, 3H). LRMS (ESI) calc'd for C$_{26}$H$_{22}$FN$_5$O$_3$S [M+H]$^+$, 504.2; found 504.1.

EXAMPLE 74

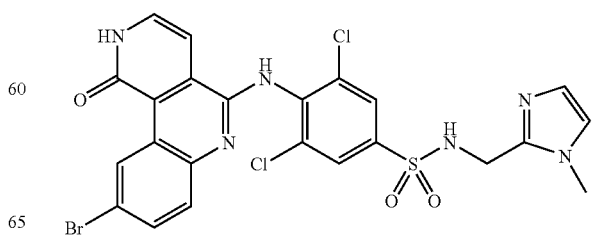

4-[(9-Bromo-1-oxo-1,2-dihydrobenzo[c]-2,6-naphthyridin-5-yl)amino]-3,5-dichloro-N-[(1H-methyl-1H-imidazol-2-yl)methyl]benzenesulfonamide

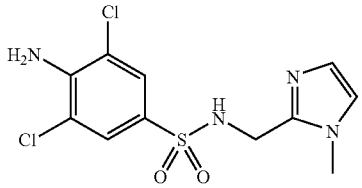 [SMILES: Cn1ccnc1CNS(=O)(=O)c1cc(Cl)c(N)c(Cl)c1]

Step 1: 4-Amino-3,5-dichloro-N-[(1-methyl-1H-imidazol-2-yl)methyl]benzenesulfonamide 4-Amino-3,5-dichlorobenzenesulfonic acid (3.0 g, 12.4 mmol) was dissolved in thionyl chloride (18 mL) and DMF (0.3 mL). The reaction was warmed to 80° C. and stirred for four hours. The reaction was then cooled and the excess thionyl chloride was removed in vacuo azeotroping with toluene three times to afford the sulfonyl chloride. To a solution of the unpurified sulfonyl chloride (1.0 g, 3.84 mmol) in dichloromethane (7.7 mL) was added pyridine (0.9 mL, 11.5 mmol) and 1-(1-methyl-1H-imidazol-2-yl)methanamine (1.3 g, 11.5 mmol). The reaction was stirred at room temperature for 18 hours and then quenched by the addition of sat. aq. NaHCO₃ solution. The mixture was extracted with EtOAc and the organic extracts were dried over Na₂SO₄ and concentrated in vacuo. Purification of the residue by silica gel column chromatography (0-10% MeOH/DCM) afforded the title compound.

¹H NMR (600 MHz, CD₆SO) δ 7.91 (s, 1H), 7.51 (s, 1H), 6.98 (s, 1H), 6.69 (s, 1H), 6.35 (s, 1H), 3.96 (s, 2H), 3.51 (s, 3H). LRMS (ESI) calc'd for $C_{11}H_{12}Cl_2N_4O_2S$ [M+H]⁺, 335.0; found 335.0.

Step 2: 4-[(9-Bromo-1-chlorobenzo[c]-2,6-naphthyridin-5-yl)amino]-3,5-dichloro-N-[(1-methyl-1H-imidazol-2-yl)methyl]benzenesulfonamide To a solution of 9-bromo-1,5-dichlorobenzo[c]-2,6-naphthyridine (100 mg, 0.31 mmol) (Example 1, Step 5) and 4-amino-3,5-dichloro-N-[(1-methyl-1H-imidazol-2-yl)methyl]benzenesulfonamide (123 mg, 0.37 mmol) in DMA (1.2 mL) was added NaHMDS (0.7 mL, 1 M in THF, 0.7 mmol). The reaction was stirred at room temperature for ten minutes and then heated in the microwave to 100° C. for 15 minutes. The reaction was then quenched by the addition of sat. aq. NaHCO₃ solution. The mixture was extracted with EtOAc and the organic extracts were dried over Na₂SO₄ and concentrated in vacuo. Purification of the residue by silica gel column chromatography (0-10% MeOH/DCM) afforded the title compound.

LRMS (ESI) calc'd for $C_{23}H_{16}BrCl_3N_6O_2S$ [M+H]⁺, 624.9; found 624.9.

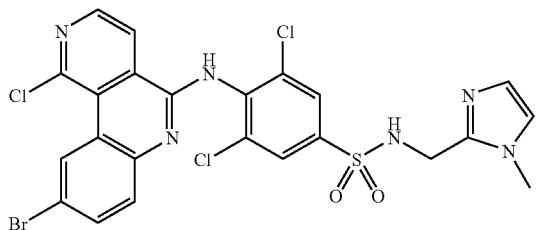 [SMILES: Cn1ccnc1CNS(=O)(=O)c1cc(Cl)c(Nc2nc3ccc(Br)cc3c3c(Cl)nccc23)c(Cl)c1]

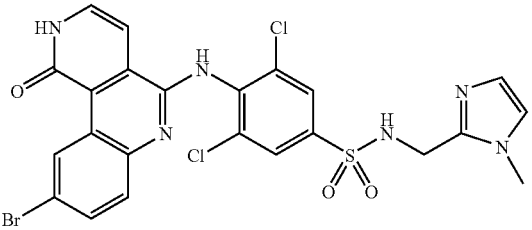 [SMILES: Cn1ccnc1CNS(=O)(=O)c1cc(Cl)c(Nc2nc3ccc(Br)cc3c3c(=O)[nH]ccc23)c(Cl)c1]

Step 3: 4-[(9-Bromo-1-oxo-1,2-dihydrobenzo[c]-2,6-naphthyridin-5-yl)amino]-3,5-dichloro-N-[(1H-methyl-1H-imidazol-2-yl)methyl]benzenesulfonamide 4-[(9-Bromo-1-chlorobenzo[c]-2,6-naphthyridin-5-yl)amino]-3,5-dichloro-N-[(1-methyl-1H-imidazol-2-yl)methyl]benzenesulfonamide (190 mg, 0.3 mmol) was dissolved in THF (3.8 mL) and 6N HCl (3.8 mL) and warmed to 85° C. After 2.5 hours, the reaction was cooled and quenched by the addition of sat. aq. NaHCO₃ solution. The mixture was extracted with EtOAc and the organic extracts were dried over Na₂SO₄ and concentrated in vacuo. Purification of the residue by silica gel column chromatography (0-10% MeOH/DCM) afforded the title compound.

LRMS (ESI) calc'd for $C_{23}H_{17}BrCl_2N_6O_3S$ [M+H]⁺, 607.0; found 609.9.

Additional analogues shown below were prepared using procedures similar to those described in the above examples.

TABLE 2

| Example | Structure | Compound Name | LCMS (M + H)⁺ |
|---|---|---|---|
| 75 | 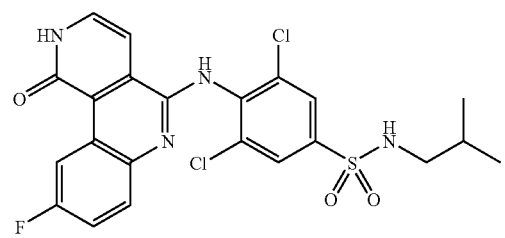 [SMILES: CC(C)CNS(=O)(=O)c1cc(Cl)c(Nc2nc3ccc(F)cc3c3c(=O)[nH]ccc23)c(Cl)c1] | 3,5-dichloro-4-[(9-fluoro-1-oxo-1,2-dihydrobenzo[c]-2,6-naphthyridin-5-yl)amino]-N-isobutylbenzenesulfonamide | Calc'd 509.1, found 509.0 |

TABLE 2-continued

| Example | Structure | Compound Name | LCMS (M + H)+ |
|---|---|---|---|
| 76 | 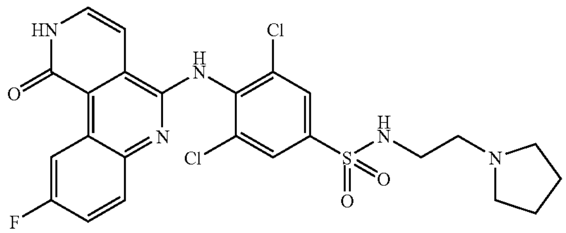 [SMILES: O=c1[nH]ccc2c(Nc3c(Cl)cc(S(=O)(=O)NCCN4CCCC4)cc3Cl)nc3ccc(F)cc3c12] | 3,5-dichloro-4-[(9-fluoro-1-oxo-1,2-dihydrobenzo[c]-2,6-naphthyridin-5-yl)amino]-N-(2-pyrrolidin-1-ylethyl)benzenesulfonamide | Calc'd 550.1, found 550.0 |
| 77 | 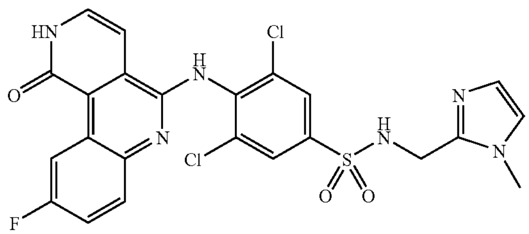 [SMILES: Cn1ccnc1CNS(=O)(=O)c1cc(Cl)c(Nc2nc3ccc(F)cc3c3c(=O)[nH]ccc23)c(Cl)c1] | 3,5-dichloro-4-[(9-fluoro-1-oxo-1,2-dihydrobenzo[c]-2,6-naphthyridin-5-yl)amino]-N-[(1-methyl-1-imidazol-2-yl)methyl]benzenesulfonamide | Calc'd 547.1, found 547.1 |
| 78 | 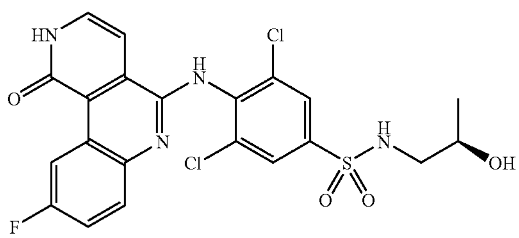 [SMILES: C[C@@H](O)CNS(=O)(=O)c1cc(Cl)c(Nc2nc3ccc(F)cc3c3c(=O)[nH]ccc23)c(Cl)c1] | 3,5-dichloro-4-[(9-fluoro-1-oxo-1,2-dihydrobenzo[c]-2,6-naphthyridin-5-yl)amino]-N-[(2R)-2-hydroxypropyl]benzenesulfonamide | Calc'd 511.0, found 511.0 |
| 79 | 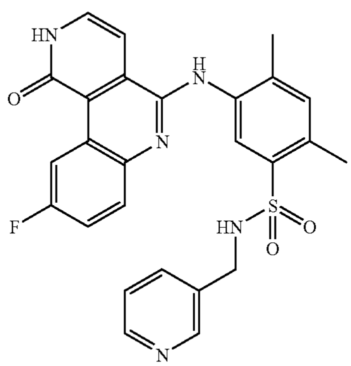 [SMILES: Cc1cc(C)c(S(=O)(=O)NCc2cccnc2)cc1Nc1nc2ccc(F)cc2c2c(=O)[nH]ccc12] | 5[(9-fluoro-1-oxo-1,2-dihydrobenzo[c]-2,6-naphthyridin-5-yl)amino]-2,4-dimethyl-N-(pyridin-3-ylmethyl)benzenesulfonamide | Calc'd 504.2, found 504.1 |
| 80 | 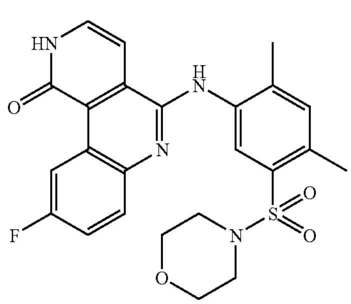 [SMILES: Cc1cc(C)c(S(=O)(=O)N2CCOCC2)cc1Nc1nc2ccc(F)cc2c2c(=O)[nH]ccc12] | 5-{[2,4-dimethyl-5-(morpholin-4-ylsulfonyl)phenyl]amino}-9-fluorobenzo[c]-2,6-naphthyridin-1(2H)-one | Calc'd 483.2, found 483.1 |

| Example | Structure | Compound Name | LCMS (M + H)+ |
|---|---|---|---|
| 81 | 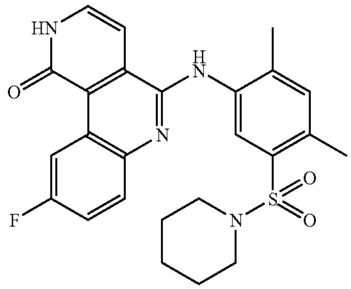 [SMILES: Cc1cc(C)c(S(=O)(=O)N2CCCCC2)cc1Nc1nc2ccc(F)cc2c2c(=O)[nH]ccc12] | 5-{[2,4-dimethyl-5-(piperidin-1-ylsulfonyl)phenyl]amino}-9-fluorobenzo[c]-2,6-naphthyridin-1(2H)-one | Calc'd 481.2, found 481.1 |
| 82 | 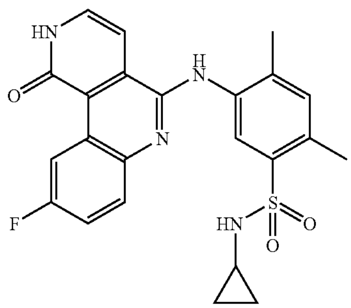 [SMILES: Cc1cc(C)c(S(=O)(=O)NC2CC2)cc1Nc1nc2ccc(F)cc2c2c(=O)[nH]ccc12] | N-cyclopropyl-5-[(9-fluoro-1-oxo-1,2-dihydrobenzo[c]-2,6-naphthyridin-5-yl)amino]-2,4-dimethylbenzenesulfonamide | Calc'd 453.1, found 453.1 |
| 83 | 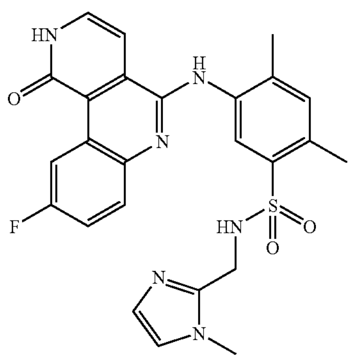 [SMILES: Cc1cc(C)c(S(=O)(=O)NCc2nccn2C)cc1Nc1nc2ccc(F)cc2c2c(=O)[nH]ccc12] | 5-[(9-fluoro-1-oxo-1,2-dihydrobenzo[c]-2,6-naphthyridin-5-yl)amino]-2,4-dimethyl-N-[(1-methyl-1H-imidazol-2-yl)methyl]benzenesulfonamide | Calc'd 507.2, found 507.1 |

EXAMPLES 84 and 85

3-[(9-Fluoro-1-oxo-1,2-dihydrobenzo[c]-2,6-naphthyridin-5-yl)amino]-4-methylbenzoic acid and Methyl 3-[(9-fluoro-1-oxo-1,2-dihydrobenzo[c]-2,6-naphthyridin-5-yl)amino]-4-methylbenzoate

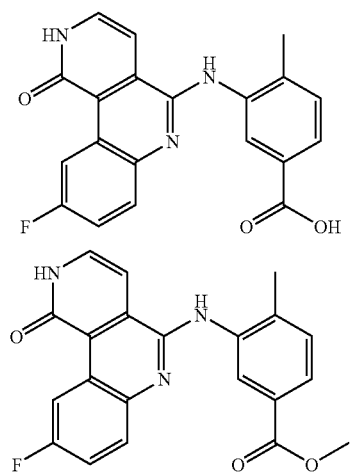

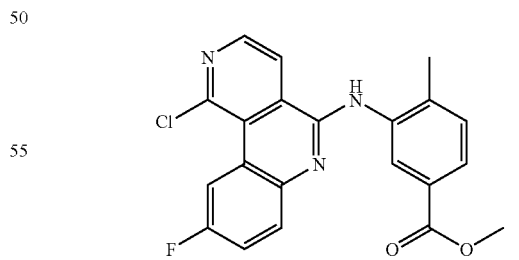

Step 1: Methyl 3-[(1-chloro-9-fluorobenzo[c]-2,6-naphthyridin-5-yl)amino]-4-methylbenzoate To a solution of 1,5-dichloro-9-fluorobenzo[c]-2,6-naphthytidine (Example 1, Step 5) (500 mg, 1.87 mmol) and methyl 3-amino-4-methylbenzoate (340 mg, 2.06 mmol) in THF (9.3 mL) was added sodium tert-butoxide (396 mg, 4.12 mmol). The reaction stirred at room temperature for ten minutes and was then quenched by the addition of sat. aq. NaHCO$_3$ solution. The mixture was extracted with EtOAc and the extracts were washed with brine, dried over MgSO$_4$ and concentrated in vacuo. Purification by silica gel column chromatography (0-30% EtOAc/heptane) afforded the title compound.

LRMS (ESI) calc'd for $C_{21}H_{15}ClFN_3O_2$ [M+H]$^+$, 396.1; found 396.1.

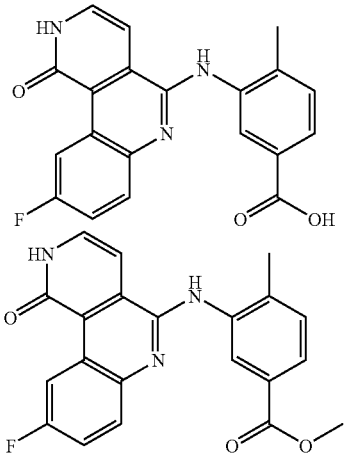

Step 2: 3-[(9-Fluoro-1-oxo-1,2-dihydrobenzo[c]-2,6-naphthyridin-5-yl)amino]-4-methylbenzoic acid and Methyl 3-[(9-fluoro-1-oxo-1,2-dihydrobenzo[c]-2,6-naphthyridin-5-yl)amino]-4-methylbenzoate Methyl 3-[(1-chloro-9-fluorobenzo[c]-2,6-naphthyridin-5-yl)amino]-4-methylbenzoate (115 mg, 0.29 mmol) was taken up in THF (3.6 ml) and 6N HCl (3.6 ml) and warmed to 85° C. After three hours, the reaction was cooled and quenched by the addition of sat. aq. NaHCO$_3$ solution. The mixture was extracted with EtOAc and the extracts were washed with brine, dried over MgSO$_4$ and concentrated in vacuo. Purification by reverse phase HPLC afforded both title compounds.

For the carboxylic acid: LRMS (ESI) calc'd for $(C_{20}H_{14}FN_3O_3)$ [M+H]$^+$, 364.1; found 364.1. For the ester: $^1$H NMR (600 MHz, CD$_6$SO) δ 9.46 (d, 1H) 8.99 (s, 1H) 7.96 (d, 1H) 7.69-7.73 (m, 2H), 7.41-7.44 (m, 2H), 7.36 (m, 1H), 7.22 (d, 1H), 3.81 (s, 3H), 2.20 (s, 3H). LRMS (ESI) calc'd for $C_{21}H_{16}FN_3O_3$ [M+H]$^+$, 378.1; found 378.1.

EXAMPLE 86

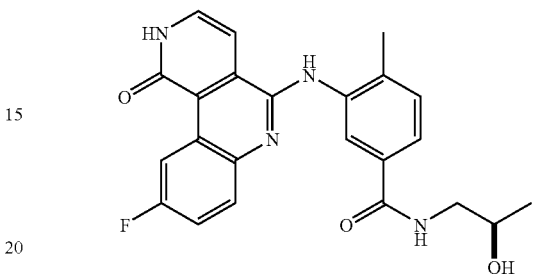

3-[(9-Fluoro-1-oxo-1,2-dihydrobenzo[c]-2,6-naphthyridin-5-yl)amino]-N-[(2R)-2-hydroxypropyl]-4-methylbenzamide Step 1: To a solution of 3-[(9-fluoro-1-oxo-1,2-dihydrobenzo[c]-2,6-naphthyridin-5-yl)amino]-4-methylbenzoic acid (Example 1, Step 5) (25 mg, 0.07 mmol) and (2R)-1-aminopropan-2-ol (8 mg, 0.1 mmol) in DMF (0.7 mL) was added BOP (91 mg, 0.21 mmol) and Hunig's base (0.4 mL, 0.21 mmol). The reaction was warmed to 60° C. and the reaction stirred for 18 hours and was then quenched by the addition of sat. aq. NaHCO$_3$ solution. The mixture was extracted with EtOAc and the extracts were washed with brine, dried over MgSO$_4$ and concentrated in vacuo. Purification by silica gel column chromatography (0-10% MeOH/CH$_2$Cl$_2$) afforded the title compound.

$^1$H NMR (600 MHz, CD$_6$SO) δ 12.21 (s, 1H), 9.45 (dd, 1H), 8.97 (s, 1H) 8.30 (t, 1H), 7.83 (s, 1H), 7.69 (t, 1H), 7.65 (d, 1H), 7.41 (m, 1H), 7.33-7.35 (m, 2H), 7.22 (d, 1H), 4.69 (d, 1H), 3.17 (t, 2H), 2.16 (s, 3H), 1.01 (d, 3H). LRMS (ESI) calc'd for $(C_{23}H_{21}FN_4O_3)$ [M+H]$^+$, 412.2; found 421.2.

Additional analogues shown below were prepared using procedures similar to those described in the above examples and general methods.

TABLE 3

| Example | Structure | Compound Name | LCMS (M + H)$^+$ |
|---|---|---|---|
| 87 | 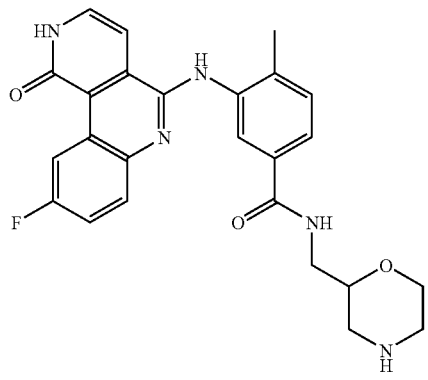 [SMILES: Cc1ccc(C(=O)NCC2CNCCO2)cc1Nc1nc2ccc(F)cc2c2c(=O)[nH]ccc12] | 3-[(9-fluoro-1-oxo-1,2-dihydrobenzo[c]-2,6-naphthyridin-5-yl)amino]-4-methyl-N-(morpholin-2-ylmethyl)benzamide | Calc'd 462.2, found 462.2 |

EXAMPLE 88

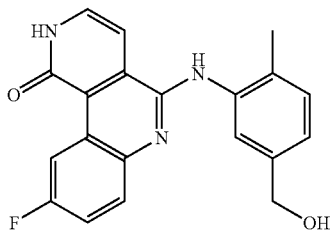 [SMILES: Cc1ccc(CO)cc1Nc1nc2ccc(F)cc2c2c(=O)[nH]ccc12]

9-Fluoro-5-{[5-(hydroxymethyl)-2-methylphenyl]amino}benzo[c]-2,6-naphthyridin-1(2H)-one

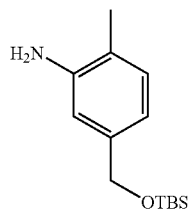 [SMILES: Cc1ccc(CO[Si](C)(C)C(C)(C)C)cc1N]

Step 1: 5-({[tert-Butyl(dimethyl)silyl]oxy}methyl)-2-methylaniline

To a solution of (3-amino-4-methylphenyl)methanol (1.0 g, 7.3 mmol) in DMF (7.3 mL) was added tert-butyldimethylchlorosilane (1.2 g, 8.1 mmol) and imidazole (0.65 g, 9.5 mmol). The reaction stirred at room temperature for 18 hours and then was poured into a separatory funnel with water and EtOAc. The mixture was extracted with EtOAc and the extracts were washed with brine, dried over MgSO$_4$ and concentrated in vacuo. Purification by silica gel column chromatography (0-40% EtOAc/heptane) afforded the title compound.

$^1$H NMR (600 MHz, CD$_6$SO) δ 6.80 (d, 1H), 6.51 (s, 1H), 6.35 (dd, 1H), 4.73 (s, 2H), 4.48 (s, 2H), 1.97 (s, 3H), 0.85 (s, 9H), 0.01 (s, 6H). LRMS (ESI) calc'd for (C$_{14}$H$_{25}$NOSi) [M+H]$^+$, 252.2; found 252.2.

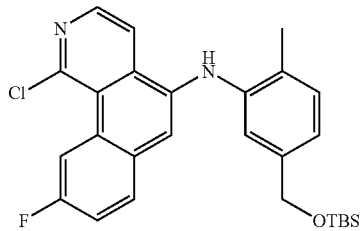 [SMILES: Cc1ccc(CO[Si](C)(C)C(C)(C)C)cc1Nc1cc2ccc(F)cc2c2c(Cl)nccc12]

Step 2: N-[5-({[tert-Butyl(dimethyl)silyl]oxy}methyl)-2-methylphenyl]-1-chloro-9-fluorobenzo[h]isoquinolin-5-amine To a solution of 1,5-dichloro-9-fluorobenzo[c]-2,6-naphthyridine (Example 1, Step 5) (150 mg, 0.56 mmol) and 5-({[tert-butyl(dimethyl)silyl]oxy}methyl)-2-methylaniline (155 mg, 0.62 mmol) in THF (9.3 mL) was added sodium tert-butoxide (65 mg, 0.67 mmol). The reaction stirred at 60° C. for 30 minutes was then quenched by the addition of sat. aq. NaHCO$_3$ solution. The mixture was extracted with EtOAc and the extracts were washed with brine, dried over MgSO$_4$ and concentrated in vacuo. Purification by silica gel column chromatography (0-50% EtOAc/heptane) afforded the title compound.

$^1$H NMR (600 MHz, CD$_6$SO) δ 9.26 (s, 1H), 9.12 (d, 1H), 8.73 (d, 1H), 8.54 (d, 1H), 7.50 (d, 1H), 7.29 (s, 1H), 7.24 (d, 1H), 7.09 (d, 1H), 4.68 (s, 2H), 2.12 (s, 3H), 0.85 (s, 9H), 0.05 (s, 6H). LRMS (ESI) calc'd for (C$_{27}$H$_{30}$ClFN$_2$OSi) [M+H]$^+$, 482.2; found 482.2

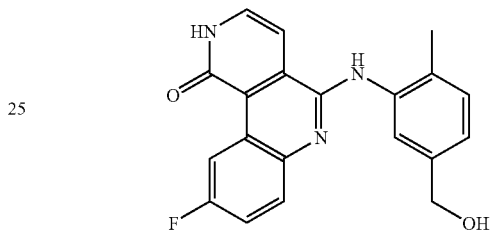

Step 3: 9-Fluoro-5-{[5-(hydroxymethyl)-2-methylphenyl]amino}benzo[c]-2,6-naphthyridin-1(2H)-one N-[5-({[tert-butyl(dimethyl)silyl]oxy}methyl)-2-methylphenyl]-1-chloro-9-fluorobenzo[h]isoquinolin-5-amine (25 mg, 0.05 mmol) was taken up in THF (0.6 mL) and 6N HCl (0.6 mL) and warmed to 85° C. After three hours, the reaction was cooled and quenched by the addition of sat. aq. NaHCO$_3$ solution. The mixture was extracted with EtOAc and the extracts were washed with brine, dried over MgSO$_4$ and concentrated in vacuo. Purification by silica gel column chromatographpy (0-50% EtOAc/heptane) afforded the title compound.

$^1$H NMR (600 MHz, CD$_6$SO) δ 12.18 (s, 1H), 9.44 (dd, 1H), 8.83 (s, 1H), 7.67 (d, 1H), 7.41 (m, 1H), 7.33 (m, 1H), 7.27 (s, 1H), 7.21 (m, 2H), 7.07 (m, 1H), 5.13 (t, 1H), 4.45 (d, 2H), 2.09 (s, 3H). LRMS (ESI) calc'd for (C$_{27}$H$_{31}$FN$_2$O$_2$Si) [M+H]$^+$, 350.1; found 350.1.

Additional analogues shown below were prepared using procedures similar to those described in the above examples and general methods.

TABLE 4

| Example | Structure | Compound Name | LCMS (M + H)$^+$ |
|---|---|---|---|
| 89 | 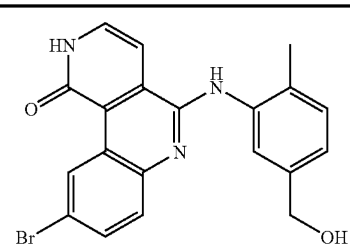 | 9-bromo-5-{[5-(hydroxymethyl)-2-methylphenyl]amino}benzo[c]-2,6-naphthyridin-1(2H)-one | Calc'd 410.1, found 410.0 |

TABLE 4-continued

| Example | Structure | Compound Name | LCMS (M + H)+ |
|---|---|---|---|
| 90 | 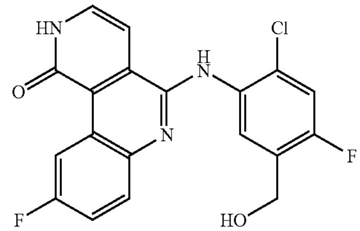 [SMILES: O=c1[nH]ccc2c(Nc3cc(CO)c(F)cc3Cl)nc3ccc(F)cc3c12] | 5-{[2-chloro-4-fluoro-5-(hydroxymethyl)phenyl]amino}-9-fluorobenzo[c]-2,6-naphthyridin-1(2H)-one | Calc'd 388.1, found 388.0 |
| 91 | 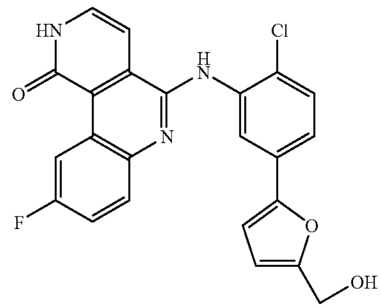 [SMILES: O=c1[nH]ccc2c(Nc3cc(-c4ccc(CO)o4)ccc3Cl)nc3ccc(F)cc3c12] | 5-({2-chloro-5-[5-(hydroxymethyl)-2-furyl]phenyl}amino)-9-fluorobenzo[c]-2,6-naphthyridin-1(2H)-one | Calc'd 436.1, found 436.1 |

EXAMPLE 92

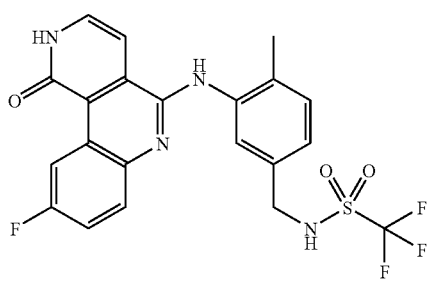 [SMILES: Cc1ccc(CNS(=O)(=O)C(F)(F)F)cc1Nc1nc2ccc(F)cc2c2c(=O)[nH]ccc12]

1,1,1-Trifluoro-N-{3-[(9-fluoro-1-oxo-1,2-dihydrobenzo[c]-2,6-naphthyridin-5-yl)amino]-4-methylbenzyl}methanesulfonamide Step 1: 3-[(1-Chloro-9-fluorobenzo[h]isoquinolin-5-yl)amino]-4-methylbenzonitrile To a solution of 1,5-dichloro-9-fluorobenzo[c]-2,6-naphthyridine (Example 1, Step 5) (250 mg, 0.94 mmol) and 3-amino-4-methylbenzonitrile (136mg, 1.03 mmol) in THF (9.3 mL) at 0° C. was added NaHMDS (1.8 mL, 1 M in THF, 1.80 mmol). The reaction stirred at 0° C. for 15 minutes and then quenched by the addition of sat. aq. NaHCO₃ solution. The precipitated solid was collected by filtration, washed with EtOAc and dried under vacuum.

$^1$H NMR (600 MHz, CD$_6$SO) δ 9.40 (s, 1H), 9.15 (dd, 1H), 8.78 (d, 1H), 8.52 (d, 1H), 7.86 (s, 1H), 7.62 (dd, 1H), 7.50-7.58 (m, 3H), 2.25 (s, 3H). LRMS (ESD calc'd for (C$_{20}$H$_{12}$ClFN$_4$) [M+H]+, 363.1; found 363.1.

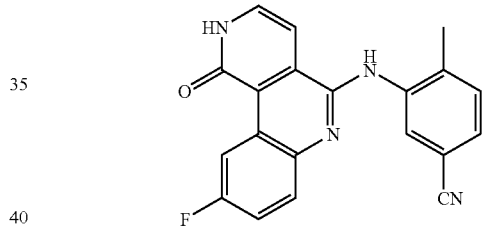

Step 2: 3-[(9-Fluoro-1-oxo-1,2-dihydrobenzo[c]-2,6-naphthyridin-5-yl)amino]-4-methylbenzonitrile 3-[(1-Chloro-9-fluorobenzo[h]isoquinolin-5-yl)amino]-4-methylbenzonitrile (135 mg, 0.37 mmol) was taken up in THF (4.7 mL) and 6N HCl (4.7 mL) and warmed to 85° C. After 90 minutes, the reaction was cooled and quenched by the addition of sat. aq. NaHCO₃ solution. The precipitated solid was then collected by filtration and washed with EtOAc to afford the title compound.

$^1$H NMR (600 MHz, CD$_6$SO) δ 12.26 (d, 1H), 9.46 (d, 1H), 8.97 (s, 1H), 7.83 (s, 1H), 7.71 (m, 1H), 7.58 (d, 1H), 7.49 (m, 2H), 7.39 (m, 1H), 7.19 (d, 1H), 2.22 (s, 3H). LRMS (ESI) calc'd for C$_{20}$H$_{13}$FN$_4$O [M+H]+, 345.1; found 345.1.

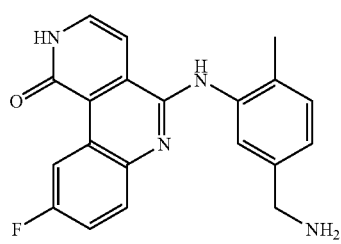 [SMILES: Cc1ccc(CN)cc1Nc1nc2ccc(F)cc2c2c(=O)[nH]ccc12]

Step 3: 5-{[5-(Aminomethyl)-2-methylphenyl]amino}-9-fluorobenzo[c]-2,6-naphthyridin-1(2H)-one To a solution of 3-[(9-fluoro-1-oxo-1,2-dihydrobenzo[c]-2,6-naphthyridin-5-yl)amino]-4-methylbenzonitrile (40 mg, 0.12 mmol) in THF (1.1 mL) at 0° C. was added lithium aluminum hydride (0.4 mL, 1 M, 0.40 mmol). The reaction was stirred for 18 hours and then quenched by the addition of 0.02 mL water, then 0.02 mL 10% aq. NaOH and finally 0.05 mL water. The mixture was then poured into a separatory funnel with water and EtOAc. The mixture was extracted with EtOAc and the extracts were washed with brine, dried over $MgSO_4$ and concentrated in vacuo. Purification by silica gel column chromatographpy (0-10% $MeOH/CH_2Cl_2$ (with 1% $NH_4OH$)) afforded the title compound.
$^1$NMR (600 MHz, $CD_6SO$) δ 9.45 (d, 1H), 8.83 (s, 1H), 7.67 (dd, 1H), 7.42 (m, 1H), 7.33 (m, 1H), 7.28 (s, 1H), 7.22 (d, 1 H), 7.18 (d, 1H), 7.08 (dd, 1H), 3.69 (s, 2H), 3.30 (s (br), 2H), 2.09 (s, 3H). LRMS (ESI) calc'd for ($C_{20}H_{17}FN_4O$) [M+H]$^+$, 349.1; found 349.1.

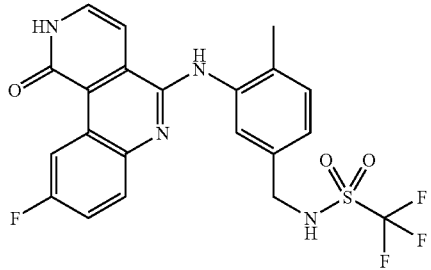 [SMILES: Cc1ccc(CNS(=O)(=O)C(F)(F)F)cc1Nc1nc2ccc(F)cc2c2c(=O)[nH]ccc12]

Step 4: 1,1,1-Trifluoro-N-{3-[(9-fluoro-1-oxo-1,2-dihydrobenzo[c]-2,6-naphthyridin-5-yl)amino]-4-methylbenzyl}methanesulfonamide To a solution of 5-{[5-(aminomethyl)-2-methylphenyl]amino}-9-fluorobenzo[c]-2,6-naphthyridin-1(2H)-one (35 mg, 0.10 mmol) in THF (1.0 mL) at 0° C. was added triethylamine (0.03 mL, 0.20 mmol) and trifluoromethanesufonyl chloride (0.01 mL, 0.11 mmol). The reaction was stirred for one hour and then quenched by the addition of citric acid. The mixture was extracted with EtOAc/water and the extracts were washed with brine, dried over $MgSO_4$ and concentrated in vacuo. Purification by silica gel column chromatographpy (0-10% $MeOH/CH_2Cl_2$) afforded the title compound. $^1$H NMR (600 MHz, $CD_6SO$) δ 12.21 (d, 1H), 9.92 (s, 1H), 9.45 (dd, 1H), 8.85 (s, 1H), 7.68 (m, 1H), 7.45 (m, 1H), 7.34-7.38 (m, 2H), 7.26 (d, 1H), 7.22 (d, 1H), 7.09 (d, 1H), 4.32 (s, 2H), 2.12 (s, 3H). LRMS (ESI) calc'd for $C_{21}H_{16}F_4N_4O_3$ [M+H]$^+$, 481.1; found 481.0.

EXAMPLE 93

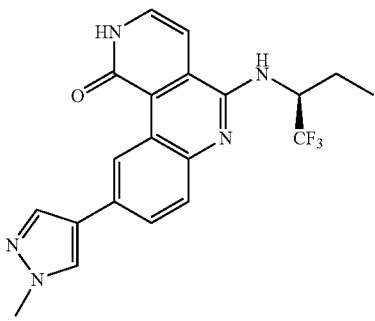 [SMILES: CC[C@H](Nc1nc2ccc(-c3cnn(C)c3)cc2c2c(=O)[nH]ccc12)C(F)(F)F]

9-(1-Methyl-1H-pyrazol-4-yl)-5-{[(1S)-1-(trifluoromethyl)propyl]amino}benzo[c]-2,6-naphthyridin-1(2H)-one Method E: General Procedure for Suzuki Coupling:
To a solution of 9-bromo-5-{[(1S)-1-(trifluoromethyl)propyl]amino}benzo[c]-2,6-naphthyridin-1(2H)-one (Example 22) (50 mg, 0.13 mmol) in DMF (2 mL) were added lithium chloride (32 mg, 0.75 mmol), 1-methyl-4-(4,4,5,5-tetramethyl-1,3,2-dioxaborolan)-1H-pyrazole-1-methylpyrazole-4-boronic acid pinacol ester (52 mg, 0.25 mmol), and tetrakis(triphenylphosphine)palladium (43 mg, 0.04 mmol). The solution was degassed by bubbling nitrogen through the vessel which was subsequently sealed and heated in the microwave for 1 hr at 130° C. The reaction mixture was filtered and purified by reverse phase HPLC to afford the title compound.
$^1$H NMR (600 MHz, $CD_6SO$) δ 12.1 (d, 1H), 9.90 (s, 1H), 8.10 (s, 1H), 7.80 (l, 1H), 7.75, (dd, 1H), 7.60 (m, 2H), 7.35 (d, 1H), 7.20 (d, 1H), 5.35 (m, 1H), 3.89 (s, 3H), 1.90 (q, 2H), 0.9 (t, 3H). LRMS (ESI) calc'd for ($C_{20}H_{19}F_3N_5O$) [M+H]$^+$, 402.2; found 402.1.

EXAMPLES 94 and 95

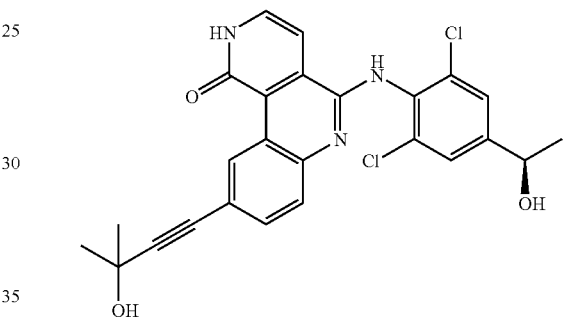

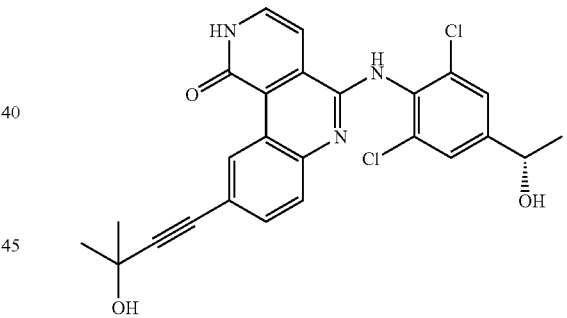

5-({2,6-Dichloro-4-[(1R)-1-hydroxyethyl]phenyl}amino)-9-(3-hydroxy-3-methylbut-1-yn-1-yl)benzo[c]-2,6-naphthyridin-1(2H)-one and 5-({2,6-Dichloro-4-[(1S)-1-hydroxyethyl]phenyl}amino)-9-(3-hydroxy-3-methylbut-1-yn-1-yl)benzo[c]-2,6-naphthyridin-1(2H)-one

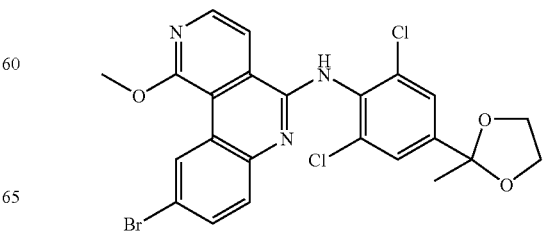

Step 1: 9-Bromo-N-[2,6-dichloro-4-(2-methyl-1,3-dioxolan-2-yl)phenyl]-1-methoxybenzo[c]-2,6-naphthyridin-5-amine To a solution of 9-bromo-1,5-dichlorobenzo[c]-2,6-naphthyridine (Example 3, Step 3) (3.0 g, 9.15 mmol) in THF (40 mL) was added 2,6-dichloro-4-(2-methyl-1,3-dioxo-2-yl)aniline (example 144 and 145, Step 1) (2.27 g, 9.15 mmol) followed by sodium tert-butoxide (2.64 g, 27.4 mmol). The reaction mixture was heated to 85° C. for 45 min. The mixture was cooled and extracted with EtOAc and water. The organic layers were collected, dried over MgSO$_4$, filtered, and concentrated under reduced pressure. Purification by column chromatography on silica gel (100% hexane to 100% EtOAc) afforded the desired product. The residue was dissolved in methanol (40 mL) followed by addition of 25% sodium methoxide in methanol (9 mL) and the mixture was heated to 100° C. for 45 min. After cooling to room temperature, the mixture was concentrated. The residue was diluted with EtOAc and washed with 10% NH$_4$Cl. The organic layers were combined, dried over MgSO$_4$, filtered, and concentrated to afford the title product. LRMS (ESI) calc'd for (C$_{23}$H$_{19}$BrCl$_2$N$_3$O$_3$) [M+H]$^+$ 534.0; found 533.9.

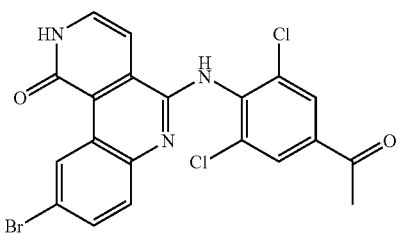 [SMILES: CC(=O)c1cc(Cl)c(Nc2nc3ccc(Br)cc3c3c(=O)[nH]ccc23)c(Cl)c1]

Step 2: 5-[(4-Acetyl-2,6-dichlorophenyl)amino]-9-bromobenzo[c]-2,6-naphthyridin-1(2H)-one To a solution of 9-bromo-N-[2,6-dichloro-4-(2-methyl-1,3-dioxolan-2-yl)phenyl]-1-methoxybenzo[c]-2,6-naphthyridin-5-amine (1.40 g, 2.62 mmol) in THF (24 mL) was added 6 N HCl (8mL) and the reaction mixture was heated to 85° C. for 45 min. The solution was cooled to room temperature and neutralized with sat. NaHCO$_3$. The mixture was extracted with a mixture of 1:3 iPrOH/CHCl$_3$. The organic layers were combined, dried over MgSO$_4$, filtered, and concentrated to afford the title compound.
LRMS (ESD calc'd for C$_{20}$H$_{13}$BrCl$_2$N$_3$O$_2$ [M+H]$^+$, 475.9; found 475.9.

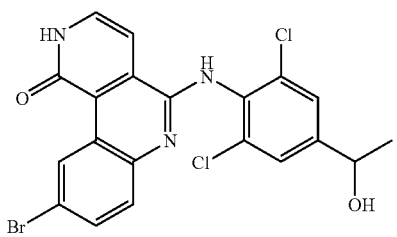 [SMILES: CC(O)c1cc(Cl)c(Nc2nc3ccc(Br)cc3c3c(=O)[nH]ccc23)c(Cl)c1]

Step 3: 9-Bromo-5-{[2,6-dichloro-4-(1-hydroxyethyl)phenyl]amino}benzo[c]-2,6-naphthyridin-1(2H)-one To a solution of 5-[(4-acetyl-2,6-dichlorophenyl)amino]-9-bromobenzo[c]-2,6-naphthyridin-1(2H)-one (700 mg, 1.47 mmol) in methanol (10 mL) was added sodium borohydride (444 mg, 11.7 mmol) at 0° C. and the reaction mixture was stirred for 30 min. The solution was extracted with EtOAc and water, dried over MgSO$_4$, filtered, and concentrated to afford the crude material. Purification by column chromatography on silica gel (100% CH$_2$Cl$_2$ to 70% CH$_2$Cl$_2$/30% MeOH) afforded the title compound.
LRMS (ESD calc'd for C$_{20}$H$_{14}$BrCl$_2$N$_3$O$_2$ [M+H]$^+$, 477.9; found 477.9.

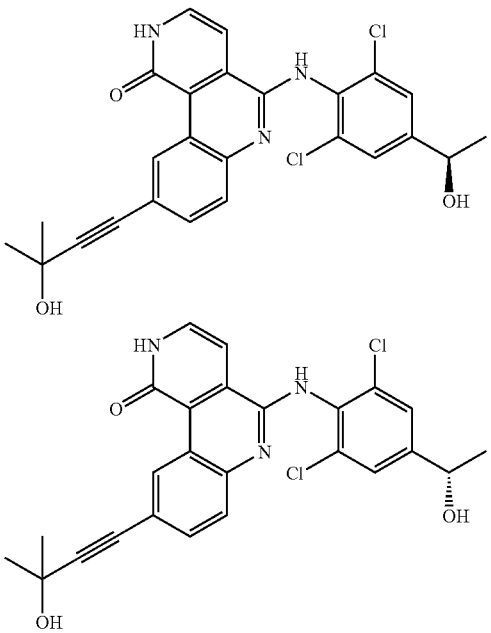

Step 4: 5-({2,6-Dichloro-4-[(1R)-1-hydroxyethyl]phenyl}amino)-9-(3-hydroxy-3-methylbut-1-yn-1-yl)benzo[c]-2,6-naphthyridin-1(2H)-one and 5-({2,6-Dichloro-4-[(1S)-1-hydroxyethyl]phenyl}amino)-9-(3-hydroxy-3-methylbut-1-yn-1-yl)benzo[c]-2,6-naphthyridin-1(2H)-one To a solution of 9-bromo-5-{[2,6-dichloro-4-(1-hydroxyethyl)phenyl]amino}benzo[c]-2,6-naphthyridin-1(2H)-one (292 mg, 0.61 mmol) in DMF (3 mL) were added triethylamine (0.255 mL, 1.83 mmol), copper iodide (23 mg, 0.12 mmol), tetrakis(triphenylphosphine)palladium (0) (70 mg, 0.06 mmol), and 2-methyl-3-butyn-2-ol (0.179 mL, 1.83 mmol). The solution was degassed by bubbling nitrogen gas and heated to 65° C. for 14 hr. The solution was diluted with EtOAc and washed with water, dried with Na$_2$SO$_4$, filtered, and concentrated under reduced pressure. Purification with column chromatography on silica gel (100% CH$_2$Cl$_2$ to 70% CH$_2$Cl$_2$/30% MeOH) provided 5-{[2,6-dichloro-4-(1-hydroxyethyl)phenyl]amino}-9-(3-hydroxy-3-methylbut-1-yn-1-yl)benzo[c]-2,6-naphthyridin-1(2H)-one as a mixture of enantiomers. The enantiomers were separated on Chiral Technology AD 2×25 cm column at 12 mL/min using 1:1 iPrOH/Heptane in a 25 min run. First enantiomer has a retention time of 7.57 min and the second enantiomer has a retention time of 15.74 min. For both enantiomers: $^1$H NMR (500 MHz, CD$_3$OD) δ 9.80 (d, 1H), 7.60 (d, 1H), 7.50-7.40 (m, 3H), 7.34 (d, 1H), 3.90 (m, 1H), 1.48 (s, 3H), 1.47 (s, 3H), 1.12 (d, 3 H). LRMS (ESI) calc'd for C$_{25}$H$_{22}$Cl$_2$N$_3$O$_3$ [M+H]$^+$, 482.1; found 482.1.

EXAMPLES 96 and 97

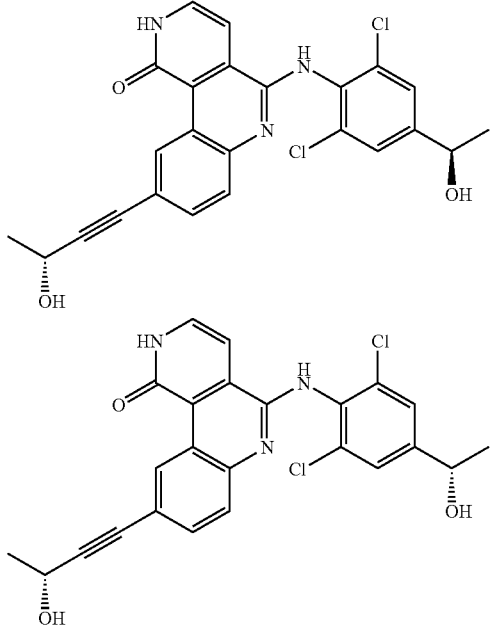

5-({2,6-Dichloro-4-[(1R)-1-hydroxyethyl]
phenyl}amino)-9-[(3R)-3-hydroxybut-1-yn-1-yl]
benzo[c]-2,6-naphthyridin-1(2H)-one and 5-({2,6-
Dichloro-4-[(1S)-1-hydroxyethyl]phenyl}amino)-9-
[(3R)-3-hydroxybut-1-yn-1-yl]benzo[c]-2,6-
naphthyridin-1(2H)-one Step 1: The title compounds were synthesized following the procedure from Examples 94 and 95, Steps 4 using 9-bromo-5-([2,6-dichloro-4-(1-hydroxyethyl)phenyl]amino)benzo[c]-2,6-naphthyridin-1(2H)-one and (2R)-but-3-yn-2-ol as starting materials. The diastereomers were separated on a Chiralpak AD column 10 mL/min using 1:1 IPA/heptane at 1 mL/injection over 25 minutes.

For both diastereomers: $^1$H NMR (500 MHz, CD$_3$OD) δ 9.80 (d, 1H), 7.60 (d, 1H), 7.50-7.40 (m, 4H), 7.30 (d, 1H), 4.84 (m, 1H) 4.65 (m, 1H), 1.50 (t, 6H). LRMS (ESI) calc'd for C$_{24}$H$_{20}$Cl$_2$N$_3$O$_3$ [M+H]$^+$, 468.1; found 468.1.

EXAMPLES 98 and 99

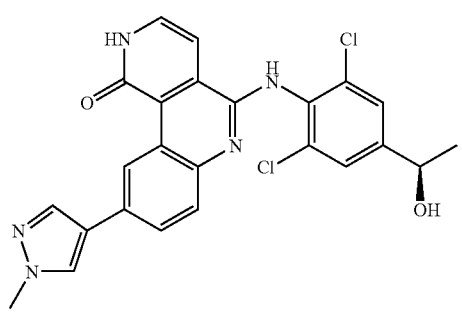

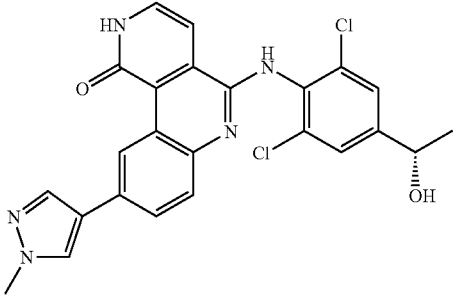

5-({2,6-Dichloro-4-[(1R)-1-hydroxyethyl]
phenyl}amino)-9-(1-methyl-1H-pyrazol-4-yl)benzo
[c]-2,6-naphthyridin-1(2H)-one and 5-({2,6-
Dichloro-4-[(1S)-1-hydroxyethyl]phenyl}amino)-9-
(1-methyl-1H-pyrazol-4-yl)benzo[c]-2,6-
naphthyridin-1(2H)-one Step 1: To a solution of 9-bromo-5-{[2,6-dichloro-4-(1-hydroxyethyl)phenyl]amino}benzo[c]-2,6-naphthyridin-1(2H)-one (Examples 94 and 95, Step 3) (300 mg, 0.63 mmol) in DMF (3 mL) were added sodium carbonate (0.3 mL, 2 M) and 1-methyl-4-(4,4,5,5-tetramethyl-1,3,2-dioxaborolan-2-yl)-1H-pyrazole (208 mg, 1.00 mmol), followed by tetrakis(triphenylphosphine)palladium (0) (145 mg, 0.13 mmol). The solution was degassed by bubbling nitrogen gas for 5 min. The reaction vessel was sealed and heated to 80° C. overnight. The reaction mixture was extracted with 3:1 (CHCl$_3$/iPrOH) and water. The organic layers were combined and dried with MgSO$_4$, filtered, and concentrated under reduced pressure. Purification with column chromatography on silica gel (100% CH$_2$Cl$_2$ to 70% CH$_2$Cl$_2$/30% MeOH) afforded 5-{[2,6-dichloro-4-(1-hydroxyethyl)phenyl]amino}-9-(1-methyl-1H-pyrazol-4-yl)benzo[c]-2,6-naphthyridin-1(2H)-one as racemates. The enantiomers were separated using a Chiralpak AD 10 mm×250 mm column with 40% iPrOH/60% Heptane with a flow rate of 10 ml/min in a 25 min run. The first enantiomer has a retention time of 8.47 min and the second enantiomer has a retention time of 11.68 min.

For both enantiomers: LRMS (ESI) calc'd for (C$_{24}$H$_{20}$Cl$_2$N$_5$O$_2$) [M+H]$^+$, 480.1; found 480.1.

EXAMPLE 100

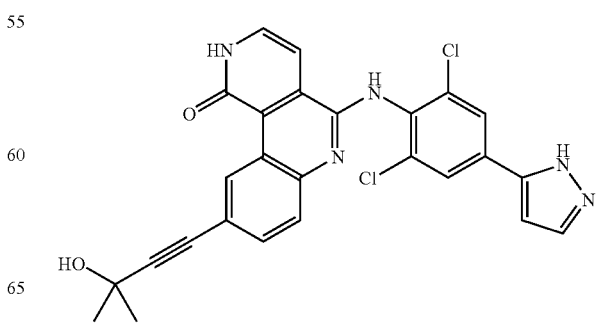

5-{[2,6-Dichloro-4-(1H-pyrazol-5-yl)phenyl]amino}-9-(3-hydroxy-3-methylbut-1-yn-1-yl)benzo[c]-2,6-naphthyridin-1(2H)-one

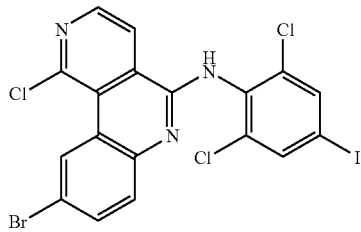 [SMILES: Clc1cc(I)cc(Cl)c1Nc1nc2ccc(Br)cc2c2c(Cl)nccc12]

Step 1: 9-Bromo-1-chloro-N-(2,6-dichloro-4-iodophenyl)benzo[c]-2,6-naphthyridin-5-amine The title compound was prepared according to the procedure in (Example 3, Method C, Step 4) using 9-bromo-1,5-dichlorobenzo[c]-2,6-naphthyridine and 2,6-dichloro-4-iodoaniline as the starting materials.

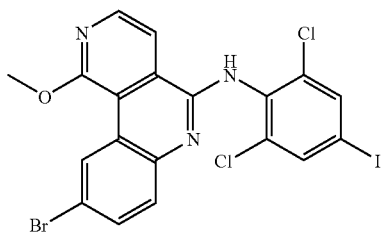 [SMILES: COc1nccc2c(Nc3c(Cl)cc(I)cc3Cl)nc3ccc(Br)cc3c12]

Step 2: 9-Bromo-N-(2,6-dichloro-4-iodophenyl)-1-methoxybenzo[c]-2,6-naphthyridin-5-amine To a solution of 9-bromo-1-chloro-N-(2,6-dichloro-4-iodophenyl)benzo[c]-2,6-naphthyridin-5-amine (1.56 g, 2.69 mmol) in methanol (30 mL) was added sodium methoxide (10 mL, 25% in methanol) and heated the reaction to 100° C. for 45min. The reaction was cooled to room temperature and a few drops of water were added to quench the reaction. The organic layer was evaporated under vacuum and the residue was diluted with ethyl acetate and extracted with water. The organic layer was separated, dried with sodium sulfate, filtered and evaporated. The residue was taken to the next step without purification.
LRMS (APCI) calc'd for $C_{19}H_{11}BrCl_2IN_3O$ [M+H]$^+$, 573.8; found 573.8.

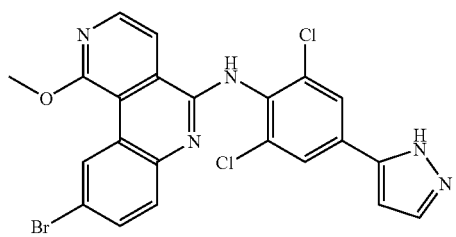 [SMILES: COc1nccc2c(Nc3c(Cl)cc(-c4ccn[nH]4)cc3Cl)nc3ccc(Br)cc3c12]

Step 3: 9-Bromo-N-[2,6-dichloro-4-(1H-pyrazol-5-yl)phenyl]-1-methoxybenzo[c]-2,6-naphthyridin-5-amine To a solution of 9-bromo-N-(2,6-dichloro-4-iodophenyl)-1-methoxybenzo[c]-2,6-naphthyridin-5-amine (500 mg, 0.87 mmol) in DMF (20 mL), was added 1H-pyrazol-5-ylboronic acid (107 mg, 0.96 mmol), PdCl$_2$(dppf)-CH$_2$Cl$_2$ adduct (142 mg, 0.17 mmol) and sodium carbonate (0.87 mL, 1.74 mmol, 2M in water). The solution was heated to 100° C. in the microwave in a sealed tube for 45 min. The reaction was diluted with ethyl acetate:THF (2:1) and extracted with water followed by brine. The organic layer was dried with sodium sulfate, filtered and concentrated under reduced pressure. The residue was purified by column chromatography on silica gel eluting with THF in hexanes(10-50%) to afford the title compound.
LRMS (ESI) calc'd for $C_{22}H_{15}BrCl_2N_5O$ [M+H]$^+$, 513.9; found 514.0.

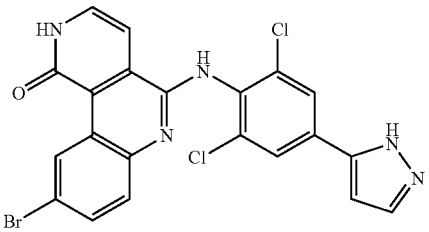 [SMILES: O=c1[nH]ccc2c(Nc3c(Cl)cc(-c4ccn[nH]4)cc3Cl)nc3ccc(Br)cc3c12]

Step 4: 9-Bromo-5-{[2,6-dichloro-4-(1H-pyrazol-5-yl)phenyl]amino}benzo[c]-2,6-naphthyridin-1(2H)-one To a slurry of 9-bromo-N-[2,6-dichloro-4-(1H-pyrazol-5-yl)phenyl]-1-methoxybenzo[c]-2,6-naphthyridin-5-amine (800 mg, 1.55 mmol) in dichloroethane (15 mL) was added boron tribromide (10.9 mL, 10.87 mmol, 1M in dichloromethane). The reaction mixture was heated at 85° C. for 45 min. After cooling to room temperature, the reaction was diluted with ethyl acetate and extracted with saturated aqueous sodium bicarbonate, followed by brine. The organic layer was dried with sodium sulfate, filtered and concentrated under reduced pressure. The residue was purified by column chromatography on silica gel eluting with THF in hexanes (0-50%) to afford the title compound.
LRMS (ESI) calc'd for $C_{21}H_{13}BrCl_2N_5O$ [M+H]$^+$, 499.9; found 499.9.

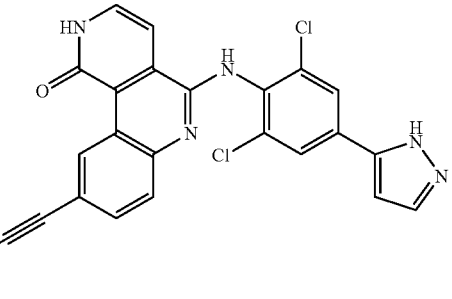

Step 5: 5-{[2,6-Dichloro-4-(1H-pyrazol-5-yl)phenyl]amino}-9-(3-hydroxy-3-methylbut-1-yn-1-yl)benzo[c]-2,6-naphthyridin-1(2H)-one A solution of 9-bromo-5-{[2,6-dichloro-4-(1H-pyrazol-5-yl)phenyl]amino}benzo[c]-2,6-naphthyridin-1(2H)-one (125 mg, 0.25 mmol) in DMF (3 mL) was degassed with nitrogen. Triethylamine (0.07 ml, 0.50 mmol), 2-methylbut-3-yn-2-ol (42.0 mg, 0.499 mmol), Pd(Ph$_3$P)$_4$ (28.8 mg, 0.025 mmol) and copper(I) iodide (9.50 mg, 0.050 mmol) were added and the reaction was heated to 75° C. for 16 h. After cooling to room temperature, the reaction was diluted with ethyl acetate and extracted with water. The organic layer was dried with sodium sulfate, filtered and concentrated under reduced pressure. The residue was dissolved in THF/MeOH, filtered and purified by reverse phase HPLC to afford the title compound.

LRMS (ESI) calc'd for $C_{26}H_{20}Cl_2N_5O_2$ [M+H]$^+$, 504.1; found 504.1

EXAMPLE 101

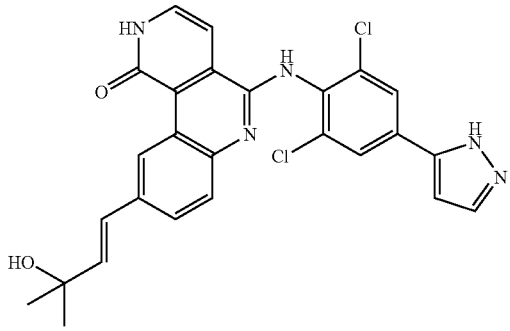 [SMILES: CC(C)(O)/C=C/c1ccc2nc(Nc3c(Cl)cc(-c4ccn[nH]4)cc3Cl)c3cc[nH]c(=O)c3c2c1]

5-{[2,6-Dichloro-4-(1H-pyrazol-5-yl)phenyl]amino}-9-[(1E)-3-hydroxy-3-methylbut-1-en-1-yl]benzo[c]-2,6-naphthyridin-1(2H)-one Step 1: To a solution of 9-bromo-5-{[2,6-dichloro-4-(1H-pyrazol-5-yl)phenyl]amino}benzo[c]-2,6-naphthyridin-1(2H)-one (Example 100, Step 4) (125 mg, 0.25 mmol) in THF (4 mL) was added [(1E)-3-hydroxy-3-methylbut-1-en-1-yl]boronic acid (65 mg, 0.45 mmol), Pd(Ph$_3$P)$_4$ (58 mg, 0.05 mmol) and sodium carbonate (0.125 mL, 0.25 mmol, 2M in water). The reaction was heated to 80° C. for 16 h. The reaction was diluted with ethyl acetate and washed with water. The organic layer was dried with sodium sulfate, filtered and concentrated under reduced pressure. The residue was dissolved in THF and methanol, filtered and purified by reverse phase HPLC to afford the title compound.

$^1$H NMR (500 MHz, DMSO-D6) δ 13.15 (bs, 1H), 12.19 (bs, 1H), 9.71 (bs, 1H), 9.13 (s, 1H), 8.01 (s, 2H), 7.88 (m, 1H), 7.64 (m, 2H), 7.31 (m, 2H), 6.94 (s, 1H), 6.61 (d, 1H), 6.40 (d, 1H), 4.73 (s, 1H), 1.28(s, 6H). LRMS (ESD calc'd for ($C_{26}H_{22}Cl_2N_5O_2$) [M+H]$^+$, 506.1; found 506.1

EXAMPLE 102

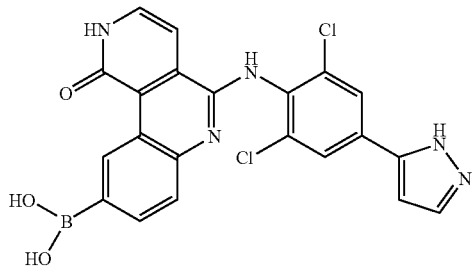 [SMILES: O=c1[nH]ccc2c(Nc3c(Cl)cc(-c4ccn[nH]4)cc3Cl)nc3ccc(B(O)O)cc3c12]

(5-{[2,6-Dichloro-4-(1H-pyrazol-5-yl)phenyl]amino}-1-oxo-1,2-dihydrobenzo[c]-2,6-naphthyridin-9-yl)boronic acid

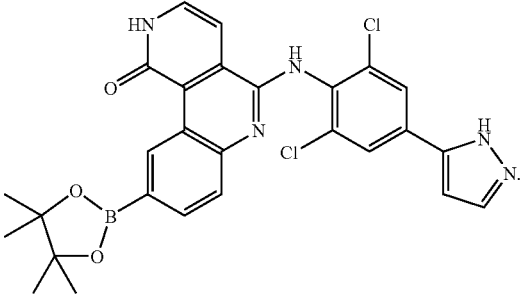 [SMILES: CC1(C)OB(c2ccc3nc(Nc4c(Cl)cc(-c5ccn[nH]5)cc4Cl)c4cc[nH]c(=O)c4c3c2)OC1(C)C]

Step 1: 5-{[2,6-Dichloro-4-(1H-pyrazol-5-yl)phenyl]amino}-9-(4,4,5,5-tetramethyl-1,3,2-dioxaborolan-2-yl)benzo[c]-2,6-naphthyridin-1(2H)-one To a solution of 9-bromo-5-{[2,6-dichloro-4-(1H-pyrazol-5-yl)phenyl]amino}benzo[c]-2,6-naphthyridin-1(2H)-one (Example 100, Step 4) (320 mg, 0.64 mmol) in 1,4-dioxane (6 mL) was added tricyclohexylphosphine (72 mg, 0.25 mmol), Pd$_2$(dba)$_3$ (117 mg, 0.13 mmol), potassium acetate (313 mg, 3.19 mmol) and 4,4,4',4',5,5,5',5'-octamethyl-2,2'-bi-1,3,2-dioxaborolane (519 mg, 2.04 mmol). The reaction was heated to 100° C. for 1.5 h. After cooling to room temperature, the reaction was diluted with ethyl acetate and extracted with water. The organic layer was dried with sodium sulfate, filtered and concentrated under reduced pressure. The residue was purified by column chromatography on silica gel eluting with ethyl acetate in hexanes (0-50%) followed by THF in hexanes (30-60%) to afford the title compound.

LRMS (ESI) calc'd for $C_{27}H_{25}BCl_2N_5O_3$ [M+H]$^+$, 548.1; found 548.1.

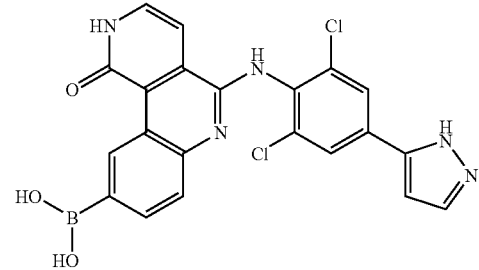 [SMILES: O=c1[nH]ccc2c(Nc3c(Cl)cc(-c4ccn[nH]4)cc3Cl)nc3ccc(B(O)O)cc3c12]

Step2: (5-{[2,6-Dichloro-4-(1H-pyrazol-5-yl)phenyl]amino}-1-oxo-1,2-dihydrobenzo[c]-2,6-naphthyridin-9-yl)boronic acid To a solution of 5-{[2,6-dichloro-4-(1H-pyrazol-5-yl)phenyl]amino}-9-(4,4,5,5-tetramethyl-1,3,2-dioxaborolan-2-yl)benzo[c]-2,6-naphthyridin-1(21)-one (175 mg, 0.32 mmol) in methanol (3 mL) was added potassium hydrogenfluoride (0.40 mL, 1.79 mmol, 4.5 M in water). The reaction was stirred at room temperature for 1 h and then concentrated under reduced pressure. The residue was suspended in THF (3 mL) and to this was added water (0.2 mL) and TFA (0.49 mL, 6.38 mmol). The reaction was stirred at room temperature for 30 min and then concentrated under reduced pressure. The residue was dissolved in THF and methanol, filtered, and purified by reverse phase HPLC to afford the title compound.

LRMS (ESI) calc'd for $C_{21}H_{15}BCl_2N_5O_3$ [M+H]$^+$, 466.1; found 466.0.

EXAMPLE 103

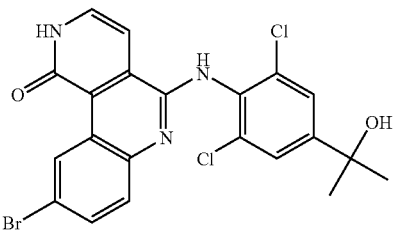 [SMILES: CC(C)(O)c1cc(Cl)c(Nc2nc3ccc(Br)cc3c3c(=O)[nH]ccc23)c(Cl)c1]

9-Bromo-5-{[2,6-dichloro-4-(1-hydroxy-1-methyl-ethyl)phenyl]amino}benzo[c]-2,6-naphthyridin-1(2H)-one Step 1: To a solution of 5-[(4-acetyl-2,6-dichlorophenyl)amino]-9-bromobenzo[c]-2,6-naphthyridin-1(2H)-one (Examples 94 and 95, Step 2) (109 mg, 0.23 mmol) in THF (3 mL) at −10° C. under nitrogen atmosphere was added methyl magnesium bromide (0.61 mL, 3.0 M in THF/toluene). The reaction mixture was stirred for 1 h keeping temperature between −5° C.-0° C. After allowing to warm to room temperature, the solution was quenched with water and diluted with 1:3 iPrOH/CHCl$_3$ and neutralized with sat. NaHCO$_3$. The organic layer was dried with Na$_2$SO$_4$, filtered, and concentrated under reduced pressure. The residue was purified by column chromatography on silica gel eluting with methanol in dichloromethane to afford the title compound.

LRMS (ESI) calc'd for $C_{21}H_{17}BrCl_2N_3O_2$ [M+H]$^+$, 491.9; found 491.9.

EXAMPLE 104

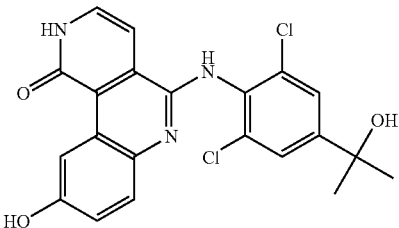

5-{[2,6-Dichloro-4-(1-hydroxy-1-methylethyl)phenyl]amino}-9-hydroxybenzo[c]-2,6-naphthyridin-1(2H)-one

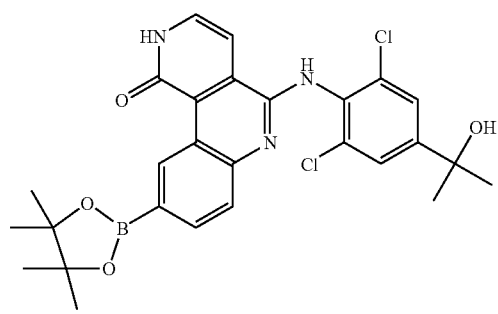 [SMILES: CC(C)(O)c1cc(Cl)c(Nc2nc3ccc(B4OC(C)(C)C(C)(C)O4)cc3c3c(=O)[nH]ccc23)c(Cl)c1]

Step 1: 5-{[2,6-Dichloro-4-(1-hydroxy-1-methyl-ethyl)phenyl]amino}-9-(4,4,5,5-tetramethyl-1,3,2-dioxaborolan-2-yl)benzo[c]-2,6-naphthyridin-1(2H)-one The title compound was made according to the procedure in Example 102, Step 1 using 9-bromo-5-{[2,6-dichloro-4-(1-hydroxy-1-methylethyl)phenyl]amino}benzo[c]-2,6-naphthyridin-1(2H)-one as the starting material.

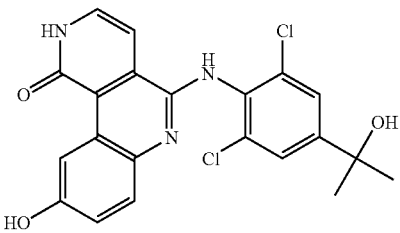 [SMILES: CC(C)(O)c1cc(Cl)c(Nc2nc3ccc(O)cc3c3c(=O)[nH]ccc23)c(Cl)c1]

Step 2: 5-{[2,6-Dichloro-4-(1-hydroxy-1-methyl-ethyl)phenyl]amino}-9-hydroxybenzo[c]-2,6-naphthyridin-1(2H)-one To a solution of 5-{[2,6-dichloro-4-(1-hydroxy-1-methylethyl)phenyl]amino}-9-(4,4,5,5-tetramethyl-1,3,2-dioxaborolan-2-yl)benzo[c]-2,6-naphthyridin-1(21)-one (68 mg, 0.126 mmol) in methanol (1 mL) was added potassiumhydrogenfluoride (0.157 mL, 0.705 mmol, 4.5 M in water). The reaction was stirred at room temperature for 1 h and then concentrated under reduced pressure. The residue was combined with hot acetone, filtered and concentrated under reduced pressure. To a solution of the residue in a mixture of acetonitrile (1 mL) and THF (0.25 mL) was added lithium hydroxide (11 mg, 0.458 mmol) and water (0.5 mL). The reaction was stirred at room temperature for 16 h. The reaction was diluted with ethyl acetate and washed with saturated ammonium chloride. The organic layer was dried with sodium sulfate, filtered and concentrated under reduced pressure. The residue was purified by column chromatography on silica gel eluting with methanol in dichloromethane to afford the title compound.

$^1$NMR (500 MHz, CD$_3$OD) δ 9.15 (s, 1H), 7.60 (s, 2H), 7.56 (d, 1H), 7.47 (d, 1H), 7.30 (d, 1H), 7.09 (dd, 1H), 1.58 (s, 6H). LRMS (ESI) calc'd for $C_{21}H_{18}Cl_2N_3O_3$ [M+H]$^+$, 430.1; found 430.0.

EXAMPLE 105

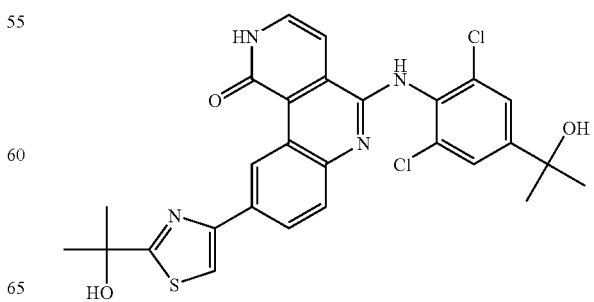

5-{[2,6-Dichloro-4-(1-hydroxy-1-methylethyl)phenyl]amino}-9-[2-(1-hydroxy-1-methylethyl)-1,3-thiazol-4-yl]benzo[c]-2,6-naphthyridin-1(2H)-one

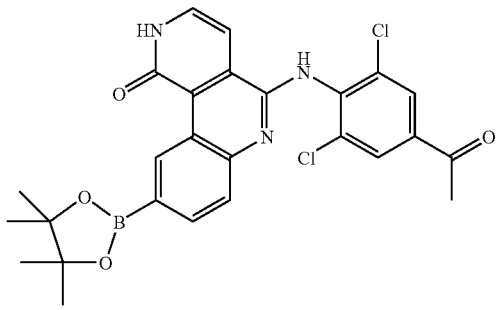 [SMILES: CC(=O)c1cc(Cl)c(Nc2nc3ccc(B4OC(C)(C)C(C)(C)O4)cc3c3c(=O)[nH]ccc23)c(Cl)c1]

Step 1: 5-[(4-Acetyl-2,6-dichlorophenyl)amino]-9-(4,4,5,5-tetramethyl-1,3,2-dioxaborolan-2-yl)benzo[c]-2,6-naphthyridin-1(2H)-one The title compound was prepared according to the procedure in (Example 102, Step 1) using 5-[(4-acetyl-2,6-dichlorophenyl)amino]-9-bromobenzo[c]-2,6-naphthyridin-1(2H)-one and 4,4,4',4',5,5,5',5'-octamethyl-2,2'-bi-1,3,2-dioxaborolane as the starting materials.

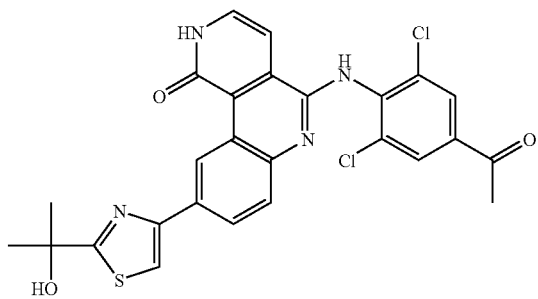 [SMILES: CC(=O)c1cc(Cl)c(Nc2nc3ccc(-c4csc(C(C)(C)O)n4)cc3c3c(=O)[nH]ccc23)c(Cl)c1]

Step 2: 5-[(4-Acetyl-2,6-dichlorophenyl)amino]-9-[2-(1-hydroxy-1-methylethyl)-1,3-thiazol-4-yl]benzo[c]-2,6-naphthyridin-1(2H)-one To a solution of 5-[(4-acetyl-2,6-dichlorophenyl)amino]-9-(4,4,5,5-tetramethyl-1,3,2-dioxaborolan-2-yl)benzo[c]-2,6-naphthyridin-1(2H)-one (135 mg, 0.26 mmol) in THF (4 mL) was added 2-(4-bromo-1,3-thiazol-2-yl)propan-2-ol (114 mg, 0.52 mmol), Pd(Ph$_3$P)$_4$ (60 mg, 0.05 mmol) and sodium carbonate (0.129 mL, 0.26 mmol, 2M in water). The reaction was heated to 80° C. for 16 h. The reaction was diluted with ethyl acetate and extracted with water. The organic layer was dried with sodium sulfate, filtered and concentrated under reduced pressure to afford the title compound.

LRMS (ESI) calc'd for C$_{26}$H$_{21}$Cl$_2$N$_4$O$_3$S [M+H]$^+$, 539.1; found 539.0.

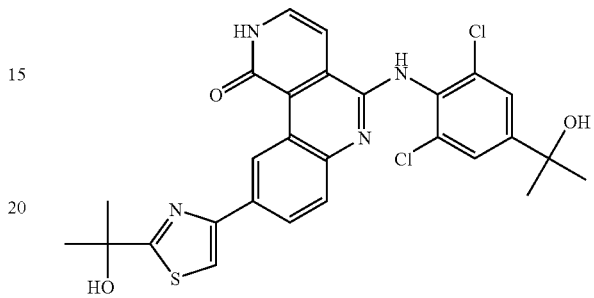

Step 2: 5-{[2,6-Dichloro-4-(1-hydroxy-1-methylethyl)phenyl]amino}-9-[2-(1-hydroxy-1-methylethyl)-1,3-thiazol-4-yl]benzo[c]-2,6-naphthyridin-1(2H)-one A solution of 5-[(4-acetyl-2,6-dichlorophenyl)amino]-9-[2-(1-hydroxy-1-methylethyl)-1,3-thiazol-4-yl]benzo[c]-2,6-naphthyridin-1(2H)-one (75 mg, 0.14 mmol) in THF (2 mL) was cooled to −10° C. and methyl magnesium bromide (0.79 mL, 1.11 mmol, 1.4 M in toluene/THF) was added. The reaction was stirred rapidly keeping the temperature between −5 & 0° C. for 1 h. After warming to room temperature, the reaction was quenched with water, diluted with ethyl acetate/THF (1:3), and extracted with water. The organic layer was dried with sodium sulfate, filtered and concentrated under reduced pressure. The residue was purified by column chromatography on silica gel eluting with methanol in dichloromethane followed by reverse phase HPLC to afford the title compound.

$^1$H NMR (500 MHz, CD$_3$OD) δ 10.38 (m, 1H), 8.24 (m, 1H), 7.77 (m, 5H), 7.33 (m, 1H), 1.69 (s, 6H), 1.61 (s, 6H). LRMS (ESI) calc'd for C$_{27}$H$_{25}$Cl$_2$N$_4$O$_3$S [M+H]$^+$, 555.1; found 555.0

Additional analogues shown below were prepared using procedures similar to those described in the above examples.

TABLE 5

| Example | Structure | Compound Name | LRMS (M + H)$^+$ |
|---|---|---|---|
| 106 | 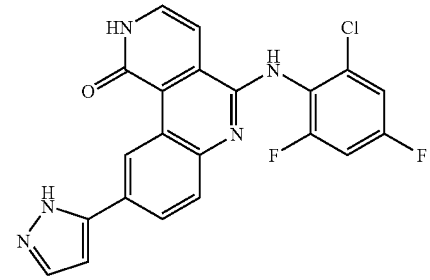 [SMILES: O=c1[nH]ccc2c(Nc3c(F)cc(F)cc3Cl)nc3ccc(-c4ccn[nH]4)cc3c12] | 5-[(2-chloro-4,6-difluorophenyl)amino]-9-(1H-pyrazol-5-yl)benzo[c]-2,6-naphthyridin-1(2H)-one | Calc'd: 424.1, found: 424.0 |

TABLE 5-continued

| Example | Structure | Compound Name | LRMS (M + H)+ |
|---|---|---|---|
| 107 | 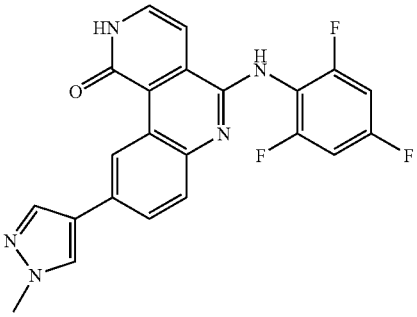 [SMILES: Cn1cc(-c2ccc3nc(Nc4c(F)cc(F)cc4F)c4cc[nH]c(=O)c4c3c2)cn1] | 9-(1-methyl-1H-pyrazol-4-yl)-5-[(2,4,6-trifluorophenyl)amino]benzo[c]-2,6-naphthyridin-1(2H)-one | Calc'd: 422.1, found: 422.1 |
| 108 | 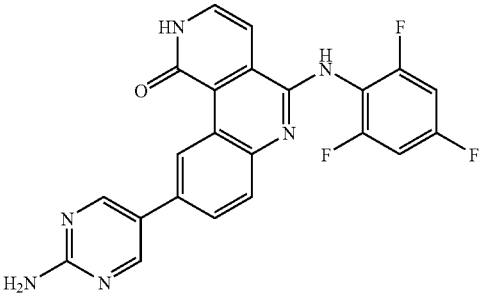 [SMILES: Nc1ncc(-c2ccc3nc(Nc4c(F)cc(F)cc4F)c4cc[nH]c(=O)c4c3c2)cn1] | 9-(2-Aminopyrimidin-5-yl)-5-[(2,4,6-trifluorophenyl)amino]benzo[c]-2,6-naphthyridin-1(2H)-one | Calc'd: 435.1, found: 435.1 |
| 109 | 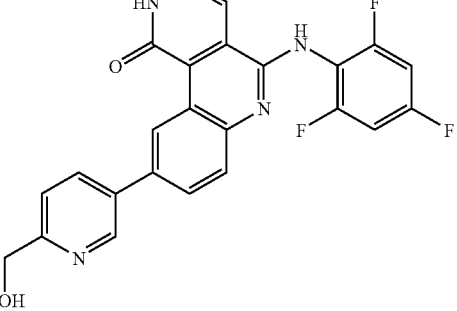 | 9-[6-(hydroxymethyl)pyridin-3-yl]-5-[(2,4,6-trifluorophenyl)amino]benzo[c]-2,6-naphthyridin-1(2H)-one | Calc'd: 449.4, found: 449.1 |
| 110 | 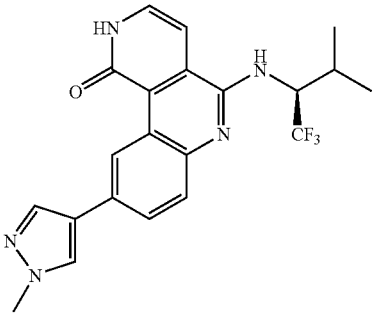 [SMILES: CC(C)[C@H](Nc1nc2ccc(-c3cnn(C)c3)cc2c2c(=O)[nH]ccc12)C(F)(F)F] | 9-(1-Methyl-1H-pyrazol-4-yl)-5-{[(1S)-2-methyl-1-(trifluoromethyl)propyl]amino}benzo[c]-2,6-naphthyridin-1(2H)-one | Calc'd: 416.4, found: 416.1 |
| 111 | 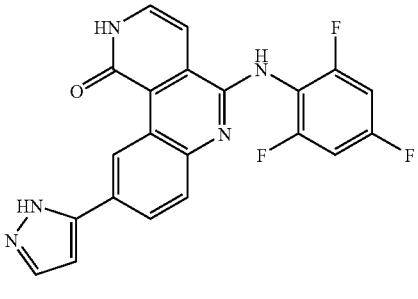 [SMILES: O=c1[nH]ccc2c(Nc3c(F)cc(F)cc3F)nc3ccc(-c4ccn[nH]4)cc3c12] | 9-(1H-Pyrazol-5-yl)-5-[(2,4,6-trifluorophenyl)amino]benzo[c]-2,6-naphthyridin-1(2H)-one | Calc'd: 408.1, found: 408.1 |

TABLE 5-continued

| Example | Structure | Compound Name | LRMS (M + H)+ |
|---|---|---|---|
| 112 | 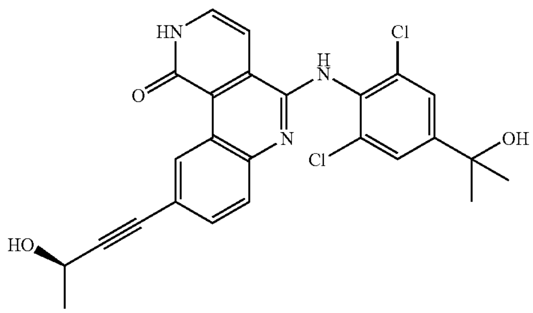 [SMILES: C[C@@H](O)C#Cc1ccc2nc(Nc3c(Cl)cc(C(C)(C)O)cc3Cl)c3cc[nH]c(=O)c3c2c1] | 5-{[2,6-dichloro-4-(1-hydroxy-1-methylethyl)phenyl]amino}-9-[(3R)-3-hydroxybut-1-yn-1-yl]benzo[c]-2,6-naphthyridin-1(2H)-one | Calc'd 482.1, found 482.0 |
| 113 | 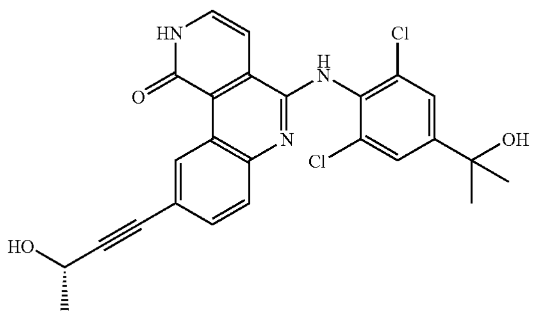 [SMILES: C[C@H](O)C#Cc1ccc2nc(Nc3c(Cl)cc(C(C)(C)O)cc3Cl)c3cc[nH]c(=O)c3c2c1] | 5-{[2,6-dichloro-4-(1-hydroxy-1-methylethyl)phenyl]amino}-9-[(3S)-3-hydroxybut-1-yn-1-yl]benzo[c]-2,6-naphthyridin-1(2H)-one | Calc'd 482.1, found 482.0 |
| 114 | 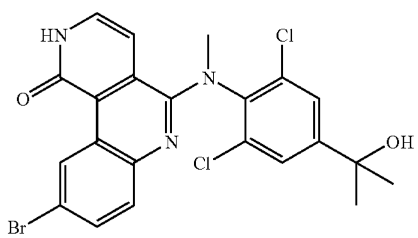 [SMILES: CN(c1c(Cl)cc(C(C)(C)O)cc1Cl)c1nc2ccc(Br)cc2c2c(=O)[nH]ccc12] | 9-bromo-5-{[2,6-dichloro-4-(1-hydroxy-1-methylethyl)phenyl](methyl)amino}benzo[c]-2,6-naphthyridin-1(2H)-one | Calc'd 506.0, found 506.0 |
| 115 | 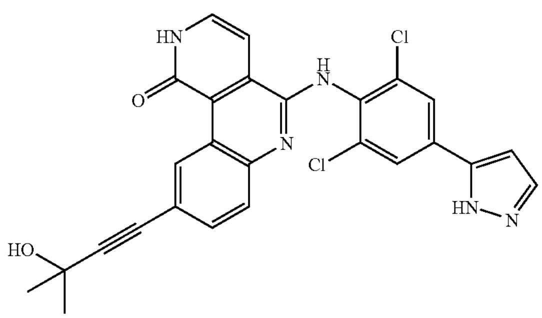 [SMILES: CC(C)(O)C#Cc1ccc2nc(Nc3c(Cl)cc(-c4ccn[nH]4)cc3Cl)c3cc[nH]c(=O)c3c2c1] | 5-{[2,6-dichloro-4-(1H-pyrazol-5-yl)phenyl]amino}-9-(3-hydroxy-3-methylbut-1-yn-1-yl)benzo[c]-2,6-naphthyridin-1(2H)-one | Calc'd 504.1, found 504.1 |
| 116 | 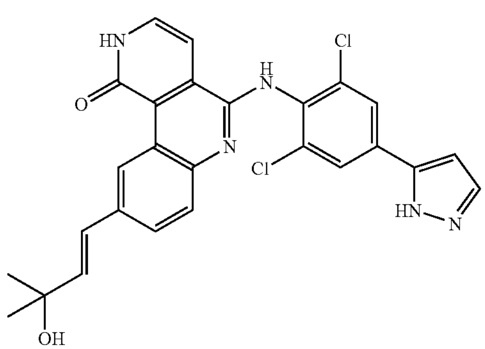 [SMILES: CC(C)(O)/C=C/c1ccc2nc(Nc3c(Cl)cc(-c4ccn[nH]4)cc3Cl)c3cc[nH]c(=O)c3c2c1] | 5-{[2,6-dichloro-4-(1H-pyrazol-5-yl)phenyl]amino}-9-[(1E)-3-hydroxy-3-methylbut-1-en-1-yl]benzo[c]-2,6-naphthyridin-1(2H)-one | Calc'd 506.1, found 506.1 |

TABLE 5-continued

| Example | Structure | Compound Name | LRMS (M + H)+ |
|---|---|---|---|
| 117 | 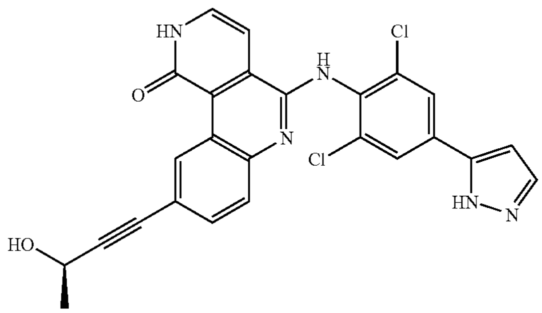 [SMILES: C[C@@H](O)C#Cc1ccc2nc(Nc3c(Cl)cc(-c4ccn[nH]4)cc3Cl)c3cc[nH]c(=O)c3c2c1] | 5-{[2,6-dichloro-4-(1H-pyrazol-5-yl)phenyl]amino}-9-[(3R)-3-hydroxybut-1-yn-1-yl]benzo[c]-2,6-naphthyridin-1(2H)-one | Calc'd 490.1, found 490.1 |
| 118 | 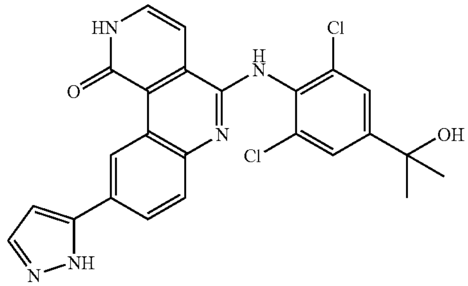 [SMILES: CC(C)(O)c1cc(Cl)c(Nc2nc3ccc(-c4ccn[nH]4)cc3c3c(=O)[nH]ccc23)c(Cl)c1] | 5-{[2,6-dichloro-4-(1-hydroxy-1-methylethyl)phenyl]amino}-9-(1H-pyrazol-5-yl)benzo[c]-2,6-naphthyridin-1(2H)-one | Calc'd 480.1, found 480.0 |
| 119 | 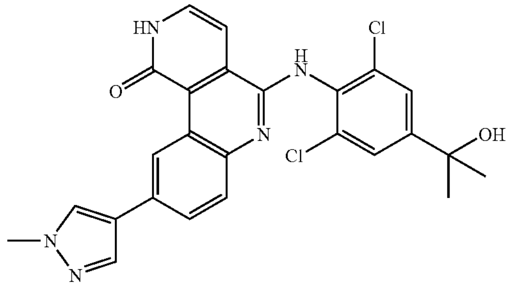 [SMILES: Cn1cc(-c2ccc3nc(Nc4c(Cl)cc(C(C)(C)O)cc4Cl)c4cc[nH]c(=O)c4c3c2)cn1] | 5-{(2,6-dichloro-4-(1-hydroxy-1-methylethyl)phenyl]amino}-9-(1-methyl-1H-pyrazol-4-yl)benzo[c]-2,6-naphthyridin-1(2H)-one | Calc'd 494.1, found 494.0 |
| 120 | 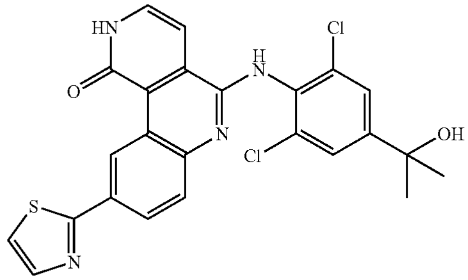 [SMILES: CC(C)(O)c1cc(Cl)c(Nc2nc3ccc(-c4nccs4)cc3c3c(=O)[nH]ccc23)c(Cl)c1] | 5-{[2,6-dichloro-4-(1-hydroxy-1-methylethyl)phenyl]amino}-9-(1,3-thiazol-2-yl)benzo[c]-2,6-naphthyridin-1(2H)-one | Calc'd 497.1, found 497.0 |
| 121 | 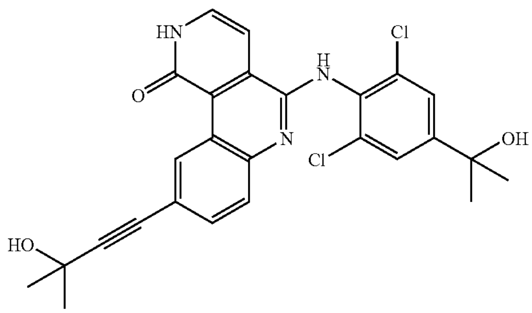 [SMILES: CC(C)(O)C#Cc1ccc2nc(Nc3c(Cl)cc(C(C)(C)O)cc3Cl)c3cc[nH]c(=O)c3c2c1] | 5-{[2,6-dichloro-4-(1-hydroxy-1-methylethyl)phenyl]amino}-9-(3-hydroxy-3-methylbut-1-yn-1-yl)benzo[c]-2,6-naphthyridin-1(2H)-one | Calc'd 496.1, found 496.0 |

TABLE 5-continued

| Example | Structure | Compound Name | LRMS (M + H)+ |
|---|---|---|---|
| 122 | 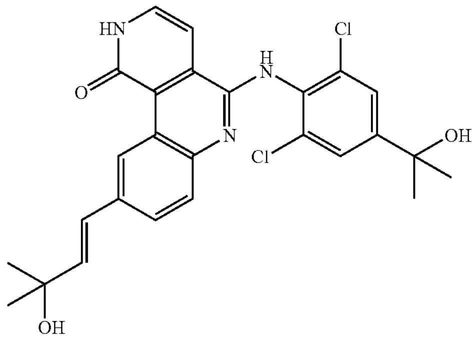 [SMILES: CC(C)(O)/C=C/c1ccc2nc(Nc3c(Cl)cc(C(C)(C)O)cc3Cl)c3cc[nH]c(=O)c3c2c1] | 5-{[2,6-dichloro-4-(1-hydroxy-1-methylethyl)phenyl]amino}-9-[(1E)-3-hydroxy-3-methylbut-1-en-1-yl]benzo[c]-2,6-naphthyridin-1(2H)-one | Calc'd 498.1, found 498.1 |
| 123 | 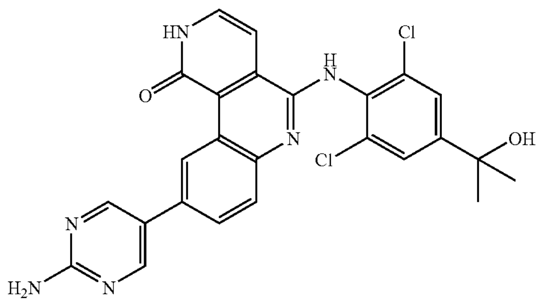 [SMILES: CC(C)(O)c1cc(Cl)c(Nc2nc3ccc(-c4cnc(N)nc4)cc3c3c(=O)[nH]ccc23)c(Cl)c1] | 9-(2-aminopyrimidin-5-yl)-5-{[2,6-dichloro-4-(1-hydroxy-1-methylethyl)phenyl]amino}benzo[c]-2,6-naphthyridin-1(2H)-one | Calc'd 507.1, found 507.0 |
| 124 | 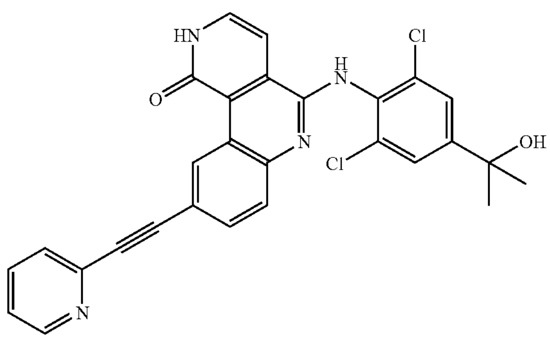 [SMILES: CC(C)(O)c1cc(Cl)c(Nc2nc3ccc(C#Cc4ccccn4)cc3c3c(=O)[nH]ccc23)c(Cl)c1] | 5-{[2,6-dichloro-4-(1-hydroxy-1-methylethyl)phenyl]amino}-9-(pyridin-2-ylethynyl)benzo[c]-2,6-naphthyridin-1(2H)-one | Calc'd 515.1, found 515.0 |
| 125 | 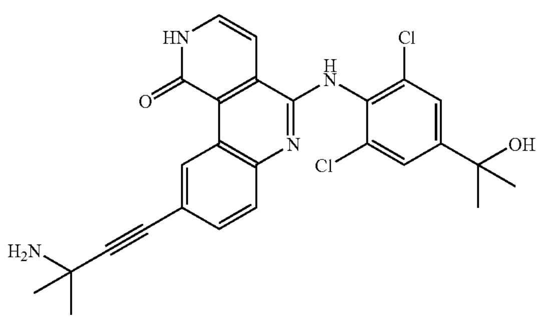 [SMILES: CC(C)(N)C#Cc1ccc2nc(Nc3c(Cl)cc(C(C)(C)O)cc3Cl)c3cc[nH]c(=O)c3c2c1] | 9-(3-amino-3-methylbut-1-yn-1-yl)-5-{[2,6-dichloro-4-(1-hydroxy-1-methylethyl)phenyl]amino}benzo[c]-2,6-naphthyridin-1(2H)-one | Calc'd 495.1, found 495.1 |
| 126 | 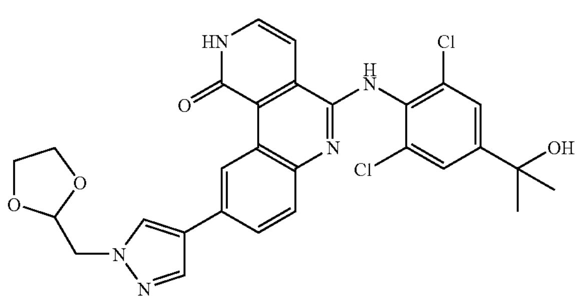 [SMILES: CC(C)(O)c1cc(Cl)c(Nc2nc3ccc(-c4cnn(CC5OCCO5)c4)cc3c3c(=O)[nH]ccc23)c(Cl)c1] | 5-{[2,6-dichloro-4-(1-hydroxy-1-methylethyl)phenyl]amino}-9-[1-(1,3-dioxolan-2-ylmethyl)-1H-pyrazol-4-yl]benzo[c]-2,6-naphthyridin-1(2H)-one | Calc'd 566.1, found 566.1 |

TABLE 5-continued

| Example | Compound Name | LRMS (M + H)+ |
|---|---|---|
| 127 | 5-{[2,6-dichloro-4-(1-hydroxy-1-methylethyl)phenyl]amino}-9-(1-isobutyl-1H-pyrazol-4-yl)benzo[c]-2,6-naphthyridin-1(2H)-one | Calc'd 536.2, found 536.1 |
| 128 | ethyl [4-(5-{[2,6-dichloro-4-(1-hydroxy-1-methylethyl)phenyl]amino}-1-oxo-1,2-dihydrobenzo[c]-2,6-naphthyridin-9-yl)-1H-pyrazol-1-yl]acetate | Calc'd 566.1, found 566.1 |
| 129 | 5-{[2,6-dichloro-4-(1-hydroxy-1-methylethyl)phenyl]amino}-9-[1-(2-morpholin-4-ylethyl)-1H-pyrazol-4-yl]benzo[c]-2,6-naphthyridin-1(2H)-one | Calc'd 593.2, found 593.1 |
| 130 | 3,5-dichloro-4-{[9-(3-hydroxy-3-methylbut-1-yn-1-yl)-1-oxo-1,2-dihydrobenzo[c]-2,6-naphthyridin-5-yl]amino}benzenesulfonamide | Calc'd 517., found 517.0 |
| 131 | 3,5-dichloro-4-[[1,2-dihydro-9-(1-methyl-1H-pyrazol-4-yl)-1-oxobenzo[c][2,6]naphthyridin-5-yl]amino]-benzenesulfonamide | Calc'd 515.0, found 515.0 |

| Example | Structure | Compound Name | LRMS (M + H)+ |
|---|---|---|---|
| 132 | 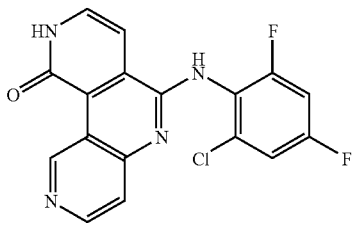 | 5-{[2,6-dichloro-4-(1-hydroxy-1-methylethyl)phenyl]amino}-9-[6-(1-hydroxy-1-methylethyl)pyridin-2-yl]benzo[c]-2,6-naphthyridin-1(2H)-one | Calc'd 549.1, found 549.1 |

EXAMPLE 133

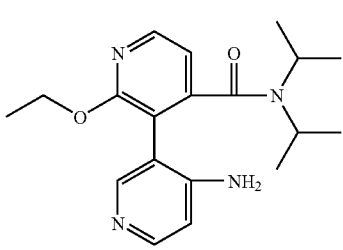 [SMILES: CCOc1nccc(C(=O)N(C(C)C)C(C)C)c1-c1cnccc1N]

6-[(2-Chloro-4,6-difluorophenyl)amino]pyrido[4,3-c]-1,6-naphthyridin-10(9H)-one

Step 1: 4'-Amino-2-ethoxy-N,N-diisopropyl-3,3'-bipyridine-4-carboxamide

[2-Ethoxy-6-(methoxycarbonyl)phenyl]boronic acid was converted to 4'-amino-2-ethoxy-N,N-diisopropyl-3,3'-bipyridine-4-carboxamide using the same procedure as shown in Example 3, Step 1 using 3-iodopyridin-4-amine as the coupling partner. The product was purified by trituration with diethyl ether and filtered.

LRMS (APCI) calc'd for $C_{19}H_{27}N_4O_2$ [M+H]+, 343.2; found 343.0.

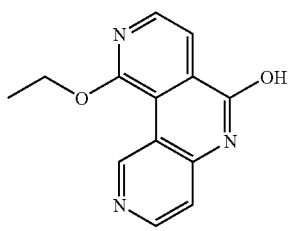 [SMILES: CCOc1nccc2c(O)nc3ccncc3c12]

Step 2: 10-Ethoxypyrido[4,3-c]-1,6-naphthyridin-6-ol

4'-Amino-2-ethoxy-N,N-diisopropyl-3,3'-bipyridine-4-carboxamide was converted to methyl 2-(4-aminopyridin-3-yl)-3-ethoxybenzoate using the same procedure as shown in (Example 3, Step 2). The product was triturated with diethyl ether.

$^1$H NMR (600 MHz, CD$_3$OD) δ 10.1 (s, 1H), 8.23 (dd, 2H), 7.86 (d, 1H), 7.3 (d, 1H), 7.35 (m, 3H), 4.66 (q, 2H), 1.5 (t, 3H). LRMS (ESI) calc'd for $C_{13}H_{12}N_3O_2$ [M+H]+, 242.1; found 242.1.

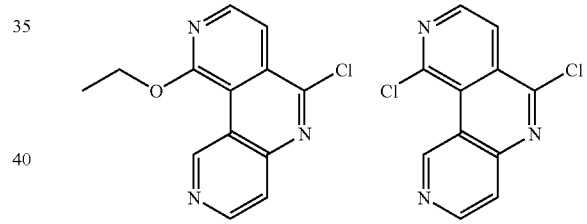

Step 3: 6-Chloro-10-ethoxypyrido[4,3-c]-1,6-naphthyridine and 6,10-Dichloropyrido[4,3-c]-1,6-naphthyridine To a solution of 10-ethoxypyrido[4,3-c]-1,6-naphthyridin-6-ol (500 mg, 2.07 mmol) in acetonitrile (13 mL) were added pyridine (0.335 mL, 4.15 mmol) and phosphorous oxychloride (1.92 mL, 20.7 mmol). The solution was heated in a microwave reactor for 1 hr at 135° C. and the reaction mixture was quenched by the dropwise addition to a solution of ammonium hydroxide in ice. The precipitate was filtered and dried on high vacuum overnight to produce a 1.5:1 mixture of 6-chloro-10-ethoxypyrido[4,3-c]-1,6-naphthyridine and 6,10-dichloropyrido[4,3-c]-1,6-naphthyridine.

$^1$H NMR for 6-chloro-10-ethoxypyrido[4,3-c]-1,6-naphthyridine (600 MHz, CD$_6$SO) δ 10.8 (s, 1H), 10.5 (s, 1H), 9.96 (d, 1H), 8.86 (d, 1H), 8.83 (d, 1H), 8.53 (d, 1H), 8.39 (d, 1H), 8.01 (d, 1H), 7.95 (d, 1H), 7.86 (d, 1H), 4.70 (q, 2H), 1.54 (t, 3H).). LRMS (ESI) calc'd for $C_{19}H_{14}ClF_2N_4O$ [M+H]+, 387.1; found 260.0, calc'd for $C_{17}H_9Cl_2F_2N_4$ [M+H]+, 377.0; found 377.0.

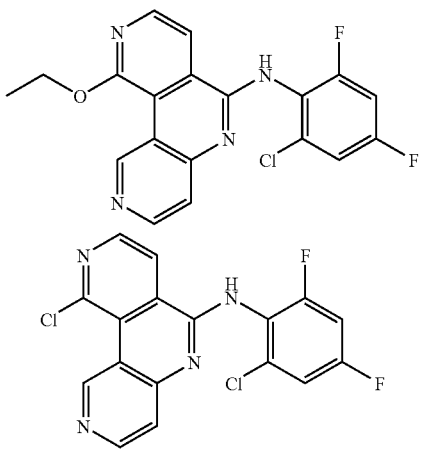

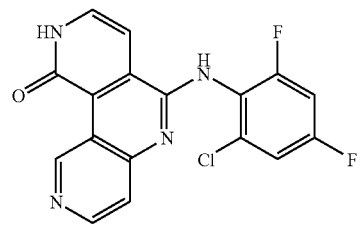

Step 4: N-(2-Chloro-4,6-difluorophenyl)-10-ethoxy-pyrido[4,3-c]-1,6-naphthyridin-6-amine and 10-Chloro-N-(2-chloro-4,6-difluorophenyl)pyrido[4,3-c]-1,6-naphthyridin-6-amine To a solution of 1.5:1 mixture of 6-chloro-10-ethoxypyrido[4,3-c]-1,6-naphthyridine and 6,10-dichloropyrido[4,3-c]-1,6-naphthyridine (1.5 g) in THF (25 mL) was added 2-chloro-4,6 difluoro aniline (945 mg, 5.78 mmol) and sodium tert-butoxide (1.65 g, 17 mmol). The solution was heated to 85° C. for 40 min then cooled to room temperature and extracted with EtOAc and brine. The organic layers were dried with $MgSO_4$, filtered, and concentrated under reduced pressure. The crude residue was purified on silica gel (100% hexanes to 100% EtOAc, gradient elution) which provided N-(2-chloro-4,6-difluorophenyl)-10-ethoxypyrido[4,3-c]-1,6-naphthyridin-6-amine and 10-chloro-N-(2-chloro-4,6-difluorophenyl)pyrido[4,3-c]-1,6-naphthyridin-6-amine.

LRMS (ESI) calc'd for $C_{13}H_{11}ClN_3O$ $[M+H]^+$, 260.1; found 260.0, calc'd for $C_{11}H_6Cl_2N_3$ $[M+H]^+$, 250.0; found 250.0.

Step 5: 6-[(2-Chloro-4,6-difluorophenyl)amino]pyrido[4,3-c]-1,6-naphthyridin-10(9H)-one To a solution of N-(2-chloro-4,6-difluorophenyl)-10-ethoxypyrido[4,3-c]-1,6-naphthyridin-6-amine and 10-chloro-N-(2-chloro-4,6-difluorophenyl)pyrido[4,3-c]-1,6-naphthyridin-6-amine (1.3 g) in 8 mL methanol was added sodium methoxide (5 mL, 2.06 mmol, 25% weight in methanol) and the mixture was heated to 100° C. for 1 hr. The solution was cooled to room temperature, concentrated, and redissolved with 3:1 $CHCl_3$/i-PrOH followed by a wash with saturated $NH_4Cl$. The organic layers were combined, dried with $MgSO_4$, filtered, and concentrated under reduced pressure. A portion of the crude solution (540 mg) was taken up in $CHCl_3$ (8 mL) and boron tribromide (1M in $CH_2Cl_2$, 7 mL, 7.0 mmol) and heated to 85° C. for 1 hr. The solution was cooled to room temperature, extracted with 3:1 $CHCl_3$/i-PrOH, and washed with saturated $NaHCO_3$. The organic layers were dried with $MgSO_4$, filtered, and concentrated to afford the crude product. The crude residue was purified on silica gel (100% $CH_2Cl_2$ to 25% MeOH, gradient elution) which afforded the title compound.

$^1$H NMR (600 MHz, $CD_3OD$) δ 12.4 (br s, 1H), 10.7 (s, 1H), 9.70 (br s, 1H), 8.48 (d, 1H), 7.80 (m, 1H), 7.56 (m, 2H), 7.40 (d, 1H), 7.29 (d, 1H). LRMS (ESI) calc'd for $C_{17}H_{10}ClF_2N_4O$ $[M+H]^+$, 359.1; found 359.0.

Additional analogues shown below were prepared using procedures similar to those described in the above examples and general methods (A-F).

TABLE 6

| Example | Structure | Compound Name | LCMS (M + H)+ | Method |
|---|---|---|---|---|
| 134 | 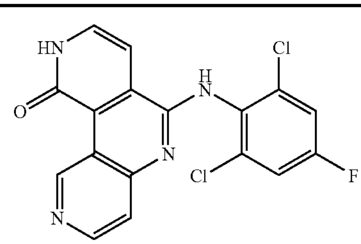 | 6-[(2,6-Dichloro-4-fluorophenyl)amino]pyrido[4,3-c]-1,6-naphthyridin-10(9H)-one | Calc'd: 375.0, found: 375.0 | C |
| 135 | 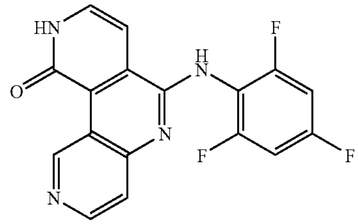 [SMILES: O=c1[nH]ccc2c(Nc3c(F)cc(F)cc3F)nc3ccncc3c12] | 6-[(2,4,6-Trifluorophenyl)amino]pyrido[4,3-c]-1,6-naphthyridin-10(9H)-one | Calc'd: 343.1, found: 343.0 | C |

TABLE 6-continued

| Example | Structure | Compound Name | LCMS (M + H)+ | Method |
|---|---|---|---|---|
| 136 | 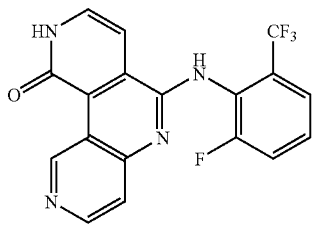 [SMILES: O=c1[nH]ccc2c(Nc3c(F)cccc3C(F)(F)F)nc3ccncc3c12] | 6-{[2-fluoro-6-(Trifluoromethyl)phenyl]amino}pyrido[4,3-c]-1,6-naphthyridin-10(9H)-one | Calc'd: 375.1, found: 375.1 | C |
| 137 | 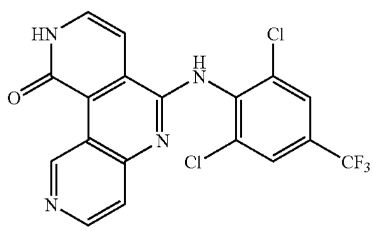 [SMILES: O=c1[nH]ccc2c(Nc3c(Cl)cc(C(F)(F)F)cc3Cl)nc3ccncc3c12] | 6-{[2,6-Dichloro-4-(trifluoromethyl)phenyl]amino}pyrido[4,3-c]-1,6-naphthyridin-10(9H)-one | Calc'd: 425.0, found: 425.0 | C |
| 138 | 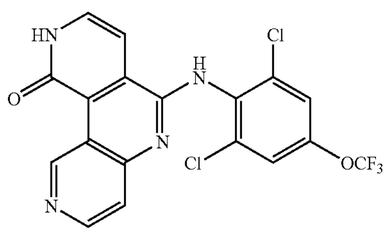 [SMILES: O=c1[nH]ccc2c(Nc3c(Cl)cc(OC(F)(F)F)cc3Cl)nc3ccncc3c12] | 6-{[2,6-Dichloro-4-(trifluoromethoxy)phenyl]amino}pyrido[4,3-c]-1,6-naphthyridin-10(9H)-one | Calc'd: 441.0, found: 441.0 | C |
| 139 | 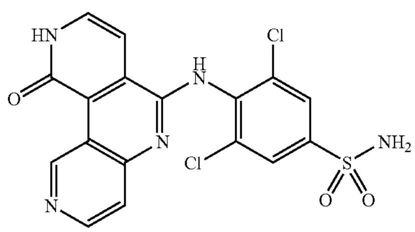 [SMILES: NS(=O)(=O)c1cc(Cl)c(Nc2nc3ccncc3c3c(=O)[nH]ccc23)c(Cl)c1] | 3,5-dichloro-4-[(10-oxo-9,10-dihydropyrido[4,3-c]-1,6-naphthyridin-6-yl)amino]benzenesulfonamide | Calc'd: 436.0, found: 436.0 | C |
| 140 | 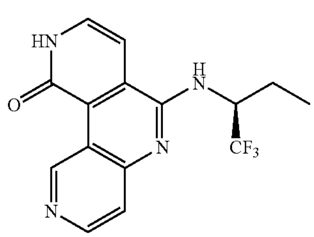 [SMILES: CC[C@H](Nc1nc2ccncc2c2c(=O)[nH]ccc12)C(F)(F)F] | 6-{[(1S)-1-(trifluoromethyl)propyl]amino}pyrido[4,3-c]-1,6-naphthyridin-10(9H)-one | Calc'd: 323.1, found: 321.1 | B |
| 141 | 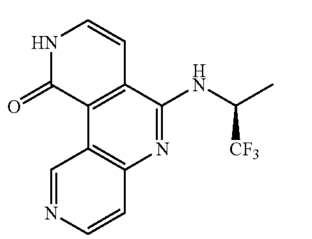 [SMILES: C[C@H](Nc1nc2ccncc2c2c(=O)[nH]ccc12)C(F)(F)F] | 6-{[(1S)-2,2,2-trifluoro-1-methylethyl]amino}pyrido[4,3-c]-1,6-naphthyridin-10(9H)-one | Calc'd: 309.1, found: 309.1 | B |

TABLE 6-continued

| Example | Structure | Compound Name | LCMS (M + H)+ | Method |
|---|---|---|---|---|
| 142 | 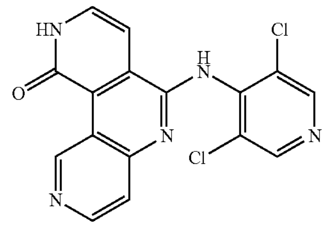 [SMILES: O=c1[nH]ccc2c(Nc3c(Cl)cncc3Cl)nc3ccncc3c12] | 6-[(3,5-dichloropyridin-4-yl)amino]pyrido[4,3-c]-1,6-naphthyridin10(9H)-one | Calc'd: 358.0, found: 358.0 | C |
| 143 | 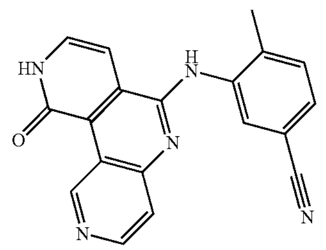 [SMILES: Cc1ccc(C#N)cc1Nc1nc2ccncc2c2c(=O)[nH]ccc12] | 4-methyl-3-[(10-oxo-9,10-dihydropyrido[4,3-c]-1,6-naphthyridin-6-yl)amino]benzonitrile | Calc'd 328.1, found 328.1 | D |

EXAMPLES 144 and 145

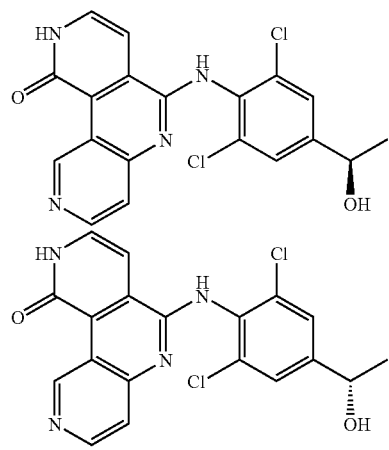

6-({2,6-Dichloro-4-[(1R)-1-hydroxyethyl]phenyl}amino)pyrido[4,3-c]-1,6-naphthyridin-10(9H)-one and 6-({2,6-Dichloro-4-[(1S)-1-hydroxyethyl]phenyl}amino)pyrido[4,3-c]-1,6-naphthyridin-10(9H)-one

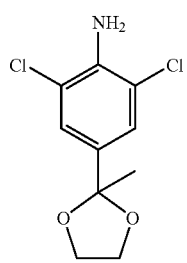

Step 1:
2,6-Dichloro-4-(2-methyl-1,3-dioxolan-2-yl)aniline 1-(4-Amino-3,5-dichlorophenyl)ethanone (15 g, 73.5 mmol), pyridinium p-toluene sulfonic acid (5.5 g, 22 mmol), and ethylene glycol (6.2 mL, 110 mmol) were heated together in benzene (250 mL) with a Dean Stark trap at 100° C. overnight. The benzene was distilled off until ~75 mL remained and the reaction mixture was extracted with EtOAc and saturated NaHCO₃. The organic layer was separated, dried with MgSO₄, filtered, and concentrated under rotary evaporation to afford a oily residue. The crude mixture was purified on silica gel chromatography (100% Hex to 100% EtOAc) to afford the desired product.

¹H NMR (600 MHz, CDCl₃) δ 7.28 (s, 2H), 4.00 (m, 2H), 3.76 (m, 2H), 1.57 (s, 3H). LRMS (ESI) calc'd for $C_{10}H_{12}Cl_2NO_2$ [M+H]⁺, 248.0; found 248.0.

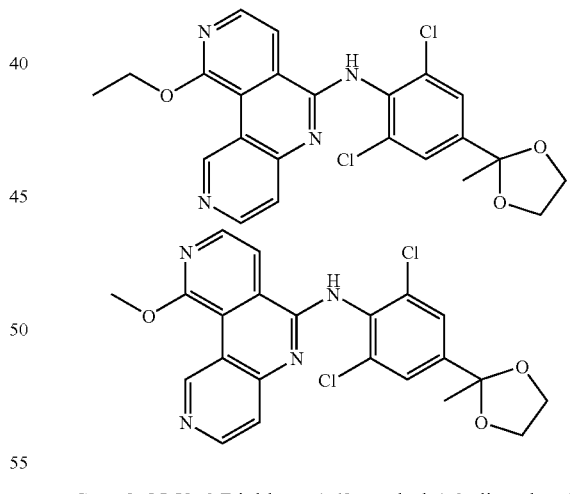

Step 2: N-[2,6-Dichloro-4-(2-methyl-1,3-dioxolan-2-yl)phenyl]-10-ethoxypyrido[4,3-c]-1,6-naphthyridin-6-amine and N-[2,6-dichloro-4-(2-methyl-1,3-dioxolan-2-yl)phenyl]-10-methoxypyrido[4,3-c]-1,6-naphthyridin-6-amine To a solution of 6-chloro-10-ethoxypyrido[4,3-c]-1,6-naphthyridine and 6,10-dichloropyrido[4,3-c]-1,6-naphthyridine (Example 133, Step 3) (2.0 g, 8.00 mmol) in THF (40 mL) was added 2,6-dichloro-4-(2-methyl-1,3-dioxolan-2-yl)aniline (4.2 g, 17 mmol) followed by sodium tert-butoxide (4.44 g, 46 mmol) and the mixture was heated to 85° C. for 1 hr. After cooling to room temperature, the mixture was extracted with EtOAc and water. The organic layers were combined, dried with MgSO₄, filtered, and concentrated under rotary evaporation. Purification by column chromatography on silica gel (100% hexane to 100% EtOAc) afforded the desired products as a mixture. The mixture was taken up in methanol (40 mL) and 25% sodium methoxide in methanol (12 mL) was added. The reaction mixture was heated to 100° C. for 1 hr then cooled to room temperature. The mixture was concentrated, diluted with EtOAc and washed with 10% NH₄Cl. The organic layers were combined, dried with MgSO₄, filtered, and concentrated to afford the desired products.

LRMS (ESI) calc'd for $C_{23}H_{21}Cl_2N_4O_3$ [M+H]⁺, 471.1; found 471.1 and $C_{22}H_{19}Cl_2N_4O_3$ [M+H]⁺, 457.1; found 457.0.

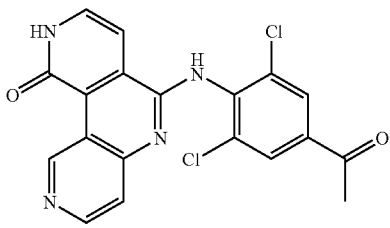 [SMILES: CC(=O)c1cc(Cl)c(Nc2nc3ccncc3c3c(=O)[nH]ccc23)c(Cl)c1]

Step 3: 6-[(4-Acetyl-2,6-dichlorophenyl)amino]pyrido[4,3-c]-1,6-napthyridin-10(9H)-one To a solution of N-[2,6-dichloro-4-(2-methyl-1,3-dioxolan-2-yl)phenyl]-10-ethoxypyrido[4,3-c]-1,6-naphthyridin-6-amine and N-[2,6-dichloro-4-(2-methyl-1,3-dioxolan-2-yl)phenyl]-10-methoxypyrido[4,3-c]-1,6-naphthyridin-6-amine (3.0 g) in THF (30 mL) was added 6 N HCl (20 mL) and the mixture was heated to 85° C. for 3.5 hr. After cooling to room temperature, the mixture was neutralized with saturated NaHCO3 and extracted with 1:1 THF/EtOAc. The precipitate between the organic and aqueous layers were collected and determined to be pure by LCMS. The organic layer was concentrated and purified by column chromatography (100% CH₂Cl₂ to 30% MeOH).

LRMS (ESI) calc'd for $C_{19}H_{13}Cl_2N_4O_2$ [M+H]⁺, 399.0; found 399.0.

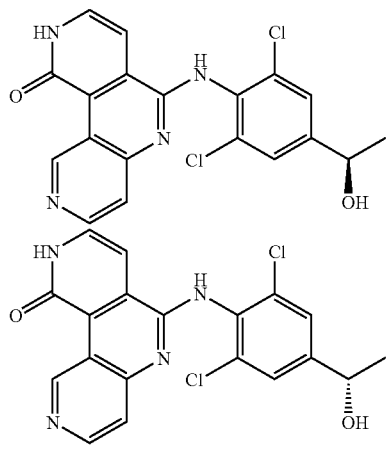

Step 4: 6-({2,6-Dichloro-4-[(1R)-1-hydroxyethyl]phenyl}amino)pyrido[4,3-c]-1,6-naphthyridin-10(9H)-one and 6-({2,6-dichloro-4-[(1S)-1-hydroxyethyl]phenyl}amino)pyrido[4,3-c]-1,6-naphthyridin-10(9H)-one To a solution of 6-[(4-acetyl-2,6-dichlorophenyl)amino]pyrido[4,3-c]-1,6-naphthyridin-10(9H)-one (375 mg, 0.93 mmol) in methanol (10 mL) was added sodium borohydride (107 mg, 2.82 mmol) and the reaction mixture was stirred for 30 min at room temperature. The solution was quenched with 1N citric acid and extracted with 3:1 CHCl₃/iPrOH. The organic layers were dried with MgSO₄, filtered, and concentrated under reduced pressure to afford the crude product. Purification by column chromatography (100% CH₂Cl₂ to 70% CH₂Cl₂/30% MeOH) afforded the racemic alcohol. Chiral separation with AD column at 10 mL/min 30% iPrOH/70% Heptane 25 minute afforded the separate enantiomers at retention time 7.1 and 10.8 minutes.

For both enantiomers: ¹H NMR (600 MHz, CD₃OD) δ 10.54 (s, 1H), 8.40 (d, 1H), 7.54 (d, 1H), 7.50 (s, 2H), 7.40 (d, 1H), 7.35 (d, 2H), 1.5 (d, 3H). LRMS (ESI) calc'd for $C_{19}H_{15}Cl_2N_4O_2$ [M+H]⁺, 401.1; found 401.0.

EXAMPLE 146

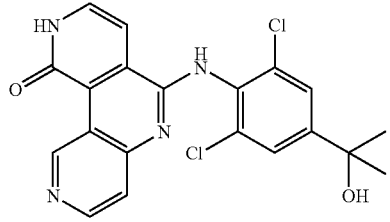 [SMILES: CC(C)(O)c1cc(Cl)c(Nc2nc3ccncc3c3c(=O)[nH]ccc23)c(Cl)c1]

6-{[2,6-Dichloro-4-(1-hydroxy-1-methylethyl)phenyl]amino}pyrido[4,3-c]-1,6-naphthyridin-10(9H)-one Step 1: To a solution of 6-[(4-acetyl-2,6-dichlorophenyl)amino]pyrido[4,3-c]-1,6-naphthyridin-10(9H)-one (Examples 144 and 145, Step 3) (1.3 g, 3.26 mmol) in THF (30 mL) at 0° C. under nitrogen atmosphere was added methyl magnesium bromide (11.6 mL, 1.4 M in THF/toluene) and the reaction mixture stirred for 30 min. The solution was quenched with 1 N citric acid, diluted with 1:1 THF/EtOAc, and neutralized with saturated NaHCO₃. The organic layer was concentrated, triturated with diethyl ether, and filtered to afford the desired product as a yellow powder.

For the 4:1 mixture of rotamers: ¹H NMR (600 MHz, CD₆SO) δ 12.4 (br s, 1H), 10.74 (s, 1H), 10.6 (br s, 0.2H)*, 10.4 (br s, 0.2H)*, 9.54 (s, 1H), 8.44 (d, 1H), 8.36 (d, 0.30)*, 7.76 (d, 1H), 7.66 (d, 2H), 7.56 (d, 0.3 H)*, 7.50 (s, 0.5)*, 7.34 (d, 0.3H)*, 7.30 (d, 1H), 7.24 (d,1H), 7.24 (d, 0.4 H)*, 5.4 (s, 1H), 5.24 (s, 0.2H)*, 1.48 (s, 6H), 1.44 (s, 1.6H)*. LRMS (ESI) calc'd for $C_{20}H_{17}Cl_2N_4O_2$ [M+H]⁺, 415.1; found 415.0.

Additional analogues shown below were prepared using procedures similar to those described in the above examples and general methods.

TABLE 7

| Example | Structure | Compound Name | LCMS (M + H)+ |
|---|---|---|---|
| 147 | 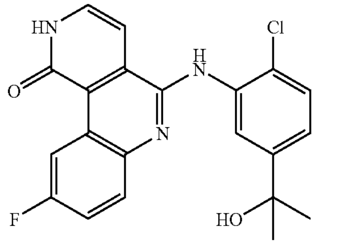 [SMILES: CC(C)(O)c1ccc(Cl)c(Nc2nc3ccc(F)cc3c3c(=O)[nH]ccc23)c1] | 5-{[2-chloro-5-(1-hydroxy-1-methylethyl)phenyl]amino}-9-fluorobenzo[c]-2,6-naphthyridin-1(2H)-one | Calc'd 398.1, found 398.1 |
| 148 | 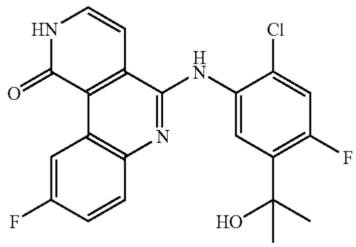 [SMILES: CC(C)(O)c1cc(Nc2nc3ccc(F)cc3c3c(=O)[nH]ccc23)c(Cl)cc1F] | 5-{[2-chloro-4-fluoro-5-(1-hydroxy-1-methylethyl)phenyl]amino}-9-fluorobenzo[c]-2,6-naphthyridin-1(2H)-one | Calc'd 416.1, found 416.1 |
| 149 | 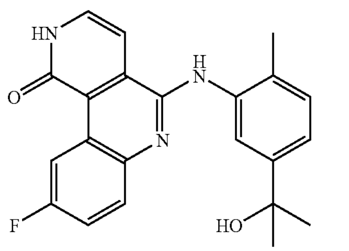 [SMILES: Cc1ccc(C(C)(C)O)cc1Nc1nc2ccc(F)cc2c2c(=O)[nH]ccc12] | 9-fluoro-5-{[5-(1-hydroxy-1-methylethyl)-2-methylphenyl]amino}benzo[c]-2,6-naphthyridin-1(2H)-one | Calc'd 378.2, found 378.1 |

EXAMPLE 150

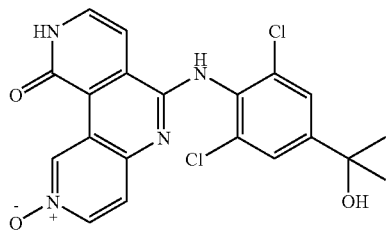

6-{[2,6-Dichloro-4-(1-hydroxy-1-methylethyl)phenyl]amino}pyrido[4,3-c]-1,6-naphthyridin-10(9H)-one 2-oxide Step 1: To a solution of 6-{[2,6-dichloro-4-(1-hydroxy-1-methylethyl)phenyl]amino}pyrido[4,3-c]-1,6-naphthyridin-10(9H)-one (Example 146, Step 1) (30 mg, 0.07 mmol) in $CH_2Cl_2$ (3 mL) at 0° C. was added m-CPBA (40.5 mg, 0.18 mmol, 77% max) and stirred for 2 hr. 10% Sodium sulfite and saturated $NaHCO_3$ were added and stirred for 30 min. The solution was extracted with 3:1 $CHCl_3$/iPrOH, dried with $MgSO_4$, filtered, and concentrated under reduced pressure. Column chromatography (100% $CH_2Cl_2$ to 30% MeOH, 70% $CH_2Cl_2$) provided the desired product.

LRMS (ESI) calc'd for $C_{20}H_{17}Cl_2N_4O_3$ [M+H]+, 431.1; found 431.1.

EXAMPLE 151

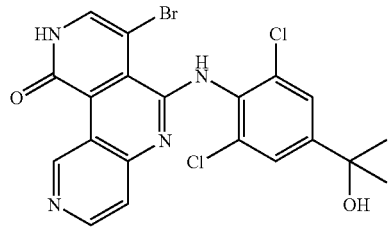 [SMILES: CC(C)(O)c1cc(Cl)c(Nc2nc3ccncc3c3c(=O)[nH]cc(Br)c23)c(Cl)c1]

7-Bromo-6-{[2,6-dichloro-4-(1-hydroxy-1-methylethyl)phenyl]amino}pyrido[4,3-c]-1,6-naphthyridin-10(9H)-one Step 1: To a solution of 6-{[2,6-dichloro-4-(1-hydroxy-1-methylethyl)phenyl]amino}pyrido[4,3-c]-1,6-naphthyridin-10(9H)-one (Example 146, Step 1) (86, 0.21 mmol) in DMF (4 mL) at 0° C. was added NBS (44 mg, 0.25 mmol) and the reaction mixture was stirred for 1.5 hr. The solution was quenched with 10% sodium thiosulfate and saturated $NaHCO_3$ and stirred for 30 min. The reaction mixture was diluted with $CH_2Cl_2$ and the layers were separated. The organic layers were dried with $MgSO_4$, filtered, and concentrated under reduced pressure. Purification by silica gel chromatography (100% $CH_2Cl_2$ to 65% $CH_2Cl_2$/35% MeOH) afforded the desired product.

LRMS (ESI) calc'd for $C_{20}H_{16}Cl_2N_4O_2$ [M+H]+, 493.0; found 493.0

EXAMPLE 152

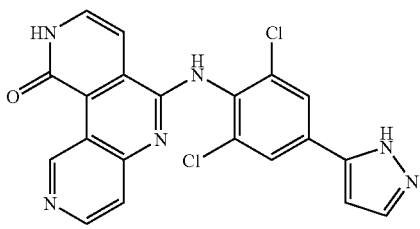 [SMILES: O=c1[nH]ccc2c(Nc3c(Cl)cc(-c4ccn[nH]4)cc3Cl)nc3ccncc3c12]

6-{[2,6-Dichloro-4-(1H-pyrazol-5-yl)phenyl]amino}pyrido[4,3-c]-1,6-naphthyridin-10(9H)-one

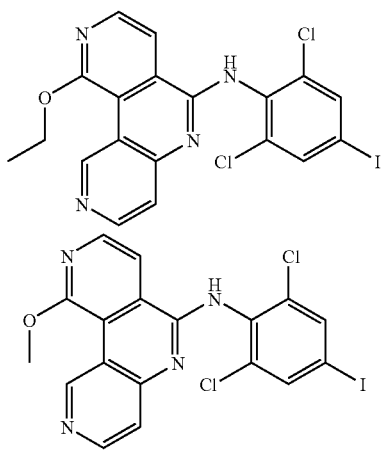

Step 1: N-(2,6-Dichloro-4-iodophenyl)-10-ethoxypyrido[4,3-c]-1,6-naphthyridin-6-amine and N-(2,6-Dichloro-4-iodophenyl)-10-methoxypyrido[4,3-c]-1,6-naphthyridin-6-amine To a mixture of 6-chloro-10-ethoxypyrido[4,3-c]-1,6-naphthyridine (Example 133, Step 3) (200 mg, 0.770 mmol) and 6,10-dichloropyrido[4,3-c]-1,6-naphthyridine (Example 133, Step 3)(193, 0.770 mmol) in THF (12 mL) were added 2,6-dichloro-4-iodoaniline (443 mg, 1.54 mmol) and sodium tert-butoxide (444 mg, 4.62 mmol) and the mixture was heated to 85° C. for 1 hr. After cooling to room temperature, the mixture was extracted with EtOAc. The organic layers were dried with MgSO$_4$, filtered, and concentrated under reduced pressure. Column chromatography (100% hexane to 100% EtOAc) provided 10-chloro-N-(2,6-dichloro-4-iodophenyl)pyrido[4,3-c]-1,6-naphthyridin-6-amine and N-(2,6-dichloro-4-iodophenyl)-10-ethoxypyrido[4,3-c]-1,6-naphthyridin-6-amine. Most instances 10-chloro-N-(2,6-dichloro-4-iodophenyl)pyrido[4,3-c]-1,6-naphthyridin-6-amine and N-(2,6-dichloro-4-iodophenyl)-10-ethoxypyrido[4,3-c]-1,6-naphthyridin-6-amine were carried on as a mixture, however, the mixtures can be separated and carried on separately. This mixture (282 mg) was taken up in methanol (5 mL) and 25% sodium methoxide (3 mL) and heated at 100° C. for 1 hr. After cooling to room temperature, the solution was concentrated and then taken up in EtOAc and washed with water. The organic layers were dried with MgSO$_4$, filtered, and concentrated to afford the title compounds.

LRMS (ESI) calc'd for $C_{19}H_{14}Cl_2N_4O$ [M+H]$^+$, 511.0; found 511.0 and LRMS (ESI) calc'd for $C_{18}H_{12}Cl_2N_4O$ [M+H]$^+$, 497.0; found 497.0.

Step 2: 6-{[2,6-Dichloro-4-(1H-pyrazol-5-yl)phenyl]amino}pyrido[4,3-c]-1,6-naphthyridin-10(9H)-one To a solution of N-(2,6-dichloro-4-iodophenyl)-10-ethoxypyrido[4,3-c]-1,6-naphthyridin-6-amine (200 mg, 0.40 mmol) were added 1H-pyrazol-5-ylboronic acid (48 mg, 0.43 mmol) 2.0 M solution of NaHCO$_3$ (1 mL) and tetrakis(triphenylphosphine)palladium (0) (90 mg, 0.78 mmol) and the mixture was heated to 80° C. for 4 hr. After cooling to room temperature, the reaction mixture was extracted with EtOAc and water. Column chromatography (100% Hex to 100% EtOAc) afforded the cross-coupled product. This purified material (79 mg) was taken up in chloroform (5 mL) followed by the addition of BBr$_3$ (1.40 mL, 1M in CH$_2$Cl$_2$) and heated to 85° C. for 1 hr. The solution was cooled to room temperature, extracted with 3:1 CHCl$_3$/IPrOH and washed with saturated NaHCO$_3$. The organic layers were dried with MgSO$_4$, filtered, and concentrated under reduced pressure. Purification by column chromatography (100% CH$_2$Cl$_2$ to 35% MeOH/65% CH$_2$Cl$_2$) afforded the title compound as a mixture of rotamers.

LRMS (ESI) calc'd for $C_{20}H_{13}Cl_2N_6O$ [M+H]$^+$, 423.1; found 423.1.

Additional analogues shown below were prepared using procedures similar to those described in the above examples and general methods.

TABLE 8

| Example | Structure | Compound Name | LCMS (M + H)$^+$ |
|---|---|---|---|
| 153 | 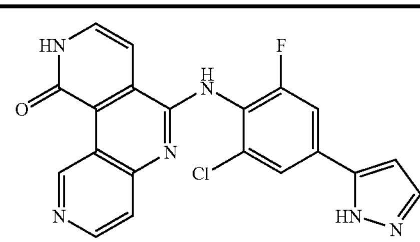 | 6-{[2-Chloro-6-fluoro-4-(1H-pyrazol-5-yl)phenyl]amino}pyrido[4,3-c]-1,6-naphthyridin-10(9H)-one | Calc'd 407.1, found 407.1 |

EXAMPLE 154

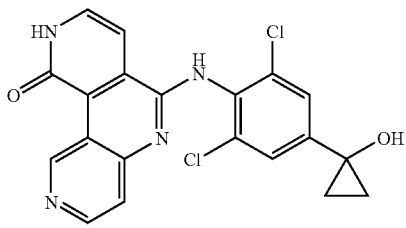 [SMILES: O=c1[nH]ccc2c(Nc3c(Cl)cc(C4(O)CC4)cc3Cl)nc3ccncc3c12]

6-{[2,6-Dichloro-4-(1-hydroxycyclopropyl)phenyl]amino}pyrido[4,3-c]-1,6-naphthyridin-10(9H)-one

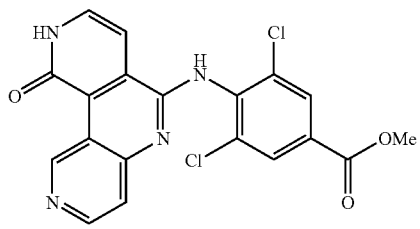 [SMILES: COC(=O)c1cc(Cl)c(Nc2nc3ccncc3c3c(=O)[nH]ccc23)c(Cl)c1]

Step 1: Methyl 3,5-dichloro-4-[(10-oxo-9,10-dihydropyrido[4,3-c]-1,6-naphthyridin-6-yl)amino]benzoate The carbonylation reaction was conducted following the procedure described in *J. Comb.* 2003, 5, 350. To a solution of N-(2,6-dichloro-4-iodophenyl)-10-ethoxypyrido[4,3-c]-1,6-naphthyridin-6-amine (Example 152, Step 1) (130 mg, 0.39 mmol) and N-(2,6-dichloro-4-iodophenyl)-10-methoxypyrido[4,3-c]-1,6-naphthyridin-6-amine (Example 152, Step 1) (66 mg, 0.13 mol) in methanol (5 mL) were added dimethylamino pyridine (96 mg, 0.78 mmol), diisopropylethylamine (137 uL, 0.78 mmol), molybdenumhexacarbonyl (106 mg, 0.39 mmol) and palladium (II) acetate (9 mg, 0.39 mmol). The solution was heated in a microwave reactor at 150° C. for 15 min. The black solution was extracted with EtOAc and water, dried with MgSO$_4$, filtered, and concentrated under reduced pressure. Purification by chromatography on silica gel (100% hexanes to 100% EtOAc) afforded methyl 3,5-dichloro-4-[(10-ethoxypyrido[4,3-c]-1,6-naphthyridin-6-yl)amino]benzoate and methyl 3,5-dichloro-4-[(10-methoxypyrido[4,3-c]-1,6-naphthyridin-6-yl)amino]benzoate. The mixture of esters (117 mg, 0.27 mmol) were suspended in CHCl$_3$ (5 mL) followed by addition of BBr$_3$ (1.91 mL, 1.91 mmol). The reaction mixture was heated to 85° C. for 45 min. After cooling to room temperature, the solution was extracted with EtOAc and saturated NaHCO$_3$, dried with MgSO$_4$, filtered, and concentrated. Purification by chromatography on silica gel (100% CH$_2$Cl$_2$ to 70% CH$_2$Cl$_2$/30% MeOH) afforded the title compound.

LRMS (ESI) calc'd for $C_{19}H_{13}Cl_2N_4O_3$ [M+H]$^+$, 415.; found 415.0.

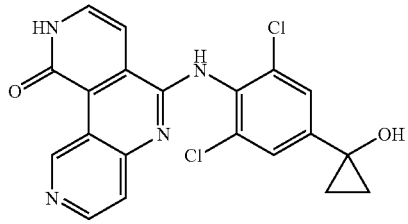 [SMILES: O=c1[nH]ccc2c(Nc3c(Cl)cc(C4(O)CC4)cc3Cl)nc3ccncc3c12]

Step 2: 6-{[2,6-Dichloro-4-(1-hydroxycyclopropyl)phenyl]amino}pyrido[4,3-c]-1,6-naphthyridin-10(9H)-one To a solution of methyl 3,5-dichloro-4-[(10-oxo-9,10-dihydropyrido[4,3-c]-1,6-naphthyridin-6-yl)amino]benzoate (67 mg, 0.16 mmol) and titanium (IV) isoproxide (46 mg, 0.16 mmol) in THF (4 mL) was added ethylmagnesium bromide (1.29 mL, 1.29 mmol, 1.0 M in THF) dropwise. The solution was stirred at room temperature overnight and extracted with 3:1 CHCl$_3$/iPrOH. Column chromatography on silica gel (100% CH$_2$Cl$_2$ to 70% CH$_2$Cl$_2$/30% MeOH) afforded the title compound.

$^1$H NMR (600 MHz, CD$_3$OD) 10.67 (s, 1H), 8.40 (d, 1H), 7.70 (d, 1H), 7.40 (s, 2H), 7.30 (d, 1H) 1.28 (br s, 2H), 1.30 (br s, 1.10) LRMS (ESI) calc'd for $C_{20}H_{15}Cl_2N_4O_2$ [M+H]$^+$, 413.0; found 413.0.

EXAMPLE 155

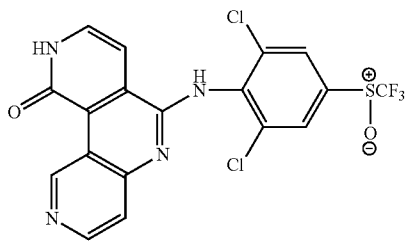

{3,5-Dichloro-4-[(10-oxo-9,10-dihydropyrido[4,3-c]-1,6-naphthyridin-6-yl)amino]phenyl}(trifluoromethyl)sulfoniumolate

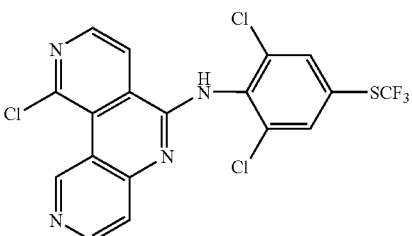

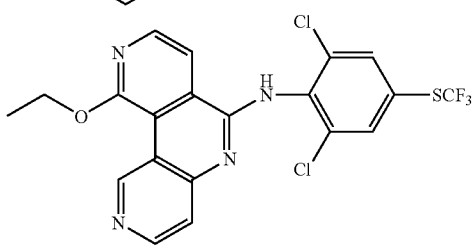

Step 1: 10-Chloro-N-{2,6-dichloro-4-[(trifluoromethyl)thio]phenyl}pyrido[4,3-c]-1,6-naphthyridin-6-amine and N-{2,6-Dichloro-4-[(trifluoromethyl)thio]phenyl}-10-ethoxypyrido[4,3-c]-1,6-naphthyridin-6-amine 6-Chloro-10-ethoxypyrido[4,3-c]-1,6-naphthyridine (128.5 mg, 0.495 mmol) (Example 133, Step 3), 6,10-dichloropyrido[4,3-c]-1,6-naphthyridine (124 mg, 0.495 mmol) (Example 133, Step 3), 2,6-dichloro-4-[(trifluoromethyl)thio]aniline (259 mg, 0.990 mmol), and sodium t-butyl (285 mg, 2.97 mmol) were combined in tetrahydrofuran (10 ml). The reaction mixture was heated to 85° C. for 45 minutes. After cooling to room temperature, the crude reaction mixture was diluted with 200 ml ethyl acetate and washed with 75 ml water. The reaction mixture was extracted three additional times with 75 ml ethyl acetate. The combined organic layers were dried with magnesium sulfate and concentrated under reduced pressure. Column chromatography (100% hexanes to 100% ethyl acetate) afforded the title compounds.

LRMS (ESD: Calculated for $C_{20}H_{13}Cl_2F_3N_4OS$ [M+H]+: 485, found 485.

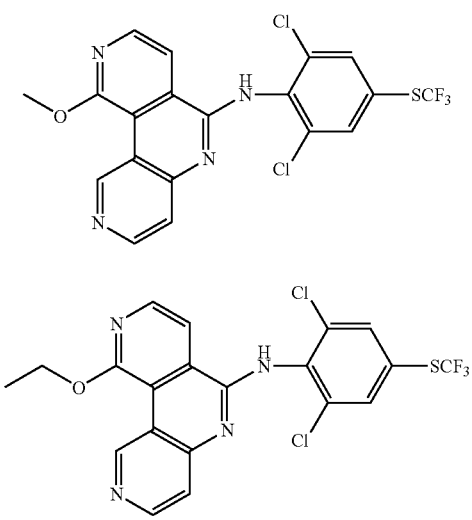

Step 2: N-{2,6-Dichloro-4-[(trifluoromethyl)thio]phenyl}-10-methoxypyrido[4,3-c]-1,6-naphthyridin-6-amine and N-{2,6-Dichloro-4-[(trifluoromethyl)thio]phenyl}-10-ethoxypyrido[4,3-c]-1,6-naphthyridin-6-amine A solution of N-{2,6-dichloro-4-[(trifluoromethyl)thio]phenyl}-10-ethoxypyrido[4,3-c]-1,6-naphthyridin-6-amine (15.5 mg, 0.032 mmol), 10-chloro-N-{2,6-dichloro-4-[(trifluoromethyl)thio]phenyl}pyrido[4,3-c]-1,6-naphthyridin-6-amine (15.19 mg, 0.032 mmol), and sodium methoxide (1 ml) was stirred in a microwave vial. The vial was heated to 100° C. for one hour. The crude reaction mixture was extracted with 3:1 chloroform:isopropanol and washed with water. The combined organics were concentrated under reduced pressure to afford the title compounds.

LRMS (ESI): Calculated for $C_{20}H_{13}Cl_2F_3N_4OS$ [M+H]+: 485, found 485.

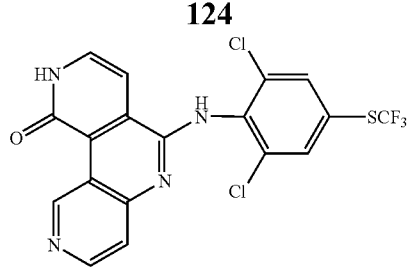

Step 3: 6-({2,6-Dichloro-4-[(trifluoromethyl)thio]phenyl}amino)pyrido[4,3-c]-1,6-naphthyridin-10(9H)-one A solution of N-{2,6-dichloro-4-[(trifluoromethyl)thio]phenyl}-10-methoxypyrido[4,3-c]-1,6-naphthyridin-6-amine (15 mg, 0.03 mmol), N-{2,6-dichloro-4-[(trifluoromethyl)thio]phenyl}-10-ethoxypyrido[4,3-c]-1,6-naphthyridin-6-amine (15 mg, 0.03 mmol) and boron tribromide (0.256 ml, 0.26 mmol) in chloroform (10 ml) was stirred in a microwave vial. The vial was sealed and heated to 85° C. for 45 minutes. The crude reaction mixture was washed with sodium bicarbonate and extracted with 3:1 chloroform:isopropanol. Combined organics were concentrated under reduced pressure to afford the title compound.

LRMS (ESI): Calculated for $C_{18}H_9Cl_2F_3N_4OS$ [M+H]+: 457, found 457.

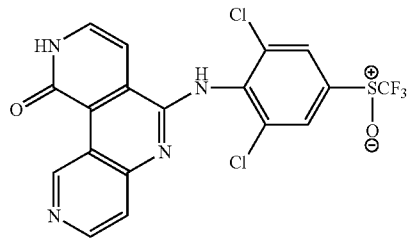

Step 4: 3,5-Dichloro-4-[(10-oxo-9,10-dihydropyrido[4,3-c]-1,6-naphthyridin-6-yl)amino]phenyl}(trifluoromethyl)sulfoniumolate A solution of 6-({2,6-dichloro-4-[(trifluoromethyl)thio]phenyl}amino)pyrido[4,3-c]-1,6-naphthyridin-10(9H)-one (10.4 mg, 0.02 mmol) and meta-Chloroperoxybenzoic acid (6.12 mg, 0.03 mmol) were stirred at 0° C. for 30 minutes. Sodium thiosulfate and sodium bicarbonate were added to neutralize and the mixture was stirred for an additional 30 minutes at room temperature. The organic layer was extracted with 3:1 chloroform:isopropanol and concentrated under reduced pressure to afford the title compound.

LRMS (ESI): Calculated for $C_{18}H_9Cl_2P_3N_4O_4S$ [M+H]+: 473, found 473.

EXAMPLE 156

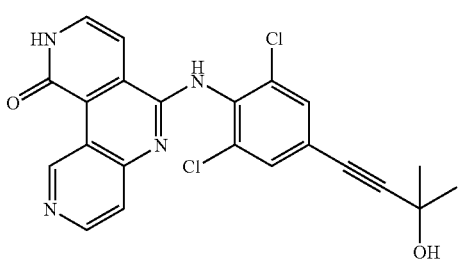 [SMILES: CC(C)(O)C#Cc1cc(Cl)c(Nc2nc3ccncc3c3c(=O)[nH]ccc23)c(Cl)c1]

6-{[2,6-Dichloro-4-(3-hydroxy-3-methylbut-1-yn-1-yl)phenyl]amino}pyrido[4,3-c]-1,6-naphthyridin-10(9H)-one

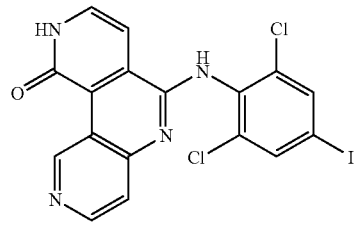 [SMILES: O=c1[nH]ccc2c(Nc3c(Cl)cc(I)cc3Cl)nc3ccncc3c12]

Step 1: 6-[(2,6-Dichloro-4-iodophenyl)amino]pyrido[4,3-c]-1,6-naphthyridin-10(9H)-one The title compound was synthesized following the procedure in Example 155, Steps 1, 2, and 3 using 6-chloro-10-ethoxypyrido[4,3-c]-1,6-naphthyridine (Example 133, Step 3), 6,10-dichloropyrido[4,3-c]-1,6-naphthyridine (124 mg, 0.495 mmol) (Example 133, Step 3), and 2,6-dichloro-4-iodoaniline as the starting materials.

LRMS (ESI) calc'd for $C_{17}H_{10}Cl_2IN_4O$ [M+H]$^+$, 482.9; found 483.0.

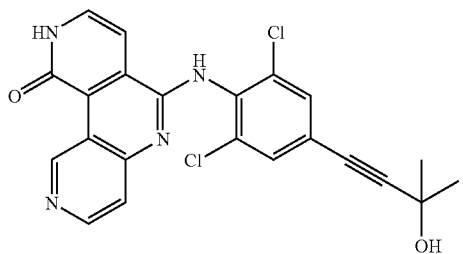

Step 2: 6-{[2,6-Dichloro-4-(3-hydroxy-3-methylbut-1-yn-1-yl)phenyl]amino}pyrido[4,3-c]-1,6-naphthyridin-10(9H)-one To a solution of 6-[(2,6-dichloro-4-iodophenyl)amino]pyrido[4,3-c]-1,6-naphthyridin-10(9H)-one (50 mg, 0.10 mmol) in DMF (4 mL) were added CuI (3.94 mg, 0.02 mmol), triethylamine (30 uL, 0.20 mmol), tetrakis(triphenylphosphine)palladium (0) (12 mg, 10.4 umol), and 2-methylbut-3-yn-2-ol (17.4 mg, 0.21 mmol). The mixture was degassed by bubbling nitrogen gas and heated to 80° C. overnight. After cooling to room temperature, the mixture was diluted with water and extracted with EtOAc. The organic layers were combined, dried with MgSO$_4$, filtered, and concentrated under reduced pressure. Purification by column chromatography on silica gel (100% CH$_2$Cl$_2$ to 70% CH$_2$Cl$_2$/30% MeOH) afforded the title compound.

LRMS (ESI) calc'd for $C_{22}H_{17}Cl_2N_4O_2$ [M+H]$^+$, 439.1; found 439.1.

EXAMPLE 157

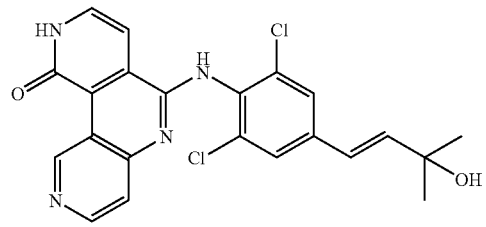 [SMILES: CC(C)(O)/C=C/c1cc(Cl)c(Nc2nc3ccncc3c3c(=O)[nH]ccc23)c(Cl)c1]

6-({2,6-Dichloro-4-[(1E)-3-hydroxy-3-methylbut-1-en-1-yl]phenyl}amino)pyrido[4,3-c]-1,6-naphthyridin-10(9H)-one Step 1: To a solution of 6-[(2,6-dichloro-4-iodophenyl)amino]pyrido[4,3-c]-1,6-naphthyridin-10(9H)-one (Example 156, Step 1) (30 mg, 0.06 mmol) in DMF (1.5 mL) were added sodium carbonate (2 M, 0.5 mL), tetrakis(triphenylphosphine)palladium (0) (14.3 mg, 0.12 mmol), and (3E)-2-methyl-4-(4,4,5,5-tetramethyl-1,3,2-dioxaborolan-2-yl)but-3-en-2-ol (13.2 mg, 0.06 mmol). The solution was degassed by bubbling nitrogen gas and heated to 80° C. overnight. After cooling to room temperature, the mixture was extracted with 3:1 CHCl$_3$/iPrOH. The organic layers were combined, dried with MgSO$_4$, filtered, and concentrated under reduced pressure. Purification by column chromatography on silica gel (100% CH$_2$Cl$_2$ to 70% CH$_2$Cl$_2$/30% MeOH) afforded the title compound.

LRMS (ESI) calc'd for $C_{22}H_{19}Cl_2N_4O_2$ [M+H]$^+$, 441.1; found 441.0

EXAMPLES 158 AND 159

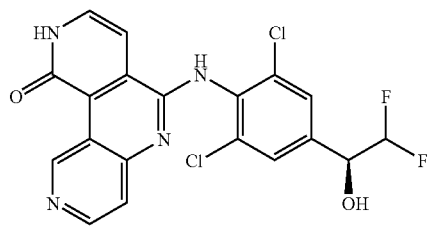

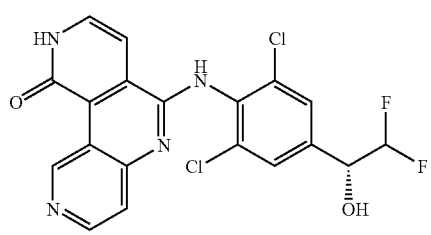

6-({2,6-Dichloro-4-[(1S)-2,2-difluoro-1-hydroxy-ethyl]phenyl}amino)pyrido[4,3-c]-1,6-naphthyridin-10(9H)-one and 6-({2,6-Dichloro-4-[(1R)-2,2-difluoro-1-hydroxyethyl]phenyl}amino)pyrido[4,3-c]-1,6-naphthyridin-10(9H)-one

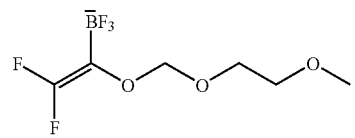

Step 1: Potassium {2,2-difluoro-1-[(2-methoxyethoxy)methoxy]vinyl(trifluoro)borate(1−)

To a solution of isopropylamine (4.77 ml, 33.5 mmol) in THF (20 mL) at −78° C. was added n-BuLi (13.4 mL, 33.5 mmol, 2.5 M in Hexanes). The solution was stirred at −78° C. for 15 min then 1,1,1-trifluoro-2-[(2-methoxyethoxy)methoxy]ethane, *Tetrahendron* 1995, 51, 9210 (3 g, 16 mmol) in THF (1 mL) was added followed by 1 mL THF wash. The solution was allowed to stir for 30 min then triisopropyl borate (7.40 mL, 32 mmol) was added and the solution was allowed to warm to −30° C. over 1.5 hr. The solution was quenched with NH$_4$Cl (5 mL) and warmed to room temperature. The solution was extracted with ether and water and the aqueous layer was acidified to pH=5 with concentrated HCl. The solution was extracted with ether 3× then dried with MgSO$_4$, filtered, and concentrated under reduced pressure. The yellow oil was taken up in acetone and water and stirred with postassium hydrogen fluoride (7.46 g, 96 mmol) for 1 hr and concentrated in a water bath at 35° C. on the rotavap. The solid was taken up in hot acetone and filtered to afford a yellow solution. The solution was concentrated under reduced pressure and taken up in 5 mL MeCN and 10 mL ether was slowly added. The precipitate was filtered and dried on high vacuum to afford the title compound.

$^1$H NMR (600 MHz, CD$_6$SO) 4.70 (s, 2H), 3.56 (m, 2H), 3.40 (m, 2H), 3.20 (s, 3H).

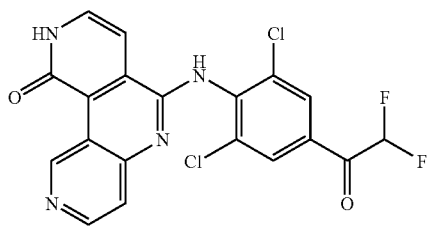

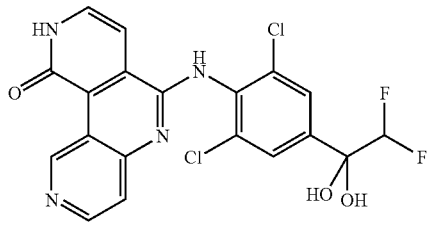

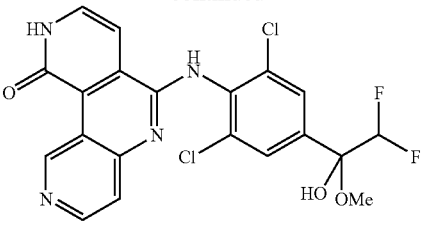

Step 2: 6-{[2,6-Dichloro-4-(difluoroacetyl)phenyl]amino}pyrido[4,3-c]-1,6-naphthyridin-10(9H)-one and 6-{[2,6-Dichloro-4-(2,2-difluoro-1,1-dihydroxyethyl)phenyl]amino}pyrido[4,3-c]-1,6-naphthyridin-10(9H)-one and 6-{[2,6-Dichloro-4-(2,2-difluoro-1-hydroxy-1-methoxyethyl)phenyl]amino}pyrido[4,3-c]-1,6-naphthyridin-10(9H)-one To a solution of 1:1 mixture of N-(2,6-dichloro-4-iodophenyl)-10-ethoxypyrido[4,3-c]-1,6-naphthyridin-6-amine and N-(2,6-dichloro-4-iodophenyl)-10-methoxypyrido[4,3-c]-1,6-naphthyridin-6-amine (Example 152, Step 1) (300 mg, 0.59 mmol and 300 mg, 0.60 mmol) in n-PrOH (12 mL) were added triethylamine (0.491 mL, 3.52 mmol), potassium {2,2-difluoro-1-[(2-methoxyethoxy)methoxy]vinyl}(trifluoro)borate(1−) (708 mg, 2.58 mmol), and PdCl$_2$(dppf)-CH$_2$Cl$_2$ adduct (96 mg, 0.12 mmol). The solution was degassed by bubbling nitrogen gas and heated to 90° C. overnight. After cooling to room temperature, the solution was extracted with EtOAc and water. The organic layer was dried with MgSO$_4$, filtered, and concentrated under reduced pressure. Purification by chromatography on silica gel (100% hexanes to 100% EtOAc) afforded a mixture of N-(2,6-dichloro-4-{2,2-difluoro-1-[(2-methoxyethoxy)methoxy]vinyl}phenyl)-10-methoxypyrido[4,3-c]-1,6-naphthyridin-6-amine and N-(2,6-dichloro-4-{2,2-difluoro-1-[(2-methoxyethoxy)methoxy]vinyl}phenyl)-10-ethoxypyrido[4,3-c]-1,6-naphthyridin-6-amine. This mixture (528 mg) was taken up in CHCl$_3$ (10 mL) and added BBr$_3$ (3.35 mL, 3.35 mmol, 1.0M in CH$_2$Cl$_2$). The solution was heated to 85° C. for 40 min then cooled to room temperature. The reaction mixture was extracted with 3:1 CHCl$_3$/iPrOH and washed with saturated NaHCO$_3$. The organic layer was dried with MgSO$_4$, filtered, and concentrated under reduced pressure. Purification by chromatography on silica gel (100% CH$_2$Cl$_2$ to 70% CH$_2$Cl$_2$/30% MeOH) afforded a 1:1:1 mixture of 6-{[2,6-dichloro-4-(difluoroacetyl)phenyl]amino}pyrido[4,3-c]-1,6-naphthyridin-10(9H)-one and an inseperable mixture of 6-{[2,6-dichloro-4-(2,2-difluoro-1,1-dihydroxyethyl)phenyl]amino}pyrido[4,3-c]-1,6-naphthyridin-10(9H)-one and 6-{[2,6-dichloro-4-(2,2-difluoro-1-hydroxy-1-methoxyethyl)phenyl]amino}pyrido[4,3-c]-1,6-naphthyridin-10(9H)-one.

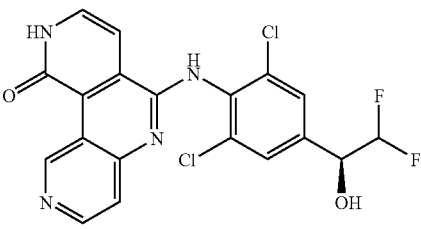

-continued

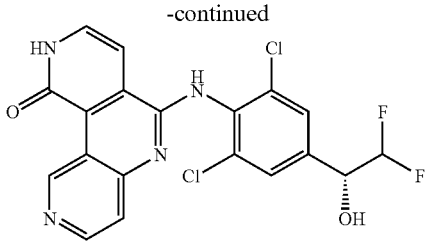

Step 3: 6-({2,6-Dichloro-4-[(1S)-2,2-difluoro-1-hydroxyethyl]phenyl}amino)pyrido[4,3-c]-1,6-naphthyridin-10(9H)-one and 6-({2,6-dichloro-4-[(1R)-2,2-difluoro-1-hydroxyethyl]phenyl}amino)pyrido[4,3-c]-1,6-naphthyridin-10(9H)-one To an inseparable mixture of 6-{[2,6-dichloro-4-(2,2-difluoro-1,1-dihydroxyethyl)phenyl]amino}pyrido[4,3-c]-1,6-naphthyridin-10(9H)-one and 6-{[2,6-dichloro-4-(2,2-difluoro-1-hydroxy-1-methoxyethyl)phenyl]amino}pyrido[4,3-c]-1,6-naphthyridin-10(9H)-one (100 mg) at 0° C. in MeOH (5 mL) was added sodium borohydride (25 mg, 0.66 mmol) and the reaction was stirred for 30 min. The solution was concentrated and dry loaded onto a silica gel column for purification (100% $CH_2Cl_2$ to 70% $CH_2Cl_2$ 30% MeOH). The racemates were separated using a chiralpak AD column eluting with 75% Hex/25% iPrOH isochratic. The first peak has a retention time of 8.58 min and the second peak has a retention time of 14.59 min.

For both enantiomers LRMS (ESI) calc'd for $C_{19}H_{13}Cl_2F_2N_4O_2$ $[M+H]^+$, 437.0; found 437.0.

EXAMPLE 160

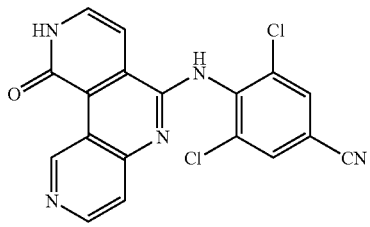 [SMILES: N#Cc1cc(Cl)c(Nc2nc3ccncc3c3c(=O)[nH]ccc23)c(Cl)c1]

3,5-Dichloro-4-[(10-oxo-9,10-dihydropyrido[4,3-c]-1,6-naphthyridin-6-yl)amino]benzonitrile

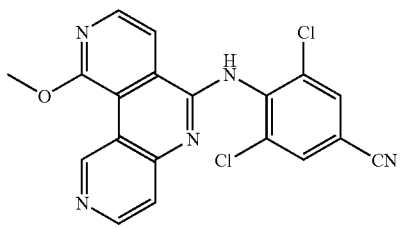 [SMILES: COc1nccc2c(Nc3c(Cl)cc(C#N)cc3Cl)nc3ccncc3c12]

Step 1: 3,5-Dichloro-4-[(10-methoxypyrido[4,3-c]-1,6-naphthyridin-6-yl)amino]benzonitrile To a solution of N-(2,6-dichloro-4-iodophenyl)-10-methoxypyrido[4,3-c]-1,6-naphthyridin-6-amine (Example 152, Step 1) (1.0 g, 2.01 mmol) in DMF (10 mL) was added zinc cyanide (283 mg, 2.41 mmol) and $Pd(Ph_3P)_4$ (465 mg, 0.402 mmol). The reaction was stirred at 80° C. for 2.5 h in a sealed tube. After cooling to room temperature, the reaction was diluted with ethyl acetate and washed with water followed by brine. The organic layer was dried with sodium sulfate, filtered and concentrated under reduced pressure. The residue was purified by column chromatography on silica gel eluting with methanol in dichloromethane to afford the title compound.

LRMS (ESI) calc'd for $C_{19}H_{12}Cl_2N_5O$ $[M+H]^+$, 396.0; found 396.0.

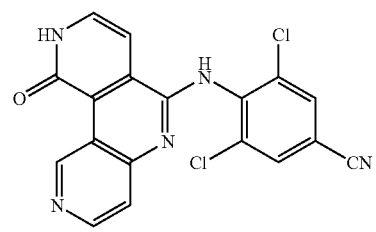 [SMILES: N#Cc1cc(Cl)c(Nc2nc3ccncc3c3c(=O)[nH]ccc23)c(Cl)c1]

Step 2: 3,5-Dichloro-4-[(10-oxo-9,10-dihydropyrido[4,3-c]-1,6-naphthyridin-6-yl)amino]benzonitrile To a solution of 3,5-dichloro-4-[(10-methoxypyrido[4,3-c]-1,6-naphthyridin-6-yl)amino]benzonitrile (140 mg, 0.35 mmol) in chloroform (3 mL) was added boron tribromide (2.5 mL, 2.5 mmol, 1M in dichloromethane) and the mixture was heated at 85° C. for 45 min in a sealed tube. After cooling to room temperature, the reaction was diluted with ethyl acetate and washed with saturated aqueous sodium bicarbonate, followed by brine. The organic layer was dried with sodium sulfate, filtered and concentrated under reduced pressure. The residue was purified by column chromatography on silica gel eluting with MeOH in dichloromethane to afford the title compound.

LRMS (ESI) calc'd for $C_{18}H_{10}Cl_2N_5O$ $[M+H]^+$, 382.0; found 382.0.

EXAMPLE 161

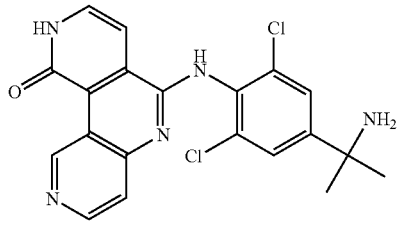 [SMILES: CC(C)(N)c1cc(Cl)c(Nc2nc3ccncc3c3c(=O)[nH]ccc23)c(Cl)c1]

6-{[4-(1-Amino-1-methylethyl)-2,6-dichlorophenyl]amino}pyrido[4,3-c]-1,6-naphthyridin-10(9H)-one Step 1: A suspension of cerium(III) chloride (80 mg, 0.32 mmol) in THF (2 ml) was heated to 45° C. for 3 h. After cooling to room temperature, 3,5-dichloro-4-[(10-oxo-9,10-dihydropyrido[4,3-c]-1,6-naphthyridin-6-yl)amino]benzonitrile (Example 160, Step 2) (40 mg, 0.11 mmol) was added. The mixture was cooled to −30° C. and methyllithium (0.33 ml, 0.53 mmol, 1.6 M in diethyl ether) was added dropwise keeping the temp between −30 and −15° C. The reaction was stirred for an additional 45 min keeping the temperature between −15-0° C. The reaction was warmed to 10° C. and stirred for 40 min. The reaction was quenched with NH$_4$OH, warmed to room temperature and stirred for 1 hr. The reaction was diluted with iPrOH/CHCl3 (1:3), and washed with water, followed by brine. The organic layer was dried with sodium sulfate, filtered and concentrated under reduced pressure. The residue was purified by column chromatography on silica gel eluting with MeOH in dichloromethane to afford the title compound.

LRMS (ESI) calc'd for $C_{20}H_{18}Cl_2N_5O$ [M+H]$^+$, 414.1; found 414.0.

Additional analogues shown below were prepared using procedures similar to those described in the above examples and general methods.

Step 1: 3,5-Dichloro-4-[(10-ethoxypyrido[4,3-c]-1,6-naphthyridin-6-yl)amino]-N'-hydroxybenzenecarboximidamide To a solution of 3,5-dichloro-4-[(10-ethoxypyrido[4,3-c]-1,6-naphthyridin-6-yl)amino]benzonitrile (Example 160, Step 1) (200 mg, 0.49 mmol) in ethanol (6 mL) was added triethylamine (0.285 mL, 2.04 mmol) and hydroxyammonium chloride (105 mg, 1.51 mmol). The reaction mixture was heated to 80° C. for 3 h in a sealed tube. After cooling to room temperature, the solid was filtered, washed with ethanol and water and dried under vacuum to afford the title compound.

LRMS (ESI) calc'd for $C_{20}H_{17}Cl_2N_6O_2$ [M+H]$^+$, 443.1; found 443.0.

TABLE 9

| Example | Structure | Compound Name | LCMS (M + H)$^+$ |
|---|---|---|---|
| 162 | 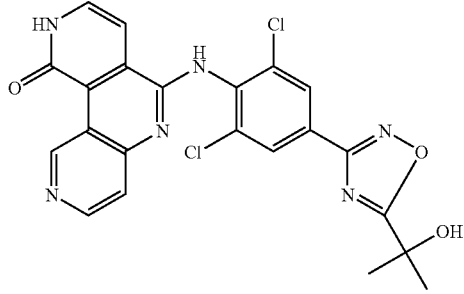 [SMILES: CC(C)(O)c1nc(-c2cc(Cl)c(Nc3nc4ccncc4c4c(=O)[nH]ccc34)c(Cl)c2)no1] | 5-{[5-(1-amino-1-methylethyl)-2-methylphenyl]amino}-9-bromobenzo[c]-2,6-naphthyridin-1(2H)-one | Calc'd 437.1, found 437.1 |

EXAMPLE 163

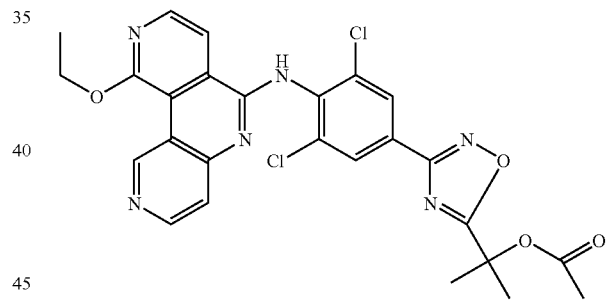

6-({2,6-Dichloro-4-[5-(1-hydroxy-1-methylethyl)-1,2,4-oxadiazol-3-yl]phenyl}amino)pyrido[4,3-c]-1,6-naphthyridin-10(9H)-one

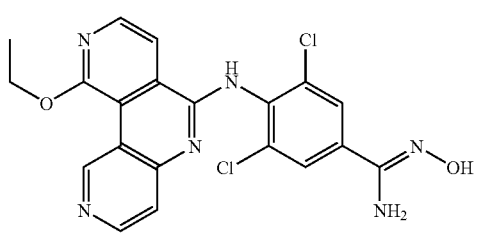 [SMILES: CCOc1nccc2c(Nc3c(Cl)cc(/C(N)=N/O)cc3Cl)nc3ccncc3c12]

Step 2: 1-(3-{3,5-Dichloro-4-[(10-ethoxypyrido[4,3-c]-1,6-naphthyridin-6-yl) amino]phenyl}-1,2,4-oxadiazol-5-yl)-1-methylethyl acetate To a solution of 3,5-dichloro-4-[(10-ethoxypyrido[4,3-c]-1,6-naphthyridin-6-yl)amino]-N'-hydroxybenzenecarboximidamide (50 mg, 0.11 mmol) in 1,4-dioxane (1 mL) was added pyridine (0.1 mL) and 2-chloro-1,1-dimethyl-2-oxoethyl acetate (0.016 mL, 0.11 mmol). The reaction was heated to 110° C. for 4 h in a sealed tube. After cooling to room temperature, the solvents were evaporated and the residue was dissolved in THF/MeOH, filtered and purified by reverse phase HPLC to afford the title compound.

LRMS (ESI) calc'd for $C_{26}H_{23}Cl_2N_6O_4$ [M+H]$^+$, 553.1; found 553.0.

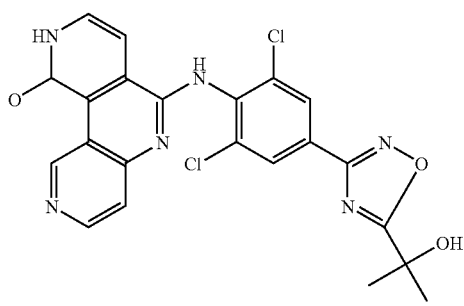 [SMILES: CC(C)(O)c1nc(-c2cc(Cl)c(Nc3nc4ccncc4c4c3C=CNC4O)c(Cl)c2)no1]

Step 3: 6-({2,6-Dichloro-4-[5-(1-hydroxy-1-methyl-ethyl)-1,2,4-oxadiazol-3-yl]phenyl}amino)pyrido[4,3-c]-1,6-naphthyridin-10(9H)-one To a solution of 1-(3-{3,5-dichloro-4-[(10-ethoxypyrido[4,3-c]-1,6-naphthyridin-6-yl)amino]phenyl}-1,2,4-oxadiazol-5-yl)-1-methylethyl acetate (63 mg, 0.11 mmol) in THF (3 mL) was added HCl (0.188 mL, 1.13 mmol, 6M in water) and the mixture was heated to 60° C. for 45 min in a sealed tube. After cooling to room temperature, the reaction was diluted with ethyl acetate/THF (3:1) and washed with saturated aqueous sodium bicarbonate, followed by brine. The organic layer was dried with sodium sulfate, filtered and concentrated under reduced pressure. The residue was purified by column chromatography on silica gel eluting with MeOH in dichloromethane to afford the title compound.

LRMS (ESI) calc'd for $C_{22}H_{17}Cl_2N_6O_3$ [M+H]$^+$, 483.1; found 483.0.

EXAMPLE 164

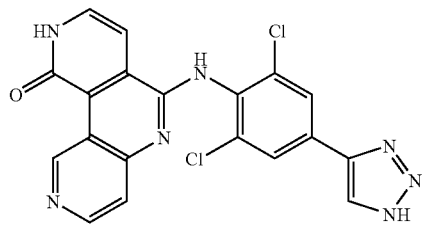 [SMILES: O=c1[nH]ccc2c(Nc3c(Cl)cc(-c4c[nH]nn4)cc3Cl)nc3ccncc3c12]

6-{[2,6-Dichloro-4-(1H-1,2,3-triazol-4-yl)phenyl]amino}pyrido[4,3-c]-1,6-naphthyridin-10(9H)-one

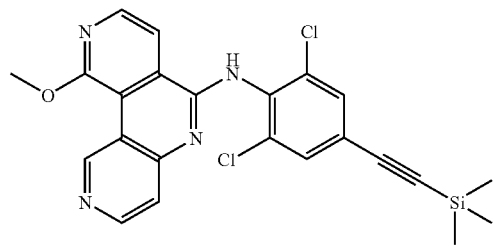

Step 1: N-{2,6-Dichloro-4-[(trimethylsilyl)ethynyl]phenyl}-10-methoxypyrido[4,3-c]-1,6-naphthyridin-6-amine A solution of N-(2,6-dichloro-4-iodophenyl)-10-methoxypyrido[4,3-c]-1,6-naphthyridin-6-amine (Example 152, Step 1) (125 mg, 0.25 mmol) in DMF (3 mL) was degassed with nitrogen. Triethylamine (0.070 ml, 0.50 mmol), 2-methylbut-3-yn-2-ol (42.0 mg, 0.50 mmol), Pd(Ph$_3$P)$_4$ (29 mg, 0.03 mmol) and copper(I) iodide (9.50 mg, 0.050 mmol) were added and the reaction mixture was heated to 65° C. for 16 h. After cooling to room temperature, the reaction was diluted with ethyl acetate and washed with water. The organic layer was dried with sodium sulfate, filtered and concentrated under reduced pressure. The residue was purified by column chromatography on silica gel eluting with ethyl acetate in hexanes to afford the title compound.

LRMS (ESI) calc'd for $C_{23}H_{21}Cl_2N_4OSi$ [M+H]$^+$, 467.1; found 467.0

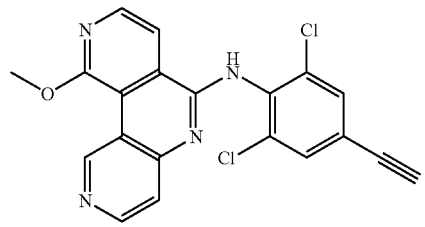 [SMILES: C#Cc1cc(Cl)c(Nc2nc3ccncc3c3c(OC)nccc23)c(Cl)c1]

Step 2: N-(2,6-Dichloro-4-ethynylphenyl)-10-methoxypyrido[4,3-c]-1,6-naphthyridin-6-amine To a solution of N-{2,6-dichloro-4-[(trimethylsilyl)ethynyl]phenyl}-10-methoxypyrido[4,3-c]-1,6-naphthyridin-6-amine (118 mg, 0.25 mmol) in methanol (3 mL) was added K$_2$CO$_3$ (38.4 mg, 0.28 mmol) and stirred at room temperature overnight. The solvents were evaporated and the residue was diluted with ethyl acetate and washed with water followed by brine. The organic layer was dried with sodium sulfate, filtered and concentrated under reduced pressure to afford the title compound.

LRMS (ESI) calc'd for $C_{20}H_{13}Cl_2N_4O$ [M+H]$^+$, 395.1; found 395.0.

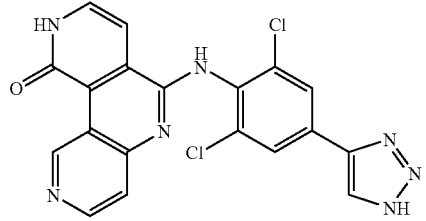 [SMILES: O=c1[nH]ccc2c(Nc3c(Cl)cc(-c4c[nH]nn4)cc3Cl)nc3ccncc3c12]

Step 3: 6-{[2,6-Dichloro-4-(1H-1,2,3-triazol-4-yl)phenyl]amino}pyrido[4,3-c]-1,6-naphthyridin-10(9H)-one N-(2,6-Dichloro-4-ethynylphenyl)-10-methoxypyrido[4,3-c]-1,6-naphthyridin-6-amine (66 mg, 0.167 mmol) and TMS-N$_3$ (1.5 mL, 11.30 mmol) were combined and heated in a sealed tube to 150° C. for 16 h. Volatiles were evaporated under vacuum. To the residue was added chloroform (1 mL) and boron tribromide (1.2 mL, 1.2 mmol, 1M in dichloromethane) and the mixture was heated at 85° C. for 45 min in a sealed tube. After cooling to room temperature, the reaction was diluted with ethyl acetate and washed with saturated aqueous sodium bicarbonate, followed by brine. The organic layer was dried with sodium sulfate, filtered and concentrated under reduced pressure. The residue was dissolved in THF/MeOH, filtered and purified by reverse phase HPLC to afford the title compound.

$^1$H NMR (500 MHz, CD$_3$OD) δ 10.93 (bs, 1H), 8.52 (dd, 1H), 8.36 (bs, 1H), 8.10 (bs, 2H), 7.92 (bs, 1H), 7.79 (m, 1H), 7.41 (m, 1H). LRMS (APCI) calc'd for ($C_{21}H_{18}Cl_2N_3O_3$) [M+H]$^+$, LRMS (ESI) calc'd for $C_{19}H_{12}Cl_2N_7O$ [M+H]$^+$, 424.1; found 424.0.

EXAMPLE 165

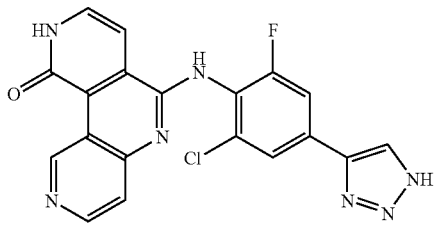 [SMILES: O=c1[nH]ccc2c(Nc3c(F)cc(-c4c[nH]nn4)cc3Cl)nc3ccncc3c12]

6-{[2-Chloro-6-fluoro-4-(1H-1,2,3-triazol-4-yl)phenyl]amino}pyrido[4,3-c]-1,6-naphthyridin-10(9H)-one Step 1: The title compound was synthesized using the procedure from (Example 164, Step 2) using N-[2-chloro-6-fluoro-4-(1H-1,2,3-triazol-4-yl)phenyl]-10-methoxypyrido[4,3-c]-1,6-naphthyridin-6-amine as a starting material (46 mg, 0.108 mmol).

LRMS (ESI) calc'd for $C_{19}H_{12}ClFN_7O$ [M+H]$^+$, 408.1; found 408.0.

EXAMPLE 166

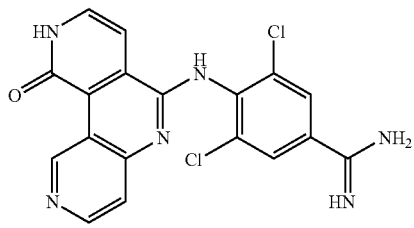 [SMILES: N=C(N)c1cc(Cl)c(Nc2nc3ccncc3c3c(=O)[nH]ccc23)c(Cl)c1]

3,5-Dichloro-4-[(10-oxo-9,10-dihydropyrido[4,3-c]-1,6-naphthyridin-6-yl)amino]benzenecarboximidamide Step 1: To a solution of 3,5-dichloro-4-[(10-ethoxypyrido[4,3-c]-1,6-naphthyridin-6-yl)amino]benzonitrile (Example 160, Step 1) (50 mg, 0.12 mmol) in THF (3 mL) was added LiHMDS (1.22 mL, 1.22 mmol, 1M in THF) and the mixture was stirred at room temperature overnight. The mixture was diluted with EtOAc and water. Extraction with EtOAc followed by drying of the organic layers with MgSO$_4$, filtering, and concentration to under reduced pressure afforded the amidine. The crude amidine (40 mg, 0.094 mmol) in CHCl$_3$ (2 mL) was heated with BBr$_3$ (0.93 mL, 0.93 mmol) for 40 min then extracted with saturated NaHCO$_3$ and EtOAc. The compound was purified by reverse phase HPLC (100% H$_2$O to 100% MeCN) to afford the title compound.

LRMS (ESI) calc'd for $C_{18}H_{13}Cl_2N_6O$ [M+H]$^+$, 399.1; found 399.0.

EXAMPLE 167

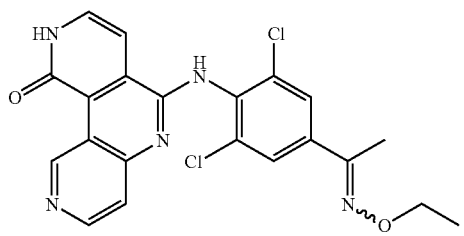 [SMILES: CCON=C(C)c1cc(Cl)c(Nc2nc3ccncc3c3c(=O)[nH]ccc23)c(Cl)c1]

E/Z mixture 6-({2,6-Dichloro-4-[N-ethoxyethanimidoyl]phenyl}amino)pyrido[4,3-c]-1,6-naphthyridin-10(9H)-one Step 1: To a solution of 6-[(4-acetyl-2,6-dichlorophenyl)amino]pyrido[4,3-c]-1,6-naphthyridin-10(9H)-one (Examples 144 and 145, Step 3) (20 mg, 0.50 mmol) in MeOH (1 mL) was added N-hydroxyethanamine HCl (24 mg, 0.25 Minot) and sodium acetate (21 mg, 0.25 mmol). The solution was heated to 85° C. for 1 hr then cooled to room temperature and extracted with 3:1 CHCl$_3$/iPrOH and water. The organic layers were dried with MgSO$_4$, filtered, and concentrated under reduced pressure. Purification by silica gel chromatography (100% CH$_2$Cl$_2$ to 70% CH$_2$Cl$_2$ 30% MeOH) provided the product as a mixture of rotamers and E/Z isomers.

LRMS (ESI) calc'd for $C_{21}H_{18}Cl_2N_5O_2$ [M+H]$^+$, 442.1; found 442.1.

Additional analogues shown below were prepared using procedures similar to those described in the above example.

TABLE 10

| Example | Structure | Compound Name | LRMS (M + H)$^+$ |
|---|---|---|---|
| 168 | ![structure] | 6-({2,6-dichloro-4-[(N-(2-morpholin-4-yl-2-oxoethoxy)ethanimidoyl]phenyl}amino)pyrido[4,3-c]-1,6-naphthyridin-10(9H)-one | Calc'd: 541.1 found: 541.1 |

TABLE 10-continued

| Example | Structure | Compound Name | LRMS (M + H)+ |
|---|---|---|---|
| 169 | 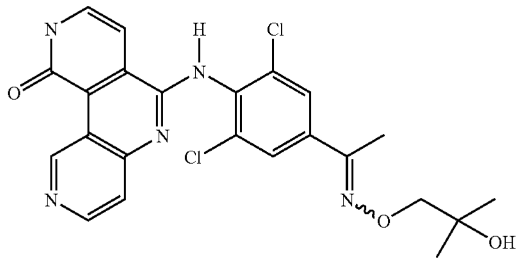 [SMILES: CC(=NOCC(C)(C)O)c1cc(Cl)c(Nc2nc3ccncc3c3c(=O)[nH]ccc23)c(Cl)c1] | 6-({2,6-dichloro-4-[(N-(2-hydroxy-2-methylpropoxy)ethanimidoyl]phenyl}amino)pyrido[4,3-c]-1,6-naphthyridin-10(9H)-one | Calc'd: 486.1 found: 486.1 |
| 170 | 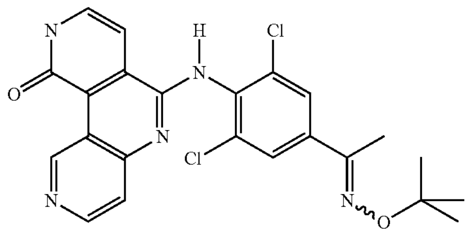 [SMILES: CC(=NOC(C)(C)C)c1cc(Cl)c(Nc2nc3ccncc3c3c(=O)[nH]ccc23)c(Cl)c1] | 6-({4-[N-(tert-butoxy)ethanimidoyl]-2,6-dichlorophenyl}amino)pyrido[4,3-c]-1,6-naphthyridin-10(9H)-one | Calc'd: 470.1 found: 470.1 |
| 171 | 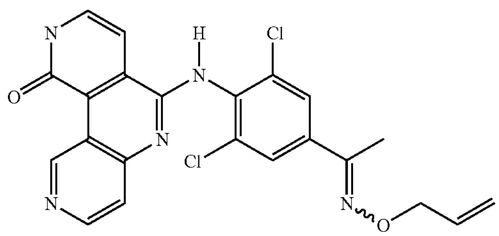 [SMILES: C=CCON=C(C)c1cc(Cl)c(Nc2nc3ccncc3c3c(=O)[nH]ccc23)c(Cl)c1] | 6-({4-[N-(allyloxy)ethanimidoyl]-2,6-dichlorophenyl}amino)pyrido[4,3-c]-1,6-naphthyridin-10(9H)-one | Calc'd: 454.1 found: 454.1 |

EXAMPLE 172

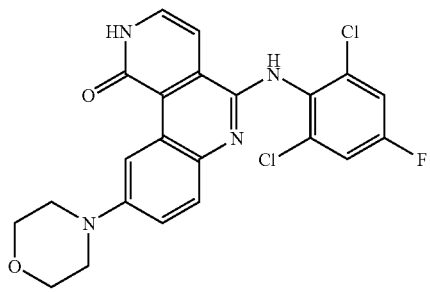 [SMILES: O=c1[nH]ccc2c(Nc3c(Cl)cc(F)cc3Cl)nc3ccc(N4CCOCC4)cc3c12]

5-[(2,6-Dichloro-4-fluorophenyl)amino]-9-morpholin-4-ylbenzo[c]-2,6-naphthyridin-1(2H)-one

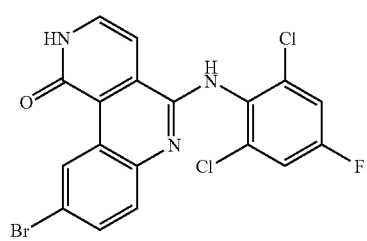 [SMILES: O=c1[nH]ccc2c(Nc3c(Cl)cc(F)cc3Cl)nc3ccc(Br)cc3c12]

Step 1: 9-Bromo-5-[(2,6-dichloro-4-fluorophenyl)amino]benzo[c]-2,6-naphthyridin-1(2H)-one The title compound was prepared according to the procedure in (Example 4, Step 4) using 9-bromo-N-(2,6-dichloro-4-fluorophenyl)-1-methoxybenzo[c]-2,6-naphthyridin-5-amine as the starting material.

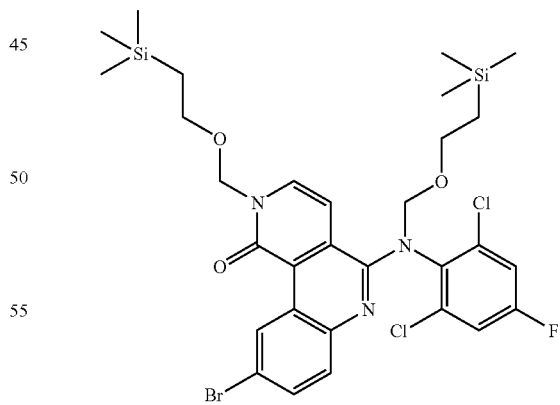

Step 1: 9-Bromo-5-(((2,6-dichloro-4-fluorophenyl){[2-(trimethylsilyl)ethoxy]methyl}amino)-2-{[2-(trimethylsilyl)ethoxy]methyl}benzo[c]-2,6-naphthyridin-1(2H)-one To a slurry of NaH (252 mg, 6.29 mmol) in THF (20 ml) was added 9-bromo-5-[(2,6-dichloro-4-fluorophenyl)amino]

benzo[c]-2,6-naphthyridin-1(2H)-one (950 mg, 2.097 mmol) and the mixture was stirred for 5 min. [2-(Chloromethoxy) ethyl](trimethyl)silane (1.116 ml, 6.29 mmol) was added and the mixture was stirred at room temperature overnight. The solution was quenched with MeOH and concentrated under reduced pressure. The residue was purified by flash chromatography (0-30% ethyl acetate in hexanes) to afford the title compound.

LRMS (APCI) calc'd for $C_{30}H_{38}BrCl_2FN_3O_3Si_2$ [M+H]$^+$, 712.1; found 712.8.

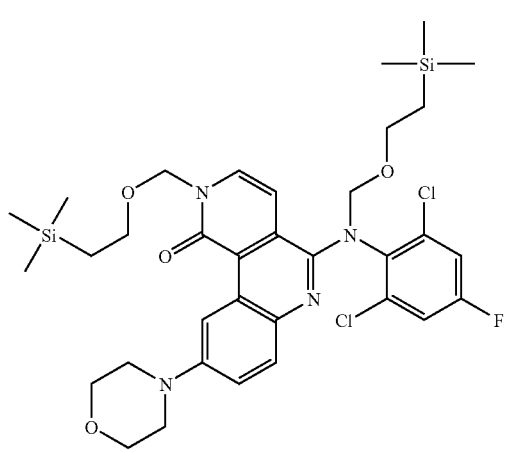 [SMILES: C[Si](C)(C)CCOCN(c1c(Cl)cc(F)cc1Cl)c1nc2ccc(N3CCOCC3)cc2c2c(=O)n(COCC[Si](C)(C)C)ccc12]

Step 2: 5-((2,6-Dichloro-4-fluorophenyl){[2-(trimethylsilyl)ethoxy]methyl}amino)-9-morpholin-4-yl-2-{[2-(trimethylsilyl)ethoxy]methyl}benzo[c]-2,6-naphthyridin-1(2H)-one To a solution of 9-bromo-5((2,6-dichloro-4-fluorophenyl){[2-(trimethylsilyl)ethoxy]methyl}amino)-2-{[2-(trimethylsilyl)ethoxy]methyl}benzo[c]-2,6-naphthyridin-1(2H)-one (58 mg, 0.08 mmol) in dioxane (2 ml) was added morpholine (14.16 mg, 0.16 mmol), xantphos (9.41 mg, 0.02 mmol), cesium carbonate(79 mg, 0.24 mmol) and $Pd_2(dba)_3$ (7.44 mg, 8.13 µmol). The solution was degassed by bubbling nitrogen for few minutes and heated to 100° C. in a sealed tube for 16 h. After cooling to room temperature, the reaction mixture was filtered and the filtrate was evaporated under vacuum to afford the title compound.

LRMS (ESI calc'd for $C_{34}H_{46}Cl_2FN_4O_4Si_2$ [M+H]$^+$, 719.24; found 719.0.

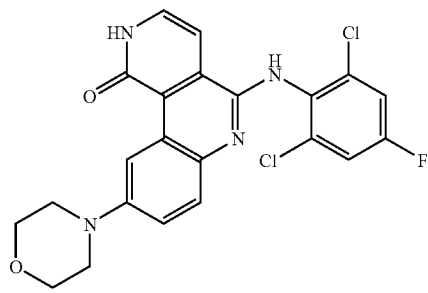 [SMILES: O=c1[nH]ccc2c(Nc3c(Cl)cc(F)cc3Cl)nc3ccc(N4CCOCC4)cc3c12]

Step 3: 5-[(2,6-Dichloro-4-fluorophenyl)amino]-9-morpholin-4-ylbenzo[c]-2,6-naphthyridin-1(2H)-one To a solution of 5-((2,6-dichloro-4-fluorophenyl){[2-(trimethylsilyl)ethoxy]methyl}amino)-9-morpholin-4-yl-2-{[2-(trimethylsilyl)ethoxy]methyl}benzo[c]-2,6-naphthyridin-1(2H)-one (58 mg, 0.08 mmol) in dichloromethane (3 mL) was added TFA (2 ml) and the mixture was stirred at room temperature for 2.5 h. The solvents were evaporated and the residue was dissolved in MeOH, filtered and purified by reverse phase HPLC to afford the title compound.

$^1$H NMR (600 MHz, CD$_3$OD) δ 9.59 (s, 1H), 7.74 (m, 2H), 7.57 (m, 3H), 7.28 (d, 1H), 3.91 (m, 4H), 3.42 (m, 4H). LRMS (ESI) calc'd for $C_{22}H_{18}Cl_2FM_4O_2$ [M+H]$^+$, 459.08; found 459.0.

Additional analogues shown below were prepared using procedures similar to those described in the above examples and general methods.

TABLE 11

| Example | Structure | Compound Name | LRMS (M + H)$^+$ |
|---|---|---|---|
| 173 | 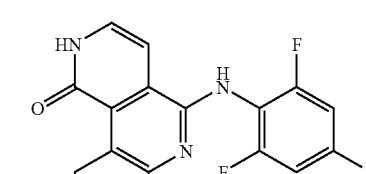 | 4-(2-hydroxyethyl)-N-{1-oxo-5-[(2,4,6-trifluorophenyl)amino]-1,2-dihydrobenzo[c]-2,6-naphthyridin-9-yl}piperazine-1-carboxamide | Calc'd: 513.2, found: 513.1 |

TABLE 11-continued

| Example | Structure | Compound Name | LRMS (M + H)+ |
|---|---|---|---|
| 174 | 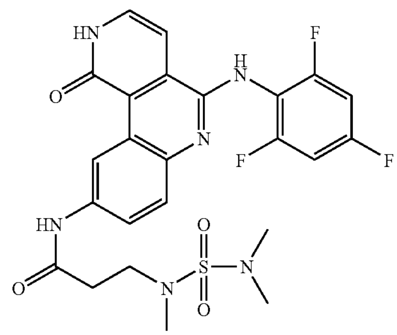 [SMILES: CN(C)S(=O)(=O)N(C)CCC(=O)Nc1ccc2nc(Nc3c(F)cc(F)cc3F)c3cc[nH]c(=O)c3c2c1] | N3-[(dimethylamino)sulfonyl]-N3-methyl-N-{1-oxo-5-[(2,4,6-trifluorophenyl)amino]-1,2-dihydrobenzo[c]-2,6-naphthyridin-9-yl}-b-alaninamide | Calc'd: 549.1, found: 549.1 |
| 175 | 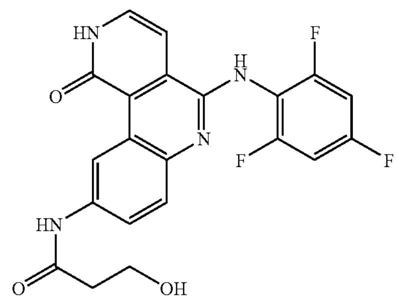 [SMILES: O=C(CCO)Nc1ccc2nc(Nc3c(F)cc(F)cc3F)c3cc[nH]c(=O)c3c2c1] | 3-hydroxy-N-{1-oxo-5-[(2,4,6-trifluorophenyl)amino]-1,2-dihydrobenzo[c]-2,6-naphthyridin-9-yl}propanamide | Calc'd: 429.1, found: 429.2 |
| 176 | 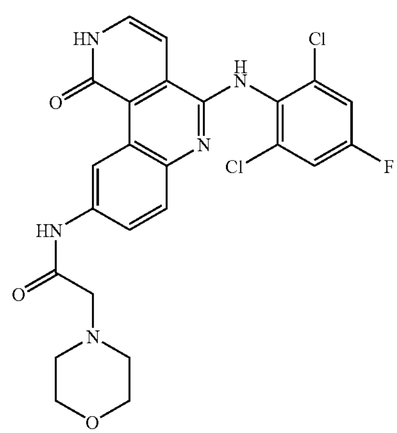 [SMILES: O=C(CN1CCOCC1)Nc1ccc2nc(Nc3c(Cl)cc(F)cc3Cl)c3cc[nH]c(=O)c3c2c1] | N-{5-[(2,6-dichloro-4-fluorophenyl)amino]-1-oxo-1,2-dihydrobenzo[c]-2,6-naphthyridin-9-yl}-2-morpholin-4-ylacetamide | Calc'd: 516.1, found: 516.0 |
| 177 | 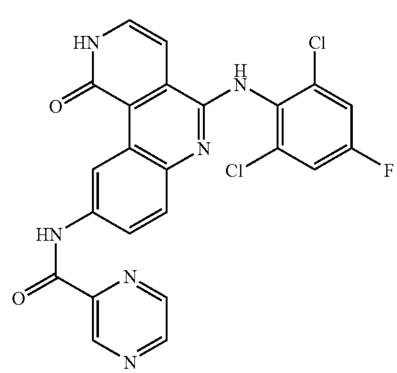 [SMILES: O=C(Nc1ccc2nc(Nc3c(Cl)cc(F)cc3Cl)c3cc[nH]c(=O)c3c2c1)c1cnccn1] | N-{5-[(2,6-dichloro-4-fluorophenyl)amino]-1-oxo-1,2-dihydrobenzo[c]-2,6-naphthyridin-9-yl}pyrazine-2-carboxamide | Calc'd: 495.1, found: 495.0 |

TABLE 11-continued

| Example | Structure | Compound Name | LRMS (M + H)+ |
|---|---|---|---|
| 178 | 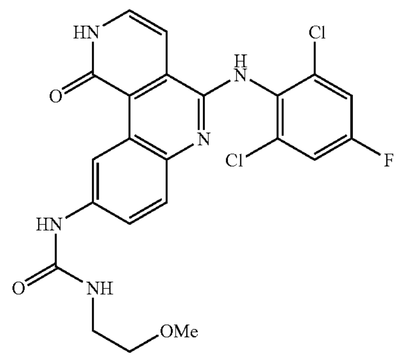 [SMILES: COCCNC(=O)Nc1ccc2nc(Nc3c(Cl)cc(F)cc3Cl)c3cc[nH]c(=O)c3c2c1] | N-{5-[(2,6-dichloro-4-fluorophenyl)amino]-1-oxo-1,2-dihydrobenzo[c]-2,6-naphthyridin-9-yl}-N'-(2-methoxyethyl)urea | Calc'd: 490.1, found: 490.0 |
| 179 | 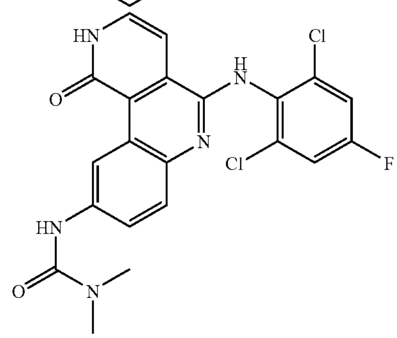 | N'-{5-[(2,6-dichloro-4-fluorophenyl)amino]-1-oxo-1,2-dihydrobenzo[c]-2,6-naphthyridin-9-yl}-N,N-dimethylurea | Calc'd: 460.1, found: 460.0 |
| 180 | 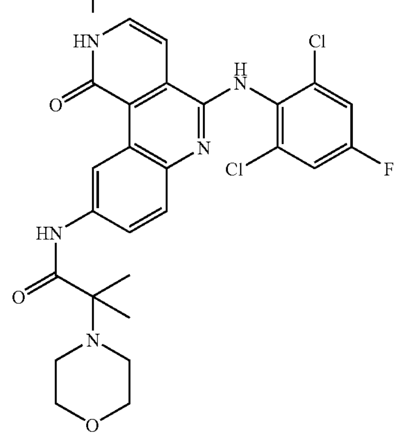 | N-{5-[(2,6-dichloro-4-fluorophenyl)amino]-1-oxo-1,2-dihydrobenzo[c]-2,6-naphthyridin-9-yl}-2-methyl-2-morpholin-4-ylpropanamide | Calc'd: 544.1, found: 544.1 |

EXAMPLE 181

5-[(2,6-Dichloro-4-fluorophenyl)amino]-9-[(2-hydroxy-2-pyrazin-2-ylethyl)amino]benzo[c]-2,6-naphthyridin-1(2H)-one

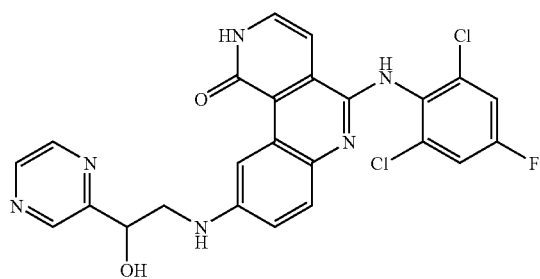 [SMILES: O=c1[nH]ccc2c(Nc3c(Cl)cc(F)cc3Cl)nc3ccc(NCC(O)c4cnccn4)cc3c12]

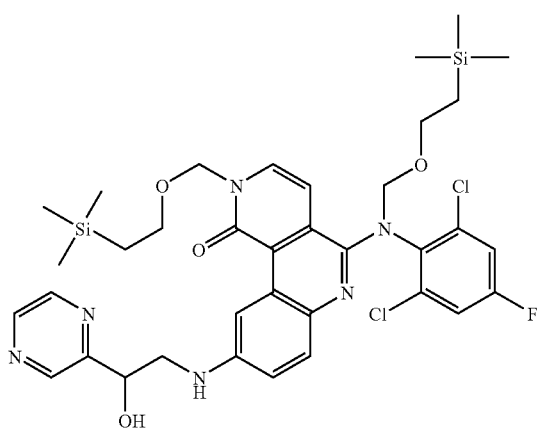 [SMILES: C[Si](C)(C)CCOCN(c1c(Cl)cc(F)cc1Cl)c1nc2ccc(NCC(O)c3cnccn3)cc2c2c(=O)n(COCC[Si](C)(C)C)ccc12]

Step 1: 5-((2,6-Dichloro-4-fluorophenyl){[2-(trimethylsilyl)ethoxy]methyl}amino)-9-[(2-hydroxy-2-pyrazin-2-ylethyl)amino]-2-{[2-(trimethylsilyl)ethoxy]methyl}benzo[c-]-2,6-naphthyridin-1(2H)-one To a solution of 9-bromo-5((2,6-dichloro-4-fluorophenyl){[2-(trimethylsilyl)ethoxy]methyl}amino)-2-{[2-(trimethylsilyl)ethoxy]methyl}benzo[c]-2,6-naphthyridin-1(2H)-one (Example 172, Step 1) (50 mg, 0.07 mmol) and 2-amino-1-pyrazin-2-ylethanol (14.6 mg, 0.11 mmol) in DMSO (1 ml) was added L-proline (2 mg, 0.014 mmol), potassium carbonate (29.7 mg, 0.14 mmol) and CuI (1.3 mg, 7.01 μmol). The solution was heated to 100° C. in a sealed tube for 16 h. After cooling to room temperature, the reaction was diluted with ethyl acetate and washed with water. The organic layer was dried with sodium sulfate, filtered and concentrated under reduced pressure to afford the title compound.

LRMS (ESI) calc'd for $C_{36}H_{46}C_{12}FN_6O_4Si_2$ [M+H]$^+$ 771.25; 771.2

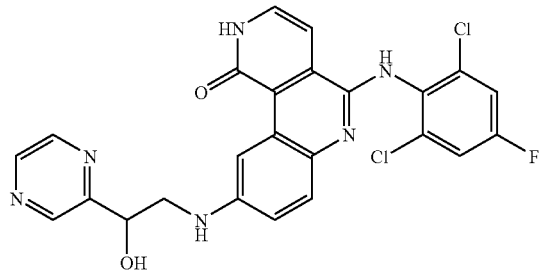 [SMILES: O=c1[nH]ccc2c(Nc3c(Cl)cc(F)cc3Cl)nc3ccc(NCC(O)c4cnccn4)cc3c12]

Step 1: 5-[(2,6-Dichloro-4-fluorophenyl)amino]-9-[(2-hydroxy-2-pyrazin-2-ylethyl)amino]benzo[c]-2,6-naphthyridin-1(2M-one To a solution of 5-((2,6-dichloro-4-fluorophenyl){[2-(trimethylsilyl)ethoxy]methyl}amino)-9-[(2-hydroxy-2-pyrazin-2-ylethyl)amino]-2-{[2-(trimethylsilyl)ethoxy]methyl}benzo[c]-2,6-naphthyridin-1(2H)-one (54 mg, 0.070 mmol) in dichloromethane (3 mL) was added TFA (2 mL) and the mixture was stirred at room temperature for 2.5 h. The solvents were evaporated and the residue was dissolved in MeOH, filtered and purified by reverse phase HPLC to afford the title compound.

$^1$H NMR (600 MHz, CD3OD) δ 9.31 (s, 1H), 8.8 (s, 1H), 8.57 (s, 1H), 8.48 (s, 1H), 7.7 (d, 2H), 7.59 (d, 1H), 7.52 (m, 2H), 7.28 (m, 1H), 7.24 (d, 1H), 5.08 (t, 1H), 3.76 (m, 1H), 3.67 (m, 1H).

LRMS (ESI) calc'd for $C_{24}H_{18}Cl_2FN_6O_2$ [M+H]$^+$, 511.09; found 511.0.

Additional analogues shown below were prepared using procedures similar to those described in the above examples and general methods.

TABLE 12

| Example | Structure | Compound Name | LRMS (M + H)$^+$ |
|---|---|---|---|
| 182 | 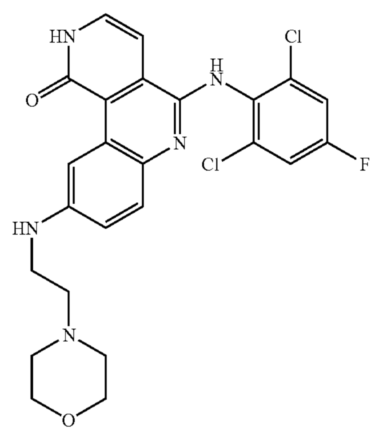 [SMILES: O=c1[nH]ccc2c(Nc3c(Cl)cc(F)cc3Cl)nc3ccc(NCCN4CCOCC4)cc3c12] | 5-[(2,6-dichloro-4-fluorophenyl)amino]-9-[(2-morpholin-4-ylethyl)amino]benzo[c]-2,6-naphthyridin-1(2H)-one | Calc'd: 502.1, found: 502.0 |
| 183 | 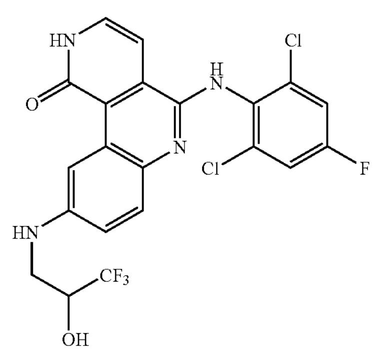 [SMILES: O=c1[nH]ccc2c(Nc3c(Cl)cc(F)cc3Cl)nc3ccc(NCC(O)C(F)(F)F)cc3c12] | 5-[(2,6-dichloro-4-fluorophenyl)amino]-9-[(3,3,3-trifluoro-2-hydroxypropyl)amino]benzo[c]-2,6-naphthyridin-1(2H)-one | Calc'd: 501.1, found: 501.0 |

TABLE 12-continued

| Example | Structure | Compound Name | LRMS (M + H)+ |
|---|---|---|---|
| 184 | 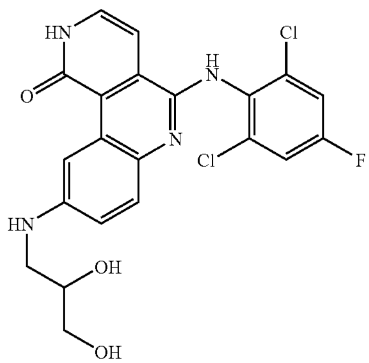 [SMILES: O=c1[nH]ccc2c(Nc3c(Cl)cc(F)cc3Cl)nc3ccc(NCC(O)CO)cc3c12] | 5-[(2,6-dichloro-4-fluorophenyl)amino]-9-[(2,3-dihydroxypropyl)amino]benzo[c]-2,6-naphthyridin-1(2H)-one | Calc'd: 463.1, found: 463.0 |
| 185 | 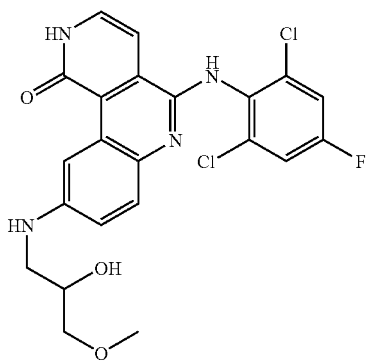 [SMILES: COCC(O)CNc1ccc2nc(Nc3c(Cl)cc(F)cc3Cl)c3cc[nH]c(=O)c3c2c1] | 5-[(2,6-dichloro-4-fluorophenyl)amino]-9-[(2-hydroxy-3-methoxypropyl)amino]benzo[c]-2,6-naphthyridin-1(2H)-one | Calc'd: 477.1, found: 477.0 |
| 186 | 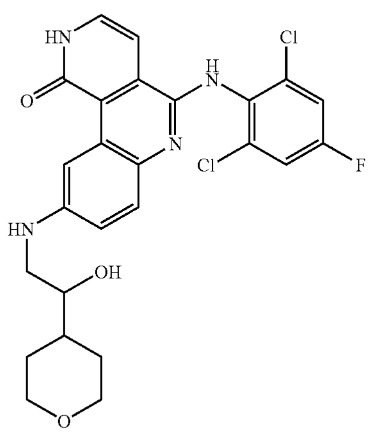 [SMILES: O=c1[nH]ccc2c(Nc3c(Cl)cc(F)cc3Cl)nc3ccc(NCC(O)C4CCOCC4)cc3c12] | 5-[(2,6-dichloro-4-fluorophenyl)amino]-9-{[2-hydroxy-2-(tetrahydro-2H-pyran-4-yl)ethyl]amino}benzo[c]-2,6-naphthyridin-1(2H)-one | Calc'd: 517.1, found: 517.1 |
| 187 | 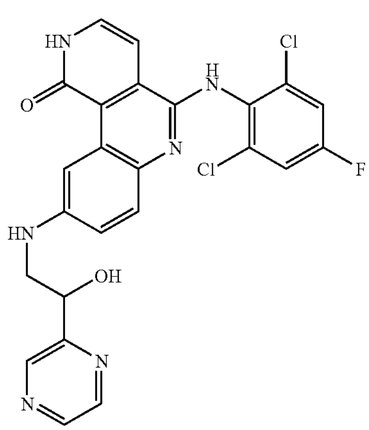 [SMILES: O=c1[nH]ccc2c(Nc3c(Cl)cc(F)cc3Cl)nc3ccc(NCC(O)c4cnccn4)cc3c12] | 5-[(2,6-dichloro-4-fluorophenyl)amino]-9-[(2-hydroxy-2-pyrazin-2-ylethyl)amino]benzo[c]-2,6-naphthyridin-1(2H)-one | Calc'd: 511.1, found: 511.0 |

TABLE 12-continued

| Example | Structure | Compound Name | LRMS (M + H)+ |
|---|---|---|---|
| 188 | 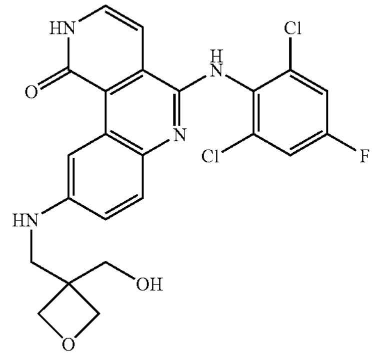 [SMILES: O=c1[nH]ccc2c(Nc3c(Cl)cc(F)cc3Cl)nc3ccc(NCC4(CO)COC4)cc3c12] | 5-[(2,6-dichloro-4-fluorophenyl)amino]-9-({[3-(hydroxymethyl)oxetan-3-yl]methyl}amino)benzo[c]-2,6-naphthyridin-1(2H)-one | Calc'd: 489.1, found: 489.0 |
| 189 | 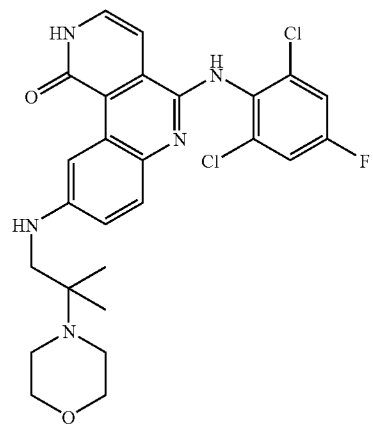 [SMILES: CC(C)(CNc1ccc2nc(Nc3c(Cl)cc(F)cc3Cl)c3cc[nH]c(=O)c3c2c1)N1CCOCC1] | 5-[(2,6-dichloro-4-fluorophenyl)amino]-9-[(2-methyl-2-morpholin-4-ylpropyl)amino]benzo[c]-2,6-naphthyridin-1(2H)-one | Calc'd: 530.1, found: 530.1 |

Pharmaceutical Composition

As a specific embodiment of this invention, 100 mg of 6-{[2,6-Dichloro-4-(1-hydroxy-1-methylethyl)phenyl]amino}pyrido[4,3-c]-1,6-naphthyridin-10(9H)-one is formulated with sufficient finely divided lactose to provide a total amount of 580 to 590 mg to fill a size 0, hard-gelatin capsule.

BIOLOGICAL ASSAYS

JAK1 Enzyme Assay

For the JAK1 enzyme assay, reactions (50 uL) contained 5× IVGN buffer (50 mM Hepes, pH 7.5, 10 mM $MgCl_2$, 0.01% Brij-35, 1 mM EGTA, 0.1 mg/ml BSA), 2mM DTT, 2.0 μM peptide substrate, 25 μM MgATP, 400 pM JAK1 enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103)

Peptide substrate is amino hexanoyl biotin-EQEDE-PEGDYFEWLE-NH2 (SEQ. ID NO.: 1); in DMSO.

JAK2 Kinase Activity Inhibition Assay and Determination of $IC_{50}$

The kinase activity was measured using a modified version of the homogeneous time-resolved tyrosine kinase assay described in Park et al. *Anal. Biochem.* 269, 94-104 (1999).

The procedure for determining the potency of a compound to inhibit JAK2 kinase comprises the following steps:

1. prepare 3-fold serial diluted compound/inhibitor solutions in 100% (DMSO) at 20× of the final desired concentrations in a 96 well plate;
2. prepare a master reaction mix containing 6.67 mM $MgCl_2$, 133.3 mM NaCl, 66.7 mM Tris-HCl (pH 7.4), 0.13 mg/ml BSA, 2.67 mM dithiothreitol, 0.27 recombinant JAK2 and 666.7 nM biotinylated synthetic peptide substrate (biotin-ahx-EQEDEPEGDYFEWLE-$CONH_2$) (SEQ. ID NO.: 1);
3. in a black assay plate, add 2.5 μl compound/inhibitor (or DMSO) and 37.5 μl master reaction mix per well; initiate the kinase reaction by adding 10 μl of 75 μM MgATP per well, allow the reactions to proceed for 80 minutes at room temperate; (the final conditions for the reactions are: 50 nM JAK2 JH1 domain (Upstate), 2.0 μM substrate, 15 μM MgATP, 5 mM $MgCl_2$, 100 mM NaCl, 2 mM DTT, 0.1 mg/ml BSA, 50 mM Tris (pH 7.4) and 5% DMSO);
4. stop the kinase reaction with 50 μl of Stop/Detection buffer containing 10 mM EDTA, 25 mM HEPES, 0.1% TRITON X-100, 0.126 μg/ml Eu-chelate labeled anti-phosphotyrosine antibody PY20 (cat. #AD0067, PerkinElmer) and 45 μg/ml Streptavidin-allophycocyanin conjugate (cat. #PJ25S, Prozyme); and
5. read HTRF signals on a Victor reader (PerkinElmer) in HTRF mode after 60 minutes.

$IC_{50}$ was obtained by fitting the observed relationship between compound/inhibitor concentration and HTRF signal with a 4-parameter logistic equation.

Compounds of the instant invention described in Examples 1-189 are potent inhibitors of recombinant purified JAK2 kinase activity with an $IC_{50}$ of approximately 0.1 nM-30 µM. Compounds of the instant invention described in Examples 115-171 are potent inhibitors of recombinant purified JAK2 kinase activity with an $IC_{50}$ of approximately 0.2 nM-500 nM.

JAK3 Enzyme Assay

For the JAK3 enzyme assay, reactions (50 uL) contained 5× IVON buffer (50 mM Hepes, pH 7.5, 10 mM $MgCl_2$, 0.01% Brij-35, 1 mM EGTA, 0.1 mg/ml BSA), 2 mM DTT, 2.0 µM peptide substrate, 25 µM MgATP, 400 pM JAK3 enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103)

Peptide substrate is amino hexanoyl biotin-EQEDE-PEGDYFEWLE-NH2 (SEQ. ID NO.: 1); in DMSO.

TYK2 Enzyme Assay

For the TYK2 enzyme assay, reactions (50 uL) contained 5× IVGN buffer (50 mM Hepes, pH 7.5, 10 mM $MgCl_2$, 0.01% Brij-35, 1 mM EGTA, 0.1 mg/ml BSA), 2 mM DTT, 2.0 µM peptide substrate, 15 µM MgATP, 125 pM enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103)

Peptide substrate is amino hexanoyl biotin-EQEDE-PEGDYFEWLE-NH2 (SEQ. ID NO.: 1); in DMSO.

Assay for JAK Family Protein Kinase Activity

Materials: Streptavidin•allophycocyanin conjugate (SA•APC) and Europium•cryptate (Eu•K) were from Packard Instrument Company: Eu•K conjugated pY20 was produced as described in Cummings, R. T.; McGovern, H. M.; Zheng, S.; Park, Y. W. and Hermes, J. D. Use Of A Phosphotyrosine-Antibody Pair As A General Detection Method In Homogeneous Time Resolved Fluorescence-Application To Human Immunodeficiency Viral Protease. *Analytical Biochemistry* 1999, 33, 79-93. Homogenous time resolved fluorescence (HTRF) measurements were made using the Discovery instrument from Packard. T-stim Culture Supplement was from Collaborative Biomedical Research. Recombinant mouse IL2 was from Phanningen or R & D.

JAK family kinase expression: JAK3, TYK2 and JAK2 kinase domains with N-terminal "Flag" affinity tags were expressed in Sf9 cells using standard baculovirus methods. The human JAK3 gene and the human TYK2 gene can be purchased from Update (now part of Millpore Corporation). Human JAK2 kinase domain was cloned from a MOLT4 cDNA library (Clonetech).

Assay for JAK family protein kinase activity: Tyrosine kinase activity was measured by detection of the tyrosine phosphorylated peptide amino hexanoyl biotin-EQEDE-PEGDYFEWLE-NH2 (SEQ. ID NO.: 1); (S, hereafter) detected by time-resolved fluorescence using a europium labeled antibody to phosphotyrosine (pY20). The JAK3(JH1) catalyzed phosphorylation reactions were carried out in a 30 uL total reaction volume. The compound was run at 5% DMSO and preincubated with enzyme buffer (EB). The EB comprised Invitrogen 5× kinase buffer (50 mM Hepes, pH 7.5, 10 mM $MgCl_2$, 0.01% Brij-35, 1 mM EGTA, 0.1 mg/ml BSA), 2 mM (final) DTT, 2 µM (final) S, and 250 pM (final) JAK3 enzyme. The assay was run at ATP $K_m$ (5 µM final) for 40 to 80 minutes. Reactions were run at ambient temperature and quenched with an equal volume of quench buffer (QB) (10 mM EDTA, 25 mM HEPES, 0.1% TRITON X-100) containing 50 µg/mL SA•APC conjugate and 0.75 nM Eu•K conjugated pY20. This mixture was incubated at ambient temperature for at least 60 minutes and read on an optimized fluorescent reader at Ex=320 nm and $Em_1$=665 nm (SA-APC) and $Em_2$=615 nM (Eu). The data was analyzed by using a standard 4P fit on the ratio of the Em results: $(Em_1 \div Em_2)$ *10,000.

JAK2 384-Well HEL Irf1-Bla AlphaScreen™ SureFire™ p-STAT5 Assay:

Principle: When JAK2 is activated and dimerized, it phosphorylates STAT5 which translocates to the nucleus and actives the transcription of target genes. AlphaScreen™ SureFire™ p-STAT5 assay (Perkin Elmer and TGR Biosciences) uses both biotinylated anti-phospho-STAT5 antibody, which is captured by Streptavidin-coated Donor beads, and anti-total STAT5 antibody, which is captured by Protein A conjugated Acceptor beads. The irf1-bla HEL CellSensor™ cell line was created by transducing parental HEL 92.1.7 cells (ATCC) with the pLenti-bsd/irf1-bla CellSensor™ vector. When both antibodies bind to phospho-STAT5 proteins released from HEL irf1-bla cells, the Donor and Acceptor beads are brought into the close proximity (<=200 nm) and a cascade of chemical reactions is initiated to produce a greatly amplified signal. Upon laser excitation, a photosensitizer in the donor bead converts ambient oxygen to a more excited singlet state. The singlet state oxygen molecules diffuse across to react with a chemiluminescer in the acceptor bead that further activates flurophores contained within the same bead. The fluorophores subsequently emit light at 520-620 nm. The emitted light intensity is directly proportional to the amount of phospho-STAT5 proteins released from HEL irf1-bla cells.

Growth Medium: RPMI Medium 1640 (Invitrogen) with 10% dialyzed FBS (Invitrogen), 1 µg/ml blasticidin, 0.1 mM NEAA, 1 mM sodium pyruvate and 1% Pen-Strep.

Method: On day 1, split HEL irf1-bla cells at density of 500,000 cells/ml. Incubate cells in a tissue culture flask at 37° C., 5% $CO_2$ overnight. On day 2, harvest cells and wash the once with HBSS (Invitrogen) containing 0.5% dialyzed FBS. Next, seed cells at a density of 100,000 cells/well in 8 ul of HBSS w/0.5% dialyzed FBS in 384-well microtiter plates. Temporarily put these cell plates in a 37° C., 5% $CO_2$ incubator. To prepare a compound plate, prepare serially diluted compounds in DMSO at a 500× stock concentration. Transfer 2 uL of the serially diluted compounds from the compound plate to an intermediate dilution plate containing 198 uL of HBSS w/0.5% dialyzed FBS. Next, transfer 2 uL of intermediately diluted compounds to each well of the cell plate to get 1:500 final dilution of each test compound and controls. Incubate the cell plates at 37° C., 5% $CO_2$ for 1 hr. Add 2.5 ul/well of 5× lysis buffer from the kit to cell plates. Gently agitate the plates for 5-10 min.

Make detection reagent mixture A by adding together 800 uL reaction buffer, 20 uL acceptor beads, and 200 uL activation buffer. Add 15 uL/well of detection mixture A to the cell plates and gently agitate the plates for 1-2 min. Seal the plates with an adhesive cover and incubate at room temperature for 2 hr, avoiding exposure to light. Make detection mixture B by adding together 400 uL dilution buffer and 20 uL donor beads. Add 6 uL/well of mixture B to the cell plates and gently agitate the plates for 1-2 min. Seal the plates with an adhesive cover and incubate at room temperature for 2 hr, avoiding exposure to light. Read the plates on an AlphaScreen-capable plate reader.

Compounds of the instant invention are potent inhibitors of pSTAT5 in the HEL irf1-bla AlphaScreen™ SureFire™ p-STAT5 Assay activity with an inflexion point (IP) of <30 μM. Compounds of the instant invention described in Examples 115-154 are potent inhibitors of pSTAT5 in the HEL irf1-bla AlphaScreen™ SureFire™ p-STAT5 Assay activity with an inflexion point (IP) of between 5 nM and 5000 nM.

Cellular proliferation assays: CTLL-2 cells (ATCC) were maintained in 6% T-stim Culture Supplement (source of IL2) in RPMI-1640 supplemented with 10% fetal bovine serum, 1 mM sodium pyruvate, 50 μM β-mercaptoethanol, 1.4 mM L-glutamine, 10 mM HEPES, 1 mg/ml dextrose, 0.04 mM essential amino acids, 0.02 mM nonessential amino acids, penicillin and streptomycin (H10). The day before use in the proliferation assay, cells were washed and resuspended in 0.2% Tstim at a cell concentration of $5\times10^5$/ml. The next day, cells were washed and plated at $0.2-1\times10^5$ cells/well in a 96 well tissue culture plate (CoStar). 0.05 ng/ml mouse recombinant IL2 (Pharmingen), with or without a test compound, or 20 ng/ml PMA (Sigma) and 1 μCi/well [$^3$H]-thymidine were added. After overnight culture, cells were harvested with a glass fiber Filtermat (Wallac) and a Tomtek cell harvester. Tritium incorporation was measured by liquid scintillation counting on a Topcount scintillation counter (Packard).

Compounds of the instant invention described in Examples 1-189 are potent inhibitors of recombinant purified JAK3 kinase activity with an $IC_{50}$ of approximately 0.8 nM->3 μM.

While a number of embodiments of this invention have been described, it is apparent that the basic examples may be altered to provide other embodiments, encompassed by the present invention. Therefore, it will be appreciated that the scope of this invention is to be defined by the appended claims rather than by the specific embodiments, which have been represented by way of example.

What is claimed is:

1. A compound of the formula I:

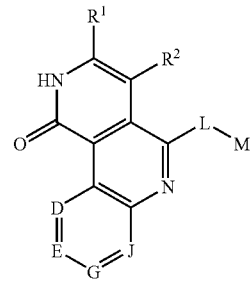

wherein D is $CR^3$;
E is N or $CR^3$;
G is $CR^3$;
J is $CR^3$;
L is —NH—;
M is
(a) hydrogen,
(b) halo,
(c) hydroxyl,
(d) $C_{1-6}$ alkyl, optionally substituted with one to four substituents independently selected from the group consisting of halo, hydroxyl, $SO_2NR^4R^5$, $Si(CH_3)_3$ and $Si(CH_3)_3O(C_{1-6}$ haloalkyl),
(e) $C_{2-6}$ alkenyl,
(f) $C_{1-6}$ haloalkyl, which is optionally substituted with $C_{3-8}$ cycloalkyl,
(g) $C_{3-8}$ cycloalkyl,
(h) $(C_{1-6}$ alkyl)$C_{3-8}$ cycloalkyl,
(i) aryl, which is optionally substituted with one to four substituents independently selected from the group consisting of halo, hydroxyl, cyano, $C_{1-6}$ alkyl which is optionally substituted with one to three substituents independently selected from the group consisting of cyano, halo, hydroxyl and $NR^4R^5$, $C_{2-6}$ alkenyl which is optionally substituted with hydroxyl, $C_{2-6}$ alkynyl which is optionally substituted with hydroxyl or $Si(CH_3)_3$, $O(C_{1-6}$ haloalkyl), $C_{3-8}$ cycloalkyl which is optionally substituted with hydroxyl, heteroaryl which is optionally substituted on either the carbon or heteroatom with $R^8$, $SO_mNHR^7$, $SO_mR^7$, $(C_{1-6}$ alkyl)NH-

---

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Completely synthetic amino acid
<220> FEATURE:
<221> NAME/KEY: AMIDATION
<222> LOCATION: (15)...(15)
<223> OTHER INFORMATION: Glutamic acid amide

<400> SEQUENCE: 1

Glu Gln Glu Asp Glu Pro Glu Gly Asp Tyr Phe Glu Trp Leu Glu
 1               5                   10                  15

SO$_m$R$^7$, (C=O)R$^8$, (C=O)OR$^8$, (C=O)NHR$^8$, (C=O)NH-C$_{1-3}$ alkyl-heterocyclyl, (C=NH)NHR$^8$, (C=NOR$^8$)C$_{1-3}$ alkyl, (C=NO-C$_{1-3}$ alkyl-(C=O)heterocyclyl)C$_{1-3}$ alkyl, and (C=NO-C$_{2-6}$ alkenyl)C$_{1-3}$ alkyl,
(j) heteroaryl, which optionally substituted on either the carbon or heteroatom with one to three substituents independently selected from the group consisting of halo, oxo, aryl and R$^8$;
(k) heterocyclyl,
(l) (C$_{1-6}$ alkyl)aryl, which is optionally substituted on either the alkyl or aryl group with a substituent selected from the group consisting of one to two halo and SO$_m$-NHR$^7$,
(m) C(O)R$^8$, or
(n) NR$^4$R$^5$;
R$^1$ is hydrogen;
R$^2$ is hydrogen;
R$^3$ is
  (a) hydrogen,
  (b) halo,
  (c) hydroxyl,
  (d) C$_{1-6}$ alkyl,
  (e) C$_{2-6}$ alkenyl, optionally substituted with one to three hydroxyl,
  (f) C$_{2-6}$ alkynyl, optionally substituted with one to two substituents independently selected from the group consisting of hydroxyl, heteroaryl and NR$^4$R$^5$,
  (g) C$_{1-6}$ haloalkyl,
  (h) O(C$_{1-6}$ alkyl),
  (i) O(C$_{1-6}$ haloalkyl),
  (j) aryl,
  (k) heteroaryl, optionally substituted on either the carbon or heteroatom with one to three substituents independently selected from the group consisting of hydroxyl, R$^8$, C$_{1-6}$ alkyl(heterocyclyl), CH$_2$(C=O)OR$^8$ and NR$^4$R$^5$,
  (l) heterocyclyl,
  (m) B(OH)$_2$,
  (n) NR$^4$R$^5$,
  (o) NHR$^6$ or
  (p) NH(C=O)R$^6$;
R$^4$ is hydrogen or C$_{1-6}$ alkyl;
R$^5$ is hydrogen or C$_{1-6}$ alkyl;
R$^6$ is hydrogen, C$_{1-6}$ alkyl, NR$^4$R$^5$, —NH(C$_{1-6}$ alkyl)OR$^8$, aryl, heteroaryl or heterocyclyl which is optionally substituted on either the carbon or heteroatom with R$^8$, wherein said alkyl groups are optionally substituted with one to four substituents selected from hydroxy, halo, OR$^8$, NR$^8$SO$_2$NR$^4$R$^5$, heteroaryl or heterocyclyl;
R$^7$ is hydrogen, C$_{1-6}$ alkyl, (C$_{3-6}$ cycloalkyl), heterocyclyl, (C$_{1-6}$ alkyl)heterocyclyl or (C$_{1-6}$ alkyl)heteroaryl, wherein said alkyl group is optionally substituted with one to four substituents selected from the group consisting of halo and hydroxy, and said heteroaryl group is optionally substituted with C$_{1-6}$ alkyl;
R$^8$ is hydrogen or C$_{1-6}$ alkyl, wherein said alkyl is optionally substituted with one to two hydroxyl; and,
m is an integer from zero to two;
or a pharmaceutically acceptable salt or stereoisomer thereof.

2. The compound of claim 1, wherein E is N; or a pharmaceutically acceptable salt or stereoisomer thereof.

3. The compound of claim 2, wherein M is C$_{1-6}$ alkyl, optionally substituted with one to four substituents independently selected from the group consisting of halo, hydroxyl and SO$_2$NR$^4$R$^5$; aryl, which is optionally substituted with one to four substituents independently selected from the group consisting of halo, hydroxyl, cyano, C$_{1-6}$ alkyl which is optionally substituted with one to three substituents independently selected from the group consisting of halo and hydroxyl, O(C$_{1-6}$ haloalkyl), C$_{3-8}$ cycloalkyl which is optionally substituted with hydroxyl, heteroaryl and SO$_m$NHR$^7$; or heteroaryl, which is optionally substituted with halo; or a pharmaceutically acceptable salt or stereoisomer thereof.

4. The compound of claim 3, wherein M is aryl, which is optionally substituted with one to four substituents independently selected from the group consisting of halo, hydroxyl, cyano, C$_{1-6}$ alkyl which is optionally substituted with one to three substituents independently selected from the group consisting of halo and hydroxyl, O(C$_{1-6}$ haloalkyl), C$_{3-8}$ cycloalkyl which is optionally substituted with hydroxyl, heteroaryl and SO$_m$NHR$^7$, or a pharmaceutically acceptable salt or stereoisomer thereof.

5. The compound of claim 2, wherein R$^3$ is hydrogen, halo, C$_{2-6}$ alkenyl optionally substituted with one to three hydroxyl, C$_{2-6}$ alkynyl optionally substituted with one to two substituents independently selected from the group consisting of hydroxyl, heteroaryl and NR$^4$R$^5$, heteroaryl optionally substituted on either the carbon or heteroatom with one to three substituents independently selected from the group consisting of hydroxyl, R$^8$, C$_{1-6}$ alkyl(heterocyclyl), CH$_2$(C=O)OR$^8$ and NR$^4$R$^5$, or B(OH)$_2$; or a pharmaceutically acceptable salt or stereoisomer thereof.

6. The compound of claim 1 selected from:
5-(Cyclopropylamino)-9-fluorobenzo[c]-2,6-naphthyridin-1(2H)-one;
9-Fluoro-5-{[(1S)-2-methyl-1-(trifluoromethyl)propyl]amino}benzo[c]-2,6-naphthyridin-1(2H)-one;
9-Bromo-5-[(2,4,6-trifluorophenyl)amino]benzo[c]-2,6-naphthyridin-1(2H)-one;
5-[(5-tert-Butyl-2-methylphenyl)amino]-9-fluorobenzo[c]-2,6-naphthyridin-1(2H)-one;
9-Fluoro-5-[(1,2,2-trimethylpropyl)amino]benzo[c]-2,6-naphthyridin-1(2H)-one;
5-[(2,2-Dimethylpropyl)amino]-9-fluorobenzo[c]-2,6-naphthyridin-1(2H)-one;
5-[(2,6-Dichlorobenzyl)amino]-9-fluorobenzo[c]-2,6-naphthyridin-1(2H)-one;
9-Fluoro-5- {[(1R)-2-methyl-1-(trifluoromethyl)propyl]amino}benzo[c]-2,6-naphthyridin-1(2H)-one;
5-[(2-Chloro-3,6-difluorophenyl)amino]-9-fluorobenzo[c]-2,6-naphthyridin-1(2H)-one;
9-Fluoro-5-{[(1S)-1-(trifluoromethyl)propyl]amino}benzo[c]-2,6-naphthyridin-1(2H)-one;
9-Fluoro-5-{[(1R)-1-(trifluoromethyl)propyl]amino}benzo[c]-2,6-naphthyridin-1(2H)-one;
9-Fluoro-5-{[(trimethylsilyl)methyl]amino}benzo[c]-2,6-naphthyridin-1(2H)-one;
9-Fluoro-5-[(1-methylprop-2-en-1-yl)amino]benzo[c]-2,6-naphthyridin-1(2H)-one;
9-Fluoro-5-[(3,3,3-trifluoro-2-hydroxypropyl)amino]benzo[c]-2,6-naphthyridin-1(2H)-one;
5-[(2-Chloro-4,6-difluorophenyl)amino]-9-fluorobenzo[c]-2,6-naphthyridin-1(2H)-one;
9-Bromo-5-{[(1S)-1-cyclopropyl-2,2,2-trifluoroethyl]amino}benzo[c]-2,6-naphthyridin-1(2H)-one;
9-Bromo-5-{[(1R)-1-cyclopropyl-2,2,2-trifluoroethyl]amino}benzo[c]-2,6-naphthyridin-1(2H)-one;
9-Fluoro-5-[(1,3,5-trimethyl-1H-pyrazol-4-yl)amino]benzo[c]-2,6-naphthyridin-1(2H)-one;
5-[(1-Ethyl-3,5-dimethyl-1H-pyrazol-4-yl)amino]-9-fluorobenzo[c]-2,6-naphthyridin-1(2H)-one;
5-[(5-Tert-butylisoxazol-4-yl)amino]-9-fluorobenzo[c]-2,6-naphthyridin-1(2H)-one;

5-[(2,6-Difluorophenyl)amino]-9-fluorobenzo[c]-2,6-naphthyridin-1(2H)-one;
9-Bromo-5-{[(1S)-1-(trifluoromethyl)propyl]amino}benzo[c]-2,6-naphthyridin-1(2H)-one;
9-Fluoro-5-(methylamino)benzo[c]-2,6-naphthyridin-1(2H)-one;
5-{[2-(2,3-Difluorophenyl)ethyl]amino}-9-fluorobenzo[c]-2,6-naphthyridin-1(2H)-one;
5-{[2-(2,5-Difluorophenyl)ethyl]amino}-9-fluorobenzo[c]-2,6-naphthyridin-1(2H)-one;
5-{[2-(3,4-Difluorophenyl)ethyl]amino}-9-fluorobenzo[c]-2,6-naphthyridin-1(2H)-one;
9-Fluoro-5-{[2-(3,4,5-trifluorophenyl)ethyl]amino}benzo[c]-2,6-naphthyridin-1(2H)-one;
5-{[2-(3-Chloro-2-fluorophenyl)ethyl]amino}-9-fluorobenzo[c]-2,6-naphthyridin-1(2H)-one;
5-{[(1S)-1-(2,6-Dichlorophenyl)ethyl]amino}-9-fluorobenzo[c]-2,6-naphthyridin-1(2H)-one;
5-{[(1R)-1-(2,6-Dichlorophenyl)ethyl]amino}-9-fluorobenzo[c]-2,6-naphthyridin-1(2H)-one;
9-Bromo-5-{[(1R)-1-(2,6-dichlorophenyl)ethyl]amino}benzo[c]-2,6-naphthyridin-1(2H)-one;
9-Bromo-5-{[(1S)-1-(2,6-dichlorophenyl)ethyl]amino}benzo[c]-2,6-naphthyridin-1(2H)-one;
4-{[(9-Bromo-1-oxo-1,2-dihydrobenzo[c]-2,6-naphthyridin-5-yl)amino]methyl}benzenesulfonamide;
3,5-Dichloro-4-[(9-fluoro-1-oxo-1,2-dihydrobenzo[c]-2,6-naphthyridin-5-yl)amino]benzenesulfonamide;
5-{[2,6-Dichloro-4-(ethylthio)phenyl]amino}-9-fluorobenzo[c]-2,6-naphthyridin-1(2H)-one;
4-[(9-Bromo-1-oxo-1,2-dihydrobenzo[c]-2,6-naphthyridin-5-yl)amino]-3,5-dichlorobenzenesulfonamide;
9-Bromo-5-[(2-methyl-1-naphthyl)amino]benzo[c]-2,6-naphthyridin-1(2H)-one;
9-Bromo-5-[(2,6-dichlorophenyl)amino]benzo[c]-2,6-naphthyridin-1(2H)-one;
9-Fluoro-5-[(4-fluoro-2,6-dimethylphenyl)amino]benzo[c]-2,6-naphthyridin-1(2H)-one;
5-[(2-Chloro-6-methylphenyl)amino]-9-fluorobenzo[c]-2,6-naphthyridin-1(2H)-one;
9-Fluoro-5-[(2-methyl-1-naphthyl)amino]benzo[c]-2,6-naphthyridin-1(2H)-one;
5-[(2,6-Dichlorophenyl)amino]-9-fluorobenzo[c]-2,6-naphthyridin-1(2H)-one;
5-[(2-tert-Butylpyridin-4-yl)amino]-9-fluorobenzo[c]-2,6-naphthyridin-1(2H)-one;
3-[(9-Bromo-1-oxo-1,2-dihydrobenzo[c]-2,6-naphthyridin-5-yl)amino]-4-methylbenzonitrile;
9-Bromo-5-[(2,5-dimethylphenyl)amino]benzo[c]-2,6-naphthyridin-1(2H)-one;
3-[(9-Bromo-1-oxo-1,2-dihydrobenzo[c]-2,6-naphthyridin-5-yl)amino]-4-chlorobenzonitrile;
5-[(3-tert-Butyl-1-methyl-1H-pyrazol-5-yl)amino]-9-fluorobenzo[c]-2,6-naphthyridin-1(2H)-one;
9-Fluoro-5-[(2-phenylpyridin-4-yl)amino]benzo[c]-2,6-naphthyridin-1(2H)-one;
9-Bromo-5-[(2-chloro-5-methylphenyl)amino]benzo[c]-2,6-naphthyridin-1(2H)-one;
5-[(4-Bromo-5-tert-butyl-2-methylphenyl)amino]-9-fluorobenzo[c]-2,6-naphthyridin-1(2H)-one;
9-Fluoro-5-[(5-isopropyl-2-methylphenyl)amino]benzo[c]-2,6-naphthyridin-1(2H)-one;
2-{3-[(9-Bromo-1-oxo-1,2-dihydrobenzo[c]-2,6-naphthyridin-5-yl)amino]-4-chlorophenyl}-2-methylpropanenitrile;
9-Bromo-5-[(5-tert-butyl-2-methylphenyl)amino]benzo[c]-2,6-naphthyridin-1(2H)-one;
5-Anilino-9-fluorobenzo[c]-2,6-naphthyridin-1(2H)-one;
9-Fluoro-5-[(5-methyl-1,1-dioxido-2,3-dihydro-1-benzothien-6-yl)amino]benzo[c]-2,6-naphthyridin-1(2H)-one;
5-{[2,4-Dimethyl-5-(methylsulfonyl)phenyl]amino}-9-fluorobenzo[c]-2,6-naphthyridin-1(2H)-one;
5-[(Cyclohexylmethyl)amino]-9-fluorobenzo[c]-2,6-naphthyridin-1(2H)-one;
9-Fluoro-5-{[(1R)-1-phenylethyl]amino}benzo[c]-2,6-naphthyridin-1(2H)-one;
5-{[1-(2,6-Dichlorophenyl)ethyl]amino}-9-fluorobenzo[c]-2,6-naphthyridin-1(2H)-one;
5-(Benzylamino)-9-bromobenzo[c]-2,6-naphthyridin-1(2H)-one;
9-Bromo-5-{[(1R)-1-phenylethyl]amino}benzo[c]-2,6-naphthyridin-1(2H)-one;
9-Bromo-5-{[(1S)-1-phenylethyl]amino}benzo[c]-2,6-naphthyridin-1(2H)-one;
9-Bromo-5-{[1-(2,6-dichlorophenyl)ethyl]amino}benzo[c]-2,6-naphthyridin-1(2H)-one;
9-Bromo-5-[(2-phenylethyl)amino]benzo[c]-2,6-naphthyridin-1(2H)-one;
5-{[2-Chloro-5-(methylsulfonyl)phenyl]amino}-9-fluorobenzo[c]-2,6-naphthyridin-1(2H)-one;
9-Fluoro-5-{[2-fluoro-4-methyl-5-(methylsulfonyl)phenyl]amino}benzo[c]-2,6-naphthyridin-1(2H)-one;
9-Fluoro-5-{[2-fluoro-5-(methylsulfonyl)phenyl]amino}benzo[c]-2,6-naphthyridin-1(2H)-one;
5-[(5-Acetyl-2-methylphenyl)amino]-9-fluorobenzo[c]-2,6-naphthyridin-1(2H)-one;
5-[(5-Acetyl-2-chlorophenyl)amino]-9-fluorobenzo[c]-2,6-naphthyridin-1(2H)-one;
9-Fluoro-5-{[5-(1-hydroxyethyl)-2-methylphenyl]amino}benzo[c]-2,6-naphthyridin-1(2H)-one;
5-{[2-Chloro-5-(1-hydroxyethyl)phenyl]amino}-9-fluorobenzo[c]-2,6-naphthyridin-1(2H)-one;
5-{[2-Chloro-4-fluoro-5-(1-hydroxyethyl)phenyl]amino}-9-fluorobenzo[c]-2,6-naphthyridin-1(2H)-one;
5-[(9-Fluoro-1-oxo-1,2-dihydrobenzo[c]-2,6-naphthyridin-5-yl)amino]-2,4-dimethyl-N-(pyridin-3-ylmethyl)benzenesulfonamide;
4-[(9-Bromo-1-oxo-1,2-dihydrobenzo[c]-2,6-naphthyridin-5-yl)amino]-3,5-dichloro-N-[(1H-methyl-1H-imidazol-2-yl)methyl]benzenesulfonamide;
3,5-Dichloro-4-[(9-fluoro-1-oxo-1,2-dihydrobenzo[c]-2,6-naphthyridin-5-yl)amino]-N-isobutylbenzenesulfonamide;
3,5-Dichloro-4-[(9-fluoro-1-oxo-1,2-dihydrobenzo[c]-2,6-naphthyridin-5-yl)amino]-N-(2-pyrrolidin-1-ylethyl)benzenesulfonamide;
3,5-Dichloro-4-[(9-fluoro-1-oxo-1,2-dihydrobenzo[c]-2,6-naphthyridin-5-yl)amino]-N-[(1-methyl-1H-imidazol-2-yl)methyl]benzenesulfonamide;
3,5-Dichloro-4-[(9-fluoro-1-oxo-1,2-dihydrobenzo[c]-2,6-naphthyridin-5-yl)amino]-N-[(2R)-2-hydroxypropyl]benzenesulfonamide;
5-[(9-Fluoro-1-oxo-1,2-dihydrobenzo[c]-2,6-naphthyridin-5-yl)amino]-2,4-dimethyl-N-(pyridin-3-ylmethyl)benzenesulfonamide;
5-{[2,4-Dimethyl-5-(morpholin-4-ylsulfonyl)phenyl]amino}-9-fluorobenzo[c]-2,6-naphthyridin-1(2H)-one;
5-{[2,4-Dimethyl-5-(piperidin-1-ylsulfonyl)phenyl]amino}-9-fluorobenzo[c]-2,6-naphthyridin-1(2H)-one;
N-Cyclopropyl-5-[(9-fluoro-1-oxo-1,2-dihydrobenzo[c]-2,6-naphthyridin-5-yl)amino]-2,4-dimethylbenzenesulfonamide;

5-[(9-Fluoro-1-oxo-1,2-dihydrobenzo[c]-2,6-naphthyridin-5-yl)amino]-2,4-dimethyl-N-[(1-methyl-1H-imidazol-2-yl)methyl]benzenesulfonamide;
3-[(9-Fluoro-1-oxo-1,2-dihydrobenzo[c]-2,6-naphthyridin-5-yl)amino]-4-methylbenzoic acid;
Methyl 3-[(9-fluoro-1-oxo-1,2-dihydrobenzo[c]-2,6-naphthyridin-5-yl)amino]-4-methylbenzoate;
3-[(9-Fluoro-1-oxo-1,2-dihydrobenzo[c]-2,6-naphthyridin-5-yl)amino]-N-[(2R)-2-hydroxypropyl]-4-methylbenzamide;
3-[(9-Fluoro-1-oxo-1,2-dihydrobenzo[c]-2,6-naphthyridin-5-yl)amino]-4-methyl-N-(morpholin-2-ylmethyl)benzamide;
9-Fluoro-5-{[5-(hydroxymethyl)-2-methylphenyl]amino}benzo[c]-2,6-naphthyridin-1(2H)-one;
9-Bromo-5-{[5-(hydroxymethyl)-2-methylphenyl]amino}benzo[c]-2,6-naphthyridin-1(2H)-one;
5-{[2-Chloro-4-fluoro-5-(hydroxymethyl)phenyl]amino}-9-fluorobenzo[c]-2,6-naphthyridin-1(2H)-one;
5-({2-Chloro-5-[5-(hydroxymethyl)-2-furyl]phenyl}amino)-9-fluorobenzo[c]-2,6-naphthyridin-1(2H)-one;
1,1,1-Trifluoro-N-{3-[(9-fluoro-1-oxo-1,2-dihydrobenzo[c]-2,6-naphthyridin-5-yl)amino]-4-methylbenzyl}methanesulfonamide;
9-(1-Methyl-1H-pyrazol-4-yl)-5-{[(1S)-1-(trifluoromethyl)propyl]amino}bezo[c]-2,6-naphthyridin-1(2H)-one;
5-({2,6-Dichloro-4-[(1R)-1-hydroxyethyl]phenyl}amino)-9-(3-hydroxy-3-methylbut-1-yn-1-yl)benzo[c]-2,6-naphthyridin-1(2H)-one;
5-({2,6-Dichloro-4-[(1S)-1-hydroxyethyl]phenyl}amino)-9-(3-hydroxy-3-methylbut-1-yn-1-yl)benzo[c]-2,6-naphthyridin-1(2H)-one;
5-({2,6-Dichloro-4-[(1R)-1-hydroxyethyl]phenyl}amino)-9-[(3R)-3-hydroxybut-1-yn-1-yl]benzo[c]-2,6-naphthyridin-1(2H)-one;
5-({2,6-Dichloro-4-[(1S)-1-hydroxyethyl]phenyl}amino)-9-[(3R)-3-hydroxybut-1-yn-1-yl]benzo[c]-2,6-naphthyridin-1(2H)-one;
5-({2,6-Dichloro-4-[(1R)-1-hydroxyethyl]phenyl}amino)-9-(1-methyl-1H-pyrazol-4-yl)benzo[c]-2,6-naphthyridin-1(2H)-one;
5-({2,6-Dichloro-4-[(1S)-1-hydroxyethyl]phenyl}amino)-9-(1-methyl-1H-pyrazol-4-yl)benzo[c]-2,6-naphthyridin-1(2H)-one;
5-{[2,6-Dichloro-4-(1H-pyrazol-5-yl)phenyl]amino}-9-(3-hydroxy-3-methylbut-1-yn-1-yl)benzo[c]-2,6-naphthyridin-1(2H)-one;
5-{[2,6-Dichloro-4-(1H-pyrazol-5-yl)phenyl]amino}-9-[(1E)-3-hydroxy-3-methylbut-1-en-1-yl]benzo[c]-2,6-naphthyridin-1(2H)-one;
(5-{[2,6-Dichloro-4-(1H-pyrazol-5-yl)phenyl]amino}-1-oxo-1,2-dihydrobenzo[c]-2,6-naphthyridin-9-yl)boronic acid;
9-Bromo-5-{[2,6-dichloro-4-(1-hydroxy-1-methylethyl)phenyl]amino}benzo[c]-2,6-naphthyridin-1(2H)-one;
5-{[2,6-Dichloro-4-(1-hydroxy-1-methylethyl)phenyl]amino}-9-hydroxybenzo[c]-2,6-naphthyridin-1(2H)-one;
5-{[2,6-Dichloro-4-(1-hydroxy-1-methylethyl)phenyl]amino}-9-[2-(1-hydroxy-1-methylethyl)-1,3-thiazol-4-yl]benzo[c]-2,6-naphthyridin-1(2H)-one;
5-[(2-Chloro-4,6-difluorophenyl)amino]-9-(1H-pyrazol-5-yl)benzo[c]-2,6-naphthyridin-1(2H)-one;
9-(1-Methyl-1H-pyrazol-4-yl)-5-[(2,4,6- trifluorophenyl)amino]benzo[c]-2,6-naphthyridin-1(2H)-one;
9-(2-Aminopyrimidin-5-yl)-5-[(2,4,6-trifluorophenyl)amino]benzo[c]-2,6-naphthyridin-1(2H)-one;
9-[6-(Hydroxymethyl)pyridin-3-yl]-5-[(2,4,6-trifluorophenyl)amino]benzo[c]-2,6-naphthyridin-1(2H)-one;
9-(1-Methyl-1H-pyrazol-4-yl)-5-{[(1S)-2-methyl-1-(trifluoromethyl)propyl]amino}benzo[c]-2,6-naphthyridin-1(2H)-one;
9-(1H-Pyrazol-5-yl)-5-[(2,4,6-trifluorophenyl)amino]benzo[c]-2,6-naphthyridin-1(2H)-one;
5-{[2,6-Dichloro-4-(1-hydroxy-1-methylethyl)phenyl]amino}-9-[(3R)-3-hydroxybut-1-yn-1-yl]benzo[c]-2,6-naphthyridin-1(2H)-one;
5-{[2,6-Dichloro-4-(1-hydroxy-1-methylethyl)phenyl]amino}-9-[(3S)-3-hydroxybut-1-yn-1-yl]benzo[c]-2,6-naphthyridin-1(2H)-one;
5-{[2,6-Dichloro-4-(1H-pyrazol-5-yl)phenyl]amino}-9-(3-hydroxy-3-methylbut-1-yn-1-yl)benzo[c]-2,6-naphthyridin-1(2H)-one;
5-{[2,6-Dichloro-4-(1H-pyrazol-5-yl)phenyl]amino}-9-[(1E)-3-hydroxy-3-methylbut-1-en-1-yl]benzo[c]-2,6-naphthyridin-1(2H)-one;
5-{[2,6-Dichloro-4-(1H-pyrazol-5-yl)phenyl]amino}-9-[(3R)-3-hydroxybut-1-yn-1-yl]benzo[c]-2,6-naphthyridin-1(2H)-one;
5-{[2,6-Dichloro-4-(1-hydroxy-1-methylethyl)phenyl]amino}-9-(1H-pyrazol-5-yl)benzo[c]-2,6-naphthyridin-1(2H)-one;
5-{[2,6-Dichloro-4-(1-hydroxy-1-methylethyl)phenyl]amino}-9-(1-methyl-1H-pyrazol-4-yl)benzo[c]-2,6-naphthyridin-1(2H)-one;
5-{[2,6-Dichloro-4-(1-hydroxy-1-methylethyl)phenyl]amino}-9-(1,3-thiazol-2-yl)benzo[c]-2,6-naphthyridin-1(2H)-one;
5-{[2,6-Dichloro-4-(1-hydroxy-1-methylethyl)phenyl]amino}-9-(3-hydroxy-3-methylbut-1-yn-1-yl)benzo[c]-2,6-naphthyridin-1(2H)-one;
5-{[2,6-Dichloro-4-(1-hydroxy-1-methylethyl)phenyl]amino}-9-[(1E)-3-hydroxy-3-methylbut-1-en-1-yl]benzo[c]-2,6-naphthyridin-1(2H)-one;
9-(2-Aminopyrimidin-5-yl)-5-{[2,6-dichloro-4-(1-hydroxy-1-methylethyl)phenyl]amino}benzo[c]-2,6-naphthyridin-1(2H)-one;
5-{[2,6-Dichloro-4-(1-hydroxy-1-methylethyl)phenyl]amino}-9-(pyridin-2-ylethynyl)benzo[c]-2,6-naphthyridin-1(2H)-one;
9-(3-Amino-3-methylbut-1-yn-1-yl)-5-{[2,6-dichloro-4-(1-hydroxy-1-methylethyl)phenyl]amino}benzo[c]-2,6-naphthyridin-1(2H)-one;
5-{[2,6-Dichloro-4-(1-hydroxy-1-methylethyl)phenyl]amino}-9-[1-(1,3-dioxolan-2-ylmethyl)-1H-pyrazol-4-yl]benzo[c]-2,6-naphthyridin-1(2H)-one;
5-{[2,6-Dichloro-4-(1-hydroxy-1-methylethyl)phenyl]amino}-9-(1-isobutyl-1H-pyrazol-4-yl)benzo[c]-2,6-naphthyridin-1(2H)-one;
Ethyl[4-(5-{[2,6-dichloro-4-(1-hydroxy-1-methylethyl)phenyl]amino}-1-oxo-1,2-dihydrobenzo[c]-2,6-naphthyridin-9-yl)-1H-pyrazol-1-yl]acetate;
5-{[2,6-Dichloro-4-(1-hydroxy-1-methylethyl)phenyl]amino}-9-[1-(2-morpholin-4-ylethyl)-1H-pyrazol-4-yl]benzo[c]-2,6-naphthyridin-1(2H)-one;
3,5-Dichloro-4-{[9-(3-hydroxy-3-methylbut-1-yn-1-yl)-1-oxo-1,2-dihydrobenzo[c]-2,6-naphthyridin-5-yl]amino}benzenesulfonamide;
3,5-Dichloro-4-[[1,2-dihydro-9-(1-methyl-1H-pyrazol-4-yl)-1-oxobenzo[c][2,6]napthyridin-5-yl]amino]-benzenesulfonamide;

5-{[2,6-Dichloro-4-(1-hydroxy-1-methylethyl)phenyl]
amino}-9-[6-(1-hydroxy-1-methylethyl)pyridin-2-yl]
benzo[c]-2,6-naphthyridin-1(2H)-one;
6-[(2-Chloro-4,6-difluorophenyl)amino]pyrido[4,3-c]-1,
6-naphthyridin-10(9H)-one;
6-[(2,6-Dichloro-4-fluorophenyl)amino]pyrido[4,3-c]-1,
6-naphthyridin-10(9H)-one;
6-[(2,4,6-Trifluorophenyl)amino]pyrido[4,3-c]-1,6-naphthyridin-10(9H)-one;
6-{[2-Fluoro-6-(Trifluoromethyl)phenyl]amino}pyrido
[4,3-c]-1,6-naphthyridin-10(9H)-one;
6-{[2,6-Dichloro-4-(trifluoromethyl)phenyl]
amino}pyrido[4,3-c]-1,6-naphthyridin-10(9H)-one;
6-{[2,6-Dichloro-4-(trifluoromethoxy)phenyl]
amino}pyrido[4,3-c]-1,6-naphthyridin-10(9H)-one;
3,5-Dichloro-4-[(10-oxo-9,10-dihydropyrido[4,3-c]-1,6-
naphthyridin-6-yl)amino]benzenesulfonamide;
6-{[(1S)-1-(Trifluoromethyl)propyl]amino}pyrido[4,3-
c]-1,6-naphthyridin-10(9H)-one;
6-{[(1S)-2,2,2-Trifluoro-1-methylethyl]amino}pyrido[4,
3-c]-1,6-naphthyridin-10(9H)-one;
6-[(3,5-Dichloropyridin-4-yl)amino]pyrido[4,3-c]-1,6-
naphthyridin10(9H)-one;
4-Methyl-3-[(10-oxo-9,10-dihydropyrido[4,3-c]-1,6-
naphthyridin-6-yl)amino]benzonitrile;
6-({2,6-Dichloro-4-[(1R)-1-hydroxyethyl]phenyl}amino)
pyrido[4,3-c]-1,6-naphthyridin-10(9H)-one;
6-({2,6-Dichloro-4-[(1S)-1-hydroxyethyl]phenyl}amino)
pyrido[4,3-c]-1,6-naphthyridin-10(9H)-one;
6-{[2,6-Dichloro-4-(1-hydroxy-1-methylethyl)phenyl]
amino}pyrido[4,3-c]-1,6-naphthyridin-10(9H)-one;
5-{[2-Chloro-5-(1-hydroxy-1-methylethyl)phenyl]
amino}-9-fluorobenzo[c]-2,6-naphthyridin-1(2H)-one;
5- {[2-Chloro-4-fluoro-5-(1-hydroxy-1-methylethyl)phenyl]amino}-9-fluorobenzo[c]-2,6-naphthyridin-1(2H)-one;
9-Fluoro-5-{[5-(1-hydroxy-1-methylethyl)-2-methylphenyl]amino}benzo[c]-2,6-naphthyridin-1(2H)-one;
6-{[2,6-Dichloro-4-(1-hydroxy-1-methylethyl)phenyl]
amino}pyrido[4,3-c]-1,6-naphthyridin-10(9H)-one
2-oxide;
6-{[2,6-Dichloro-4-(1H-pyrazol-5-yl)phenyl]
amino}pyrido[4,3-c]-1,6-naphthyridin-10(9H)-one;
6-{[2-Chloro-6-fluoro-4-(1H-pyrazol-5-yl)phenyl]
amino}pyrido[4,3-c]-1,6-naphthyridin-10(9H)-one;
6-{[2,6-Dichloro-4-(1-hydroxycyclopropyl)phenyl]
amino}pyrido[4,3-c]-1,6-naphthyridin-10(9H)-one;
{3,5-Dichloro-4-[(10-oxo-9,10-dihydropyrido[4,3-c]-1,
6-naphthyridin-6-yl)amino]phenyl}(trifluoromethyl)
sulfoniumolate;
6-{[2,6-Dichloro-4-(3-hydroxy-3-methylbut-1-yn-1-yl)
phenyl]amino}pyrido[4,3-c]-1,6-naphthyridin-10(9H)-
one;
6-({2,6-Dichloro-4-[(1E)-3-hydroxy-3-methylbut-1-en-
1-yl]phenyl}amino)pyrido[4,3-c]-1,6-naphthyridin-10
(9H)-one;
6-({2,6-Dichloro-4-[(1S)-2,2-difluoro-1-hydroxyethyl]
phenyl}amino)pyrido[4,3-c]-1,6-naphthyridin-10(9H)-
one;
6-({2,6-Dichloro-4-[(1R)-2,2-difluoro-1-hydroxyethyl]
phenyl}amino)pyrido[4,3-c]-1,6-naphthyridin-10(9H)-
one;
3,5-Dichloro-4-[(10-oxo-9,10-dihydropyrido[4,3-c]-1,6-
naphthyridin-6-yl)amino]benzonitrile;
6-{[4-(1-Amino-1-methylethyl)-2,6-dichlorophenyl]
amino}pyrido[4,3-c]-1,6-naphthyridin-10(9l)-one;
5-{[5-(1-Amino-1-methylethyl)-2-methylphenyl]amino}-
9-bromobenzo[c]-2,6-naphthyridin-1(2H)-one;
6-({2,6-Dichloro-4-[5-(1-hydroxy-1-methylethyl)-1,2,4-
oxadiazol-3-yl]phenyl}amino)pyrido[4,3-c]-1,6-naphthyridin-10(91)-one;
6-{[2,6-Dichloro-4-(1H-1,2,3-triazol-4-yl)phenyl]
amino}pyrido[4,3-c]-1,6-naphthyridin-10(9H)-one;
6-{[2-Chloro-6-fluoro-4-(1H-1,2,3-triazol-4-yl)phenyl]
amino}pyrido[4,3-c]-1,6-naphthyridin-10(9H)-one;
3,5-Dichloro-4-[(10-oxo-9,10-dihydropyrido[4,3-c]-1,6-
naphthyridin-6-yl)amino]benzenecarboximidamide;
6-({2,6-Dichloro-4-[N-ethoxyethanimidoyl]
phenyl}amino)pyrido[4,3-c]-1,6-naphthyridin-10(9H)-
one;
6-({2,6-Dichloro-4-[(N-(2-morpholin-4-yl-2-oxoethoxy)
ethanimidoyl]phenyl}amino)pyrido[4,3-c]-1,6-naphthyridin-10(9H)-one;
6-({2,6-Dichloro-4-[(N-(2-hydroxy-2-methylpropoxy)
ethanimidoyl]phenyl}amino)pyrido[4,3-c]-1,6-naphthyridin-10(9H)-one;
6-({4-[N-(tert-Butoxy)ethanimidoyl]-2,6-
dichlorophenyl}amino)pyrido[4,3-c]-1,6-naphthyridin-
10(9H)-one;
6-({4-[N-(Allyloxy)ethanimidoyl]-2,6-
dichlorophenyl}amino)pyrido[4,3-c]-1,6-naphthyridin-
10(9H)-one;
5-[(2,6-Dichloro-4-fluorophenyl)amino]-9-morpholin-4-
ylbenzo[c]-2,6-naphthyridin-1(2H)-one;
4-(2-Hydroxyethyl)-N-{1-oxo-5-[(2,4,6-trifluorophenyl)
amino]-1,2-dihydrobenzo[c]-2,6-naphthyridin-9-
yl}piperazine-1-carboxamide;
N3-[(Dimethylamino)sulfonyl]-N3-methyl-N-{1-oxo-5-
[(2,4,6-trifluorophenyl)amino]-1,2-dihydrobenzo[c]-2,
6-naphthyridin-9-yl}-b-alaninamide;
3-Hydroxy-N-{1-oxo-5-[(2,4,6-trifluorophenyl)amino]-
1,2-dihydrobenzo[c]-2,6-naphthyridin-9-
yl}propanamide;
N-{5-[(2,6-Dichloro-4-fluorophenyl)amino]-1-oxo-1,2-
dihydrobenzo[c]-2,6-naphthyridin-9-yl}-2-morpholin-
4-ylacetamide;
N-{5-[(2,6-Dichloro-4-fluorophenyl)amino]-1-oxo-1,2-
dihydrobenzo[c]-2,6-naphthyridin-9-yl}pyrazine-2-
carboxamide;
N-{5-[(2,6-Dichloro-4-fluorophenyl)amino]-1-oxo-1,2-
dihydrobenzo[c]-2,6-naphthyridin-9-yl}-N'-(2-methoxyethyl)urea;
N'-{5-[(2,6-Dichloro-4-fluorophenyl)amino]-1-oxo-1,2-
dihydrobenzo[c]-2,6-naphthyridin-9-yl}-N,N-dimethylurea;
N-{5-[(2,6-Dichloro-4-fluorophenyl)amino]-1-oxo-1,2-
dihydrobenzo[c]-2,6-naphthyridin-9-yl}-2-methyl-2-
morpholin-4-ylpropanamide;
5-[(2,6-Dichloro-4-fluorophenyl)amino]-9-[(2-hydroxy-
2-pyrazin-2-ylethyl)amino]benzo[c]-2,6-naphthyridin-
1(2H)-one;
5-[(2,6-Dichloro-4-fluorophenyl)amino]-9-[(2-morpholin-4-ylethyl)amino]benzo[c]-2,6-naphthyridin-1(2H)-
one;
5-[(2,6-Dichloro-4-fluorophenyl)amino]-9-[(3,3,3-trifluoro-2-hydroxypropyl)amino]benzo[c]-2,6-naphthyridin-1(2H)-one;
5-[(2,6-Dichloro-4-fluorophenyl)amino]-9-[(2,3-dihydroxypropyl)amino]benzo[c]-2,6-naphthyridin-1(2H)-
one;
5-[(2,6-Dichloro-4-fluorophenyl)amino]-9-[(2-hydroxy-
3-methoxypropyl)amino]benzo[c]-2,6-naphthyridin-1
(2H)-one;

5-[(2,6-Dichloro-4-fluorophenyl)amino]-9-{[2-hydroxy-2-(tetrahydro-2H-pyran-4-yl)ethyl]amino}benzo[c]-2,6-naphthyridin-1(2H)-one;

5-[(2,6-Dichloro-4-fluorophenyl)amino]-9-[(2-hydroxy-2-pyrazin-2-ylethyl)amino]benzo[c]-2,6-naphthyridin-1(2H)-one;

5-[(2,6-Dichloro-4-fluorophenyl)amino]-9-({[3-(hydroxymethyl)oxetan-3-yl]methyl}amino)benzo[c]-2,6-naphthyridin-1(2H)-one;

5-[(2,6-Dichloro-4-fluorophenyl)amino]-9-[(2-methyl-2-morpholin-4-ylpropyl)amino]benzo[c]-2,6-naphthyridin-1(2H)-one;

or a pharmaceutically acceptable salt or stereoisomer thereof.

7. A pharmaceutical composition comprising a pharmaceutically effective amount of the compound according to claim 1, and a pharmaceutically acceptable carrier.

\* \* \* \* \*